United States Patent
Puffer et al.

(10) Patent No.: US 12,221,473 B2
(45) Date of Patent: *Feb. 11, 2025

(54) POLYPEPTIDES THAT BIND COMPLEMENT COMPONENT C5 OR SERUM ALBUMIN AND FUSION PROTEINS THEREOF

(71) Applicant: Alexion Pharmaceuticals, Inc., Boston, MA (US)

(72) Inventors: Bridget Puffer, South Weymouth, MA (US); Julian Chandler, Guilford, CT (US); Nimish Gera, Waltham, MA (US); Douglas L. Sheridan, Branford, CT (US); Siddharth Jindal, Hamden, CT (US); Paul P. Tamburini, Kensington, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/938,756

(22) Filed: Oct. 7, 2022

(65) Prior Publication Data

US 2023/0235033 A1 Jul. 27, 2023

Related U.S. Application Data

(63) Continuation of application No. 16/629,687, filed as application No. PCT/US2018/041661 on Jul. 11, 2018, now Pat. No. 11,498,960.

(60) Provisional application No. 62/531,215, filed on Jul. 11, 2017.

(51) Int. Cl.
  *C07K 16/18* (2006.01)
  *A61K 38/47* (2006.01)
  *A61K 39/395* (2006.01)
  *A61K 39/00* (2006.01)

(52) U.S. Cl.
  CPC .............. *C07K 16/18* (2013.01); *A61K 38/47* (2013.01); *A61K 39/3955* (2013.01); *C12Y 302/01035* (2013.01); *A61K 2039/505* (2013.01); *C07K 2317/24* (2013.01); *C07K 2317/31* (2013.01); *C07K 2317/565* (2013.01); *C07K 2317/569* (2013.01); *C07K 2317/92* (2013.01); *C07K 2317/94* (2013.01)

(58) Field of Classification Search
  None
  See application file for complete search history.

(56) References Cited

U.S. PATENT DOCUMENTS

| | | | |
|---|---|---|---|
| 7,807,409 B2 * | 10/2010 | Kopetzki | A61K 38/162 435/320.1 |
| 8,475,792 B2 * | 7/2013 | Dall'Acqua | A61K 47/6835 530/387.9 |
| 8,921,528 B2 | 12/2014 | Holt et al. | |
| 9,079,949 B1 | 7/2015 | Andrien, Jr. et al. | |
| 11,498,960 B2 | 11/2022 | Puffer et al. | |
| 2006/0093599 A1 | 5/2006 | Gazit-Bornstein et al. | |
| 2011/0002931 A1 | 1/2011 | Tamburini | |
| 2011/0008340 A1 | 1/2011 | Bansal | |
| 2011/0064653 A1 | 3/2011 | Hansen et al. | |
| 2012/0301469 A1 | 11/2012 | Depla et al. | |
| 2013/0273052 A1 | 10/2013 | Gies et al. | |
| 2014/0212427 A1 | 7/2014 | Song | |
| 2015/0064182 A1 | 3/2015 | Silence et al. | |
| 2015/0291686 A1 | 10/2015 | Bansal | |
| 2016/0122419 A1 | 5/2016 | Bansal | |
| 2019/0352381 A1 | 11/2019 | Sheridan et al. | |

FOREIGN PATENT DOCUMENTS

| | | | |
|---|---|---|---|
| CN | 1743009 A | | 3/2006 |
| CN | 103003296 A | | 3/2013 |
| CO | 6731077 A2 | | 8/2013 |
| EA | 012622 B1 | | 10/2009 |
| EA | 201691764 A1 | | 12/2016 |
| JP | 2015-508652 A | | 3/2015 |
| JP | 2016-20345 A | | 2/2016 |
| KR | 10-2011-0038173 A | | 4/2011 |

(Continued)

OTHER PUBLICATIONS

Haller, Michael F. "Converting intravenous dosing to subcutaneous dosing with recombinant human hyaluronidase." Pharmaceutical Technology, Pharmaceutical Technology—Oct. 2, 2007, vol. 31, Issue 10, Advanstar Communications Inc. (Year: 2007).*

Vincke, Cecile, et al. "General strategy to humanize a camelid single-domain antibody and identification of a universal humanized nanobody scaffold." Journal of Biological Chemistry 284.5 (2009): 3273-3284. (Year: 2009).*

Kipriyanov, Sergey M., and Fabrice Le Gall. "Generation and production of engineered antibodies." Molecular biotechnology 26.1 (2004): 39-60. (Year: 2004).*

(Continued)

*Primary Examiner* — Michael Szperka
*Assistant Examiner* — Lia E Taylor
(74) *Attorney, Agent, or Firm* — Clark & Elbing LLP

(57) ABSTRACT

The disclosure provides engineered polypeptides that specifically bind to human complement component C5 and/or serum albumin. The disclosure also provides fusion proteins comprising such engineered polypeptides, wherein such fusion proteins may be multivalent and multi-specific fusion proteins. The disclosure further provides nucleic acid molecules that encode such engineered polypeptides or fusion proteins, and methods of making such engineered polypeptides or fusion proteins. The disclosure further provides pharmaceutical compositions that comprise such engineered polypeptides or fusion proteins, and methods of treatment using such engineered polypeptides or fusion proteins.

13 Claims, 22 Drawing Sheets

Specification includes a Sequence Listing.

(56) References Cited

FOREIGN PATENT DOCUMENTS

| | | |
|---|---|---|
| MX | 2019008827 A | 9/2019 |
| WO | WO-03/080672 A1 | 10/2003 |
| WO | WO-2007/056227 A2 | 5/2007 |
| WO | WO-2010/015608 A1 | 2/2010 |
| WO | WO-2010/151526 A1 | 12/2010 |
| WO | WO-2011/112850 A2 | 9/2011 |
| WO | WO-2012/004384 A2 | 1/2012 |
| WO | WO-2013/093762 A1 | 6/2013 |
| WO | WO-2013/126006 A1 | 8/2013 |
| WO | WO-2015/028550 A1 | 3/2015 |
| WO | WO-2015/028558 A1 | 3/2015 |
| WO | WO-2018/140956 A1 | 8/2018 |

OTHER PUBLICATIONS

Ghahroudi, M et al. "Selection and identification of single domain antibody fragments from camel heavy-chain antibodies." FEBS letters vol. 414,3 (1997): 521-6. doi:10.1016/s0014-5793(97)01062-4 (Year: 1997).*
Arbabi Ghahroudi et al., "Selection and identification of single domain antibody fragments from camel heavy-chain antibodies," FEBS Lett. 414(3):521-6 (1997).
Berglund et al., "The clinical potential of Affibody-based inhibitors of C5 for therapeutic complement disruption," Expert Rev Proteomics. 13(3):241-3 (2016).
Caravaca-Fontán et al., "Update on C3 Glomerulopathy: A Complement-Mediated Disease," Nephron. 144(6):272-280 (May 2020).
Chen et al., "Fusion protein linkers: property, design and functionality," available in PMC Oct. 15, 2014, published in final edited form as: Adv Drug Deliv Rev. 65(10):1357-1369 (2013).
Colman, "Effects of amino acid sequence changes on antibody-antigen interactions," Res Immunol. 145(1):33-6 (1994).
Extended European Search Report for European Patent Application No. 18744926.9 mailed Jul. 10, 2020 (10 pages).
Harmsen et al. "Properties, production, and applications of camelid single-domain antibody fragments," Appl Microbiol Biotechnol. 77(1):13-22 (2007).
International Preliminary Report on Patentability for International Application No. PCT/US2018/015985, issued Jul. 30, 2019 (9 pages).
International Search Report and Written Opinion for International Application No. PCT/US2018/015985, mailed Jun. 11, 2018 (16 pages).
International Search Report for International Application No. PCT/US2018/041661, mailed Sep. 24, 2018 (5 pages).
Kipriyanov et al., "Generation and Production of Engineered Antibodies," Mol Biotechnol. 26(1): 39-60 (2004).
Kontermann et al., "Bispecific antibodies," Drug Discov Today. 20(7):838-47 (Jul. 2015) (12 pages).
Maeda et al., "Engineering of functional chimeric protein G-Vargula luciferase," Anal Biochem. 249(2):147-52 (Jul. 1997).
Muller et al., "Spliceosomal Peptide P140 for Immunotherapy of Systemic Lupus Erythematosus: Results of an Early Phase II Clinical Trial," Arthritis & Rheumatism. 58(12):3873-3883 (2008).
Office Action for Chinese Patent Application No. 201880046102.3 dated Feb. 14, 2023 (13 pages).
Office Action for Colombian Patent Application No. NC2020/0000369, dated Sep. 14, 2021 (14 pages).
Office Action for Japanese Patent Application No. 2020-500686 mailed Jun. 28, 2022 (9 pages).
Office Action for Russian Patent Application No. 2020102910/10(004483) mailed Dec. 2, 2021 (19 pages) (English language translation provided).
Official Action for Russian Patent Application No. 2020102910 dated Apr. 22, 2022 (13 pages).
Ozen et al., "Broadly effective metabolic and immune recovery with C5 inhibition in CHAPLE disease," Nat Immunol. 22(2):128-39 (2021).
Pandey et al., "The link between Complement System and Anemia in Gaucher disease," J Immunol. 206(1 Supplement) 64.01 (2021). Abstract only.
Pedersen et al. "Recruitment of Properdin by Bi-Specific Nanobodies Activates the Alternative Pathway of Complement," Mol Immunol. 124:200-210 (2020).
Rother et al. "Discovery and development of the complement inhibitor eculizumab for the treatment of paroxysmal nocturnal hemoglobinuria," Nat Biotechnol. 25(11):1256-64 (2007) (10 pages).
Shen et al., "Single variable domain-IgG fusion. A novel recombinant approach to Fc domain-containing bispecific antibodies," J Biol Chem. 281(16):10706-14 (2006).
Shibuya et al., "Generation of camelid VHH bispecific constructs via in-cell intein-mediated protein trans-splicing," Protein Eng Des Sel. 30(1):15-21 (Jan. 2017) (Epub Nov. 2016).
Stork et al. "Biodistribution of a bispecific single-chain diabody and its half-life extended derivatives," J Biol Chem. 284(38):25612-9 (2009) (9 pages).
Stryer, Protein Structure and Function, *Biochemistry* (4th Edition), W.H. Freeman and Company, 18-23 (1995).
Tijink et al. "Improved Tumor Targeting of Anti-Epidermal Growth Factor Receptor Nanobodies Through Albumin Binding: Taking Advantage of Modular Nanobody Technology," Mol Cancer Ther. 7(8):2288-97 (2008).
Van Roy et al. "The preclinical pharmacology of the high affinity anti-IL-6R Nanobody® ALX-0061 supports its clinical development in rheumatoid arthritis," Arthritis Res Ther. 17:135 (2015) (16 pages).
Vincke et al., "General strategy to humanize a camelid single-domain antibody and identification of a universal humanized nanobody scaffold," J Biol Chem. 284(5):3273-84 (2009).
Written Opinion for International Application No. PCT/US2018/041661, mailed Sep. 24, 2018 (8 pages).
Office Action and Search Report for Canadian Patent Application No. 3,067,247 mailed Nov. 2, 2023 (9 pages).
Rudikoff et al., "Single amino acid substitution altering antigen-binding specificity," Proc Natl Acad Sci USA. 79(6):1979-83 (Mar. 1982).
Tamura et al., "Structural correlates of an anticarcinoma antibody: identification of specificity-determining residues (SDRs) and development of a minimally immunogenic antibody variant by retention of SDRs only," J Immunol. 164(3):1432-41 (Feb. 2000) (11 pages).
Communication pursuant to Article 94(3) EPC for European Patent Application No. 18746529.9 mailed Jul. 12, 2023 (9 pages).
Office Action for South Korean Patent Application No. 10-2020-7002889 dated Jan. 9, 2024 (15 pages).

* cited by examiner

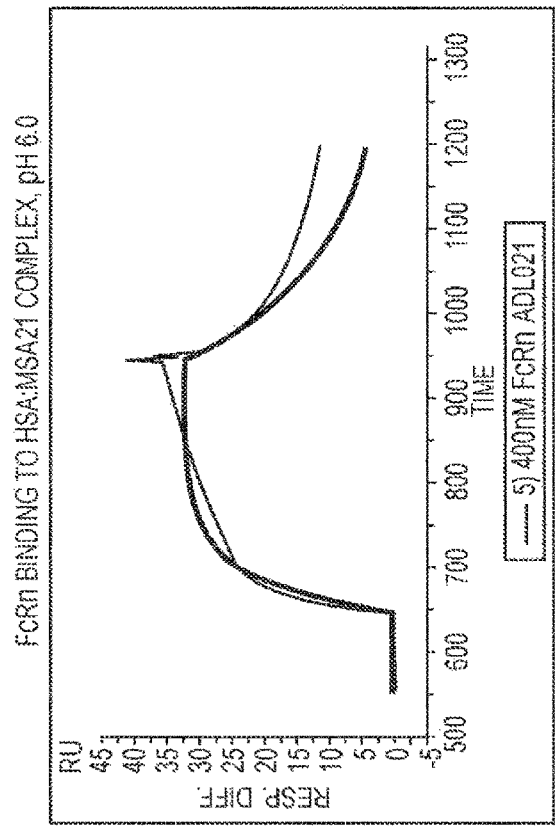
FIG. 7A
FIG. 7B
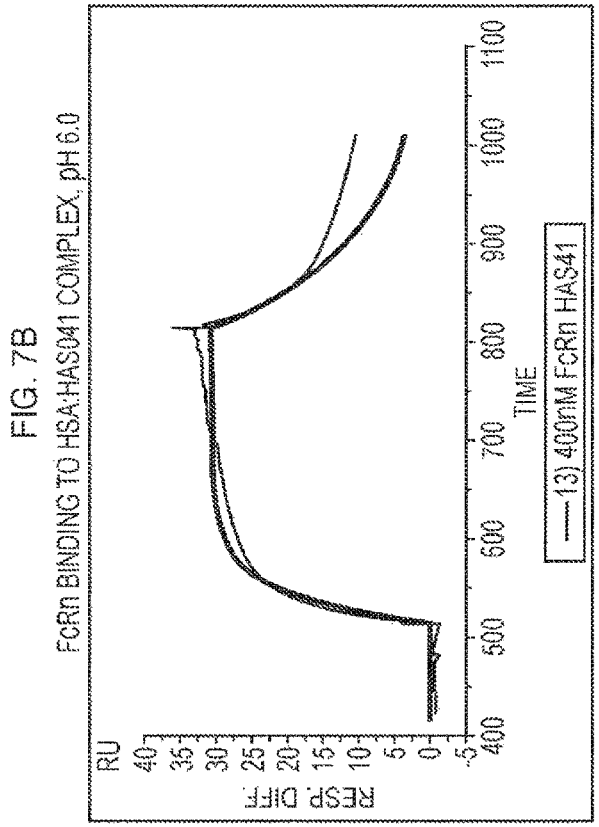
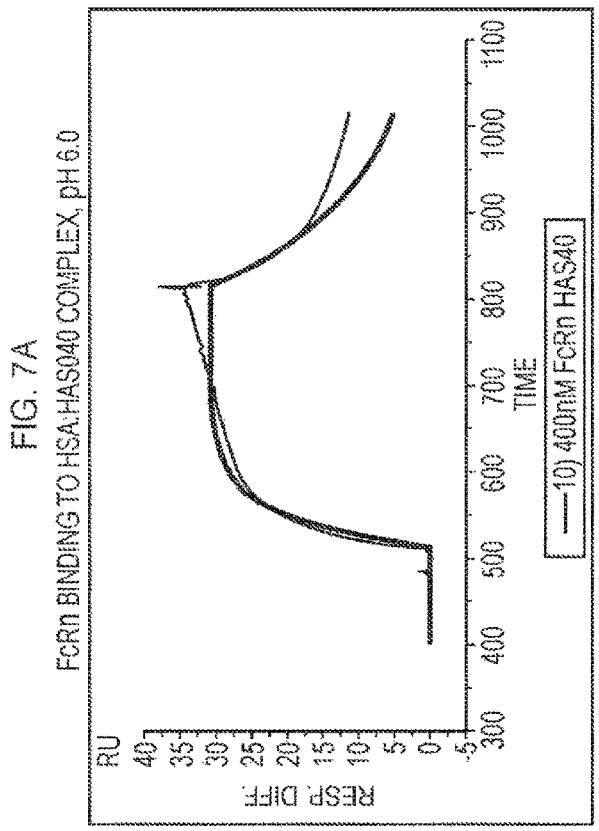
FIG. 7C
FIG. 7D

POLYPEPTIDES THAT BIND COMPLEMENT COMPONENT C5 OR SERUM ALBUMIN AND FUSION PROTEINS THEREOF

RELATED INFORMATION PARAGRAPH

This application claims the benefit of the priority date of U.S. Provisional Application No. 62/531,215, filed on Jul. 11, 2017, the content of which is hereby incorporated by reference in its entirety.

SEQUENCE LISTING

The instant application contains a Sequence Listing which has been submitted electronically in XML format and is hereby incorporated by reference in its entirety. Said XML copy, created on Sep. 30, 2022, is named 51196-005003_Sequence_Listing_9_30_22 and is 378,627 bytes in size.

BACKGROUND

Complement component 5 (C5) is the fifth component of complement, which plays an important role in inflammatory and cell killing processes. An activation peptide, C5a, which is an anaphylatoxin that possesses potent spasmogenic and chemotactic activity, is derived from the alpha polypeptide via cleavage with a C5-convertase. The C5b macromolecular cleavage product can form a complex with the C6 complement component, and this complex is the basis for formation of the membrane attack complex (MAC), which includes additional complement components.

Improperly regulated C5 can lead to immuno-compromised patients or disorders characterized by excessive cellular degradation (e.g., hemolytic disorders cause by C5-mediated hemolysis).

As misregulated C5 can lead to severe and devastating phenotypes, modulators of C5 activity with favorable pharmaceutical properties (e.g., half-life) are needed.

SUMMARY

The disclosure provides engineered polypeptides that specifically bind to complement component C5 or serum albumin, wherein such engineered polypeptides may be sdAbs or Ig variable domains. In some embodiments, the engineered polypeptides do not significantly reduce or inhibit the binding of serum albumin to FcRn or do not significantly reduce the half-life of serum albumin. The disclosure also provides fusion proteins comprising such engineered polypeptides, wherein such fusion proteins may be multivalent and multi-specific fusion proteins. The disclosure further provides nucleic acid molecules that encode such engineered polypeptides or fusion proteins, and methods of making such engineered polypeptides or fusion proteins. The disclosure further provides pharmaceutical compositions that comprise such engineered polypeptides or fusion proteins, and methods of treatment using such engineered polypeptides or fusion proteins.

In one embodiment, the disclosure is directed to a fusion protein comprising an engineered polypeptide that specifically binds to human complement component C5 and an engineered polypeptide that specifically binds to human serum albumin, wherein the engineered polypeptide that specifically binds to human complement component C5 is fused to the polypeptide that specifically binds to human serum albumin either directly or via a peptide linker. In a particular embodiment, the C-terminal residue of the polypeptide that specifically binds to human serum albumin is fused either directly or via a linker to the N-terminal residue of the polypeptide that specifically binds to human complement component C5. In a particular embodiment, the C-terminal residue of the polypeptide that specifically binds to human complement component C5 is fused either directly or via a linker to the N-terminal residue of the polypeptide that specifically binds to human serum albumin. In a particular embodiment, the polypeptide that specifically binds to human complement component C5 comprises an amino acid sequence selected from the group consisting of SEQ ID NOS:1-12 and fragments thereof; and the polypeptide that specifically binds to human serum albumin comprises an amino acid selected from the group consisting of SEQ ID NOs:22-34 and fragments thereof. In a particular embodiment, the polypeptide that specifically binds to human complement component C5 comprises the amino acid sequence of SEQ ID NO:11 and the polypeptide that specifically binds to human serum albumin comprises the amino acid sequence of SEQ ID NO:26. In a particular embodiment, the fusion proteins described herein further comprise a peptide linker having an amino acid sequence of SEQ ID NO:102 or 103. In a particular embodiment, the fusion protein comprises a sequence that is at least 95% identical to a sequence selected from the group consisting of SEQ ID NOS:96-101. In a particular embodiment, the fusion protein consists of a sequence selected from the group consisting of SEQ ID NOS:96-101. In a particular embodiment, the fusion protein consists of a polypeptide sequence of SEQ ID NO:96. In a particular embodiment, the polypeptide that specifically binds to human complement component C5 comprises three complementarity determining regions, CDR1, CDR2 and CDR3, wherein CDR1 comprises any one of the amino acid sequences of SEQ ID NOS:13-17, CDR2 comprises an amino acid sequences of SEQ ID NO:18 or 19, and CDR3 comprises an amino acid sequences of SEQ ID NO:20 or 21. In a particular embodiment, the polypeptide that specifically binds to human serum albumin comprises three complementarity determining regions, CDR1, CDR2 and CDR3, wherein CDR1 comprises any one of the amino acid sequences of SEQ ID NOS:35-43, CDR2 comprises any one of the amino acid sequences of SEQ ID NOS:44-51, and CDR3 comprises any one of the amino acid sequences of SEQ ID NOS:52-63. In some embodiments, the antigen-binding domains described herein, can be engineered or further engineered to bind antigen in a pH-dependent manner, e.g., high affinity for antigen at high pH and a lower affinity for antigen binding at lower pH, or vice versa.

In one embodiment, the disclosure is directed to a pharmaceutical composition comprising a therapeutically effective amount of a fusion protein described herein and a pharmaceutically acceptable carrier. In a particular embodiment, the pharmaceutical compositions can contain an agent that degrades or inactivates hyaluronan, e.g., hyaluronidase or a recombinant hyaluronidase.

In one embodiment, the disclosure is directed to an isolated nucleic acid molecule comprising a nucleotide sequence encoding a fusion protein described herein. The nucleic acid molecule can be, for example, an expression vector. The disclosure is directed to host cells, (e.g., Chinese hamster ovary (CHO) cells, HEK293 cells, *Pichia pastoris* cells, mammalian cells, yeast cells, plant cells) and expression systems that comprise or utilize the nucleic acids that encode a fusion proteins described herein.

In one embodiment, the disclosure is directed to an engineered polypeptide that binds to human complement component C5, wherein the engineered polypeptide comprises an amino acid sequence selected from the group consisting of SEQ ID NOS:1-12 and fragments thereof. In a particular embodiment, the engineered polypeptide comprises an amino acid sequence that is at least 90% identical (e.g., 90%, 91%, 92%, 93%, 94%, 95%, 96%, 97%, 98%, or 99% identical) to a sequence selected from the group consisting of SEQ ID NOS:1-12. For example, in one embodiment, the engineered polypeptide comprises the amino acid sequence set forth in SEQ ID NO:1 or a sequence at least 90% identical thereto. In another embodiment, the engineered polypeptide comprises the amino acid sequence set forth in SEQ ID NO:2 or a sequence at least 90% identical thereto. In another embodiment, the engineered polypeptide comprises the amino acid sequence set forth in SEQ ID NO:3 or a sequence at least 90% identical thereto. In another embodiment, the engineered polypeptide comprises the amino acid sequence set forth in SEQ ID NO:4 or a sequence at least 90% identical thereto. In another embodiment, the engineered polypeptide comprises the amino acid sequence set forth in SEQ ID NO:5 or a sequence at least 90% identical thereto. In another embodiment, the engineered polypeptide comprises the amino acid sequence set forth in SEQ ID NO:6 or a sequence at least 90% identical thereto. In another embodiment, the engineered polypeptide comprises the amino acid sequence set forth in SEQ ID NO:7 or a sequence at least 90% identical thereto. In another embodiment, the engineered polypeptide comprises the amino acid sequence set forth in SEQ ID NO:8 or a sequence at least 90% identical thereto. In another embodiment, the engineered polypeptide comprises the amino acid sequence set forth in SEQ ID NO:9 or a sequence at least 90% identical thereto. In another embodiment, the engineered polypeptide comprises the amino acid sequence set forth in SEQ ID NO:10 or a sequence at least 90% identical thereto. In another embodiment, the engineered polypeptide comprises the amino acid sequence set forth in SEQ ID NO:11 or a sequence at least 90% identical thereto. In another embodiment, the engineered polypeptide comprises the amino acid sequence set forth in SEQ ID NO:12 or a sequence at least 90% identical thereto.

In another embodiment, an engineered polypeptide is provided that binds to human complement component C5, wherein the engineered polypeptide consists of an amino acid sequence selected from the group consisting of SEQ ID NOS:1-12 and fragments thereof. For example, in one embodiment, the engineered polypeptide consists of the amino acid sequence set forth in SEQ ID NO:1. In another embodiment, the engineered polypeptide consists of the amino acid sequence set forth in SEQ ID NO:2. In another embodiment, the engineered polypeptide consists of the amino acid sequence set forth in SEQ ID NO:3. In another embodiment, the engineered polypeptide consists of the amino acid sequence set forth in SEQ ID NO:4. In another embodiment, the engineered polypeptide consists of the amino acid sequence set forth in SEQ ID NO:5. In another embodiment, the engineered polypeptide consists of the amino acid sequence set forth in SEQ ID NO:6. In another embodiment, the engineered polypeptide consists of the amino acid sequence set forth in SEQ ID NO:7. In another embodiment, the engineered polypeptide consists of the amino acid sequence set forth in SEQ ID NO:8. In another embodiment, the engineered polypeptide consists of the amino acid sequence set forth in SEQ ID NO:9. In another embodiment, the engineered polypeptide consists of the amino acid sequence set forth in SEQ ID NO:10. In another embodiment, the engineered polypeptide consists of the amino acid sequence set forth in SEQ ID NO:11. In another embodiment, the engineered polypeptide consists of the amino acid sequence set forth in SEQ ID NO:12.

In one embodiment, the disclosure is directed to an engineered polypeptide that specifically binds to human serum albumin, wherein the polypeptide comprises and amino acid sequence selected from the group consisting of SEQ ID NOS:22-34 and fragments thereof. In a particular embodiment, the engineered polypeptide comprises an amino acid sequence that is at least 90% identical (e.g., 90%, 91%, 92%, 93%, 94%, 95%, 96%, 97%, 98%, or 99% identical) to any one of the amino acid sequences of SEQ ID NOS:22-34. For example, in one embodiment, the engineered polypeptide comprises the amino acid sequence set forth in SEQ ID NO:22 or a sequence at least 90% identical thereto. In another embodiment, the engineered polypeptide comprises the amino acid sequence set forth in SEQ ID NO:23 or a sequence at least 90% identical thereto. In another embodiment, the engineered polypeptide comprises the amino acid sequence set forth in SEQ ID NO:24 or a sequence at least 90% identical thereto. In another embodiment, the engineered polypeptide comprises the amino acid sequence set forth in SEQ ID NO:25 or a sequence at least 90% identical thereto. In another embodiment, the engineered polypeptide comprises the amino acid sequence set forth in SEQ ID NO:26 or a sequence at least 90% identical thereto. In another embodiment, the engineered polypeptide comprises the amino acid sequence set forth in SEQ ID NO:27 or a sequence at least 90% identical thereto. In another embodiment, the engineered polypeptide comprises the amino acid sequence set forth in SEQ ID NO:28 or a sequence at least 90% identical thereto. In another embodiment, the engineered polypeptide comprises the amino acid sequence set forth in SEQ ID NO:29 or a sequence at least 90% identical thereto. In another embodiment, the engineered polypeptide comprises the amino acid sequence set forth in SEQ ID NO:30 or a sequence at least 90% identical thereto. In another embodiment, the engineered polypeptide comprises the amino acid sequence set forth in SEQ ID NO:31 or a sequence at least 90% identical thereto. In another embodiment, the engineered polypeptide comprises the amino acid sequence set forth in SEQ ID NO:32 or a sequence at least 90% identical thereto. In another embodiment, the engineered polypeptide comprises the amino acid sequence set forth in SEQ ID NO:33 or a sequence at least 90% identical thereto. In another embodiment, the engineered polypeptide comprises the amino acid sequence set forth in SEQ ID NO:34 or a sequence at least 90% identical thereto.

In another embodiment, the engineered polypeptide that specifically binds to human serum albumin consists of an amino acid sequence selected from the group consisting of SEQ ID NOS:22-34 and fragments thereof. For example, in one embodiment, the engineered polypeptide consists of the amino acid sequence set forth in SEQ ID NO:22. In another embodiment, the engineered polypeptide consists of the amino acid sequence set forth in SEQ ID NO:23. In another embodiment, the engineered polypeptide consists of the amino acid sequence set forth in SEQ ID NO:24. In another embodiment, the engineered polypeptide consists of the amino acid sequence set forth in SEQ ID NO:25. In another embodiment, the engineered polypeptide consists of the amino acid sequence set forth in SEQ ID NO:26. In another embodiment, the engineered polypeptide consists of the amino acid sequence set forth in SEQ ID NO:27. In another embodiment, the engineered polypeptide consists of the amino acid sequence set forth in SEQ ID NO:28. In another embodiment, the engineered polypeptide consists of the amino acid sequence set forth in SEQ ID NO:29. In another embodiment, the engineered polypeptide consists of the amino acid sequence set forth in SEQ ID NO:30. In another embodiment, the engineered polypeptide consists of the amino acid sequence set forth in SEQ ID NO:31. In another embodiment, the engineered polypeptide consists of the amino acid sequence set forth in SEQ ID NO:32. In another embodiment, the engineered polypeptide consists of the amino acid sequence set forth in SEQ ID NO:33. In another embodiment, the engineered polypeptide consists of the amino acid sequence set forth in SEQ ID NO:34.

In a particular embodiment, the engineered polypeptide that specifically binds to human serum albumin comprises three complementarity determining regions, CDR1, CDR2 and CDR3, wherein CDR1 comprises an amino acid sequence selected from the group consisting of SEQ ID NOs:35-43, CDR2 comprises an amino acid sequence selected from the group consisting of SEQ ID NOs:44-51, and CDR3 comprises an amino acid sequence selected from the group consisting of SEQ ID NOs:52-63. In a particular embodiment, the polypeptide specifically binds to the same epitope on human serum albumin as Alb1.

In one embodiment, the disclosure is directed to a method for making a fusion protein described herein, comprising expressing in a host cell at least one nucleic acid molecule comprising a nucleotide sequence encoding the fusion protein.

In one embodiment, the disclosure is directed to a therapeutic kit comprising: (a) a container comprising a label; and (b) a composition comprising the fusion protein described herein; wherein the label indicates that the composition is to be administered to a patient having, or that is suspected of having, a complement-mediated disorder. The kit can optionally comprise an agent that degrades or inactivates hyaluronan, e.g., hyaluronidase or a recombinant hyaluronidase.

In one embodiment, the disclosure is directed to a method for treating a patient having a complement-mediated disorder, the method comprising administering to the patient a therapeutically effective amount of a fusion protein described herein. In a particular embodiment, the complement-mediated disorder is selected from the group consisting of: rheumatoid arthritis; lupus nephritis; asthma; ischemia-reperfusion injury; atypical hemolytic uremic syndrome; dense deposit disease; paroxysmal nocturnal hemoglobinuria; macular degeneration; hemolysis, elevated liver enzymes, and low platelets (HELLP) syndrome; Guillain-Barré Syndrome; CHAPLE syndrome; myasthenia gravis; neuromyelitis optica; post-hematopoietic stem cell transplant thrombotic microangiopathy (post-HSCT-TMA); post-bone marrow transplant TMA (post-BMT TMA); Degos disease; Gaucher's disease; glomerulonephritis; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis.

BRIEF DESCRIPTION OF THE DRAWINGS

FIGS. 7A-7D show Biacore sensorgrams indicating the binding of FcRn at pH 6.0 in HBS-EP buffer to HSA saturated with no VHH domain (control, FIG. 7A), MSA21 (FIG. 7B), HAS040 (FIG. 7C) or HAS041 (FIG. 7D).

DETAILED DESCRIPTION

Figure 1A:
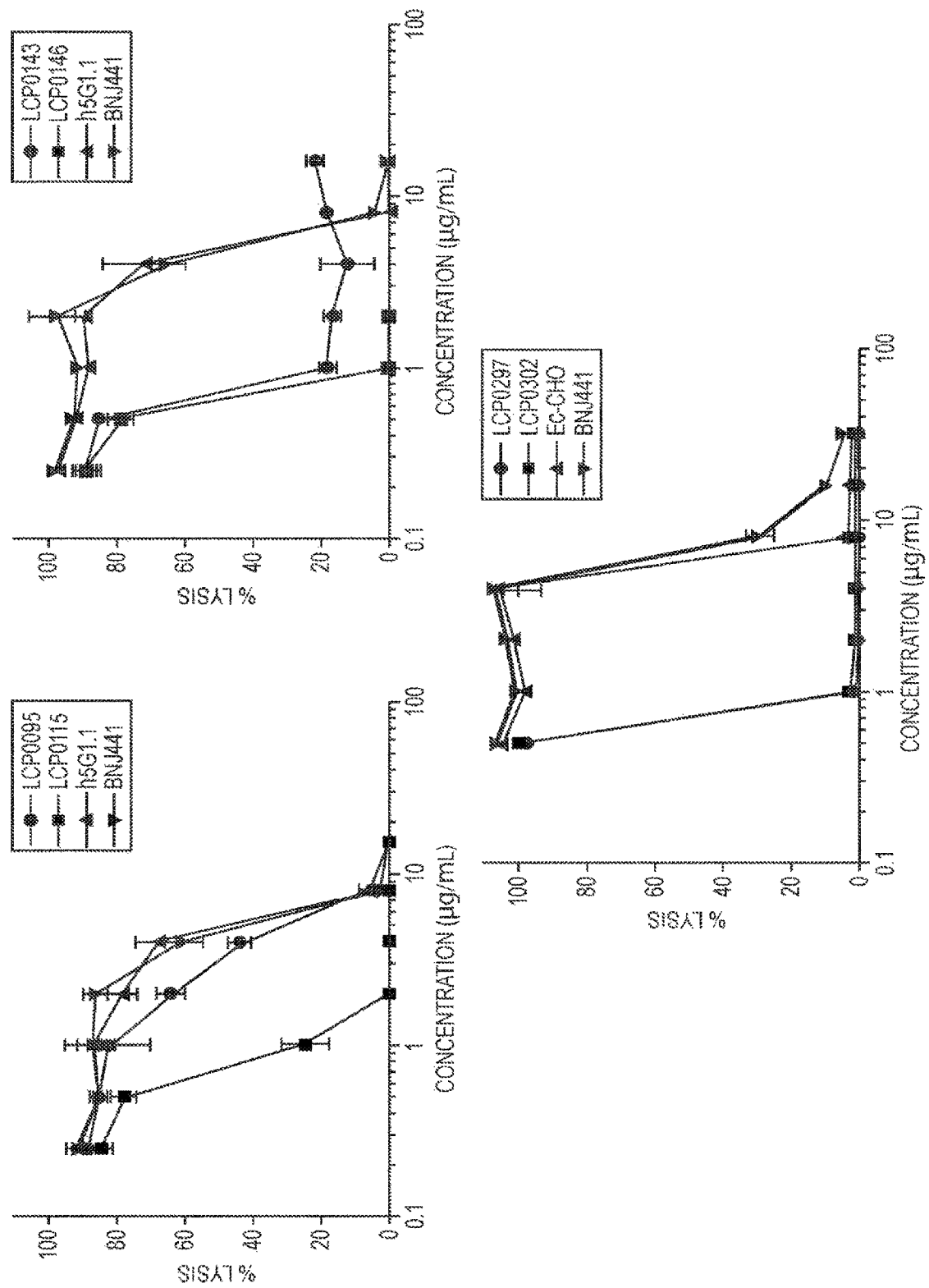
FIGS. 1A and 1B show the results of a Complement Classical Pathway (CCP) hemolysis assay for anti-C5 VHH domains.

The disclosure provides engineered polypeptides that specifically bind to serum albumin or complement component C5, wherein the engineered polypeptides can be, for example, single-domain antibodies (sdAb's) or immunoglobulin (IgG) variable domains. In some embodiments, the engineered polypeptides do not significantly reduce or inhibit the binding of serum albumin to FcRn or do not significantly reduce the half-life of serum albumin. The disclosure also provides fusion proteins comprising engineered polypeptides, wherein the fusion proteins can be, for example, multivalent and multi-specific fusion proteins. The disclosure further provides nucleic acid molecules that encode engineered polypeptides or fusion proteins, and methods of making such engineered polypeptides or fusion proteins. The disclosure further provides pharmaceutical compositions that comprise engineered polypeptides or fusion proteins, and methods of treatment using such engineered polypeptides or fusion proteins.

Standard recombinant DNA methodologies are used to construct polynucleotides encoding the engineered polypeptides or fusion proteins of the disclosure, incorporate such polynucleotides into recombinant expression vectors, and introduce such vectors into host cells to produce the engineered polypeptides or fusion proteins of the disclosure. See e.g., Sambrook et al., 2001, MOLECULAR CLONING: A LABORATORY MANUAL (Cold Spring Harbor Laboratory Press, 3rd ed.). Unless specific definitions are provided, the nomenclature utilized in connection with, and the laboratory procedures and techniques of, analytical chemistry, synthetic organic chemistry, and medicinal and pharmaceutical chemistry described herein are those known and commonly used in the art. Similarly, conventional techniques can be used for chemical syntheses, chemical analyses, pharmaceutical preparation, formulation, delivery and treatment of patients.

Definitions

As utilized in accordance with the present disclosure, the following terms, unless otherwise indicated, shall be understood to have the following meanings. Unless otherwise required by context, singular terms shall include pluralities and plural terms shall include the singular.

As used herein, the term "binding domain" refers to the portion of a protein or antibody which comprises the amino acid residues that interact with an antigen. Binding domains include, but are not limited to, antibodies (e.g., full length antibodies), as well as antigen-binding portions thereof. The binding domain confers on the binding agent its specificity and affinity for the antigen. The term also covers any protein having a binding domain which is homologous or largely homologous to an immunoglobulin-binding domain.

The term "antibody" as referred to herein includes whole antibodies and any antigen binding fragment (i.e., "antigen-binding portion") or single chain version thereof. An "antibody" refers, in one preferred embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody (or simply "antibody fragment"), as used herein, refers to one or more fragments or portions of an antibody that retain the ability to specifically bind to an antigen. Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker.

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (sFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

The term "human antibody," as used herein, refers to an immunoglobulin (Ig) that is used, for example, by the immune system to bind and neutralize pathogens. The term includes antibodies having variable and constant regions substantially corresponding to human germline Ig sequences. In some embodiments, human antibodies are produced in non-human mammals, including, but not limited to, rodents, such as mice and rats, and lagomorphs, such as rabbits. In other embodiments, human antibodies are produced in hybridoma cells. In still other embodiments, human antibodies are produced recombinantly. As used herein, human antibodies include all or a portion of an antibody, including, for example, heavy and light chains, variable regions, constant regions, proteolytic fragments, complementarity determining regions (CDRs), and other functional fragments.

As used herein, "biologically active fragment" refers to a portion of a molecule, e.g., a gene, coding sequence, mRNA, polypeptide or protein, which has a desired length or biological function. A biologically active fragment of a protein, for example, can be a fragment of the full-length protein that retains one or more biological activities of the protein. A biologically active fragment of an mRNA, for example, can be a fragment that, when translated, expresses a biologically active protein fragment. A biologically active mRNA fragment, furthermore, can comprise shortened versions of non-coding sequences, e.g., regulatory sequences, UTRs, etc. In general, a fragment of an enzyme or signaling molecule can be, for example, that portion(s) of the molecule that retains its signaling or enzymatic activity. A fragment of a gene or coding sequence, for example, can be that portion of the gene or coding sequence that produces an expression product fragment. A fragment does not necessarily have to be defined functionally, as it can also refer to a portion of a molecule that is not the whole molecule, but has some desired characteristic or length (e.g., restriction fragments, proteolytic fragment of a protein, amplification fragments, etc.).

Ordinary or conventional mammalian antibodies comprise a tetramer, which is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain," as used herein, refer to any Ig polypeptide having sufficient variable domain sequence to confer specificity for a target antigen. The N-terminal portion of each light and heavy chain typically includes a variable domain of about 100 to 110 or more amino acids that typically is responsible for antigen recognition. The C-terminal portion of each chain typically defines a constant domain responsible for effector function. Thus, in a naturally occurring antibody, a full-length heavy chain Ig polypeptide includes a variable domain ($V_H$ or VH) and three constant domains ($C_{H1}$ or CH1, $C_{H2}$ or CH2, and $C_{H3}$ or CH3), wherein the $V_H$ domain is at the N-terminus of the polypeptide and the $C_{H3}$ domain is at the C-terminus, and a full-length light chain Ig polypeptide includes a variable domain ($V_L$ or VL) and a constant domain ($C_L$ or CL), wherein the $V_L$ domain is at the N-terminus of the polypeptide and the $C_L$ domain is at the C-terminus.

Within full-length light and heavy chains, the variable and constant domains typically are joined by a "J" region of about 12 or more amino acids, with the heavy chain also including a "D" region of about 10 more amino acids. The variable regions of each light/heavy chain pair typically form an antigen-binding site. The variable domains of naturally occurring antibodies typically exhibit the same general structure of relatively conserved framework regions (FR) joined by three hypervariable regions called CDRs. The CDRs from the two chains of each pair typically are aligned by the framework regions, which enables binding to a specific epitope. From the N-terminus to the C-terminus, both light and heavy chain variable domains typically comprise the domains FR1, CDR1, FR2, CDR2, FR3, CDR3 and FR4.

The terms "substantially pure" or "substantially purified," as used herein, refer to a compound or species that is the predominant species present in a composition (i.e., on a molar basis it is more abundant than any other individual species in the composition). A substantially purified fraction, for example, can be a composition wherein the predominant species comprises at least about 50% (on a molar basis) of all macromolecular species present. A substantially pure composition, for example, can comprise a predominant species that represents more than about 80%, 85%, 90%, 95% or 99% of all macromolar species present in the composition. In other embodiments, the predominant species can be purified to substantial homogeneity (contaminant species cannot be detected in the composition by conventional detection methods) wherein the composition consists essentially of a single macromolecular species.

The terms "antigen" or "antigen target," as used herein, refer to a molecule or a portion of a molecule that is capable of being bound to by an antibody, one or more Ig binding domain, or other immunological binding moiety, including, for example, the engineered polypeptides or fusion proteins disclosed herein. An antigen is capable of being used in an animal to produce antibodies capable of binding to an epitope of that antigen. An antigen may have one or more epitopes.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from the antigen are tested for reactivity with the given antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

The terms "activity," "biological activity," or "biological property," as used in reference to the engineered polypeptides or fusion proteins of the disclosure, include, but are not limited to, epitope affinity and specificity, ability to antagonize the activity of an antigen target, the in vivo stability of the engineered polypeptides or fusion proteins of the disclosure, and the immunogenic properties of the engineered polypeptides or fusion proteins of the disclosure. Other identifiable biological properties include, for example, cross-reactivity (e.g., with non-human homologs of the antigen target, or with other antigen targets or tissues, generally), and ability to preserve high expression levels of protein in mammalian cells.

An antibody, immunoglobulin, or immunologically functional immunoglobulin fragment, or the engineered polypeptides or fusion proteins disclosed herein, are said to "specifically" bind an antigen when the molecule preferentially recognizes its antigen target in a complex mixture of proteins and/or macromolecules. The term "specifically binds," as used herein, refers to the ability of an antibody, immunoglobulin, or immunologically functional immunoglobulin fragment, or an engineered polypeptide or fusion protein of the disclosure, to bind to an antigen containing an epitope with an $K_D$ of at least about $10^{-6}$ M, $10^{-7}$ M, $10^{-8}$ M, $10^{-9}$ M, $10^{-10}$ M, $10^{-11}$ M, $10^{-12}$ M, or more, and/or to bind to an epitope with an affinity that is at least two-fold greater than its affinity for a nonspecific antigen.

The term "$K_D$," as used herein, refers to the dissociation constant of the interaction between an antibody, immunoglobulin, or immunologically functional immunoglobulin fragment, or an engineered polypeptide or fusion protein disclosed herein, and an antigen target. When an engineered polypeptide or fusion protein of the disclosure comprises a monovalent Ig sequence, the monovalent Ig sequence preferably binds to a desired antigen, for example, with a $K_D$ of $10^{-5}$ to $10^{-12}$ M or less, or $10^{-7}$ to $10^{-12}$ M or less, or $10^{-3}$ to $10^{-12}$ M, and/or with a binding affinity of at least $10^7$ M$^{-1}$, at least $10^8$ M$^{-1}$, at least $10^9$M$^{-1}$, or at least $10^{12}$ M$^{-1}$. A $K_D$ value greater than $10^{-4}$ M is generally considered to indicate non-specific binding. In some embodiments, a monovalent Ig sequence of an engineered polypeptide or fusion protein of the disclosure binds to a desired antigen with an affinity less than 500 mM, less than 200 nM, less than 10 nM, or less than 500 pM.

A $K_D$ can be determined by methods known in the art, including, for example, surface plasmon resonance (SPR). Generally, SPR analysis measures real-time binding interactions between a ligand (a target antigen on a biosensor matrix) and an analyte using, for example, the BIAcore system (Pharmacia Biosensor; Piscataway, NJ). SPR analysis can also be performed by immobilizing an analyte and presenting the ligand. Specific binding of an engineered polypeptide or fusion protein of the disclosure to an antigen or antigenic determinant can also be determined in any suitable manner known in the art, including, for example, Scatchard analysis and/or competitive binding assays, such as radioimmunoassays (RIA), enzyme immunoassays (EIA) and sandwich competition assays.

The term "bispecific" refers to a fusion protein of the disclosure that is capable of binding two antigens. The term "multivalent fusion protein" means a fusion protein comprising two or more antigen binding sites.

The term "multi-specific fusion protein" refers to a fusion protein of the disclosure that is capable of binding two or more related or unrelated targets.

The term "fused to" as used herein refers to a polypeptide made by combining more than one sequence, typically by cloning one sequence, e.g., a coding sequence, into an expression vector in frame with one or more second coding sequence(s) such that the two (or more) coding sequences are transcribed and translated into a single continuous polypeptide. In addition to being made by recombinant technology, parts of a polypeptide can be "fused to" each other by means of chemical reaction, or other means known in the art for making custom polypeptides.

The term "vector," as used herein, refers to any molecule (e.g., nucleic acid, plasmid or virus) that is used to transfer coding information to an expression system (e.g., a host cell or in vitro expression system). One type of vector is a "plasmid," which refers to a circular double-stranded DNA (dsDNA) molecule into which additional DNA segments can be inserted. Another type of vector is a viral vector, wherein additional DNA segments can be inserted into a viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of coding sequences to which they are operatively linked. Such vectors are referred to herein as "expression vectors."

The term "operably linked," as used herein, refers to an arrangement of flanking sequences wherein the flanking sequences are configured or assembled to perform a desired function. Thus, a flanking sequence operably linked to a coding sequence may be capable of effecting the replication, transcription, and/or translation of the coding sequence. A coding sequence is operably linked to a promoter, for example, where the promoter is capable of directing transcription of that coding sequence. A flanking sequence need not be contiguous with the coding sequence to be considered operably linked, so long as it functions correctly.

The term "host cell," as used herein, refers to a cell into which an expression vector has been introduced. A host cell is intended to refer not only to the particular subject cell, but also to the progeny of such a cell. Because certain modifications may occur in succeeding generations due to either mutation or environmental influences, such progeny may not be, in fact, identical to the parent cell, but such cells are still included within the scope of the term "host cell" as used herein. A wide variety of host cell expression systems can be used to express the engineered polypeptides or fusion proteins of the disclosure, including bacterial, yeast, baculoviral, and mammalian expression systems (as well as phage display expression systems).

The term "naturally occurring," as used herein and applied to a particular molecule, refers to a molecule that is found in nature and has not been manipulated by man. Similarly, the term "non-naturally occurring," as used herein, refers to a molecule that is not found in nature or that has been modified or artificially synthesized.

The term "engineered," as used herein and applied to a particular molecule, such as, for example, a polypeptide, that has been modified or manipulated, such as by mutation, truncation, deletion, substitution, addition, conjugation or by otherwise changing the primary sequence, chemical or three-dimensional structure, chemical signature, folding behavior, glycosylation state, or any other attribute of the molecule, such that the molecule differs from its naturally occurring counterpart.

The term "patient" as used herein includes human and animal subjects.

A "disorder" is any condition that would benefit from treatment using the engineered polypeptides or fusion proteins of the disclosure. "Disorder" and "condition" are used interchangeably herein.

A "complement-mediated disorder" as used herein refers to a disorder caused, directly or indirectly, by mis-regulation of the complement pathway, e.g., activation or suppression of the complement pathway, or a disorder that is mediated, directly or indirectly, by one or more components of the complement pathway, or a product generated by the complement pathway. The term also refers to a disorder that is exacerbated by one or more components of the complement pathway, or a product generated by the complement pathway.

The terms "treatment" or "treat," as used herein, refer to both therapeutic treatment and prophylactic or preventative measures. Those in need of treatment include those having the disorder as well as those at risk of having the disorder or those in which the disorder is to be prevented.

As used herein, a "therapeutically effective" amount of, for example, a fusion protein or engineered polypeptide described herein, is an amount that, when administered, results in a decrease in severity of disease symptoms (e.g., a decrease in symptoms of disorders associated with a complement-mediated disorder, an increase in frequency and duration of disease symptom free periods, or a prevention of impairment or disability due to the disease affliction. In certain embodiments, a therapeutically effective amount of a therapeutic agent described herein can include an amount (or various amounts in the case of multiple administrations) that reduces hemolysis, or improves symptoms of a complement-mediated disorder.

The terms "pharmaceutical composition" or "therapeutic composition," as used herein, refer to a compound or composition capable of inducing a desired therapeutic effect when administered to a patient.

The term "pharmaceutically acceptable carrier" or "physiologically acceptable carrier," as used herein, refers to one or more formulation materials suitable for accomplishing or enhancing the delivery of the engineered polypeptides or fusion proteins of the disclosure.

The term "therapeutically effective amount," as used in reference to a pharmaceutical composition comprising one or more engineered polypeptides or fusion proteins of the disclosure, refers to an amount or dosage sufficient to produce a desired therapeutic result. More specifically, a therapeutically effective amount is an amount of one or more engineered polypeptides or fusion proteins of the disclosure sufficient to inhibit, for some period of time, one or more of the clinically defined pathological processes associated with the condition being treated, e.g., a complement-mediated disorder. The therapeutically effective amount may vary depending on the specific engineered polypeptide or fusion protein that is being used, and depends on a variety of factors and conditions related to the patient being treated and the severity of the disorder.

Complement System

The complement system acts in conjunction with other immunological systems of the body to defend against intrusion of cellular and viral pathogens. There are at least 25 complement proteins, which are a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory and lytic functions.

The complement cascade can progress via the classical pathway (CP), the lectin pathway or the alternative pathway (AP). The lectin pathway is typically initiated with binding of mannose-binding lectin (MBL) to high mannose substrates. The AP can be antibody independent and initiated by certain molecules on pathogen surfaces. The CP is typically initiated by antibody recognition of, and binding to, an antigenic site on a target cell. These pathways converge at the C3 convertase—where complement component C3 is cleaved by an active protease to yield C3a and C3b.

Spontaneous hydrolysis of complement component C3, which is abundant in the plasma fraction of blood, can also lead to AP C3 convertase initiation. This process, known as "tickover," occurs through the spontaneous cleavage of a thioester bond in C3 to form C3i or C3($H_2$0). Tickover is facilitated by the presence of surfaces that support the binding of activated C3 and/or have neutral or positive charge characteristics (e.g., bacterial cell surfaces). Formation of C3($H_2$0) allows for the binding of plasma protein Factor B, which in turn allows Factor D to cleave Factor B into Ba and Bb. The Bb fragment remains bound to C3 to form a complex containing C3($H_2$0)Bb—the "fluid-phase" or "initiation" C3 convertase. Although only produced in small amounts, the fluid-phase C3 convertase can cleave multiple C3 proteins into C3a and C3b and results in the generation of C3b and its subsequent covalent binding to a surface (e.g., a bacterial surface). Factor B bound to the surface-bound C3b is cleaved by Factor D to form the surface-bound AP C3 convertase complex containing C3b, Bb.

The AP C5 convertase ((C3b)$_2$,Bb) is formed upon addition of a second C3b monomer to the AP C3 convertase. The role of the second C3b molecule is to bind C5 and present it for cleavage by Bb. The AP C3 and C5 convertases are stabilized by the addition of the trimeric protein properdin. Properdin binding, however, is not required to form a functioning alternative pathway C3 or C5 convertase.

The CP C3 convertase is formed upon interaction of complement component C1, which is a complex of C1q, C1r and C1s, with an antibody that is bound to a target antigen (e.g., a microbial antigen). The binding of the C1q portion of C1 to the antibody-antigen complex causes a conformational change in C1 that activates C1r. Active C1r then cleaves the C1-associated C1s to generate an active serine protease. Active C1s cleaves complement component C4 into C4b and C4a. Like C3b, the newly generated C4b fragment contains a highly reactive thiol that readily forms amide or ester bonds with suitable molecules on a target surface (e.g., a microbial cell surface). C1s also cleaves complement component C2 into C2b and C2a. The complex formed by C4b and C2a is the CP C3 convertase, which is capable of processing C3 into C3a and C3b. The CP C5 convertase (C4b,C2a,C3b) is formed upon addition of a C3b monomer to the CP C3 convertase.

In addition to its role in C3 and C5 convertases, C3b also functions as an opsonin through its interaction with complement receptors present on the surfaces of antigen-presenting cells such as macrophages and dendritic cells. The opsonic function of C3b is generally considered one of the most important anti-infective functions of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone.

The AP and CP C5 convertases cleave C5 into C5a and C5b. Cleavage of C5 releases C5a, a potent anaphylatoxin and chemotactic factor, and C5b, which allows for the formation of the lytic terminal complement complex, C5b-9. C5b combines with C6, C7 and C8 to form the C5b-8 complex at the surface of the target cell. Upon binding of several C9 molecules, the membrane attack complex (MAC, C5b-9, terminal complement complex ("TCC")) is formed. When sufficient numbers of MACs insert into target cell membranes, the openings they create (MAC pores) mediate rapid osmotic lysis of the target cells.

While a properly functioning complement system provides a robust defense against infecting microbes, inappropriate regulation or activation of the complement pathways has been implicated in the pathogenesis of a variety of disorders including, e.g., rheumatoid arthritis (RA); lupus nephritis; asthma; ischemia-reperfusion injury; atypical hemolytic uremic syndrome (aHUS); dense deposit disease (DDD); paroxysmal nocturnal hemoglobinuria (PNH); macular degeneration (e.g., age-related macular degeneration (AMD)); hemolysis, elevated liver enzymes and low platelets (HELLP) syndrome; Guillain-Barré Syndrome (GBS); protein-losing enteropathy (e.g., CHAPLE syndrome); myasthenia gravis (MG); neuromyelitis optica (NMO); post-hematopoietic stem cell transplant thrombotic microangiopathy (post-HSCT-TMA); post-bone marrow transplant TMA (post-BMT TMA); Degos disease; Gaucher's disease; glomerulonephritis; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis (Holers, V., *Immunol. Rev.*, 223:

300-16, 2008). The down-regulation of complement activation has been demonstrated to be effective in treating several disease indications in a variety of animal models (Rother, R. et al., *Nat. Biotechnol.,* 25:1256-64, 2007; Wang, Y. et al., *Proc. Natl. Acad. Sci. USA,* 93:8563-8, 1996; Wang, Y. et al., *Proc. Natl. Acad. Sci. USA,* 92:8955-9, 1995; Rinder, C. et al., *J. Clin. Invest.,* 96:1564-72, 1995; Kroshus, T. et al., *Transplantation,* 60:1194-202, 1995; Homeister, J. et al., *J. Immunol.,* 150:1055-64, 1993; Weisman, H. et al., *Science,* 249:146-51, 1990; Amsterdam, E. et al., *Am. J. Physiol.,* 268:H448-57, 1995; and Rabinovici, R. et al., *J. Immunol.,* 149:1744-50, 1992).

Human Serum Albumin and Neonatal Fc Receptor

Polypeptides that can bind to human serum albumin (HSA) to increase the half-life of therapeutically relevant proteins have been described (WO 91/01743, WO 01/45746 and WO 02/076489). The described peptide moieties, however, are of bacterial or synthetic origin, which is not preferred for use in therapeutics in humans. WO 04/041865 describes single-domain antibodies (sdAb's or Nanobodies®) directed against serum albumin (and in particular against HSA) that can be linked to other proteins (such as one or more other sdAb's directed against a desired target) to increase the half-life of the protein.

The neonatal Fc receptor (FcRn), also termed "Brambell receptor," is involved in prolonging the lifespan of albumin in circulation (Chaudhury, C. et al., *J. Exp. Med.,* 3:315-22, 2003). FcRn is an integral membrane glycoprotein consisting of a soluble light chain consisting of β2-microglobulin (β2m), non-covalently bound to a 43 kDa α chain with three extracellular domains, a transmembrane region and a cytoplasmic tail of about 50 amino acids. The cytoplasmic tail contains a dinucleotide motif endocytosis signal implicated in the internalization of the receptor. The α chain is a member of the non-classical MHC I family of proteins. The β2m association with the α chain is critical for correct folding of FcRn and exiting the endoplasmic reticulum for routing to endosomes and the cell surface.

The overall structure of FcRn is similar to that of class I molecules. The α-1 and α-2 regions resemble a platform composed of eight antiparallel strands forming a single β-sheet topped by two antiparallel α-helices very closely resembling the peptide cleft in MHC I molecules. Owing to an overall repositioning of the α-1 helix and bending of the C-terminal portion of the α-2 helix due to a break in the helix introduced by the presence of Pro162, the FcRn helices are close in proximity, occluding peptide binding. The side chain of Arg164 of FcRn also occludes the potential interaction of the peptide N-terminus with the MEW pocket. Further, salt bridge and hydrophobic interaction between the α-1 and α-2 helices may also contribute to the groove closure. FcRn therefore, does not participate in antigen presentation and the peptide cleft is empty.

FcRn binds and transports IgG across the placental syncytiotrophoblast from maternal circulation to fetal circulation and protects IgG from degradation in adults. In addition to homeostasis, FcRn controls transcytosis of IgG in tissues. FcRn is localized in epithelial cells, endothelial cells, and hepatocytes.

HSA binds FcRn to form a tri-molecular complex with IgG. Both albumin and IgG bind non-cooperatively to distinct sites on FcRn. Binding of human FcRn to Sepharose-HSA and Sepharose-hIgG is pH dependent, being maximal at pH 5 and undetectable at pH 7 through pH 8. The observation that FcRn binds albumin in the same pH-dependent fashion as it binds IgG suggests that the mechanism by which albumin interacts with FcRn and thus is protected from degradation is identical to that of IgG, and mediated via a similarly pH-sensitive interaction with FcRn. Using surface plasmon resonance to measure the capacity of individual HSA domains to bind immobilized soluble hFcRn, FcRn and albumin have been shown to interact via the D-III domain of albumin in a pH-dependent manner, on a site distinct from the IgG binding site (Chaudhury, C. et al., *Biochemistry,* 45:4983-90, 2006).

Engineered Polypeptides Specifically Bind Complement C5 or Serum Albumin

Described herein are engineered polypeptides comprising Ig sequences, e.g., Ig variable domain sequences, that can bind or otherwise associate with complement component C5 or serum albumin. Engineered polypeptides described herein can specifically bind serum albumin in such a way that, when the engineered polypeptide is bound to or otherwise associated with a serum albumin molecule, the binding of the serum albumin molecule to FcRn is not significantly reduced or inhibited as compared to the binding of the serum albumin molecule to FcRn when the polypeptide is not bound thereto. In this embodiment, "not significantly reduced or inhibited" means that the binding affinity for serum albumin to FcRn (as measured using a suitable assay, such as, for example, SPR) is not reduced by more than 50%, or by more than 30%, or by more than 10%, or by more than 5%, or not reduced at all. In this embodiment, "not significantly reduced or inhibited" also means that the half-life of the serum albumin molecule is not significantly reduced. In particular, the engineered polypeptides can to amino acid residues on serum albumin that are not involved in binding of serum albumin to FcRn. More particularly, engineered polypeptides can bind to amino acid residues or sequences of serum albumin that do not form part of domain III of serum albumin, e.g., engineered polypeptides that are capable of binding to amino acid residues or sequences of serum albumin that form part of domain I and/or domain II.

In some embodiments, the engineered polypeptides are sdAbs or suitable for use as sdAbs, and as such may be a heavy chain variable domain sequence or a light chain variable domain sequence, and in certain embodiments, are heavy chain variable domain sequences of a heavy chain antibody. In cases where the engineered polypeptides are single domain, heavy chain variable domain sequences from a heavy chain antibody, such sequences may be referred to as VHH or $V_HH$ antibodies, VHH or $V_HH$ antibody fragments, or VHH or $V_HH$ domains.

A "heavy chain antibody" refers to an antibody that consists of two heavy chains and lacks the two light chains found in conventional antibodies. Camelids (members of the biological family Camelidae, the only currently living family in the suborder Tylopoda; extant camelids include dromedary camels, Bactrian camels, wild or feral camels, llamas, alpacas, vicuñas and guanacos) are the only mammals with single chain VHH antibodies. About 50% of the antibodies in camelids are heavy chain antibodies with the other 50% being of the ordinary or conventional mammalian heavy/light chain antibody type.

"VHH domain" refers to variable domains present in naturally occurring heavy chain antibodies to distinguish them from the heavy chain variable domains that are present in conventional four chain antibodies (referred to herein as "VH domains") and from the light chain variable domains that present in conventional four chain antibodies (referred to herein as "VL domains").

VHH domains have a number of unique structural characteristics and functional properties that make isolated VHH domains (as well as sdAbs, which are based on VHH domains and share these structural characteristics and functional properties with the naturally occurring VHH domains) and proteins containing the VHH domains highly advantageous for use as functional antigen binding domains or proteins. For example, VHH domains, which bind to an antigen without the presence of a VL, and sdAbs can function as a single, relatively small, functional antigen binding structural unit, domain or protein. The small size of these molecules distinguishes VHH domains from the VH and VL domains of conventional four-chain antibodies. The use of VHH domains and sdAbs as single antigen-binding proteins or as antigen-binding domains (e.g., as part of a larger protein or polypeptide) offers a number of significant advantages over the use of conventional VH and VL domains, as well as scFv or conventional antibody fragments (such as Fab or F(ab')$_2$ fragments). Only a single domain is required to bind an antigen with high affinity and with high selectivity, for example, so that there is no need to have two separate domains present, nor to assure that these two domains are present in a particular spatial conformation and configuration (e.g., through the use of specific linkers, as with an scFv). VHH domains and sdAbs can also be expressed from a single gene and require no post-translational folding or modifications. VHH domains and sdAbs can easily be engineered into multivalent and multi-specific formats. VHH domains and sdAbs are also highly soluble and do not have a tendency to aggregate (Ward, E. et al., *Nature,* 341:544-6, 1989), and they are highly stable to heat, pH, proteases and other denaturing agents or conditions (Ewert, S. et al., *Biochemistry,* 41:3628-36, 2002). VHH domains and sdAbs are relatively easy and cheap to prepare, even on a scale required for production. For example, VHH domains, sdAbs, and polypeptides containing VHH domains or sdAbs can be produced using microbial fermentation using methods known in the art and do not require the use of mammalian expression systems, as with, for example, conventional antibody fragments. VHH domains and sdAbs are relatively small (approximately 15 kDa, or 10 times smaller than a conventional IgG) compared to conventional four-chain antibodies and antigen-binding fragments thereof, and therefore show higher penetration into tissues (including but not limited to solid tumors and other dense tissues) than conventional four-chain antibodies and antigen-binding fragments thereof. VHH domains and sdAbs can show so-called "cavity-binding" properties (due to, for example, their extended CDR3 loop) and can access targets and epitopes not accessible to conventional four-chain antibodies and antigen-binding fragments thereof. It has been shown, for example, that VHH domains and sdAbs can inhibit enzymes (WO 97/49805; Transue, T. et al., *Proteins,* 32:515-22, 1998; Lauwereys, M. et al., *EMBO J.,* 17:3512-20, 1998).

The term "single-domain antibody," or "sdAb," as used herein, is an antibody or fragment thereof consisting of a single monomeric variable antibody domain. It is not limited to a specific biological source or to a specific method of preparation. A sdAb can be obtained, for example, by (1) isolating the VHH domain of a naturally occurring heavy chain antibody; (2) expressing a nucleotide sequence encoding a naturally occurring VHH domain; (3) "humanization" of a naturally occurring VHH domain or by expression of a nucleic acid encoding such humanized VHH domain; (4) "camelization" of a naturally occurring VH domain from any animal species, in particular a species of mammal, such as from a human being, or by expression of a nucleic acid encoding such a camelized VH domain; (5) "camelization" of a "domain antibody" ("Dab") or by expression of a nucleic acid encoding such a camelized VH domain; (6) using synthetic or semi-synthetic techniques for preparing engineered polypeptides or fusion proteins; (7) preparing a nucleic acid encoding a sdAb using techniques for nucleic acid synthesis, followed by expression of the nucleic acid thus obtained; and/or (8) any combination of the above.

The engineered polypeptides or fusion proteins described herein can comprise, for example, amino acid sequences of naturally occurring VHH domains that have been "humanized," e.g., by replacing one or more amino acid residues in the amino acid sequence of the naturally occurring VHH sequence by one or more of the amino acid residues that occur at the corresponding positions in a VH domain from a human being.

The engineered polypeptides or fusion proteins described herein can comprise, for example, amino acid sequences of naturally occurring VH domains that have been "camelized," i.e., by replacing one or more amino acid residues in the amino acid sequence of a naturally occurring VH domain with one or more of the amino acid residues that occur at the corresponding positions in a VHH domain of, for example, a camelid antibody. This can be performed in a manner known in the art. Such camelization may preferentially occur at amino acid positions that are present at the VH-VL interface and at the so-called "Camelidae hallmark residues" (WO 94/04678). The VH domain or sequence that is used as a parental sequence or starting material for generating or designing the camelized sequence can be, for example, a VH sequence from a mammal, and in certain embodiments, the VH sequence of a human. It should be noted, however, that such camelized sequences can be obtained in any suitable manner known in the art and thus are not strictly limited to polypeptides that have been obtained using a polypeptide that comprises a naturally occurring parental VH domain.

Both "humanization" and "camelization" can be performed by providing a nucleotide sequence that encodes a naturally occurring VHH domain or $V_H$ domain, respectively, and then changing, in a manner known to those skilled in the art, one or more codons in the nucleotide sequence such that the new nucleotide sequence encodes a humanized or camelized sequence, respectively. Also, based on the amino acid sequence or nucleotide sequence of a naturally occurring VHH domain or VH domain, a nucleotide sequence encoding a desired humanized or camelized sequence can be designed and synthesized de novo using techniques for nucleic acid synthesis known in the art, after which the nucleotide sequence thus obtained can be expressed in a manner known in the art.

In some embodiments, the disclosure provides an engineered polypeptide that specifically binds to the same epitope on human C5 as eculizumab, or that binds to an epitope on C5 that prevents cleavage of C5 into C5a and C5b. In some embodiments, the disclosure provides an engineered polypeptide that specifically binds to human complement component C5, wherein the polypeptide comprises any one of the amino acid sequences of SEQ ID NOs:1-12 or a fragment thereof. In other embodiments, the disclosure provides an engineered polypeptide that specifically binds to human complement component C5, wherein the polypeptide comprises an amino acid sequence that is at least 90% identical to any one of the amino acid sequences of SEQ ID NOs:1-12. In other embodiments, the disclosure provides an engineered polypeptide that specifically binds to human complement component C5, wherein the polypeptide comprises an amino acid sequence that is at least 95% identical, at least 96% identical, at least 97% identical, at least 98% identical, or at least 99% identical to any one of the amino acid sequences of SEQ ID NOs:1-12. For example, in one embodiment, the engineered polypeptide comprises the amino acid sequence set forth in SEQ ID NO:1 or a sequence at least 90% identical thereto. In another embodiment, the engineered polypeptide comprises the amino acid sequence set forth in SEQ ID NO:2 or a sequence at least 90% identical thereto. In another embodiment, the engineered polypeptide comprises the amino acid sequence set forth in SEQ ID NO:3 or a sequence at least 90% identical thereto. In another embodiment, the engineered polypeptide comprises the amino acid sequence set forth in SEQ ID NO:4 or a sequence at least 90% identical thereto. In another embodiment, the engineered polypeptide comprises the amino acid sequence set forth in SEQ ID NO:5 or a sequence at least 90% identical thereto. In another embodiment, the engineered polypeptide comprises the amino acid sequence set forth in SEQ ID NO:6 or a sequence at least 90% identical thereto. In another embodiment, the engineered polypeptide comprises the amino acid sequence set forth in SEQ ID NO:7 or a sequence at least 90% identical thereto. In another embodiment, the engineered polypeptide comprises the amino acid sequence set forth in SEQ ID NO:8 or a sequence at least 90% identical thereto. In another embodiment, the engineered polypeptide comprises the amino acid sequence set forth in SEQ ID NO:9 or a sequence at least 90% identical thereto. In another embodiment, the engineered polypeptide comprises the amino acid sequence set forth in SEQ ID NO:10 or a sequence at least 90% identical thereto. In another embodiment, the engineered polypeptide comprises the amino acid sequence set forth in SEQ ID NO:11 or a sequence at least 90% identical thereto. In another embodiment, the engineered polypeptide comprises the amino acid sequence set forth in SEQ ID NO:12 or a sequence at least 90% identical thereto.

In another embodiment, an engineered polypeptide is provided that binds to human complement component C5, wherein the engineered polypeptide consists of an amino acid sequence selected from the group consisting of SEQ ID NOS:1-12 and fragments thereof. For example, in one embodiment, the engineered polypeptide consists of the amino acid sequence set forth in SEQ ID NO:1. In another embodiment, the engineered polypeptide consists of the amino acid sequence set forth in SEQ ID NO:2. In another embodiment, the engineered polypeptide consists of the amino acid sequence set forth in SEQ ID NO:3. In another embodiment, the engineered polypeptide consists of the amino acid sequence set forth in SEQ ID NO:4. In another embodiment, the engineered polypeptide consists of the amino acid sequence set forth in SEQ ID NO:5. In another embodiment, the engineered polypeptide consists of the amino acid sequence set forth in SEQ ID NO:6. In another embodiment, the engineered polypeptide consists of the amino acid sequence set forth in SEQ ID NO:7. In another embodiment, the engineered polypeptide consists of the amino acid sequence set forth in SEQ ID NO:8. In another embodiment, the engineered polypeptide consists of the amino acid sequence set forth in SEQ ID NO:9. In another embodiment, the engineered polypeptide consists of the amino acid sequence set forth in SEQ ID NO:10. In another embodiment, the engineered polypeptide consists of the amino acid sequence set forth in SEQ ID NO:11. In another embodiment, the engineered polypeptide consists of the amino acid sequence set forth in SEQ ID NO:12.

In another embodiment, the disclosure provides an engineered polypeptide that specifically binds to human complement component C5, wherein the polypeptide comprises three complementarity determining regions, CDR1, CDR2 and CDR3, wherein CDR1 comprises any one of the amino acid sequences of SEQ ID NOs:13-17 or a sequence that is at least 90% identical to SEQ ID NOs:13-17; CDR2 comprises an amino acid sequence of SEQ ID NOs:18 or 19 or a sequence that is at least 90% identical to SEQ ID NOs:18 or 19; and CDR3 comprises an amino acid sequence of SEQ ID NOs:20 or 21 or a sequence that is at least 90% identical to SEQ ID NOs:20 or 21.

In other embodiments, the disclosure provides an engineered polypeptide that specifically binds to human serum albumin, wherein the polypeptide comprises any one of the amino acid sequences of SEQ ID NOs:22-34, or a fragment thereof. In other embodiments, the disclosure provides an engineered polypeptide that specifically binds to human serum albumin, wherein the polypeptide comprises an amino acid sequence that is at least 90% identical to any one of the amino acid sequences of SEQ ID NOs:22-34. In other embodiments, the disclosure provides an engineered polypeptide that specifically binds to human serum albumin, wherein the polypeptide comprises an amino acid sequence that is at least 95% identical, at least 96% identical, at least 97% identical, at least 98% identical, or at least 99% identical to any one of the amino acid sequences of SEQ ID NOs:22-34. For example, in one embodiment, the engineered polypeptide comprises the amino acid sequence set forth in SEQ ID NO:22 or a sequence at least 90% identical thereto. In another embodiment, the engineered polypeptide comprises the amino acid sequence set forth in SEQ ID NO:23 or a sequence at least 90% identical thereto. In another embodiment, the engineered polypeptide comprises the amino acid sequence set forth in SEQ ID NO:24 or a sequence at least 90% identical thereto. In another embodiment, the engineered polypeptide comprises the amino acid sequence set forth in SEQ ID NO:25 or a sequence at least 90% identical thereto. In another embodiment, the engineered polypeptide comprises the amino acid sequence set forth in SEQ ID NO:26 or a sequence at least 90% identical thereto. In another embodiment, the engineered polypeptide comprises the amino acid sequence set forth in SEQ ID NO:27 or a sequence at least 90% identical thereto. In another embodiment, the engineered polypeptide comprises the amino acid sequence set forth in SEQ ID NO:28 or a sequence at least 90% identical thereto. In another embodiment, the engineered polypeptide comprises the amino acid sequence set forth in SEQ ID NO:29 or a sequence at least 90% identical thereto. In another embodiment, the engineered polypeptide comprises the amino acid sequence set forth in SEQ ID NO:30 or a sequence at least 90% identical thereto. In another embodiment, the engineered polypeptide comprises the amino acid sequence set forth in SEQ ID NO:31 or a sequence at least 90% identical thereto. In another embodiment, the engineered polypeptide comprises the amino acid sequence set forth in SEQ ID NO:32 or a sequence at least 90% identical thereto. In another embodiment, the engineered polypeptide comprises the amino acid sequence set forth in SEQ ID NO:33 or a sequence at least 90% identical thereto. In another embodiment, the engineered polypeptide comprises the amino acid sequence set forth in SEQ ID NO:34 or a sequence at least 90% identical thereto.

In another embodiment, the engineered polypeptide that specifically binds to human serum albumin consists of an amino acid sequence selected from the group consisting of SEQ ID NOS:22-34 and fragments thereof. For example, in one embodiment, the engineered polypeptide consists of the amino acid sequence set forth in SEQ ID NO:22. In another embodiment, the engineered polypeptide consists of the amino acid sequence set forth in SEQ ID NO:23. In another embodiment, the engineered polypeptide consists of the amino acid sequence set forth in SEQ ID NO:24. In another embodiment, the engineered polypeptide consists of the amino acid sequence set forth in SEQ ID NO:25. In another embodiment, the engineered polypeptide consists of the amino acid sequence set forth in SEQ ID NO:26. In another embodiment, the engineered polypeptide consists of the amino acid sequence set forth in SEQ ID NO:27. In another embodiment, the engineered polypeptide consists of the amino acid sequence set forth in SEQ ID NO:28. In another embodiment, the engineered polypeptide consists of the amino acid sequence set forth in SEQ ID NO:29. In another embodiment, the engineered polypeptide consists of the amino acid sequence set forth in SEQ ID NO:30. In another embodiment, the engineered polypeptide consists of the amino acid sequence set forth in SEQ ID NO:31. In another embodiment, the engineered polypeptide consists of the amino acid sequence set forth in SEQ ID NO:32. In another embodiment, the engineered polypeptide consists of the amino acid sequence set forth in SEQ ID NO:33. In another embodiment, the engineered polypeptide consists of the amino acid sequence set forth in SEQ ID NO:34.

In another embodiment, the disclosure provides an engineered polypeptide that specifically binds to human serum albumin, wherein the polypeptide comprises three complementarity determining regions, CDR1, CDR2 and CDR3, wherein CDR1 comprises any one of the amino acid sequences of SEQ ID NOs:35-43 or a sequence that is at least 90% identical to SEQ ID Nos:35-43; CDR2 comprises any one of the amino acid sequences of SEQ ID NOs:44-51 or a sequence that is at least 90% identical to SEQ ID Nos:44-51; and CDR3 comprises any one of the amino acid sequences of SEQ ID NOs:52-63 or a sequence that is at least 90% identical to SEQ ID Nos:52-63.

The engineered polypeptide disclosed herein can specifically bind, for example, to the same epitope on human serum albumin as Alb1 (AVQLVESGGG LVQPGNSLRL SCAASGFTFR SFGMSWVRQA PGKEPEWVSS ISGSGSDTLY ADSVKGRFTI SRDNAKTTLY LQMNSLKPED TAVYYCTIGG SLSRSSQGTQ VTVSS; SEQ ID NO: 149). In other embodiments, the engineered polypeptide competitively inhibits the binding of Alb1 to human serum albumin.

When the engineered polypeptide comprises an Ig, a suitable fragment of the Ig, such as an Ig variable domain, may also be used in place of a full Ig.

Methods for identifying CDRs from within a given immunoglobulin variable domain are known in the art (Wu, T. & Kabat, E., *J. Exp. Med.*, 132:211-50, 1970; Clothia, C. et al., *Nature*, 342:877-83, 1989; Al-Lazikani, B. et al., *J. Mol. Biol.*, 273:927-48, 1997; and Ofran, Y. et al., *J. Immunol.*, 181:6230-35, 2008).

Fusion Proteins That Specifically Bind Complement Component C5 and Serum Albumin Described herein are fusion proteins that comprise engineered polypeptides that specifically bind albumin and complement component C5, wherein the engineered polypeptides are fused directly or are linked via one or more suitable linkers or spacers. The term "peptide linker" as used herein refers to one or more amino acid residues inserted or included between the engineered polypeptides of the fusion protein(s). The peptide linker can be, for example, inserted or included at the transition between the engineered polypeptides of the fusion protein at the sequence level. The identity and sequence of amino acid residues in the linker may vary depending on the desired secondary structure. For example, glycine, serine and alanine are useful for linkers having maximum flexibility. Any amino acid residue can be considered as a linker in combination with one or more other amino acid residues, which may be the same as or different from the first amino acid residue, to construct larger peptide linkers as necessary depending on the desired properties. In other embodiments, the linker is GGGGAGGGGAGGGGS (SEQ ID NO:102). In other embodiments, the linker is GGGGSGGGGSGGGGS (SEQ ID NO:103). Additional peptide linkers suitable for use in creating fusion proteins described herein include, for example, $G_4S$ (SEQ ID NO:104), $(G_4S)_2$ (SEQ ID NO:105), $(G_4S)_3$ (SEQ ID NO:106), $(G_4S)_4$ (SEQ ID NO:107), $(G_4S)_5$ (SEQ ID NO:108), $(G_4S)_6$ (SEQ ID NO:109), $(EAAAK)_3$ (SEQ ID NO:110), PAPAP (SEQ ID NO:111), $G_4$SPAPAP (SEQ ID NO:112), PAPAP$G_4$S (SEQ ID NO:113), GST-SGKSSEGKG (SEQ ID NO:114), $(GGGDS)_2$ (SEQ ID NO:115), $(GGGES)_2$ (SEQ ID NO:116), GGGDSGGGGS (SEQ ID NO:117), GGGASGGGGS (SEQ ID NO:118), GGGESGGGGS (SEQ ID NO:119), ASTKGP (SEQ ID NO:120), ASTKGPSVFPLAP (SEQ ID NO:121), $G_3P$ (SEQ ID NO:122), $G_7P$ (SEQ ID NO:123), PAPNLLGGP (SEQ ID NO:124), $G_6$ (SEQ ID NO:125), $G_{12}$ (SEQ ID NO:126), APELPGGP (SEQ ID NO:127), SEPQPQPG (SEQ ID NO:128), $(G_3S_2)_3$ (SEQ ID NO:129), GGGGGGGGGSGGGS (SEQ ID NO:130), GGGGSGGGGGGGGGS (SEQ ID NO:131), $(GGSSS)_3$ (SEQ ID NO:132), $(GS_4)_3$ (SEQ ID NO:133), $G_4A(G_4S)_2$ (SEQ ID NO:134), $G_4SG_4AG_4S$ (SEQ ID NO:135), $G_3AS(G_4S)_2$ (SEQ ID NO:136), $G_4SG_3ASG_4S$ (SEQ ID NO:137), $G_4SAG_3SG_4S$ (SEQ ID NO:138), $(G_4S)_2AG_3S$ (SEQ ID NO:139), $G_4SAG_3SAG_3S$ (SEQ ID NO:140), $G_4D(G_4S)_2$ (SEQ ID NO:141), $G_4SG_4DG_4S$ (SEQ ID NO:142), $(G_4D)_2G_4S$ (SEQ ID NO:143), $G_4E(G_4S)_2$ (SEQ ID NO:144), $G_4SG_4EG_4S$ (SEQ ID NO:145) and $(G_4E)_2G_4S$ (SEQ ID NO:146). One of skill in the art can select a linker, for example, to reduce or eliminate post-translational modification, e.g., glycosylation, e.g., xylosylation. In certain embodiments, the fusion protein comprises at least two sdAbs, Dabs, VHH antibodies, VHH antibody fragments, or combination thereof wherein at least one of the sdAbs, Dabs, VHH antibodies, or VHH antibody fragments is directed against albumin and one of the sdAbs, Dabs, VHH antibodies, or VHH antibody fragments is directed against complement component C5, so that the resulting fusion protein is multivalent or multi-specific. The binding domains or moieties can be directed against, for example, HSA, cynomolgus monkey serum albumin, human C5 and/or cynomolgus monkey C5.

In some embodiments, the C-terminal residue of the albumin-binding domain of the fusion protein can be fused either directly or via a peptide to the N-terminal residue of the complement component C5 binding domain. In other embodiments, the C-terminal residue of the complement component C5 binding domain of the fusion protein can be fused either directly or via a peptide to the N-terminal residue of the albumin-binding domain.

In some embodiments, a fusion protein comprises a complement component C5 binding comprising an amino acid sequences of SEQ ID NOs:1-12 or a fragment thereof; and the polypeptide that specifically binds to human serum albumin can comprise an amino acid sequence of SEQ ID NOs:22-34 or a fragment thereof. In some embodiments, the first polypeptide is derived from an amino acid sequence set forth in any of SEQ ID NOs:1-12 and the second polypeptide is derived from an amino acid sequence set forth in any of SEQ ID NOs:22-34. The human complement component C5-binding domain can comprise, for example, the amino acid sequence of SEQ ID NO:5 or 11, and the albumin-binding domain can comprise, for example the amino acid sequence of SEQ ID NO:26. In another embodiment, the disclosure provides a fusion protein having any one of the amino acid sequences of SEQ ID NOs:64-95. In another embodiment, the disclosure provides a fusion protein having the amino acid sequence of SEQ ID NO:93. In another embodiment, the disclosure provides a fusion protein having the amino acid sequence of SEQ ID NO:77. In another embodiment, the disclosure provides for a fusion protein having any one of the amino acid sequences of SEQ ID NOs:96-101.

The fusion proteins disclosed herein can be made by expressing in a host cell at least one nucleic acid molecule comprising a nucleotide sequence encoding the fusion protein. Host cells can be mammalian, plant or microbial in origin. In addition to known mammalian host cells, yeast host cells, e.g., *Pichia pastoris, Saccharomyces cerevisiae*, and/or plant host cells can be used.

Therapeutic Compositions Comprising Polypeptides that Specifically Bind Complement C5 or Serum Albumin, or Fusion Proteins Thereof, and Administration Thereof In another embodiment, the disclosure provides engineered polypeptides comprising or consisting of an amino acid sequence as disclosed herein. In another embodiment, the disclosure provides fusion proteins and multivalent and multi-specific fusion proteins comprising or consisting of at least one engineered polypeptide of the disclosure that is linked to at least one therapeutic or targeting moiety, optionally via one or more suitable linkers or spacers.

The disclosure further relates to therapeutic uses of the engineered polypeptides of the disclosure, or fusion proteins and multivalent and multi-specific fusion proteins comprising or consisting of such engineered polypeptides, or to pharmaceutical compositions comprising such engineered polypeptides, fusion proteins, or multivalent and multi-specific fusion proteins.

In some embodiments, the therapeutic or targeting moiety can comprise, for example, at least one sdAb, Dab, VHH or fragment(s) thereof. In certain embodiments, the engineered polypeptide of the disclosure is a multivalent and/or multi-specific fusion protein comprising at least two sdAbs, Dabs, VHH antibodies, VHH antibody fragments, or combination(s) thereof.

In some embodiments, the engineered polypeptides, fusion proteins, or multivalent and multi-specific fusion proteins show an affinity for HSA that is higher than the affinity for mouse serum albumin. In certain embodiments, the engineered polypeptides, fusion proteins, or multivalent and multi-specific fusion proteins show an affinity for cynomolgus monkey serum albumin that is higher than the affinity for mouse serum albumin. In other embodiments, the engineered polypeptides, fusion proteins, or multivalent and multi-specific fusion proteins show an affinity for HSA that is higher than the affinity for cynomolgus monkey serum albumin.

In some embodiments, the engineered polypeptides, fusion proteins, or multivalent and multi-specific fusion proteins show an affinity for human C5 that is higher than the affinity for mouse C5. In certain embodiments, the engineered polypeptides, fusion proteins, or multivalent and multi-specific fusion proteins show an affinity for cynomolgus monkey C5 that is higher than the affinity for mouse C5. In other embodiments, the engineered polypeptides, fusion proteins, or multivalent and multi-specific fusion proteins show an affinity for human C5 that is higher than the affinity for cynomolgus monkey C5.

The engineered polypeptides, fusion proteins, or multivalent and multi-specific fusion proteins described herein can exhibit, for example, improved therapeutic properties, including, for example, increased efficacy, bioavailability, half-life or other therapeutically desirable properties when compared to antibody therapeutics or other therapeutics. In one embodiment, a fusion protein of the disclosure comprises at least one engineered polypeptide disclosed herein and at least one therapeutic or targeting moiety. In such fusion proteins, the fusion protein can exhibit, for example, an increased half-life compared to the therapeutic binding domain alone. Generally, such fusion proteins have a half-life that is at least 1.5 times, or at least 2 times, or at least 5 times, or at least 10 times, or more than 20 times greater than the half-life of the corresponding therapeutic or targeting moiety alone. In some embodiments, a fusion protein of the disclosure has a half-life that is increased by more than 1 hour, more than 2 hours, more than 6 hours, or more than 12 hours as compared to the half-life of the corresponding therapeutic or targeting moiety. In other embodiments, a fusion protein has a half-life that is more than 1 hour, more than 2 hours, more than 6 hours, more than 12 hours, about one day, about two days, about one week, about two weeks, about three weeks, or no more than 2 months.

The term "half-life," as used herein, refers to the time taken for the serum concentration of the engineered polypeptide, fusion protein, or multivalent and multi-specific fusion protein to be reduced by 50%, in vivo, as a result, for example, of the degradation of the molecule and/or clearance or sequestration of the molecule by physiological mechanisms. Methods for pharmacokinetic analysis and determination of half-life are known to those skilled in the art.

A general description of multivalent and multi-specific fusion proteins containing one or more VHH antibodies and their preparation are known (Els Conrath, K. et al., *J. Biol. Chem.*, 276:7346-50, 2001; Muyldermans, S., *J. Biotechnol.*, 74:277-302 2001; International Publication Nos. WO 96/34103, WO 99/23221 and WO 04/041865).

The engineered polypeptides, fusion proteins, and multivalent and multi-specific fusion proteins disclosed herein can be expressed from or associated with constructs that include, for example, one or more elements such as expression vectors (WO 04/041862).

The engineered polypeptides, fusion proteins, and multivalent and multi-specific fusion proteins disclosed herein can be expressed in, for example, isolated host cells comprising nucleic acid molecules that encode the engineered polypeptides, fusion proteins, and multivalent and multi-specific fusion proteins disclosed herein. Suitable host cells include but are not limited to mammalian and yeast cells.

The therapeutic or pharmaceutical compositions disclosed herein can comprise a therapeutically effective amount of one or more engineered polypeptides, fusion proteins, or multivalent and multi-specific fusion proteins as disclosed herein in admixture with a pharmaceutically or physiologically acceptable formulation agent selected for suitability with the mode of administration. Acceptable formulation materials are preferably nontoxic to recipients at the dosages and concentrations to be employed.

Acceptable formulation materials can be used to modify, maintain, or preserve, for example, the pH, osmolarity, viscosity, clarity, color, isotonicity, odor, sterility, stability, rate of dissolution or release, adsorption, or penetration of the composition. Acceptable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, which are incorporated herein by reference).

A skilled artisan can develop a pharmaceutical composition comprising the engineered polypeptides, fusion proteins, or multivalent and multi-specific fusion proteins disclosed herein depending upon, for example, the intended route of administration, delivery format, and desired dosage.

Since the engineered polypeptides, fusion proteins, and multivalent and multi-specific fusion proteins disclosed herein can exhibit, for example, an increased half-life, they may, in some embodiments, be administered to be in circulation. As such, they can be administered in any suitable manner, such as intravenously, subcutaneously, via injection or infusion, or in any other suitable manner that allows the engineered polypeptides, fusion proteins, or multivalent and multi-specific fusion proteins to enter circulation. The preparation of such pharmaceutical compositions is within the knowledge of one of skill in the art.

Any of the engineered polypeptides, fusion proteins, and multivalent and multi-specific fusion proteins disclosed herein, can be administered in combination with an additional therapy, i.e., combined with other agents. The term "coadministered" as used herein includes any or all of simultaneous, separate, or sequential administration of the engineered polypeptides, fusion proteins, and multivalent and multi-specific fusion proteins described herein with adjuvants and other agents, including administration as part of a dosing regimen.

Pharmaceutical compositions described herein can include one or more agents to improve, for example, delivery of the therapeutic agent. Additional agents can be co-administered, for example, as a co-injectable. Agents that degrade hyaluronan, for example, can be included in the pharmaceutical compositions described herein, or such agents can be co-administered with the pharmaceutical compositions described herein to facilitate, for example, dispersion and absorption of the therapeutic agents described herein upon administration. An example of such an agent is recombinant hyaluronidase.

The pharmaceutical compositions can also be selected for parenteral delivery. Alternatively, the compositions can be selected for inhalation or for delivery through the digestive tract, such as orally. The preparation of such pharmaceutical compositions is within the knowledge of one of skill in the art.

Additional pharmaceutical compositions will be evident to those of skill in the art, including formulations involving sustained-delivery or controlled-delivery formulations. Techniques for formulating sustained-delivery or controlled-delivery formulations, using, for example, liposome carriers, bio-erodible microparticles or porous beads, and depot injections, are known to those of skill in the art.

The disclosure also encompasses therapeutic kits comprising the engineered polypeptides, fusion proteins, and multivalent and multi-specific fusion proteins disclosed herein. In some embodiments, the kits comprise both a first container having a dried protein and a second container having an aqueous formulation. In other embodiments, the kits comprise single and multi-chambered pre-filled syringes (e.g., liquid syringes and lyosyringes).

The disclosure also encompasses an article of manufacture comprising a container comprising a label and a composition comprising the engineered polypeptides, fusion proteins, and multivalent and multi-specific fusion proteins disclosed herein wherein the label indicates that the composition is to be administered to a patient having, or that is suspected of having, a complement-mediated disorder.

In one embodiment, the disclosure provides a method for preventing and/or treating at least one disease, condition, or disorder that can be prevented or treated using an engineered polypeptide, fusion protein, or multivalent and multi-specific fusion protein disclosed herein, the method comprising administering to a patient in need thereof a therapeutically or pharmaceutically effective amount of an engineered polypeptide, fusion protein, or multivalent and multi-specific fusion protein disclosed herein. In particular embodiments, the disorder is a complement-mediated disorder such as, for example, rheumatoid arthritis (RA); lupus nephritis; asthma; ischemia-reperfusion injury; atypical hemolytic uremic syndrome (aHUS); dense deposit disease (DDD); paroxysmal nocturnal hemoglobinuria (PNH); macular degeneration (e.g., age-related macular degeneration (AMD); hemolysis, elevated liver enzymes, and low platelets (HELLP) syndrome; Guillain-Barré Syndrome (GBS); CHAPLE syndrome; myasthenia gravis (MG); neuromyelitis optica (NMO); post-hematopoietic stem cell transplant thrombotic microangiopathy (post-HSCT-TMA); post-bone marrow transplant TMA (post-BMT TMA); Degos disease; Gaucher's disease; glomerulonephritis; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis.

The effective amount of a pharmaceutical composition as disclosed herein to be employed therapeutically will depend, for example, upon the therapeutic context and objectives. One of skill in the art will appreciate that an appropriate dosage level for treatment will vary depending, in part, upon the molecule being delivered, the indication for which the composition is being used, the route of administration, and the size (body weight, body surface, or organ size) and condition (age and general health) of the patient.

EXAMPLES

The Examples that follow are illustrative of specific embodiments of the disclosure, and various uses thereof. They are set forth for explanatory purposes only, and should not be construed as limiting the scope of the invention in any way.

Example 1. Llama Immunization and Anti-C5 VHH Phage Library Construction

Llama immunizations were performed starting with a primary injection followed by secondary boosts. Briefly, primary immunization was initiated with 500 μg of human complement protein C5 and subsequent 500 μg human complement protein C5 antigen boosts administered at week 2 (boost 1), week 4 (boost 2), week 8 (boost 3), and week 12 (boost 4). Serum titers were measured by ELISA and titers after boost 3 were found to be the highest-10-fold above the pre-bleed signal at the 1:1,000,000 dilution. Peripheral blood mononuclear cells (PBMCs) were isolated from blood samples after boost 3. Cell viability was found to be 98% by trypan blue staining. Cells were lysed in RNA lysis buffer immediately after PBMC isolation. Total RNA was isolated from PBMCs and cDNA was synthesized using llama heavy chain specific primers. VHH (heavy chain only) fragments were separated from VH (conventional heavy chain) fragments via gel electrophoresis. The VHH fragments were cloned into pADL-10b (Antibody Design Labs, San Diego, CA), and the DNA library was transformed into TG1 cells. 114 colonies were randomly sequenced and 101 (89%) correct sequences were obtained. The library was scraped and suspended in 25% glycerol, then stored at −80 C.

Example 2. Phage Display Panning and Screening for Anti-C5 VHH Domains

TG1 cells containing the anti-human complement protein C5 VHH domain library were grown to logarithmic phase ($OD_{600}$=0.4-0.8) at 37 C in 2×YT media containing 100 μg/mL carbenicillin and 2% glucose. The cells were infected with M13K07 helper phage with and without shaking at 37 C for 30 minutes. Infected cells were pelleted at 4000×g for 10 minutes and resuspended in 2×YT media containing 100 μg/mL carbenicillin, 50 μg/mL kanamycin, and 1 mM IPTG, and the bacteriophage was propagated by overnight growth at 30 C and 250 rpm. The overnight culture was centrifuged at 9000×g for 10 minutes at 4 C, and phage was precipitated with one-fifth volume of a PEG-NaCl solution [20% polyethyleneglycol 6000, 1.5 M NaCl] by incubation for 1 hour on ice. Phage particles were pelleted by centrifugation at 9000×g for 15 minutes at 4 C and the supernatant was discarded. Phage particles were resuspended in superblock blocking buffer and cell debris was pelleted by centrifugation for 10 minutes at 7500×g in a microcentrifuge tube. The supernatant containing phage particles was transferred to a new tube and phage was precipitated again as described above. Concentrated phage particles were subjected to a thermal challenge for 1 hour at 70 C, and the phage titer before and after heating was determined by infection of logarithmic phase TG1 cells followed by plating on 2×YT agar plates with 100 μg/mL carbenicillin, 50 μg/mL kanamycin, and 2% glucose.

The library selection strategy included selection with biotinylated cynomolgus monkey (cyno) complement protein C5 and competition with molar equivalent non-biotinylated human complement protein C5 to obtain affinity matched anti-C5 VHH domains with reactivity to both human and cyno species. The phage display VHH library was subjected to a deselection step against Dynabeads® M-280 streptavidin for 1 hour at room temperature. The deselected phage particles were selected for matched affinity to human and cyno C5 by incubating in an equimolar solution of biotinylated cyno C5 and non-biotinylated human C5 with Dynabeads® M-280 Streptavidin for 30 minutes at room temperature. After 5 rounds of washing with PBST and PBS, phage was eluted off the beads using 0.1 M glycine (pH 2.2) with 1 mg/mL BSA. The eluted supernatant was neutralized with 1 M Tris pH 8.0. Log phase TG1 cells were infected with the neutralized phage and plated on 2YTCG medium to measure the output titer. Output and input titers were compared to calculate the enrichment ratio; a higher ratio suggested the successful isolation of C5 specific clones.

Individual clones were picked, inoculated in a 96-well deep well plate in 2×YT media with 100 μg/mL carbenicillin and 2% glucose, and grown to log phase. The cells were infected with M13K07 and cultured overnight at 30 C for the production of phage particles displaying individual VHH domains in culture supernatant. Phage ELISA screening of four 96-well plates with human C5 captured on streptavidin-coated plates suggested ~60% positive clones. 72 unique clones out of a total of 76 were selected as representatives based on sequence analysis of CDR H3. The sequences of these representative VHH clones are provided in Table 1. For cloning purposes, the N- and C-terminal amino acids were modified to match the N- and C-terminal amino acids of human VH-3 germline.

Amino acid sequences suitable for use in the engineered polypeptides of the disclosure include the amino acid sequences disclosed in Tables 1 or fragments thereof.

TABLE 1

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0081 | EVQLVESGGGLVQTGGSLRLSCAASTSGSDFSGKKMAWYRQAPGNGRE FVAIIFSNKVTDYADSVKGRFTISRDNAKKTVYLQMSSLTPTDTAVYY CHDQEISWGQGTQVTVSS (SEQ ID NO: 150) | + | − |
| LCP0082 | EVQLVESGGGLVQAGGSLRLSCAASGTSVVINSMGWYRQAPGKQRELV ATIDLSGTTNYADSAQGRFTISRDNAENLNLVYLQMNNLNPDDTAVYY CNALLSRAVSGSYVYWGQGTQVTVSS (SEQ ID NO: 151) | + | + |

TABLE 1-continued

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0083 | EVQLVESGGGLVQPGGSLRLSCTSRIGTISNIDLMNWYRQAPGKQREF VASLQSNGATNYADSVKGRFTISRDNAKNTLFLQMNSLNPEDTAVYFC HALLPRSPYNSWGQGTQVTVSS (SEQ ID NO: 152) | + | + |
| LCP0085 | EVQLVESGGGLVQAGGSLRLSCAASSIIPNIYAMGWYRQAPGKQRELV ASIENGLPANYADSVKGRFTISRDNAKNTVFLQMHSLKSEDTAVYYCY AFRPGVPTTWGQGTQVTVSS (SEQ ID NO: 153) | + | + |
| LCP0086 | EVQLVESGGGLVQAGESLRLSCAASGSISAINAMGWYRQAPGKQREFV ADITRAGVSDYADAVKGRFTISRDNAKNTFYLQMNDLKPEDTAVYYCD ALLIAGGVYWGQGTQVTVSS (SEQ ID NO: 154) | + | − |
| LCP0088 | EVQLVESGGGLVQAGGSLRLSCTASGRTISTTVMGWFRQAPGKEREFV AAVHWGDGNTVYADSVKGRFTISRDDAKNTVYLQLNYLKPEDTSVYYC AARPPTYVGTSRNSRSYDYWGQGTQVTVSS (SEQ ID NO: 155) | + | + |
| LCP0089 | EVQLVESGGGLVQAGGSLRLSCVVSGRAIDRNAMGWFRQAPGKERESV AAISASSGNTYYSDSVTGRFTISRDNTKNTVYLQMNSLKPEDTAVYYC AAGSRGSWYLFDRREYDYWGQGTQVTVSS (SEQ ID NO: 156) | + | − |
| LCP0090 | EVQLVESGGGLVQAGGSLRLTCTASETSFDINVMGWYRQAPGKQRELV AIITASGNTEYADSAKGRFTISRDNTKNTVAMQMNNLKPDDTAVYYCY VLLSGAVSGVYAHWGQGTQVTVSS (SEQ ID NO: 157) | + | + |
| LCP0091 | EVQLVESGGGLVQAGGSLTLSCAASGRTDSRYAMGWFRQAPGKERELM AAISWSGRPTYYADSVKGRFTISRDNAKNTVSLQMNSLKPEDTAVYYC AYKRLPAWYTGSAYYSQESEYDYWGQGTQVTVSS (SEQ ID NO: 158) | + | + |
| LCP0092 | EVQLVESGGGLVQPGGSLRLSCTSRIGTISNIDLMNWYRQAPGKQREF VASLQSTGTTDYADSVKGRFTISRDNAKNTLFLQMNSLNPEDTAVYYC HALIPRSPYNVWGQGTQVTVSS (SEQ ID NO: 159) | + | + |
| LCP0095 | EVQLVESGGGLVQAGGSLRLSCTASGRTISTTVMAWFRQAPGKEREFV AADHWGDAGTVYADSVKGRFTISRDNAKNTVYLQMNYLKPEDTSVYYC AARPPTYVGTSRDSRAYDYWGQGTQVTVSS (SEQ ID NO: 160) | + | + |
| LCP0097 | EVQLVESGGGLVQPGGSLRLSCAASESISSDSPMAWYRQAPGKQREMV ARILPIGPPDYADAVKDRFSISRENAKNTVYLQMNSLKPEDTAVYYCN LLHLPSGLNYWGQGTQVTVSS (SEQ ID NO: 161) | + | + |
| LCP0098 | EVQLVESGGDLVQAGGSLRLSCVASRSISSAMNWYRQPPGKQRELVAL ITRGFNTNYADSVKGRFTISRDNAKNTVYLQMNSLKPEDTGVYYCNSL NYWGQGTQVTVSS (SEQ ID NO: 162) | + | − |
| LCP0100 | EVQLVESGGGLVQAGGSLRLSCAASGRTDSMWSMGWFRQAPGQEREFV AAISWSVGTYYEDSVKGRFTLSRDDDKDTAYLEMSDLKLEDTADYYCA ASTRHGTNLVLPRDYDYWGQGTQVTVSS (SEQ ID NO: 163) | + | − |
| LCP0101 | EVQLVESGGGLVQPGGSLRLSCTSRIGTISNIDLMNWYRQAPGKQREF VASLQSTGTTDYADSVKGRFTISRDNAKNTLFLQMNSLNPEDTAVYYC HALLPRSPYNAWGQGTQVTVSS (SEQ ID NO: 164) | + | + |
| LCP0102 | EVQLVESGGGLVQAGGSLRLSCAASGIIPNIYAMGWYRQAPGKQRELV ASIENGGSTNYADSVKGRFTISRDNARNTVFLQMHSLKSEDTAVYYCY AFRPGVPTDWGQGTQVTVSS (SEQ ID NO: 165) | + | + |
| LCP0103 | EVQLVESGGGLVQAGGSLTLSCVASGRTFSNYRMGWFRQAPGAEREFV GTIYWSTGRSYYGDSVKGRFIISGDNAKNTIHLQMNSLKPEDTGVYYC ASGPENSAFDSWGQGTQVTVSS (SEQ ID NO: 166) | + | + |
| LCP0104 | EVQLVESGGGLVQAGDSLRLSCAASGRPFSSYTMGWFRQAPGKERDFV ATISWSGGIKYYADSVEGRFSISRDNAKNMVYLQMNSLKPEDTAVYYC AATELRTWSRQTFEYDYWGQGTQVTVSS (SEQ ID NO: 167) | + | − |
| LCP0105 | EVQLVESGGGLVQAGGSLRLSCTASGRTISTTVMAWFRQAPGKEREFV AAVHWGDESTVYADSVKGRFTISRDNAKNTVYLQMNYLKPEDTSVYYC AARPPTYVGSSRSSRAYDYWGQGTQVTVSS (SEQ ID NO: 168) | + | + |
| LCP0106 | EVQLVESGGGLVQAGGSLRLSCVVSGSILDINVMAWYRQAPGKQREFV ARITSGGDIDYADPVKGRFTISTNGAKNTVYLQMNSLKPEDTAAYYCN VLLSRSSAGRYTHWGQGTQVTVSS (SEQ ID NO: 169) | + | + |

TABLE 1-continued

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0111 | EVQLVESGGGLVQPGGSLRLSCAASGFPFSLYDMGWYRQAPEKQRESV AIITQSGSTDYADSVKGRFTISRDNAKNTLYLQMNSLKPEDTAVYYCR LVGVTWGQGTQVTVSS (SEQ ID NO: 170) | + | − |
| LCP0112 | EVQLVESGGGLVQAGGSLTLSCAASGRTFSSYGIGWFRQAPGKEREFV AAISRTGQTTHYADSIRFTISRDNAKNTVYLQMNSLKPEDTAVYYCAA RTGGPIYGSEYHYWGQGTQVTVSS (SEQ ID NO: 171) | + | − |
| LCP0113 | EVQLVESGGGLVQAGDSLTLSCAASGRPFSSLTMGWFRQAPGKGREFV ATTSWSGDIKYYADFVKGRFTISRDNAKNMVYLQMNSLKPEDTAVYYC AATLLRTWSRQTNEYEYWGQGTQVTVSS (SEQ ID NO: 172) | + | − |
| LCP0114 | EVQLVESGGGLVQPGGSLRLSCTSRIGTISNIDLMNWYRQAPGKQREF VASLQSTGTTDYADSVRGRFTISRDNAKNTLFLQMNSLNPEDTAVYYC HALLPRSPYNVWGQGTQVTVSS (SEQ ID NO: 173) | + | + |
| LCP0115 | EVQLVESGGGLVQAGGSLRLSCAASGRTFSGILSPYAVGWFRQAPGKG REFVSTITSGGSAIYTDSVKGRFTLSRDNAKDTVYLQMNSLKPEDTAV YYCAVRTRRYGSNLGEVPQENEYGYWGQGTQVTVSS (SEQ ID NO: 174) | + | + |
| LCP0122 | EVQLVESGGGLVQAGGSLRLSCAAPETGATINVMAWYRQAPGKQRELV ARVAIDNNTDYADHAKGRFTISRDNTKNTVYLQMNNLKPDDTAVYYCN VLLSRQISGSYGHWGQGTQVTVSS (SEQ ID NO: 175) | + | + |
| LCP0123 | EVQLVESGGGLVQAGGSLTLSCAMSGGTRPFEDYVMAWFRQATGKERE FVATITWMGETTYYKDSVNGRFAISRDNAENTVALQMNSLEPEDTAVY FCAAHSRSSFSTSGGRYNPRPTEYDYWGQGTQVTVSS (SEQ ID NO: 176) | + | + |
| LCP0125 | EVQLVESGGGLVQAGGSLRLSCTASGRTISTTVMGWFRQAPGKEREFV AAVHWGDEGTVYADSVKGRFTISRDNAKNTVYLQMNALKPEDTSVYYC AAKPPTYVGTSRSSRAYVYWGQGTQVTVSS (SEQ ID NO: 177) | + | + |
| LCP0126 | EVQLVESGGGLVQAGDSLTLSCAASGSGFSINVMAWYRQAPGKQRDLV ASMTIGGRTNYKDSLKGRFTISRDNTKNTAYLQMNSLKPEDTAVYYCY ALLDRGIGGNYVYWGQGTQVTVSS (SEQ ID NO: 178) | + | + |
| LCP0127 | EVQLVESGGGLVQAGGSLRLSCAASGLTFSDYYMGWFRQAPGKERDFL ARIGKSGIGKSYADSVRGRFTISRDNAKNTVYLQMNNLKLEDTAVYYC AADRDIAYDARLTAEYDYWGQGTQVTVSS (SEQ ID NO: 179) | + | + |
| LCP0128 | EVQLVESGGGLVQAGGSLRLSCTASGRTISTTVMGWFRQAPGKEREFV AAVHWGDESTVYADSVKGRFTISRDNAKNTVYLQMNYLKPEDTAVYYC AARPPTYVGTSRSSRAYDYWGQGTQVTVSS (SEQ ID NO: 180) | + | − |
| LCP0129 | EVQLVESGGGLVQAGGSLRLSCAASVASETIVSINDMAWYRQAPGKQR ELVASITIHNNRDYADSAKGRFTISRDDTKNTVYLQMTHLKPDDTAVY YCTVLLSRALSGSYRFWGQGTQVTVSS (SEQ ID NO: 181) | + | + |
| LCP0130 | EVQLVESGGGLVQAGGSLRLSCTGSETSGTIFNINVMGWYRQAPGKQR ELVAIMDIGGTTDYADSVKGRFTISRDNAKNTVYVQMNNLKSEDTAVY YCYCALDRAVAGRYTYWGQGTQVTVSS (SEQ ID NO: 182) | ND | ND |
| LCP0132 | EVQLVESGGGLVQPGGSLRLSCEASGISLNDYNMGWFRQAPGKDREIV AALSRRSHGIYQSDSVKYRFSISRDNTKNMVSLQMDSLRPEDTAVYYC AADGDPYFTGRDMNPEYWGQGTQVTVSS (SEQ ID NO: 183) | + | − |
| LCP0133 | EVQLVESGGGSVQAGGSLRLSCAFSGGRFSDYGMAWFRQGPGKEREFV SRISGNGRGTQYTDSVSGRFIISRDNDKNTVYLQMNDLKVEDTAIYYC ARGSGPSSFNEGSVYDYWGQGTQVTVSS (SEQ ID NO: 184) | + | + |
| LCP0134 | EVQLVESGGGLVQSGGSLTLSCVLSGSIFSSNTMGWHRQAPGKQREWV AITTSGGTTKYADSVKGRFTISRDNAKNTVYLRMNNLKPEDTGVYFCY ASLAGIWGQGTQVTVSS (SEQ ID NO: 185) | + | + |
| LCP0135 | EVQLVESGGGLVQAGGSLRLSCAAPETEATYNVMGWYRRAPGKQRELV ATMTIDYNTNYADSAKGRFTISRDNTKNTVYLQMNNLRPDDTAVYYCR VDLSRQISGSYNYWGQGTQVTVSS (SEQ ID NO: 186) | + | + |
| LCP0136 | EVQLVESGGGLVQPGESLRLSCAISGFAFTDVGMSWVRQAPGKGLEWV SSISSGSSITTYSDSVKGRFTISRDNARTLFLQMNSLKPEDTAVYYC GRYYCTGLGCHPRRDSALWGQGTQVTVSS (SEQ ID NO: 187) | + | + |

TABLE 1-continued

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0137 | EVQLVESGGGLVQPGGSLRLSCRASGFTYSTAAMGWVRQAPGKGLEWV SSISSLGSDRKSADSVKGRFTISRDNAKNTLYLQMNSLKPEDTAVYYC ARFISNRWSRDVHAPSDFGSRGQGTQVTVSS (SEQ ID NO: 188) | + | + |
| LCP0138 | EVQLVESGGGSVPAGGSLRLSCAAFGFTFDNYAIAWFRQAPGKEREGV SCLSTNDGETYYADSVKGRFTISSDHAKNTVYLQMDSLRPEDTAVYYC AAAEGSWCHKYEYDYWGQGTQVTVSS (SEQ ID NO: 189) | + | − |
| LCP0139 | EVQLVESGGGLVQAGESLRLSCAASGRTSDLYVVGWFRQTPGKEREFV AGIAWTGDASYYADSVEGRFTIARDNAENRIDLQMTSLKPEDTAVYYC AADSRARFERQRYNDMNYWGQGTQVTVSS (SEQ ID NO: 190) | + | − |
| LCP0141 | EVQLVESGGGLVQAGGSLRLSCIASVTIADINVMGWYRQAPGKQREFV ASIPTTGDKNYAESAKGRFTISRDNSQNTVAMQMNNLKPDDTAVYYCY VLLSRAVSGSYGHWGQGTQVTVSS (SEQ ID NO: 191) | + | + |
| LCP0142 | EVQLVESGGGLVQVGGSLRLSCAASGIVDIKVMGWYRQAPGNERELV ALINDADDSEYSPSMRGRFTISRDNSKNTVYLQMNSLKPEDTAAYYCA ADRDSSWFKSPYIPGSWGQGTQVTVSS (SEQ ID NO: 192) | + | + |
| LCP0143 | EVQLVESGGGLVQAGGSLRLSCAAPEMGATINVMAWYRQAPGKQRELV ARLPLDNNIDYGDFAKGRFTISRDITRNTVYLQMNNLKPDDTAVYYCN VLLSRQINGAYVHWGQGTQVTVSS (SEQ ID NO: 193) | + | + |
| LCP0144 | EVQLVESGGGLVQAGGSLRLSCAASGIDGDINVMAWYRQAPGKQRELV ASITIGGNTNYADSVKGRFTIARDNAKNRMSLEMNSLKSEDTAVYYCN TLLSRVHDGQYVFWGQGTQVTVSS (SEQ ID NO: 194) | + | + |
| LCP0145 | EVQLVESGGGLVQAGGSLRLSCVASEDAFKTDTLGWFRQAPGEEREFV AAFVWAGGPFYADSVKGRFTISMDEDRNTVYLQMNSLKPEDTGVYYCA ASLSRLRVGEITPRHMNYWGQGTQVTVSS (SEQ ID NO: 195) | + | − |
| LCP0146 | EVQLVESGGGLVQAGGSLRLSCAASGRAFSDYAMAWFRQAPGKEREFV AGIGWSGGDTLYADSVRGRFTNSKDNAKNRMSLQMNSLKPEDTAVYYC AARQGQYIYSSMRSDSYDYWGQGTQVTVSS (SEQ ID NO: 196) | + | + |
| LCP0147 | EVQLVESGGGLVQAGGSLRLSCAASGRTFSSSNMGWFRQAPGEEREFV TAIDWSGGRTYYADSVKGRFTISRDNAKNTVYLQMDSLKPEDTAVYYC AAQGSGLDWGYPWTYDYWGQGTQVTVSS (SEQ ID NO: 197) | + | + |
| LCP0149 | EVQLVESGGGLVQPGGSLKLSCATSGSVLNIDSMAWYRQAPGKQRELV AEMLWGGTKNYGDSVKGRFTISGDADWGTELQMSSLKPEDTAVYYCNA VGRGFRDAWGQGTQVTVSS (SEQ ID NO: 198) | + | − |
| LCP0150 | EVQLVESGGGLVQAGGSLRLSCVASGSGFGILDMGWYRQAPGSRRELV GYVTRDGTTNYGNSVKGRSIISEDITKNTVILQMNSLKPEDTAVYFCT AGLTNQPRAWGQGTQVTVSS (SEQ ID NO: 199) | + | + |
| LCP0151 | EVQLVESGGGLVQPGGSLRLSCAASGSVSSINVMGWYRQTPGKQRELV AAINRGGSTNVADSVKGRFTISRDNAKNTVYLQMNSLKPEDTAVYYCN AEPYGLDWRYDYWGQGTQVTVSS (SEQ ID NO: 200) | + | + |
| LCP0152 | EVQLVESGGGLEQAGGSLRLSCTASGGTDSIYQMGWFRQTPGKEREFV AAINWNYGGAYYPDSVKGRFTISRDKAKNIGFLQMNSLKPEDTAVYYC ATSQTSVDAFSVPITTARRYQYWGQGTQVTVSS (SEQ ID NO: 201) | + | − |
| LCP0153 | EVQLVESGGGLVQAGGSLTLSCVASGRTFSNYRMGWFRQAPGKEREFV GTIYWSTGRSYYGDSVKGRFIISGDNAKNTIHLQMSLKPGDTGVYYC ASGPEMSAFDSWGQGTQVTVSS (SEQ ID NO: 202) | + | + |
| LCP0154 | EVQLVESGGGLVQPGGSLRLSCAASGFTLDDYAIGWFRQAPGKEREGV SCISSSDGSTYYGDSVKGRFTISRDNAKNTMYLQMNSLKPEDTAVYYC ATGTPLSSYYGSCLDYDMAYWGQGTQVTVSS (SEQ ID NO: 203) | + | + |
| LCP0155 | EVQLVESGGGLVQAGGSLRLSCAASGVTFSNYGMAWFRQAPEKEREFV ARISSNGRRTEYADGVSKGRFTISRDNAKNTVYLQMNGLKPEDTAVYYC ARAAGPSGFHEQSIYDDWGQGTQVTVSS (SEQ ID NO: 204) | + | + |
| LCP0295 | EVQLVESGGGLVQAGGSLRLSCAVSGRSISTYVAGWFRQGPGKEREFV ALISRGGGDIQYSDSVKGRFTISRDNAKNAVYLQMNSLKPADTAVYYC SLDASFGSRLVSRWDYWGQGTQVTVSS (SEQ ID NO: 205) | + | + |

TABLE 1-continued

Representative llama-derived anti-C5 VHH domains and whether each clone binds to human complement protein C5 (hC5) and/or cyno complement protein C5 (cC5).

| VHH domain | Sequence | Binds hC5 | Binds cC5 |
|---|---|---|---|
| LCP0296 | EVQLVESGGGVVQAGDSLTLTCTAPVGTISDYGMGWFRQAPGKEREFV ASISWGGMWTDYADSVKGRFTISRDNDKNAVYLRMNSLNAEDTAVYYC GRGRMYRGIGNSLAQPKSYGYWGQGTQVTVSS (SEQ ID NO: 206) | + | + |
| LCP0297 | EVQLVESGGGLVQAGGSLRLSCAGSGFTSDDYAIAWFRQAPGKEREGV SCIGSGDGTTYYADSVKGRFIISSENAKKTVYLQMNSLKPEDTGIYYC AADLYPPADYALDHTWYDYWGQGTQVTVSS (SEQ ID NO: 207) | + | + |
| LCP0298 | EVQLVESGGGVVQPGGSLRLSCVVSGSRFSLDTVGWHHQAPGKLRELV ARIRDDGDTMYVASVKGRFIISRDDAKNTVYLQMNSLKPEDTGVYYCY FSRNGAWGQGTQVTVSS (SEQ ID NO: 208) | + | + |
| LCP0299 | EVQLVESGGGLVQAGGSLRLSCGASGRISDINVMGWYRQAPGKQREMV ADIDIRGYTNYADSVKGRFTVSRDNAETMYLEMNSLKPEDTAVYRCNA LTSRDWGTGKYVYWGQGTQVTVSS (SEQ ID NO: 209) | + | + |
| LCP0300 | EVQLVESGGDLVQVGGSLRLSCAFPGSMSSRNSVNWYRQPPGKQREWV ATISVSGFTQYADSAKGRFTISRDSAKNTVHLQMNSLKPEDTGVYYCN YMDYWGQGTQVTVSS (SEQ ID NO: 210) | + | + |
| LCP0301 | EVQLVESGGGVVRAGGSLKLSCTAAGTDINIVTVGWHRQAPGKHRELV ATIVGSGSRTNYADSVKGRFTISRDNPKNTVYLQMNSLKPEDTAVYYC YATSIGWGQGTQVTVSS (SEQ ID NO: 211) | + | + |
| LCP0302 | EVQLVESGGGLVQAGGSLRLSCAASGRTFSGILSAYAVGWFRQAPGKE REFVSTITSGGSTLSADSVKGRFTLSRDNAKDTVYLQMNSLKPEDTAV YYCAVRTWPYGSNRGEVPTENEYGHWGQGTQVTVSS (SEQ ID NO: 212) | + | + |
| LCP0303 | EVQLVESGGGSVQAGGSLRLTCTASGNVRSIFTMAWYRQAPGKQRELV ASAAKGGDTYYADSAKGRFTISRDDAKAIVSLQMNSLKPEDTAVYYCK TDGRPWFSEDYWGQGTQVTVSS (SEQ ID NO: 213) | + | + |
| LCP0304 | EVQLVESGGGLVQVGDSMRLSCAVFGNIFTRDPVMWFRQPPGKQREWV ATITPSGFANYADSVKGRFTISRYAANNTVHLQMNSLKPEDTGVYFCN FGTYWGQGTQVTVSS (SEQ ID NO: 214) | + | + |
| LCP0306 | EVQLVESGGGLVQAGGSLRLSCAASKGAFNINVMAWYRQAPGKQRELV ARVALGGTTDYADSVKGRFTISRNNAQDTVYLQMNSLKPEDTAVYYCN VLLDRGVRGSYAYWGQGTQVTVSS (SEQ ID NO: 215) | + | + |
| LCP0309 | EVQLVESGGGLVQAGGSLRLSCAASGRTYSSYVIGWFRQAPGKEREFV ASIRWAGGDSHYQESVKGRSTISKDNARNTVYLQMNSLKPEDTAVYYC AGAAPVPGQSYEWSSWGQGTQVTVSS (SEQ ID NO: 216) | + | + |
| LCP0310 | EVQLVESGGGLVQAGGSLRLSCVASGSAFYVGPMAWYRQAPGKERESV ASITKGGITNYADSVKGRFTISRDNAKNTVYLQMNSLKPEDTDVYVCN ARVKLQEDRLFRDYWGQGTQVTVSS (SEQ ID NO: 217) | + | + |
| LCP0311 | EVQLVESGGGMVQPGGSLRLSCVVSGASGNIDFVTVGWHRQAPGKHRE MVAVITGDGTRNYRDSVKGRFSISRDNAKNTIYLQMNSLKPEDTAVYY CYMSNPISSWGQGTQVTVSS (SEQ ID NO: 218) | + | + |
| LCP0312 | EVQLVESGGGLVQAGGSRRLSCAVSGRTLSSFGMGWFRQAPEKPREFV AAITWGQGGTFYADSVKGRFTISRDIVKNTVYLQMNDLKPDDTGLYFC VSAPHFHEAFPSRPPAYAYWGQGTQVTVSS (SEQ ID NO: 219) | + | + |
| LCP0313 | EVQLVESGGGLVQAGGSLRLSCAASGRTYGSYVIGWFRQAPGKEREFV ASIRWAGGDSHYGDPLKGRSTISKDNAKNTVYLQMNSLKPEDAAVYYC AGAAPVPGSSYEWTNWGQGTQVTVSS (SEQ ID NO: 220) | + | + |
| LCP0314 | EVQLVESGGGLVQAGGSLRLSCAASGSISSVNTMGWYRQAPGKQRELV AFITSGDDTNYADSMKGRFTISRDNAKNTLYLQMNSLKPEDTAVYYCV ATLGRSSSGTYTYWGQGTQVTVSS (SEQ ID NO: 221) | + | + |
| LCP0316 | EVQLVESGGGLVQAGGSLRLSCAASLRTLDNYGVGWFRQTPGREREFV SAVSWNGDRTYYQDSVKGRFTISREYAKNTVYLQMDSLKPEDTAVYYC AVNMYGSTFPGLSVESHYDYWGQGTQVTVSS (SEQ ID NO: 222) | + | + |
| LCP0317 | EVQLVESGGGLVQAGGSLRLSCAASGSIFSINAMAWYRQAQGKQRELV ADITKNDITDYADSVKGRFTIARDNAKNTVDLQMNSLKPEDTAVYYCT AALSRHPYRSWGQGTQVTVSS (SEQ ID NO: 223) | + | + |

TABLE 1-continued

Representative llama-derived anti-C5 VHH domains and
whether each clone binds to human complement protein
C5 (hC5) and/or cyno complement protein C5 (cC5).

| VHH domain | Sequence | Binds hC5 | Binds cC5 |
|---|---|---|---|
| LCP0319 | EVQLVESGGGLVQAGGSLRLSCAAAGRSLSDYYIIWFRQPPGKEYEFV SSIRWNTGSTTYGDSVKGRFTISRDNAKSTVYLQMNSLKPEDTALYWC AAGLHLTPTSRTYNYRGQGTQVTVSS (SEQ ID NO: 224) | + | + |
| LCP0320 | EVQLVESGGGLVQAGGSLRLSCAAPETIFTINSMGWYRQAPGKQRELV AFINLDGNTNYADSAKGRFTISRDNAENTVYLQMDNLKPDDTAVYYCN VLLSRAISGSYVHWGQGTQVTVSS (SEQ ID NO: 225) | + | + |

Example 3. Cloning and Expression of Anti-C5 VHH Domains

Representative anti-C5 VHH domains were subcloned into a mammalian expression vector and expressed as VHH-His-tag fusions in Expi293F cells. Culture supernatants were harvested when cell viability dropped to 50-60%. The supernatants were analyzed via SDS-PAGE under reducing conditions, followed by Coomassie brilliant blue staining. Expression levels were calculated using biolayer interferometry on an Octet (ForteBio Inc.) instrument. His-tagged VHH domains were purified by Immobilized Metal Affinity Chromatography (IMAC) on an AKTA (GE Healthcare) from the culture supernatants.

Example 4. Binding and Functional Analysis of Anti-C5 VHH Domains

Binding Analysis to Complement Component C5.

Representative anti-C5 VHH domains were sequenced, characterized, and evaluated for binding to human, cynomolgus monkey (cyno), and mouse C5 protein using Biolayer Interferometry on an Octet (ForteBio Inc.) instrument. Cell culture supernatants from expressed VHH-His domains were normalized to a concentration of 20 µg/mL in 2× kinetics buffer and loaded on anti-penta-HIS (HIS1K) biosensor tips (ForteBio Inc.) for 300 seconds to fully saturate the sensor tips. The saturated tips were then exposed to a solution containing 50 nM of soluble C5 (human, cyno or mouse) in 2× kinetics buffer each for 600 seconds in separate experiments and dissociation was followed for 600 seconds into 2× kinetics buffer. VHH domains that showed binding to human (hC5) or cyno C5 (cC5) are marked with a '+' in Table 1.

Hemolysis Assays for C5 Antagonism.

A hemolysis assay measures the release of hemoglobin from sensitized chicken erythrocytes lysed on exposure to Complement Classical Pathway (CCP)-activated serum. His-tagged VHH domains were expressed in Expi293 cells. Preliminary assays were used to select functional anti-C5 VHH domains, which were purified by IMAC. Ten purified VHH domains were analyzed for their ability to inhibit CCP-mediated hemolysis of sensitized chicken erythrocytes at different concentrations.

Figure 1B:
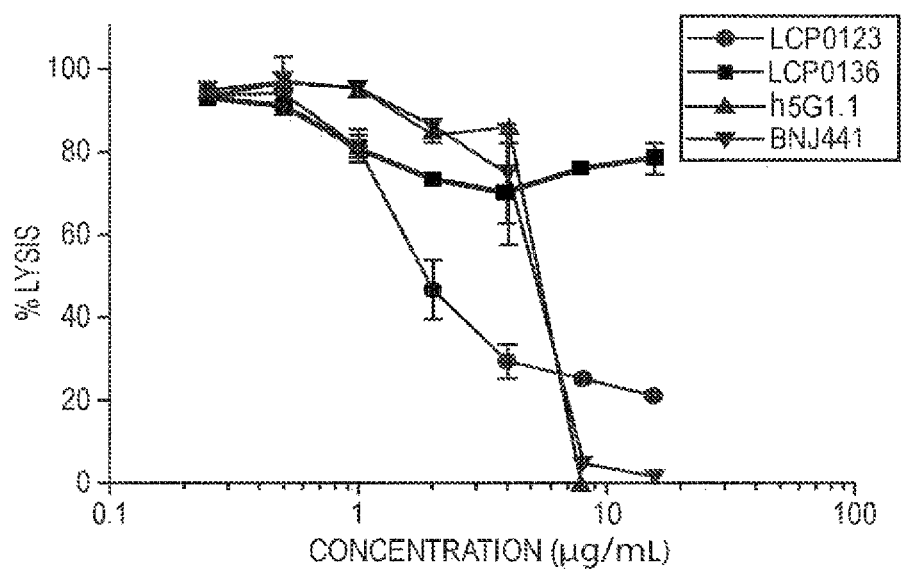
Figure 1B:
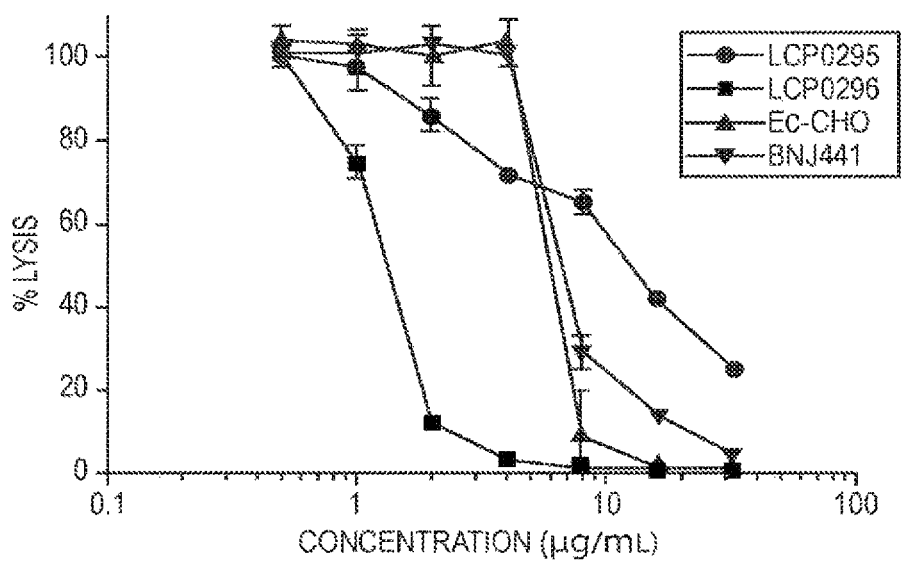

No antibody and 20 mM EDTA were used as complete lysis and no lysis controls for the assay, respectively. The ten VHH domains and the control anti-C5 IgGs (denoted h5G1.1, BNJ441 and Ec-CHO) at different concentrations (32 µg/mL to 0.5 µg/mL) were pre-incubated with 20% normal human serum (NHS) in 0.1 mL gelatin veronal buffered saline (GVB++, cat #B100, Comptech) for 30 minutes at room temperature. 400 µL chicken erythrocytes (Lampire Biologicals, cat #7201403) were washed four times with 1 mL of GVB++ and sensitized cRBCs were prepared by incubating $5 \times 10^7$ cells/mL with 1:500 (v/v) dilution of rabbit-anti-chicken IgG (cat #203-4139, Rockland) and incubated at 4 C for 15 minutes. The cells were washed twice with GVB++ and resuspended in a final volume of 3.6 mL GVB++. 30 µL of sensitized cRBCs ($2.5 \times 10^6$ cells) were added to the pre-incubated human serum and antibodies, and incubated at 37 C for 30 minutes. The cells were pelleted by centrifugation at 1700×g for 3 minutes at 4 C and the supernatant (85 µL) was transferred to a new flat bottom 96 well plate. Absorbance was measured at 415 nm. Percent lysis was calculated for each VHH domain and the control antibodies as:

$$((A_{415 sample} - A_{415\ no\ lysis})/(A_{415 complete\ lysis} - A_{415\ no\ lysis})) \times 100$$

where $A_{415 sample}$ is the absorbance at 415 nm for the sample antibody, $A_{415 no\ lysis}$ is the absorbance at 415 nm for no lysis control (20 mM EDTA), and $A_{415\ complete\ lysis}$ is the absorbance at 415 nm for complete lysis control. The results are shown in FIG. 1.

Identification of VHH Domains That Inhibit C5a Liberation.

Figure 2:
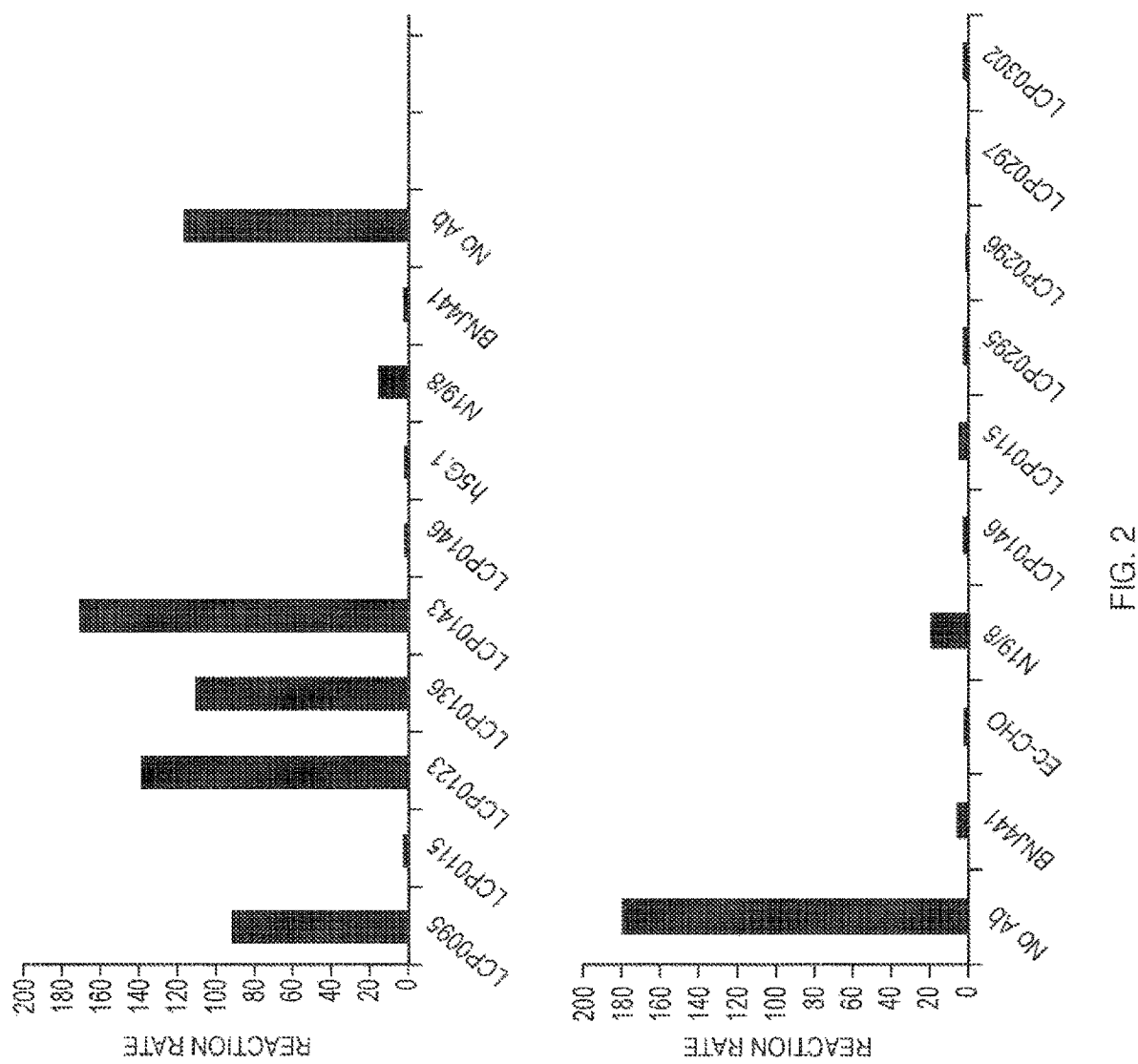
FIG. 2 shows the results of a C5a liberation assay for anti-C5 VHH domains.

Human C5 protein cleavage (e.g., C5a liberation with Complement Alternative Pathway C5 convertase deposited on CAP-activator Zymosan) was measured using a Meso Scale Discovery (MSD)-based immunoassay. Anti-C5 VHH domains were expressed and purified as in the previous section and were analyzed for their ability to block the cleavage of human C5 protein by measuring the amount of hC5a released. Optimal concentration for the sample VHH domain was determined in pilot experiments. The sample VHH domains and control antibodies (h5G1.1, N19/8, BNJ441 and Ec-CHO) were added to human C5 protein (final concentration 25 nM) (CompTech Inc.) in GVB++ buffer containing 1% gelatin, and 2.5 mM NiCl for 30 minutes at 37 C and stored at 4 C until further use. A MSD high-binding 96 well plate was coated with an anti-05a antibody at 2 µg/mL in BupH Phosphate Buffered Saline (ThermoFisher) and incubated for 1 hour. Zymosan was then added to NETS in equal proportion to activate the complement alternative pathway. This mixture of zymosan-NHS was then added to pre-incubated VHH-hC5 solution and incubated at 37 C. The reaction was stopped at different time points (0, 30, 60 and 90 minutes) by addition of futhan-EDTA. The plate was centrifuged at 3600 rpm for 2 minutes and supernatant was transferred to a new polypropylene plate. Blocker A was added for 1 hour at room temperature to block non-specific binding to the coated MSD plate. The MSD plate was washed and supernatant from samples from above were 5 added. This plate was incubated at room temperature for 15 minutes. A mixture of detection antibody biotin-Ab2942 (Abcam) at 1 µg/mL and streptavidin conjugated sulfo tag at 0.5 µg/mL was prepared and then added to each well and incubated at room temperature for 30 minutes. MSD 2x read buffer was added to each well and the electro-chemiluminescent signal was measured. Raw data was analyzed using the MSD workbench software. The results from this experiment are shown in FIG. 2.

LCP0115, LCP0146, LCP0295, LCP0296, LCP0297 and LCP0302 inhibited the release of C5a and were used for further characterization.

Example 5. Affinity Analysis of Anti-C5 VHH Domains by Biacore

Anti-C5 VHH domains were prioritized based on cross reactivity to cyno C5 and eight purified anti-C5 VHH domains were subjected to affinity analysis by Biacore. The kinetic parameters for binding to human and cyno C5 for the initial eight candidates are shown in Table 2. Out of the eight affinity-analyzed candidates, five anti-C5 domains (LCP0115, LCP0143, LCP0146, LCP0296, and LCP0302) were chosen and prioritized for humanization and further analysis based on matched affinity to human and cyno C5.

TABLE 2

Results of Biacore characterization of VHH domains.

| Sample | C5 | $k_a$ (1/Ms) | $k_d$ (1/s) | $K_D$ (M) | Chi$^2$ |
|---|---|---|---|---|---|
| LCP0095 | hC5 | 2.86e5 | 7.14e-4 | 2.50e-9 | 6.94 |
| | cC5 | 4.56e5 | 1.68e-3 | 3.69e-9 | 12.9 |
| LCP0115 | hC5 | 1.13e5 | 3.48e-5 | 3.09e-10 | 0.08 |
| | cC5 | 9.53e4 | 1.02e-5 | 1.07e-10 | 0.10 |
| LCP0123 | hC5 | 1.08e5 | 2.16e-4 | 1.99e-9 | 0.13 |
| | cC5 | 1e5 | 3.81e-4 | 3.8e-9 | 0.14 |

TABLE 2-continued

Results of Biacore characterization of VHH domains.

| Sample | C5 | $k_a$ (1/Ms) | $k_d$ (1/s) | $K_D$ (M) | Chi$^2$ |
|---|---|---|---|---|---|
| LCP0136 | hC5 | 4.86e5 | 8.82e-4 | 1.81e-9 | 2.47 |
| | cC5 | 7.89e5 | 2.51e-4 | 3.18e-10 | 1.01 |
| LCP0143 | hC5 | 6.91e5 | 5.66e-5 | 8.2e-11 | 0.90 |
| | cC5 | 7.41e5 | 1.24e-4 | 1.67e-10 | 0.81 |
| LCP0146 | hC5 | 2.24e6 | 9.75e-5 | 4.35e-11 | 0.42 |
| | cC5 | 2.64e6 | 2.44e-4 | 9.22e-11 | 0.47 |
| LCP0296 | hC5 | 9.34e4 | 3.9e-5 | 4.17e-10 | 0.06 |
| | cC5 | 6.84e4 | 1.06e-4 | 1.55e-9 | 0.03 |
| LCP0302 | hC5 | 1.14e5 | 2.22e-5 | 1.95e-10 | 0.03 |
| | cC5 | 1.03e5 | 2.38e-5 | 2.32e-10 | 0.03 |

Example 6. Humanization of Anti-C5 VHH Domains

Five prioritized anti-C5 VHH domains (LCP0115, LCP0143, LCP0146, LCP0296 and LCP0302) were humanized by CDR grafting onto human germlines with sequence similarity to the llama sequence. CDRs were based on higher amino acid coverage among the IMGT and Kabat definitions. Back mutations to llama FR2 hallmark residues were made to maintain VHH domain stability. The humanized variants were expressed in Expi293 cells and tested for binding to human C5 using biolayer interferometry.

Further back mutations to parental llama residues were introduced in selected frameworks for several of the variants to improve their affinity for human C5. Constructs were expressed in HEK293F cells and evaluated for binding by biolayer interferometry. Additional mutations were made in some of the variants to further optimize their affinity, and the N-termini were humanized to EVQLV (SEQ ID NO:147; where necessary) and the C-termini were humanized to WGQGTLVTVSS (SEQ ID NO:148; where necessary). Resulting prioritized anti-C5 VHH candidates are shown in Table 3 below. The CDRs from these candidates are shown in Table 4.

TABLE 3

Humanized anti-C5 VHH domain candidates

| VHH anti-C5 candidate name | Candidate sequence | SEQ ID NO: |
|---|---|---|
| LCP0177 | EVQLVESGGGLVQPGGSLRLSCAASGRTFSGILSPYAVGWFRQAPGQGLEAVATITSGGSAIYTDSVKGRFTISRDNSKNTLYLQMNSLRAEDTAVYYCAVRTRRYGSNLGEVPQENEYGYWGQGTLVTVSS | 226 |
| LCP0178 | EVQLVESGGGLVQPGGSLRLSCAASEMGATINVMAWFRQAPGQGLEAVARLPLDNNIDYGDFAKGRFTISRDNSKNTLYLQMNSLRAEDTAVYYCNVLLSRQINGAYVHWGQGTLVTVSS | 227 |
| LCP0179 | EVQLVESGGGLVQPGGSLRLSCAASGRAFSDYAMAWFRQAPGQGLEAVAGIGWSGGDTLYADSVRGRFTISRDNSKNTLYLQMNSLRAEDTAVYYCAARQGQYIYSSMRSDSYDYWGQGTLVTVSS | 228 |
| LCP0180 | EVQLVESGGGLVQPGGSLRLSCAASGRTFSGILSPYAVGWFRQAPGQGREFVATITSGGSAIYTDSVKGRFTISRDNSKNTLYLQMNSLRAEDTAVYYCAVRTRRYGSNLGEVPQENEYGYWGQGTLVTVSS | 229 |
| LCP0181 | EVQLVESGGGLVQPGGSLRLSCAAPEMGATINVMAWYRQAPGQQRELVARLPLDNNIDYGDFAKGRFTISRDNSKNTLYLQMNSLRAEDTAVYYCNVLLSRQINGAYVHWGQGTLVTVSS | 230 |
| LCP0182 | EVQLVESGGGLVQPGGSLRLSCAASGRAFSDYAMAWFRQAPGQEREFVAGIGWSGGDTLYADSVRGRFTISRDNSKNTLYLQMNSLRAEDTAVYYCAARQGQYIYSSMRSDSYDYWGQGTLVTVSS | 231 |

TABLE 3-continued

Humanized anti-C5 VHH domain candidates

| VHH anti-C5 candidate name | Candidate sequence | SEQ ID NO: |
|---|---|---|
| LCP0183 | EVQLVESGGGLVQPGGSLRLSCAASGRTFSGILSPYAVGWFRQ APGKGREFVSTITSGGSAIYTDSVKGRFTISRDNAKNSLYLQM NSLRAEDTAVYYCAVRTRRYGSNLGEVPQENEYGYWGQGTLVT VSS | 232 |
| LCP0184 | EVQLVESGGGLVQPGGSLRLSCAASGRTFSGILSPYAVGWFRQ APGKGLEFVSTITSGGSAIYTDSVKGRFTISRDNAKNSLYLQM NSLRAEDTAVYYCAVRTRRYGSNLGEVPQENEYGYWGQGTLVT VSS | 233 |
| LCP0185 | EVQLVESGGGLVKPGGSLRLSCAASEMGATINVMAWYRQAPGK QRELVSRLPLDNNIDYGDFAKGRFTISRDNAKNSLYLQMNSLR AEDTAVYYCNVLLSRQINGAYVHWGQGTLVTVSS | 234 |
| LCP0186 | EVQLVESGGGLVKPGGSLRLSCAASEMGATINVMAWYRQAPGK GLEVVSRLPLDNNIDYGDFAKGRFTISRDNAKNSLYLQMNSLR AEDTAVYYCNVLLSRQINGAYVHWGQGTLVTVSS | 235 |
| LCP0187 | EVQLVESGGGLVQPGRSLRLSCAASGRAFSDYAMAWFRQAPGK EREFVSGIGWSGGDTLYADSVRGRFTISRDNAKNSLYLQMNSL RAEDTALYYCAARQGQYIYSSMRSDSYDYWGQGTLVTVSS | 236 |
| LCP0188 | EVQLVESGGGLVQPGRSLRLSCAASGRAFSDYAMAWFRQAPGK GLEFVSGIGWSGGDTLYADSVRGRFTISRDNAKNSLYLQMNSL RAEDTALYYCAARQGQYIYSSMRSDSYDYWGQGTLVTVSS | 237 |
| LCP0195 | EVQLVESGGGLVQPGGSLRLSCAASGRAFSDYAMAWFRQAPGQ EREFVAGIGWSGGDTLYADSVRGRFTNSRDNSKNTLYLQMNSL RAEDTAVYYCAARQGQYIYSSMRSDSYDYWGQGTLVTVSS | 1 |
| LCP0197 | EVQLVESGGGLVQPGGSLRLSCAASGRAFSDYAMAWFRQAPGQ EREFVAGIGWSGGDTLYADSVRGRFTISRDNAKNTLYLQMNSL RAEDTAVYYCAARQGQYIYSSMRSDSYDYWGQGTLVTVSS | 2 |
| LCP0199 | EVQLVESGGGLVQPGGSLRLSCAASGRAFSDYAMAWFRQAPGQ EREFVAGIGWSGGDTLYADSVRGRFTISRDNSKNTMYLQMNSL RAEDTAVYYCAARQGQYIYSSMRSDSYDYWGQGTLVTVSS | 3 |
| LCP0203 | EVQLVESGGGLVQPGGSLRLSCAASGRAFSDYAMAWFRQAPGQ GLEFVAGIGWSGGDTLYADSVRGRFTISRDNSKNTLYLQMNSL RAEDTAVYYCAARQGQYIYSSMRSDSYDYWGQGTLVTVSS | 4 |
| LCP0207 | EVQLVESGGGLVQPGGSLRLSCAASGRTFSGILSPYAVGWFRQ APGKGLEFVSTITSGGSAIYTDSVKGRFTISRDNAKDSLYLQM NSLRAEDTAVYYCAVRTRRYGSNLGEVPQENEYGYWGQGTLVT VSS | 5 |
| LCP0208 | EVQLVESGGGLVQPGGSLRLSCAASGRTFSGILSPYAVGWFRQ APGKGLEFVSTITSGGSAIYTDSVKGRFTISRDNAKNTLYLQM NSLRAEDTAVYYCAVRTRRYGSNLGEVPQENEYGYWGQGTLVT VSS | 6 |
| LCP0209 | EVQLVESGGGLVQPGGSLRLSCAASGRTFSGILSPYAVGWFRQ APGKGLEFVSTITSGGSAIYTDSVKGRFTISRDNAKNSVYLQM NSLRAEDTAVYYCAVRTRRYGSNLGEVPQENEYGYWGQGTLVT VSS | 7 |
| LCP0212 | EVQLVESGGGLVQPGGSLRLSCAASGRTFSGILSPYAVGWFRQ APGQGLEFVATITSGGSAIYTDSVKGRFTISRDNSKNTLYLQM NSLRAEDTAVYYCAVRTRRYGSNLGEVPQENEYGYWGQGTLVT VSS | 8 |
| CRL0303 | EVQLVESGGGLVQPGGSLRLSCAASGRHFSDYAMAWFRQAPGQ EREFVAGIGWSGGDTLYADSVRGRFTISRDNSKNTLYLQMNSL RAEDTAVYYCAARQGQYIYSSMRSDSYDYWGQGTLVTVSS | 9 |
| CRL0304 | EVQLVESGGGLVQPGGSLRLSCAASGRAHSDYAMAWFRQAPGQ EREFVAGIGWSGGDTLYADSVRGRFTISRDNSKNTLYLQMNSL RAEDTAVYYCAARQGQYIYSSMRSDSYDYWGQGTLVTVSS | 10 |
| CRL0305 | EVQLVESGGGLVQPGGSLRLSCAASGRAHSDYAMAWFRQAPGQ EREFVAGIGWSGGDTLYADSVRGRFTNSRDNSKNTLYLQMNSL RAEDTAVYYCAARQGQYIYSSMRSDSYDYWGQGTLVTVSS | 11 |

TABLE 3-continued

Humanized anti-C5 VHH domain candidates

| VHH anti-C5 candidate name | Candidate sequence | SEQ ID NO: |
|---|---|---|
| CRL0307 | EVQLVESGGGLVQPGGSLRLSCAASGRHHSDYAMAWFRQAPGQ EREFVAGIGWSGGDTLYADSVRGRFTISRDNSKNTLYLQMNSL RAEDTAVYYCAARQGQYIYSSMRSDSYDYWGQGTLVTVSS | 12 |
| CRL0726 | EVQLVESGGGLVQPGGSLRLSCAASVGTISDYGMGWFRQAPGQ GLEAVASISWGGMWTDYADSVKGRFTISRDNSKNTLYLQMNSL RAEDTAVYYCGRGRMYRGIGNSLAQPKSYGYWGQGTLVTVSS | 238 |
| CRL0727 | EVQLVESGGGLVQPGGSLRLSCAASGRTFSGILSAYAVGWFRQ APGQGLEAVATITSGGSTLSADSVKGRFTISRDNSKNTLYLQM NSLRAEDTAVYYCAVRTWPYGSNRGEVPTENEYGHWGQGTLVT VSS | 239 |
| CRL0728 | EVQLVESGGGLVQPGGSLRLSCAASVGTISDYGMGWFRQAPGQ EREFVASISWGGMWTDYADSVKGRFTISRDNSKNTLYLQMNSL RAEDTAVYYCGRGRMYRGIGNSLAQPKSYGYWGQGTLVTVSS | 240 |
| CRL0729 | EVQLVESGGGLVQPGGSLRLSCAASGRTFSGILSAYAVGWFRQ APGQEREFVATITSGGSTLSADSVKGRFTISRDNSKNTLYLQM NSLRAEDTAVYYCAVRTWPYGSNRGEVPTENEYGHWGQGTLVT VSS | 241 |
| CRL0730 | EVQLVESGGGLVKPGGSLRLSCAASVGTISDYGMGWFRQAPGK EREFVSSISWGGMWTDYADSVKGRFTISRDNAKNSLYLQMNSL RAEDTAVYYCGRGRMYRGIGNSLAQPKSYGYWGQGTLVTVSS | 242 |
| CRL0731 | EVQLVESGGGLVKPGGSLRLSCAASVGTISDYGMGWFRQAPGK GLEFVSSISWGGMWTDYADSVKGRFTISRDNAKNSLYLQMNSL RAEDTAVYYCGRGRMYRGIGNSLAQPKSYGYWGQGTLVTVSS | 243 |
| CRL0732 | EVQLLESGGGLVQPGGSLRLSCAASGRTFSGILSAYAVGWFRQ APGKEREFVSTITSGGSTLSADSVKGRFTISRDNSKNTLYLQM NSLRAEDTAVYYCAVRTWPYGSNRGEVPTENEYGHWGQGTLVT VSS | 244 |
| CRL0733 | EVQLLESGGGLVQPGGSLRLSCAASGRTFSGILSAYAVGWFRQ APGKGLEFVSTITSGGSTLSADSVKGRFTISRDNSKNTLYLQM NSLRAEDTAVYYCAVRTWPYGSNRGEVPTENEYGHWGQGTLVT VSS | 245 |
| CRL0960 | QVQLVQSGAEVKKPGASVKVSCKASGRAFSDYAMAWVRQAPGQ GLEWMGGIGWSGGDTLYADSVRGYTENFKDRVTMTRDTSTSTV YMELSSLRSEDTAVYYCARQGQYIYSSMRSDSYDYWGQGTLVT VSS | 246 |
| CRL0961 | QVQLVQSGAEVKKPGASVKVSCKASGRAFSDYAMAWFRQAPGQ EREFMGGIGWSGGDTLYADSVRGYTENFKDRVTMTRDTSTSTV YMELSSLRSEDTAVYYCARQGQYIYSSMRSDSYDYWGQGTLVT VSS | 247 |
| CRL0962 | QVQLVQSGAEVKKPGASVKVSCKASGRAFSDYAMAWFRQAPGQ GLEFMGGIGWSGGDTLYADSVRGYTENFKDRVTMTRDTSTSTV YMELSSLRSEDTAVYYCARQGQYIYSSMRSDSYDYWGQGTLVT VSS | 248 |
| CRL0963 | QVQLVQSGAEVKKPGASVKVSCKASVGTISDYGMGWVRQAPGQ GLEWMGSISWGGMWTDYADSVKGYTENFKDRVTMTRDTSTSTV YMELSSLRSEDTAVYYCARGRGRMYRGIGNSLAQPKSYGYWGQ GTLVTVSS | 249 |
| CRL0964 | QVQLVQSGAEVKKPGASVKVSCKASVGTISDYGMGWFRQAPGQ EREFMGSISWGGMWTDYADSVKGYTENFKDRVTMTRDTSTSTV YMELSSLRSEDTAVYYCARGRGRMYRGIGNSLAQPKSYGYWGQ GTLVTVSS | 250 |
| CRL0965 | QVQLVQSGAEVKKPGASVKVSCKASVGTISDYGMGWFRQAPGQ GLEFMGSISWGGMWTDYADSVKGYTENFKDRVTMTRDTSTSTV YMELSSLRSEDTAVYYCARGRGRMYRGIGNSLAQPKSYGYWGQ GTLVTVSS | 251 |
| CRL0966 | QVQLVQSGAEVKKPGASVKVSCKASGRTFSGILSAYAVGWVRQ APGQGLEWMGTITSGGSTLSADSVKGYTENFKDRVTMTRDTST STVYMELSSLRSEDTAVYYCARAVRTWPYGSNRGEVPTENEYG HWGQGTLVTVSS | 252 |

TABLE 3-continued

Humanized anti-C5 VHH domain candidates

| VHH anti-C5 candidate name | Candidate sequence | SEQ ID NO: |
|---|---|---|
| CRL0967 | QVQLVQSGAEVKKPGASVKVSCKASGRTFSGILSAYAVGWFRQAPGQEREFMGTITSGGSTLSADSVKGYTENFKDRVTMTRDTSTSTVYMELSSLRSEDTAVYYCARAVRTWPYGSNRGEVPTENEYGHWGQGTLVTVSS | 253 |
| CRL0968 | QVQLVQSGAEVKKPGASVKVSCKASGRTFSGILSAYAVGWFRQAPGQGLEFMGTITSGGSTLSADSVKGYTENFKDRVTMTRDTSTSTVYMELSSLRSEDTAVYYCARAVRTWPYGSNRGEVPTENEYGHWGQGTLVTVSS | 254 |
| CRL0972 | EVQLVESGGVVRPGGSLRLSFAASGRAFSDYAMAWFRQAPGKEREFVSGIGWSGGDTLYADSVRGRFTISRDNAKNSLYLQMNSLRAEDTALYHCAARQGQYIYSSMRSDSYDYWGQGTLVTVSS | 255 |
| CRL0973 | EVQLLESGGGLVQPGGSLRLSCAASGRAFSDYAMAWFRQAPGKEREFVSGIGWSGGDTLYADSVRGRFTISRDNSKNTLYLQMNSLRAEDTAVYYCAARQGQYIYSSMRSDSYDYWGQGTLVTVSS | 256 |
| CRL0974 | EVQLVESGGVVVQPGGSLRLSCAASGRAFSDYAMAWFRQAPGKEREFVSGIGWSGGDTLYADSVRGRFTISRDNSKNSLYLQMNSLRAEDTALYYCAARQGQYIYSSMRSDSYDYWGQGTLVTVSS | 257 |
| CRL0975 | EVQLVESGGGLVQPGGSLRLSCAASVGTISDYGMGWFRQAPGKEREFVSSISWGGMWTDYADSVKGRFTISRDNSKNTLYLQMNSLRAEDTAVYYCGRGRMYRGIGNSLAQPKSYGYWGQGTQVTVSS | 258 |
| CRL0976 | EVQLVESGGGLVQPGGSLRLSCAASVGTISDYGMGWFHQAPGKEREFVSSISWGGMWTDYADSVKGRFIISRDNSRNTLYLQTNSLRAEDTAVYYCGRGRMYRGIGNSLAQPKSYGYWGQGTLVTVSS | 259 |
| CRL0977 | EVQLVESGGGVVQPGRSLRLSCAASVGTISDYGMGWFRQAPGKEREFVASISWGGMWTDYADSVKGRFTISRDNSKNTLYLQMNSLRAEDTAVYYCGRGRMYRGIGNSLAQPKSYGYWGQGTQVTVSS | 260 |
| CRL0978 | EVQLVESGGGLVKPGGSLRLSCAASGRTFSGILSAYAVGWFRQAPGKEREFVSTITSGGSTLSADSVKGRFTISRDNAKNSLYLQMNSLRAEDTAVYYCAVRTWPYGSNRGEVPTENEYGHWGQGTQVTVSS | 261 |
| CRL0979 | EVQLVESGGGLVQPGGSLRLSCAASGRTFSGILSAYAVGWFRQAPGKEREFVSTITSGGSTLSADSVKGRFTISRDNSKNTLYVQMsSLRAEDTAVYYCAVRTWPYGSNRGEVPTENEYGHWGQGTQVTVSS | 262 |
| CRL0980 | EVQLVESGGGVVQPGGSLRLSCAASGRTFSGILSAYAVGWFRQAPGKEREFVSTITSGGSTLSADSVKGRFTISRDNSKNSLYLQMNSLRTEDTALYYCAVRTWPYGSNRGEVPTENEYGHWGQGTQVTVSS | 263 |

TABLE 4

CDRs of humanized anti-C5 VHH domain candidates

| VHH domain | CDR1 sequence [SEQ ID NO:] | CDR2 sequence [SEQ ID NO:] | CDR3 sequence [SEQ ID NO:] |
|---|---|---|---|
| LCP0146 | GRAFSDYAMA | GIGWSGGDTLYADSVRG | AARQGQYIYSSMRSDSYDY |
| LCP0179 | [13] | [18] | [20] |
| LCP0182 | | | |
| LCP0187 | | | |
| LCP0188 | | | |
| LCP0195 | | | |
| LCP0197 | | | |
| LCP0199 | | | |
| LCP0203 | | | |
| CRL0960 | | | |
| CRL0961 | | | |
| CRL0962 | | | |
| CRL0972 | | | |
| CRL0973 | | | |
| CRL0974 | | | |

TABLE 4-continued

CDRs of humanized anti-C5 VHH domain candidates

| VHH domain | CDR1 sequence [SEQ ID NO:] | CDR2 sequence [SEQ ID NO:] | CDR3 sequence [SEQ ID NO:] |
|---|---|---|---|
| LCP0115<br>LCP0177<br>LCP0180<br>LCP0183<br>LCP0184<br>LCP0207<br>LCP0208<br>LCP0209<br>LCP0212 | GRTFSGILSPYAVG [14] | TITSGGSAIYTDSVKG [19] | AVRTRRYGSNLGEVPQENEYGY [21] |
| LCP0143<br>LCP0178<br>LCP0181<br>LCP0185<br>LCP0186 | EMGATINVMA [327] | RLPLDNNIDYGDFAKG [325] | NVLLSRQINGAYVH [326] |
| CRL0303 | GRHFSDYAMA [15] | GIGWSGGDTLYADSVRG [18] | AARQGQYIYSSMRSDSYDY [20] |
| CRL0304<br>CRL0305 | GRAHSDYAMA [16] | GIGWSGGDTLYADSVRG [18] | AARQGQYIYSSMRSDSYDY [20] |
| CRL0307 | GRHHSDYAMA [17] | GIGWSGGDTLYADSVRG [18] | AARQGQYIYSSMRSDSYDY [20] |
| LCP0296<br>CRL0726<br>CRL0728<br>CRL0730<br>CRL0731<br>CRL0963<br>CRL0964<br>CRL0965<br>CRL0975<br>CRL0976<br>CRL0977 | VGTISDYGMG [264] | SISWGGMWTDYADSVKG [266] | GRGRMYRGIGNSLAQPKSYGY [268] |
| LCP0302<br>CRL0727<br>CRL0729<br>CRL0732<br>CRL0733<br>CRL0966<br>CRL0967<br>CRL0968<br>CRL0978<br>CRL0979<br>CRL0980 | GRTFSGILSAYAVG [265] | TITSGGSTLSADSVKG [267] | AVRTWPYGSNRGEVPTENEYGH [269] |

Back mutations to parental llama residues were introduced in selected frameworks from humanization assessments to improve the affinity of the selected variants. The sequences of the back mutated variants are shown in Table 5. Constructs were expressed in HEK293F cells and evaluated for binding by biolayer interferometry.

TABLE 5

Anti-C5 VHH humanized variants with back mutations

| Variant name | Back mutated variant sequence | SEQ ID NO |
|---|---|---|
| LCP0115 variants | | |
| LCP0204 | EVQLVESGGGLVQAGGSLRLSCAASGRTFSGILSPYAVGWFRQAPGKGLEF VSTITSGGSAIYTDSVKGRFTISRDNAKNSLYLQMNSLRAEDTAVYYCAVR TRRYGSNLGEVPQENEYGYWGQGTLVTVSS | 270 |
| LCP0205 | EVQLVESGGGLVQPGGSLRLSCAASGRTFSGILSPYAVGWFRQAPGKGREF VSTITSGGSAIYTDSVKGRFTISRDNAKNSLYLQMNSLRAEDTAVYYCAVR TRRYGSNLGEVPQENEYGYWGQGTLVTVSS | 232 |

TABLE 5-continued

Anti-C5 VHH humanized variants with back mutations

| Variant name | Back mutated variant sequence | SEQ ID NO |
|---|---|---|
| LCP0206 | EVQLVESGGGLVQPGGSLRLSCAASGRTFSGILSPYAVGWFRQAPGKGLEF VSTITSGGSAIYTDSVKGRFTLSRDNAKNSLYLQMNSLRAEDTAVYYCAVR TRRYGSNLGEVPQENEYGYWGQGTLVTVSS | 271 |
| LCP0207 | EVQLVESGGGLVQPGGSLRLSCAASGRTFSGILSPYAVGWFRQAPGKGLEF VSTITSGGSAIYTDSVKGRFTISRDNAKDSLYLQMNSLRAEDTAVYYCAVR TRRYGSNLGEVPQENEYGYWGQGTLVTVSS | 5 |
| LCP0208 | EVQLVESGGGLVQPGGSLRLSCAASGRTFSGILSPYAVGWFRQAPGKGLEF VSTITSGGSAIYTDSVKGRFTISRDNAKNTLYLQMNSLRAEDTAVYYCAVR TRRYGSNLGEVPQENEYGYWGQGTLVTVSS | 6 |
| LCP0209 | EVQLVESGGGLVQPGGSLRLSCAASGRTFSGILSPYAVGWFRQAPGKGLEF VSTITSGGSAIYTDSVKGRFTISRDNAKNSVYLQMNSLRAEDTAVYYCAVR TRRYGSNLGEVPQENEYGYWGQGTLVTVSS | 7 |
| LCP0210 | EVQLVESGGGLVQPGGSLRLSCAASGRTFSGILSPYAVGWFRQAPGKGLEF VSTITSGGSAIYTDSVKGRFTISRDNAKNSLYLQMNSLKAEDTAVYYCAVR TRRYGSNLGEVPQENEYGYWGQGTLVTVSS | 272 |
| LCP0211 | EVQLVESGGGLVQPGGSLRLSCAASGRTFSGILSPYAVGWFRQAPGKGLEF VSTITSGGSAIYTDSVKGRFTISRDNAKNSLYLQMNSLRPEDTAVYYCAVR TRRYGSNLGEVPQENEYGYWGQGTLVTVSS | 273 |
| LCP0212 | EVQLVESGGGLVQPGGSLRLSCAASGRTFSGILSPYAVGWFRQAPGQGLEF VATITSGGSAIYTDSVKGRFTISRDNSKNTLYLQMNSLRAEDTAVYYCAVR TRRYGSNLGEVPQENEYGYWGQGTLVTVSS | 8 |

LCP0146 variants

| Variant name | Back mutated variant sequence | SEQ ID NO |
|---|---|---|
| LCP0193 | EVQLVESGGGLVQAGGSLRLSCAASGRAFSDYAMAWFRQAPGQEREFVAGI GWSGGDTLYADSVRGRFTISRDNSKNTLYLQMNSLRAEDTAVYYCAARQGQ YIYSSMRSDSYDYWGQGTLVTVSS | 274 |
| LCP0194 | EVQLVESGGGLVQPGGSLRLSCAASGRAFSDYAMAWFRQAPGKEREFVAGI GWSGGDTLYADSVRGRFTISRDNSKNTLYLQMNSLRAEDTAVYYCAARQGQ YIYSSMRSDSYDYWGQGTLVTVSS | 275 |
| LCP0195 | EVQLVESGGGLVQPGGSLRLSCAASGRAFSDYAMAWFRQAPGQEREFVAGI GWSGGDTLYADSVRGRFTNSRDNSKNTLYLQMNSLRAEDTAVYYCAARQGQ YIYSSMRSDSYDYWGQGTLVTVSS | 1 |
| LCP0196 | EVQLVESGGGLVQPGGSLRLSCAASGRAFSDYAMAWFRQAPGQEREFVAGI GWSGGDTLYADSVRGRFTISKDNSKNTLYLQMNSLRAEDTAVYYCAARQGQ YIYSSMRSDSYDYWGQGTLVTVSS | 276 |
| LCP0197 | EVQLVESGGGLVQPGGSLRLSCAASGRAFSDYAMAWFRQAPGQEREFVAGI GWSGGDTLYADSVRGRFTISRDNAKNTLYLQMNSLRAEDTAVYYCAARQGQ YIYSSMRSDSYDYWGQGTLVTVSS | 2 |
| LCP0198 | EVQLVESGGGLVQPGGSLRLSCAASGRAFSDYAMAWFRQAPGQEREFVAGI GWSGGDTLYADSVRGRFTISRDNSKNRLYLQMNSLRAEDTAVYYCAARQGQ YIYSSMRSDSYDYWGQGTLVTVSS | 277 |
| LCP0199 | EVQLVESGGGLVQPGGSLRLSCAASGRAFSDYAMAWFRQAPGQEREFVAGI GWSGGDTLYADSVRGRFTISRDNSKNTMYLQMNSLRAEDTAVYYCAARQGQ YIYSSMRSDSYDYWGQGTLVTVSS | 3 |
| LCP0200 | EVQLVESGGGLVQPGGSLRLSCAASGRAFSDYAMAWFRQAPGQEREFVAGI GWSGGDTLYADSVRGRFTISRDNSKNTLSLQMNSLRAEDTAVYYCAARQGQ YIYSSMRSDSYDYWGQGTLVTVSS | 278 |
| LCP0201 | EVQLVESGGGLVQPGGSLRLSCAASGRAFSDYAMAWFRQAPGQEREFVAGI GWSGGDTLYADSVRGRFTISRDNSKNTLYLQMNSLKAEDTAVYYCAARQGQ YIYSSMRSDSYDYWGQGTLVTVSS | 279 |
| LCP0202 | EVQLVESGGGLVQPGGSLRLSCAASGRAFSDYAMAWFRQAPGQEREFVAGI GWSGGDTLYADSVRGRFTISRDNSKNTLYLQMNSLRPEDTAVYYCAARQGQ YIYSSMRSDSYDYWGQGTLVTVSS | 280 |
| LCP0203 | EVQLVESGGGLVQPGGSLRLSCAASGRAFSDYAMAWFRQAPGQGLEFVAGI GWSGGDTLYADSVRGRFTISRDNSKNTLYLQMNSLRAEDTAVYYCAARQGQ YIYSSMRSDSYDYWGQGTLVTVSS | 4 |

Example 7. Isolation of VHH Domains Binding to Human Serum Albumin

Albumin is an abundant protein in serum and has sufficient molecular weight to avoid removal by filtration through the glomerular filtration barrier. Removal of albumin from serum by intracellular degradation is inhibited by the interaction of FcRn with albumin that occurs at low pH. This interaction results in trafficking of the albumin-FcRn complex back to the plasma membrane where albumin is released back into blood upon exposure to the more neutral pH of the blood.

Overview of the Process for Generating Anti-HSA VHH

An immune biased VHH anti-HSA phage display library was produced from B cells of an immunized llama for anti-C5 VHH domains and for anti-HSA VHH domains. Upon obtaining endpoint titers greater than 1,000,000 towards HSA, PBMCs were harvested, RNA isolated and VHH regions genetically isolated. As described in detail for anti-C5 VHH domains in Examples 2-4, these anti-HSA VHH sequences were cloned into a pIII fusion phagemid, resulting in a library of $6 \times 10^8$ independent clones. Standard phage display panning techniques were used to select VHH domains reactive towards HSA and CSA (Cynomolgus monkey serum albumin). Outputs from three rounds of panning were analyzed by ELISA and Sanger sequencing. In parallel, next generation sequencing (NGS) was used to examine populations of sequences within the original library, or sequences that were enriched by panning. A total of ~1000 clones were isolated and analyzed using these methods.

Llama Immunization and VHH Phage Library Construction.

A llama was immunized with HSA. The primary boost consisted of 500 μg antigen mixed with complete Freunds adjuvant. Boost immunizations of 500 μg antigen in incomplete Freunds adjuvant were given at 2 weeks, 4 weeks, 8 weeks and 12 weeks. Sera titers were monitored with test bleeds approximately 2 weeks after each boost. Test bleeds were analyzed by ELISA to determine titer of immune response. An anti-HSA sera titer was detected at 20× signal above the pre-bleed for the 1:100,000 dilution, therefore a production bleed of 500 mL was processed to obtain ~$7 \times 10^8$ PBMCs for RNA isolation and library production. Total RNA from PBMCs was purified with phenol/chloroform extraction, followed by a silica-spin column, and total RNA was eluted with RNase free water. Quality of RNA was evaluated by determining the $OD_{260/280}$ ratio and by agarose gel electrophoresis. cDNA was synthesized using llama heavy chain specific reverse primers. VHH (heavy chain only) fragments were separated from VH (conventional heavy chain) fragments via gel electrophoresis.

The VHH fragments were modified with SfiI sites and cloned into pADL-10b, and the DNA library was transformed into TG1 cells. A total of $6 \times 10^8$ independent clones were obtained for the library. All clones were harvested and stored in 25% glycerol at −80 C until use. Library quality was validated by analysis of 105 clones for the presence of an insert with a correct reading frame, uniqueness, and presence of primer sequences.

Phage Display Panning and Screening.

An aliquot of the anti-HSA VHH library glycerol stock comprising $3.75 \times 10^{10}$ cells was cultured in 2×YT media supplemented with 2% glucose and 100 μg/mL carbenicillin. Cells were grown at 37 C with shaking at ~250 rpm until and an $OD_{600}$ of ~0.6 was obtained. Helper phage was added at a multiplicity of infection (MOI) of 20 and the culture was incubated for 30 minutes without shaking, followed by incubation for 30 minutes with shaking at 37 C. Cells were harvested and resuspended in 2×YT media supplemented with 25 μg/mL Carbenicillin, 50 μg/mL kanamycin, and 200 μM IPTG. Cultures were shaken overnight at 30 C and 250 rpm. Media was clarified by centrifugation, phage were precipitated by addition of ¼th volume of 10% PEG-8000/2.5 M NaCl and incubation on ice for 30 minutes. Phage were pelleted by centrifugation at 7500 rpm for 15 minutes at 4 C in an SLA3000 rotor. The pellet was resuspended in Superblock (Thermo Scientific, 37515).

An aliquot of phage was deselected with M280 Streptavidin beads (Life Technologies, 11205D) for 30 minutes at room temperature, the beads were removed using a magnet, and phage-containing supernatant was transferred to a new Eppendorf tube. Phage were supplemented with 10 μg of biotinylated HSA, incubated with rotation at room temperature for 30 minutes, and then supplemented with M280 streptavidin beads to immobilize biotinylated HSA. Beads were washed 11 times with PBS/0.05% Tween wash buffer, eluted with 0.1 M glycine, pH 2.7, and then the elution buffer was neutralized with 1 M Tris, pH 9.0. Eluted phage were rescued into log phage TG1 cells and outgrowths recovered on 250 cm×250 cm LB Carbenicillin, 2% glucose trays. Titers were determined by serial dilution of an aliquot of the phage rescue. A second round of panning was performed essentially as described above, using an aliquot of the round one outgrowth and 5 μg of biotinylated HSA for selections.

To screen clones for reactivity to HSA, individual clones were picked into 96 well plates, cultured in a volume of 250 μL 2×YT supplemented with 100 μg/mL Carbenicillin and 2% glucose overnight at 37 C. Each well was subcultured by transfer of 5 μL dense overnight culture into 250 μL fresh media. An aliquot was submitted for rolling circle amplification sequence analysis to determine the encoded insert. Cells were grown to an $OD_{600}$ of ~0.6, then supplemented with M13 helper phage at an MOI of 20 for one hour. Cells were harvested by centrifugation and media replaced with 250 μL per well of 2×YT supplemented with 100 μg/mL Carbenicillin and 50 μg/mL kanamycin. Plates were then incubated overnight at 30 C with shaking at 250 rpm. Media was clarified by centrifugation to prepare phage supernatants for use in ELISA assays.

For ELISA analysis, streptavidin-coated, pre-blocked 96-well plates (Pierce, 15500) were incubated with has-Biotin at 2 μg/mL for 30 minutes at room temperature with shaking. Plates were washed and then blocking was repeated for 1 hour at room temperature. Plates were again washed and supplemented with 50 μL of clarified supernatant for 30 minutes at room temperature. Plates were washed three times, then incubated with anti-M13 HRP antibody (GE Healthcare, Cat #27-9421-01) in blocking buffer for 30 minutes at room temperature. Plates were washed four times, then supplemented with 1-step Ultra TMB-ELISA reagent (Thermo Scientific, Cat #34029), color developed, and the reaction stopped using 2 M sulfuric acid stop solutions. $OD_{450}$ readings were determined using a BioRad iMark plate reader.

NGS was used to examine populations of sequences within the original library, or sequences that were enriched by panning. For NGS, phagemid DNA was isolated from outgrowths of the initial library, round 1 panning, and round 2 panning. The VHH cassette was released from the phag emid by restriction digestion, VHH encoding bands isolated by agarose gel electrophoresis, and DNA purified using DNA affinity columns. This DNA was submitted for library production and analysis on the MiSeq 2×300 platform.

Example 8. Expression and Purification of VHH Domains Binding to HSA

VHH sequences selected using the above methodologies were synthesized with N-terminal signal peptides and C-terminal 6× His-tags (SEQ ID NO: 324) and cloned into a mammalian expression construct. The published MSA21 VHH domain (International Publication No. WO 2004/062551 A2) and genetically modified versions of individual clones (deglycosylated or humanized) were prepared by synthesis of GeneBlocks (Integrated DNA Technologies) and infusion cloning into a standard mammalian expression vector. These constructs were transfected into 293expi cells and supernatant harvested at 96 hours post-transfection. Supernatants were dialyzed against PBS and VHH-His proteins purified using standard chromatography methods. Purified proteins were buffer exchanged into PBS and quantified using OD and extinction coefficient.

Example 9. Characterization of Immobilized VHH Domains Binding to Soluble HSA, CSA and Mouse Serum Albumin Mammalian expression vectors were created for 112 VHH sequences and protein produced in the 293 expi expression system. VHH sequences were first analyzed by SDS-PAGE and Coomassie staining to determine approximate concentration relative to a known standard. Supernatant concentrations were then normalized and subjected to biolayer interferometry on an Octet HTX (Pall/ForteBio). Penta-His sensors were exposed to kinetics buffer for 60 seconds to establish baseline measurements. The sensors were then loaded with VHH-His containing supernatants for 300 seconds before a second baseline was established in kinetics buffer over 120 seconds. Tips were then incubated with 100 nM HSA or CSA in kinetics buffer for 600 seconds and dissociation measured over an additional 600 seconds.

Of the 112 VHH domains analyzed, 12 domains demonstrated binding to biotinylated HSA and three clones (HAS040, HAS041 and HAS042) interacted with both biotinylated CSA and biotinylated HSA. The sequences of these 12 anti-HSA VHH domains, including one or more humanized versions thereof, are shown in Table 6, with the CDRs of these anti-HSA VHH domains shown in Table 7.

TABLE 6

Sequences for anti-albumin VHH domains

| VHH domain | Sequence | SEQ ID NO: |
|---|---|---|
| HAS020 | QVQLVESGGGLVQAGGSLRLSCAASGRTFGSDAAGWFRQASGKEREFVASISWSGGYTYYADSVKGRFTISSDNVKNTVYLQMNSLTPEDTAVYFCATGNRYSDYRISLVTPSQYEYWGQGTLVTVS | 22 |
| HAS038 | QVQLVESGGGLVQPGGSLRLSCTGSGHSFSTYTVGWFRQAPGEERKFVASISWSGEVTLYGDSVKGRFTISRDNRKKTVYLQMHSLKPEDSAIYYCAAKRGGRPTDSSDDYFYWGQGTQVTVSS | 23 |
| HAS040 | QVQLNESGGGMVQAGGSLRLSCAASGRTVSNYAAGWFRQAPGKEREFVAAINWNKTTTYADSVKGRFIISREYAKNTVALQMNSLKPEDTAVYYCAAVFRIVAPKTQYEYDYWGQGTQVTVSS | 24 |
| HAS041 | QVQLIESGGGLVQAGGSLGLSCAASGRPVSNYAAAWFRQAPGKEREFVAAINWNKTATYADSVKGRFTISRDNAKSTVALQMNSLKPEDTAVYYCAAVFRVVAPKTQYDYDYWGQGTQVTVSS | 25 |
| HAS042 | EVQLVESGGGLVKPGGSLRLSCAASGRPVSNYAAAWFRQAPGKEREFVSAINWQKTATYADSVKGRFTISRDNAKNSLYLQMNSLRAEDTAVYYCAAVFRVVAPKTQYDYDYWGQGTLVTVSS | 26 |
| HAS044 | QVQLVESGGGLVQAGGSLRLSCAASGRTFSSYAIGWFRQAPGKAREFVARVSTIAGDTDYADSVKGRFTISRDNAKNTVYLQMNSLKPEDTAVYYCAADSYNVRLVTGEADYWGEGTQVTVSS | 27 |
| HAS077 | QVQLVESGGGLVQAGGSLRLSCAASGRTFSSYAIGWFRQAPGKAREFVARVSTIAGDTDYADSVKGRFTISRDNAKNTVYLQMNSLKPEDTAVYYCAADSYNVRLGTGEADYWGEGTQVTVSS | 28 |
| HAS079 | EVQLVESGGGLVQAGDSLRLSCAASGFTFSNYAIGWFRQAPGKAREFVARVSTIAGDTDYANAVKGRFTISRDNAKNTVYLQMNSLKPDDTAVYYCAAESYNVRLVTGEADYWGEGTQVTVSS | 29 |
| HAS080 | QVRLAESGGGRVQAGESLRLSCVASGRTFSNDAAGWFREASGKEREFVASISWSGNYTYYADSVKGRFTISEDNVKNTVYLQMTSLKPEDTAVYYCAAGNRYSDYRISLVTPRLYEYWGQGTQVTVS | 30 |
| HAS081 | QVQLVESGGGLVQAGGSLRLSCAASGRTFSSDAAGWFRQASGKEREFVAAISWSGNYTYSADSVKGRFTISSDNVKNTVYLQMNSLKPEDTAVYLCAAGNRYSDYRISLVTPSQYEYWGQGTQVTVS | 31 |
| HAS091 | QVQLVESGGGLVQAGGSLRLSCAASGRTFGSDAAGWFRQASGKEREFVASISWSGGYTYYADSGTGRFTISSDNVKNTVYLQMNSLTPEDTAVYFCATGNRSDYRISLVTPSQYEYWGQGTQVTVS | 32 |

TABLE 6-continued

Sequences for anti-albumin VHH domains

| VHH domain | Sequence | SEQ ID NO: |
|---|---|---|
| HAS093 | QVQLVESGGGLVQAGGSLRLSCAASGRTFGSDAAGWFRQASGK EREFVASISWSGGYTYYADSGKGRFTISSDNVKNTVYLQMNSL TPEDTAVYFCATGNRYSDYRISLVTPSQYDYWGQGTQVTVS | 33 |
| HAS096 | QVQLVESGGGLVQAGGSLRLSCAASGRTFGSDAAGWFRQASGK EREFVASISWSGGYTYYADSVKGRFTSSSDNVKNTVYLQMNSL TPEDTAVYFCATVNRYSDYRISLVTPSQYEYWGQGTQVTVS | 34 |

TABLE 7

CDR sequences for anti-albumin VHH domains.

| VHH domain | CDR1 sequence [SEQ ID NO:] | CDR2 sequence [SEQ ID NO] | CDR3 sequence [SEQ ID NO:] |
|---|---|---|---|
| HAS020 | GRTFGSDA [35] | ISWSGGYT [44] | ATGNRYSDYRISLVTPSQYEY [52] |
| HAS038 | GHSFSTYT [36] | ISWSGEVT [45] | AAKRGGRPTDSSDDYFY [53] |
| HAS040 | GRTVSNYA [37] | INWNKTTT [46] | AAVFRIVAPKTQYEYDY [54] |
| HAS041 | GRPVSNYA [38] | INWNKTAT [47] | AAVFRVVAPKTQYDYDY [55] |
| HAS042 | GRPVSNYA [38] | INWQKTAT [48] | AAVFRVVAPKTQYDYDY [55] |
| HAS044 | GRTFSSYA [39] | VSTIAGDT [49] | AADSYNVRLVTGEADY [56] |
| HAS077 | GRTFSSYA [39] | VSTIAGDT [49] | AADSYNVRLGTGEADY [57] |
| HAS079 | GFTFSNYA [40] | VSTIAGDT [49] | AAESYNVRLVTGEADY [58] |
| HAS080 | GRTFSNDA [41] | ISWSGNYT [50] | AAGNRYSDYRISLVTPRLYEY [59] |
| HAS081 | GRTFSSDA [42] | ISWSGNYT [50] | AAGNRYSDYRISLVTPSQYEY [60] |
| HAS091 | GRTFGSDA [43] | ISWSGGYT [51] | ATGNRDSDYRISLVTPSQYEY [61] |
| HAS093 | GRTFGSDA [43] | ISWSGGYT [51] | ATGNRYSDYRISLVTPSQYDY [62] |
| HAS096 | GRTFGSDA [43] | ISWSGGYT [51] | ATVNRYSDYRISLVTPSQYEY [63] |

Example 10. Characterization of Albumin-Binding Kinetics by Biacore

The binding kinetics of the VHH domains HAS040 and HAS041 to HSA or CSA were determined using SPR on a Biacore 3000 instrument. Biotinylated albumin was captured onto a CAP chip saturated with Biotin CAPture reagent containing deoxyribooligonucleotides (obtained from GE Healthcare). Concentrations of purified VHH domains were injected for 5 minutes at a flowrate of 50 µL/min. Three concentrations were assessed per VHH domain. Bound analyte was allowed to dissociate for 600 seconds. The chip surface was regenerated after each concentration by injecting 6 M guanidine HCl/0.25 M NaOH for 2 minutes at 10 µL/min. Kinetics were determined at pH 7.4 and pH 6.0 in HBS-EP buffer using a 1:1 Langmuir model (local $R_{max}$ and constant RI) and double reference subtraction (subtraction of a buffer concentration cycle from the sample concentration cycle and subtraction of a parallel reference flow cell). The MSA21 VHH domain (International Publication No. WO 2004/062551 A2) (sequence:

(SEQ ID NO: 322)
LEQVQLQESGGGLVQPGGSLRLSCEASGFTFSRFGMTWVRQAPGKGVEW

VSGISSLGDSTLYADSVKGRFTISRDNAKNTLYLQMNSLKPEDTAVYYC

TIGGSLNPGGQGTQVTVSS was prepared and used as a comparator in these assays.

The results of this assay are shown in Table 8. Binding affinities were observed in the 0.3-5 nM range, indicating that the HAS040 and HAS041 domains have sufficient affinity at both pH 6 and pH 7.4 to facilitate half-life extension. Furthermore, these VHH domains demonstrated binding to CSA and HSA with very similar affinities, strengthening the predictive nature of half-life extension studies to be performed in primates.

TABLE 8

Results of Biacore characterization of anti-albumin VHH domains.

| Sample | Albumin/pH | $k_a$ (1/Ms) | $k_d$ (1/s) | $K_D$ (M) | Chi² |
|---|---|---|---|---|---|
| HAS40 | CSA/pH 6.0 | 3.68E+05 | 2.81E−04 | 7.64E−10 | 0.05 |
| | CSA/pH 7.4 | 1.04E+06 | 5.62E−04 | 5.39E−10 | 0.1 |

TABLE 8-continued

Results of Biacore characterization of anti-albumin VHH domains.

| Sample | Albumin/pH | $k_a$ (1/Ms) | $k_d$ (1/s) | $K_D$ (M) | Chi² |
|---|---|---|---|---|---|
| | HSA/pH 6.0 | 4.45E+05 | 2.08E-04 | 4.66E-10 | 0.09 |
| | HSA/pH 7.4 | 1.29E+06 | 4.40E-04 | 3.41E-10 | 0.03 |
| HAS41 | CSA/pH 6.0 | 3.12E+05 | 7.39E-04 | 2.37E-09 | 0.41 |
| | CSA/pH 7.4 | 1.07E+06 | 1.23E-03 | 1.15E-09 | 0.18 |
| | HSA/pH 6.0 | 3.73E+05 | 3.87E-04 | 1.04E-09 | 0.12 |
| | HSA/pH 7.4 | 1.23E+06 | 5.66E-04 | 4.61E-10 | 0.03 |
| MSA21 | CSA/pH 6.0 | 2.80E+05 | 1.53E-03 | 5.47E-09 | 0.05 |
| | CSA/pH 7.4 | 5.61E+05 | 2.16E-03 | 3.85E-09 | 0.05 |
| | HSA/pH 6.0 | 3.30E+05 | 1.81E-03 | 5.46E-09 | 0.06 |
| | HSA/pH 7.4 | 1.13E+06 | 3.93E-03 | 3.49E-09 | 0.07 |

Example 11. Demonstration of Non-Competitive Albumin Binding by VHH and FcRn

Recycling of albumin from endocytic vesicles is mediated by interaction with FcRn. It was, therefore, important to determine whether the VHH would interfere with the interaction of HSA and FcRn. To determine whether the HAS040 and HAS041 VHH domains bind to the same epitope as FcRn, the binding of FcRn to HSA that had been saturated with anti-HSA VHH domains was analyzed on a Biacore 3000 instrument at pH 6.0 in HBS-EP buffer. HSA was directly immobilized onto a CM5 chip to reach a target density of 250 RUs (resonance units) using amine coupling. VHH domains were diluted to approximately 1-10 μg/mL and injected to achieve saturation (3 minutes at 50 μL/min). One concentration of FcRn was injected over the HSA:VHH surface to obtain kinetics for 5 minutes at 50 μL/min. Dissociation was allowed for 180 seconds before regeneration. The chip surface was regenerated by injecting 20 μL of 25 mM NaOH at 100 μL/min. Kinetics were determined using a 1:1 Langmuir model (local $R_{max}$ and constant RI) and double reference subtraction (subtraction of a buffer concentration cycle from the sample concentration cycle and subtraction of a parallel reference flow cell).

Results are shown in FIG. 7. In FIG. 7A, the direct interaction of FcRn with an HSA saturated surface resulted in a response difference of 30 RUs. Similar RUs were obtained when 400 nM FcRn was injected over surfaced saturated with complexes of HSA with MSA21 (ADL021) (FIG. 7B), HAS040 (FIG. 7C) or HAS041 (FIG. 7D). Based on these data, HAS040 and HAS041 do not to interfere with FcRn binding and are expected to be recycled from the endosome via the interaction of albumin with FcRn.

Example 12. Generation of Anti-C5 and Anti-Albumin Bispecific Fusion Proteins

Anti-C5 VHH domains were fused to an anti-albumin domain to generate bispecific molecules. Four different linker lengths $(G_4S)_3$ (SEQ ID NO: 106), $(G_4S)_4$ (SEQ ID NO: 107), $(G_4S)_5$ (SEQ ID NO: 108) and $(G_4S)_6$ (SEQ ID NO: 109), and two different orientations (N-terminal or C-terminal) of anti-albumin domain were evaluated. Constructs were expressed in HEK293F cells and purified using Protein A affinity chromatography. Purified fusion molecules were evaluated in Biacore experiments. Human C5 was biotinylated and immobilized on a biacore chip, purified bispecific molecules were injected to saturate the chip followed by three different concentrations of human serum albumin to obtain kinetics. Measured affinity to human serum albumin was used as a proxy to compare the different linker lengths. $(G_4S)_3$ (SEQ ID NO: 106) was chosen as the optimal linker length to generate bispecific fusions. N-terminal or C-terminal anti-albumin fusions were also evaluated in the same experiment. Different orientations were found to be optimal for different anti-C5 VHH domains. The N-versus C-terminal orientation of the constructs is specified below the construct name in Table 9 with (C5/HSA) indicating the anti-C5 domain is located N-terminal to the anti-HSA domain. Likewise, with (HSA/C5) indicates the anti-HSA domain is located N-terminal to the anti-C5 domain.

Figure 3A:
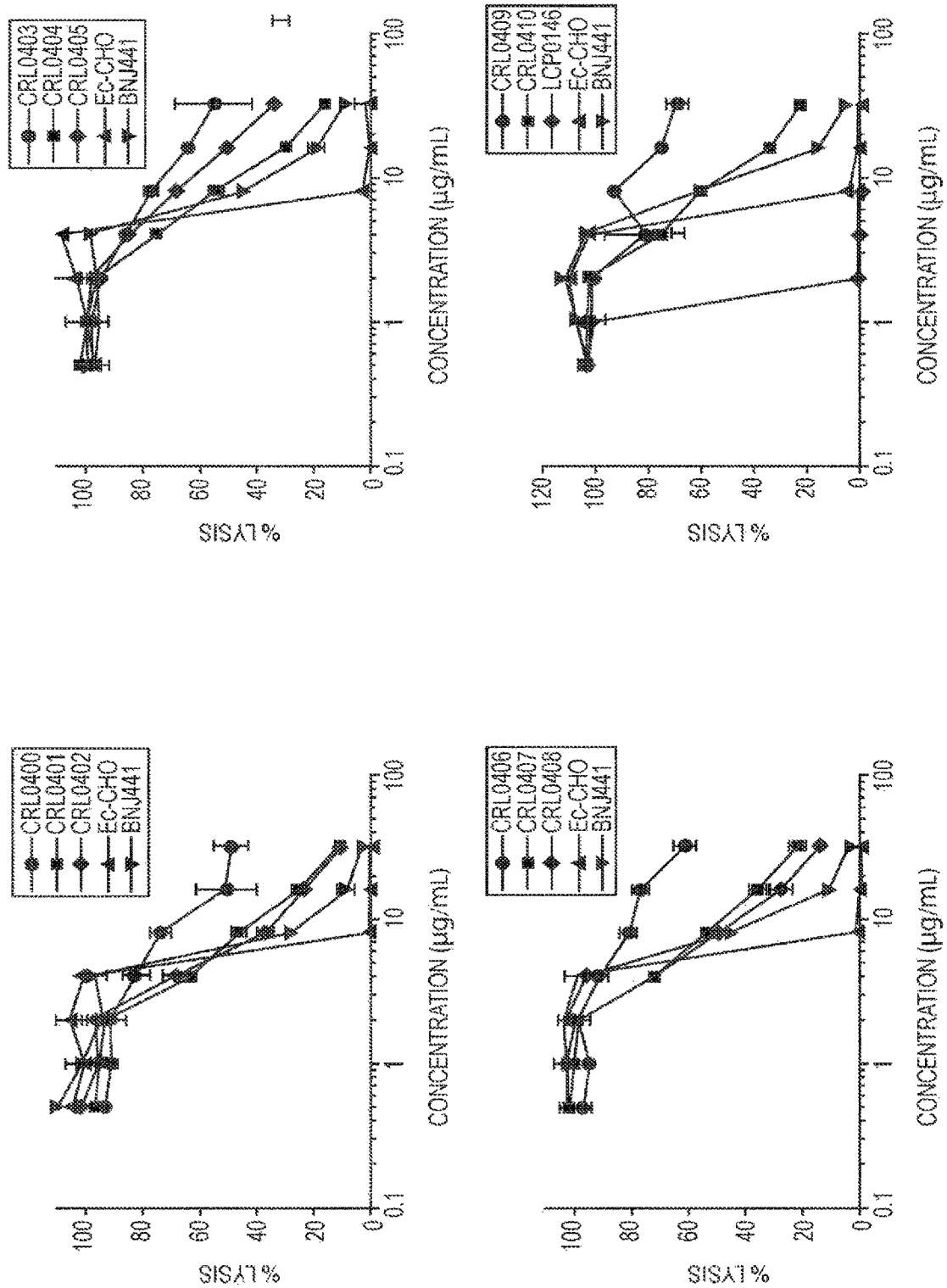
FIGS. 3A-3D show the results of a CCP hemolysis assay for bispecific fusion proteins.
Figure 3B:
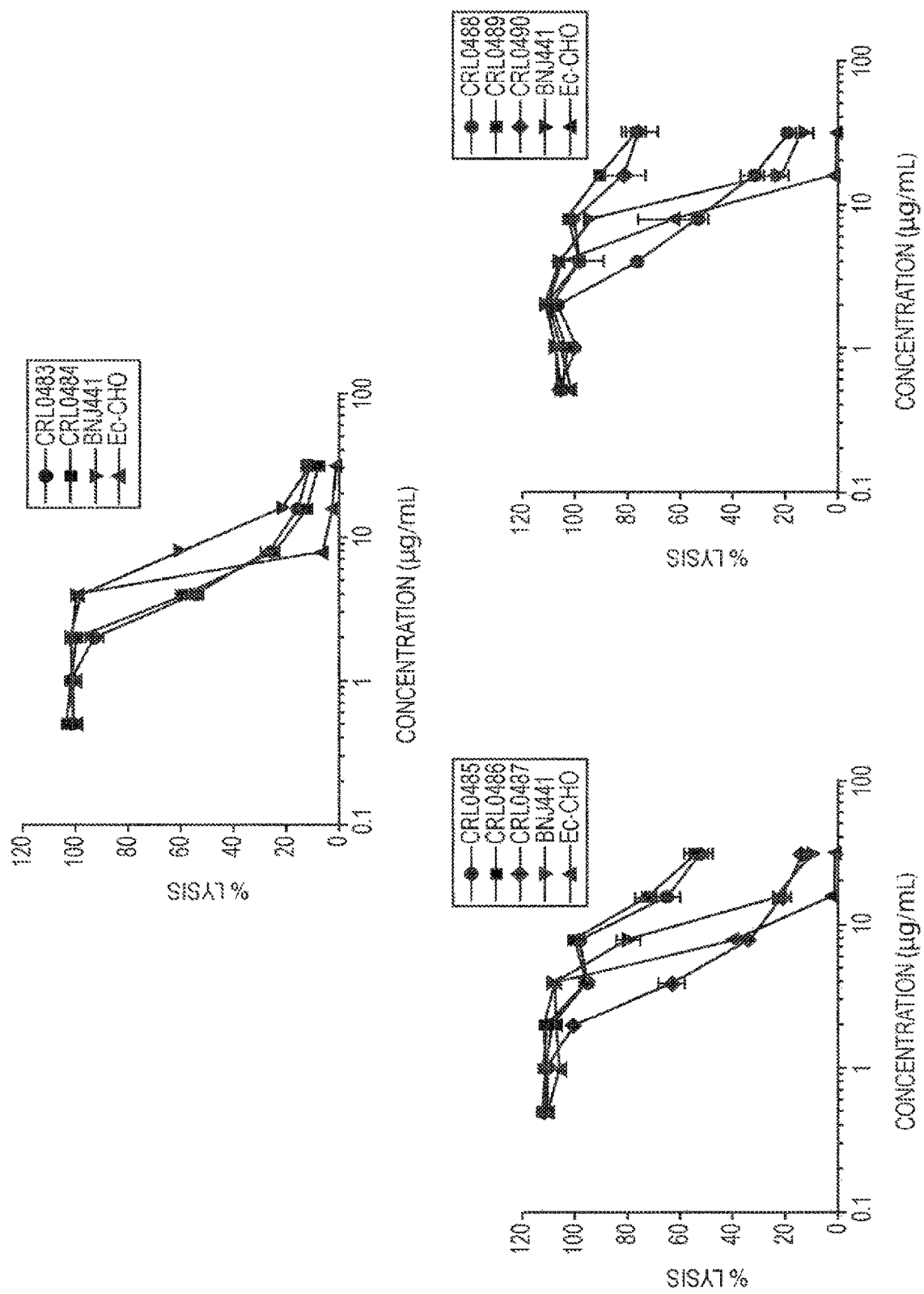
Figure 3C:
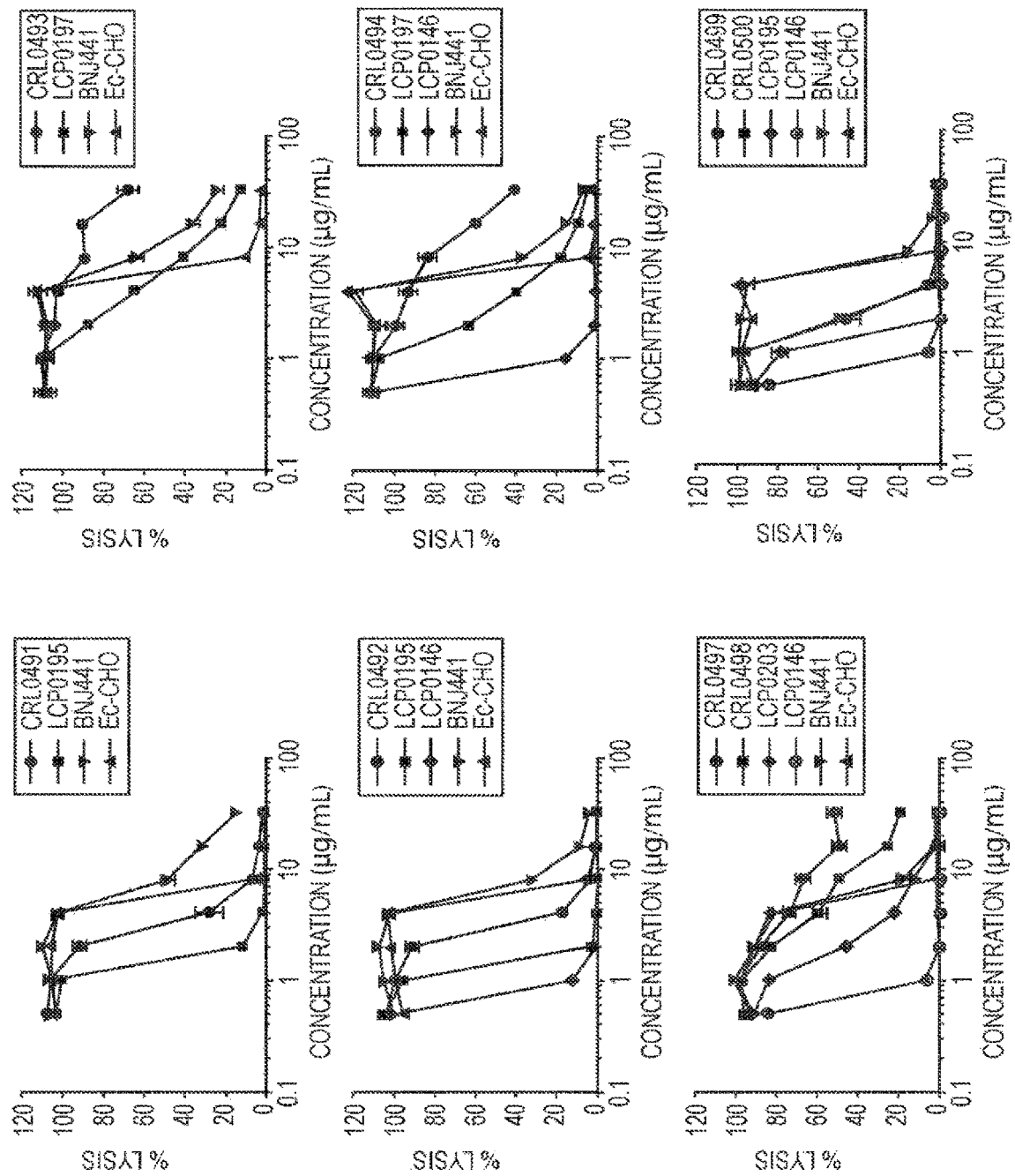
Figure 3D:
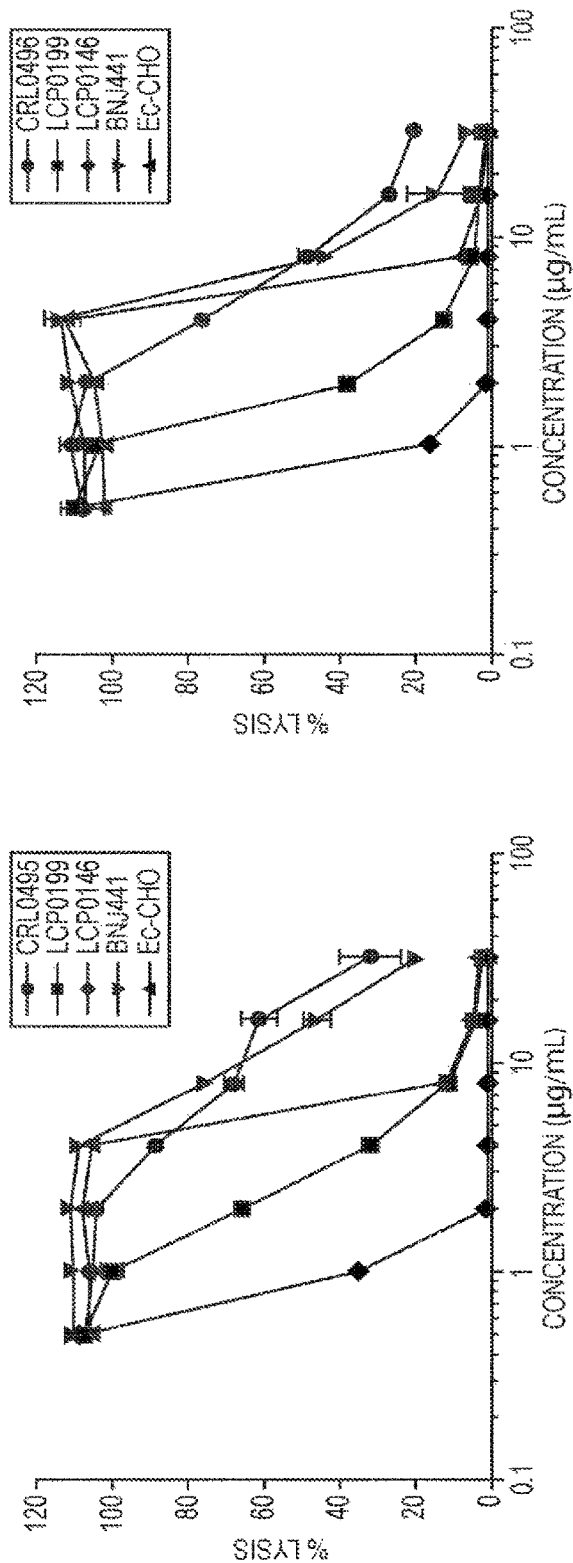
Figure 3D:
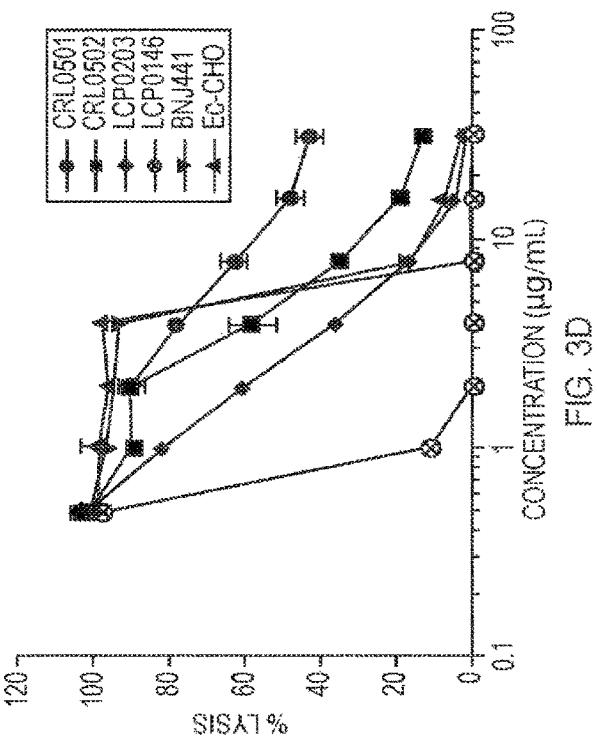

After selecting the optimal linker length, a series of different bispecific fusion molecules were generated with humanized anti-C5 VHH domains fused to two different anti-albumin domains (shown in Table 8). These constructs were expressed in Expi293 cells and purified using Protein A chromatography. Purified bispecific fusion proteins were tested in hemolysis assays and the results are shown in FIGS. 3A and 3B.

TABLE 9

Anti-C5/Anti-Albumin Fusion Proteins

| Name | Sequence | SEQ ID NO: |
|---|---|---|
| CRL0400 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRHFSDYAMAWFRQAPGQEREFVAGIGWS GGDTLYADSVRGRFTISRDNAKNTLYLQMNSLRAEDTAVYYCAARQ GQYIYSSMRSDSYDYWGQGTLVTVSS | 64 |
| CRL0401 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAHSDYAMAWFRQAPGQEREFVAGIGWS GGDTLYADSVRGRFTISRDNAKNTLYLQMNSLRAEDTAVYYCAARQ GQYIYSSMRSDSYDYWGQGTLVTVSS | 65 |
| CRL0402 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRHSDYAMAWFRQAPGQEREFVAGIGWS GGDTLYADSVRGRFTISRDNAKNTLYLQMNSLRAEDTAVYYCAARQ GQYIYSSMRSDSYDYWGQGTLVTVSS | 66 |

TABLE 9-continued

Anti-C5/Anti-Albumin Fusion Proteins

| Name | Sequence | SEQ ID NO: |
|---|---|---|
| CRL0403 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRHFSDYAMAWFRQAPGQEREFVAGIGWS GGDTLYADSVRGRFTISRDNSKNTMYLQMNSLRAEDTAVYYCAARQ GQYIYSSMRSDSYDYWGQGTLVTVSS | 67 |
| CRL0404 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAHSDYAMAWFRQAPGQEREFVAGIGWS GGDTLYADSVRGRFTISRDNSKNTMYLQMNSLRAEDTAVYYCAARQ GQYIYSSMRSDSYDYWGQGTLVTVSS | 68 |
| CRL0405 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRHHSDYAMAWFRQAPGQEREFVAGIGWS GGDTLYADSVRGRFTISRDNSKNTMYLQMNSLRAEDTAVYYCAARQ GQYIYSSMRSDSYDYWGQGTLVTVSS | 69 |
| CRL0406 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRHFSDYAMAWFRQAPGQERE FVAGIGWSGGDTLYADSVRGRFTISRDNAKNTLYLQMNSLRAEDTA VYYCAARQGQYIYSSMRSDSYDYWGQGTLVTVSS | 70 |
| CRL0407 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAHSDYAMAWFRQAPGQERE FVAGIGWSGGDTLYADSVRGRFTISRDNAKNTLYLQMNSLRAEDTA VYYCAARQGQYIYSSMRSDSYDYWGQGTLVTVSS | 71 |
| CRL0408 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRHHSDYAMAWFRQAPGQERE FVAGIGWSGGDTLYADSVRGRFTISRDNAKNTLYLQMNSLRAEDTA VYYCAARQGQYIYSSMRSDSYDYWGQGTLVTVSS | 72 |
| CRL0409 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRHFSDYAMAWFRQAPGQERE FVAGIGWSGGDTLYADSVRGRFTISRDNSKNTMYLQMNSLRAEDTA VYYCAARQGQYIYSSMRSDSYDYWGQGTLVTVSS | 73 |
| CRL0410 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAHSDYAMAWFRQAPGQERE FVAGIGWSGGDTLYADSVRGRFTISRDNSKNTMYLQMNSLRAEDTA VYYCAARQGQYIYSSMRSDSYDYWGQGTLVTVSS | 74 |
| CRL0411 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRHHSDYAMAWFRQAPGQERE FVAGIGWSGGDTLYADSVRGRFTISRDNSKNTMYLQMNSLRAEDTA VYYCAARQGQYIYSSMRSDSYDYWGQGTLVTVSS | 75 |
| CRL0483 (C5/HSA) | EVQLVESGGGLVQPGGSLRLSCAASGRTFSGILSPYAVGWFRQAPG KGLEFVSTITSGGSAIYTDSVKGRFTISRDNAKDSLYLQMNSLRAE DTAVYYCAVRTRRYGSNLGEVPQENEYGYWGQGTLVTVSSGGGGSG GGGSGGGGSEVQLLESGGGLVQPGGSLRLSCAASGFTFRSFGMSWV RQAPGKGPEWVSSISGSGSDTLYADSVKGRFTISRDNSKNTLYLQM NSLRPEDTAVYYCTIGGSLSRSSQGTLVTVSS | 76 |
| CRL0484 (C5/HSA) | EVQLVESGGGLVQPGGSLRLSCAASGRTFSGILSPYAVGWFRQAPG KGLEFVSTITSGGSAIYTDSVKGRFTISRDNAKDSLYLQMNSLRAE DTAVYYCAVRTRRYGSNLGEVPQENEYGYWGQGTLVTVSSGGGGSG GGGSGGGGSEVQLVESGGGLVKPGGSLRLSCAASGRPVSNYAAAWF RQAPGKEREFVSAINWQKTATYADSVKGRFTISRDNAKNSLYLQMN SLRAEDTAVYYCAAVFRVVAPKTQYDYDYWGQGTLVTVSS | 77 |

TABLE 9-continued

Anti-C5/Anti-Albumin Fusion Proteins

| Name | Sequence | SEQ ID NO: |
|---|---|---|
| CRL0485 (C5/HSA) | EVQLVESGGGLVQPGGSLRLSCAASGRTFSGILSPYAVGWFRQAPG KGLEFVSTITSGGSAIYTDSVKGRFTISRDNAKNTLYLQMNSLRAE DTAVYYCAVRTRRYGSNLGEVPQENEYGYWGQGTLVTVSSGGGGSG GGGSGGGGSEVQLLESGGGLVQPGGSLRLSCAASGFTFRSFGMSWV RQAPGKGPEWVSSISGSGSDTLYADSVKGRFTISRDNSKNTLYLQM NSLRPEDTAVYYCTIGGSLSRSSQGTLVTVSS | 78 |
| CRL0486 (C5/HSA) | EVQLVESGGGLVQPGGSLRLSCAASGRTFSGILSPYAVGWFRQAPG KGLEFVSTITSGGSAIYTDSVKGRFTISRDNAKNTLYLQMNSLRAE DTAVYYCAVRTRRYGSNLGEVPQENEYGYWGQGTLVTVSSGGGGSG GGGSGGGGSEVQLVESGGGLVKPGGSLRLSCAASGRPVSNYAAAWF RQAPGKEREFVSAINWQKTATYADSVKGRFTISRDNAKNSLYLQMN SLRAEDTAVYYCAAVFRVVAPKTQYDYDYWGQGTLVTVSS | 79 |
| CRL0487 (C5/HSA) | EVQLVESGGGLVQPGGSLRLSCAASGRTFSGILSPYAVGWFRQAPG KGLEFVSTITSGGSAIYTDSVKGRFTISRDNAKNSVYLQMNSLRAE DTAVYYCAVRTRRYGSNLGEVPQENEYGYWGQGTLVTVSSGGGGSG GGGSGGGGSEVQLLESGGGLVQPGGSLRLSCAASGFTFRSFGMSWV RQAPGKGPEWVSSISGSGSDTLYADSVKGRFTISRDNSKNTLYLQM NSLRPEDTAVYYCTIGGSLSRSSQGTLVTVSS | 80 |
| CRL0488 (C5/HSA) | EVQLVESGGGLVQPGGSLRLSCAASGRTFSGILSPYAVGWFRQAPG KGLEFVSTITSGGSAIYTDSVKGRFTISRDNAKNSVYLQMNSLRAE DTAVYYCAVRTRRYGSNLGEVPQENEYGYWGQGTLVTVSSGGGGSG GGGSGGGGSEVQLVESGGGLVKPGGSLRLSCAASGRPVSNYAAAWF RQAPGKEREFVSAINWQKTATYADSVKGRFTISRDNAKNSLYLQMN SLRAEDTAVYYCAAVFRVVAPKTQYDYDYWGQGTLVTVSS | 81 |
| CRL0489 (C5/HSA) | EVQLVESGGGLVQPGGSLRLSCAASGRTFSGILSPYAVGWFRQAPG QGLEFVATITSGGSAIYTDSVKGRFTISRDNSKNTLYLQMNSLRAE DTAVYYCAVRTRRYGSNLGEVPQENEYGYWGQGTLVTVSSGGGGSG GGGSGGGGSEVQLLESGGGLVQPGGSLRLSCAASGFTFRSFGMSWV RQAPGKGPEWVSSISGSGSDTLYADSVKGRFTISRDNSKNTLYLQM NSLRPEDTAVYYCTIGGSLSRSSQGTLVTVSS | 82 |
| CRL0490 (C5/HSA) | EVQLVESGGGLVQPGGSLRLSCAASGRTFSGILSPYAVGWFRQAPG QGLEFVATITSGGSAIYTDSVKGRFTISRDNSKNTLYLQMNSLRAE DTAVYYCAVRTRRYGSNLGEVPQENEYGYWGQGTLVTVSSGGGGSG GGGSGGGGSEVQLVESGGGLVKPGGSLRLSCAASGRPVSNYAAAWF RQAPGKEREFVSAINWQKTATYADSVKGRFTISRDNAKNSLYLQMN SLRAEDTAVYYCAAVFRVVAPKTQYDYDYWGQGTLVTVSS | 83 |
| CRL0491 (C5/HSA) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAFSDYAMAWFRQAPGQEREFVAGIGWS GGDTLYADSVRGRFTNSRDNSKNTLYLQMNSLRAEDTAVYYCAARQ GQYIYSSMRSDSYDYWGQGTLVTVSS | 84 |
| CRL0492 (C5/HSA) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAFSDYAMAWFRQAPGQERE FVAGIGWSGGDTLYADSVRGRFTNSRDNSKNTLYLQMNSLRAEDTA VYYCAARQGQYIYSSMRSDSYDYWGQGTLVTVSS | 85 |
| CRL0493 (C5/HSA) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAFSDYAMAWFRQAPGQEREFVAGIGWS GGDTLYADSVRGRFTISRDNAKNTLYLQMNSLRAEDTAVYYCAARQ GQYIYSSMRSDSYDYWGQGTLVTVSS | 86 |
| CRL0494 (C5/HSA) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAFSDYAMAWFRQAPGQERE FVAGIGWSGGDTLYADSVRGRFTISRDNAKNTLYLQMNSLRAEDTA VYYCAARQGQYIYSSMRSDSYDYWGQGTLVTVSS | 87 |

TABLE 9-continued

Anti-C5/Anti-Albumin Fusion Proteins

| Name | Sequence | SEQ ID NO: |
|---|---|---|
| CRL0495 (C5/HSA) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAFSDYAMAWFRQAPGQEREFVAGIGWS GGDTLYADSVRGRFTISRDNSKNTMYLQMNSLRAEDTAVYYCAARQ GQYIYSSMRSDSYDYWGQGTLVTVSS | 88 |
| CRL0496 (C5/HSA) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAFSDYAMAWFRQAPGQERE FVAGIGWSGGDTLYADSVRGRFTISRDNSKNTMYLQMNSLRAEDTA VYYCAARQGQYIYSSMRSDSYDYWGQGTLVTVSS | 89 |
| CRL0497 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAFSDYAMAWFRQAPGQGLEFVAGIGWS GGDTLYADSVRGRFTISRDNSKNTLYLQMNSLRAEDTAVYYCAARQ GQYIYSSMRSDSYDYWGQGTLVTVSS | 90 |
| CRL0498 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAFSDYAMAWFRQAPGQGLE FVAGIGWSGGDTLYADSVRGRFTISRDNSKNTLYLQMNSLRAEDTA VYYCAARQGQYIYSSMRSDSYDYWGQGTLVTVSS | 91 |
| CRL0499 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAHSDYAMAWFRQAPGQEREFVAGIGWS GGDTLYADSVRGRFTNSRDNSKNTLYLQMNSLRAEDTAVYYCAARQ GQYIYSSMRSDSYDYWGQGTLVTVSS | 92 |
| CRL0500 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAHSDYAMAWFRQAPGQERE FVAGIGWSGGDTLYADSVRGRFTNSRDNSKNTLYLQMNSLRAEDTA VYYCAARQGQYIYSSMRSDSYDYWGQGTLVTVSS | 93 |
| CRL0501 (HSA/C5) | EVQLLESGGGLVQPGGSLRLSCAASGFTFRSFGMSWVRQAPGKGPE WVSSISGSGSDTLYADSVKGRFTISRDNSKNTLYLQMNSLRPEDTA VYYCTIGGSLSRSSQGTLVTVSSGGGGSGGGGSGGGGSEVQLVESG GGLVQPGGSLRLSCAASGRAHSDYAMAWFRQAPGQGLEFVAGIGWS GGDTLYADSVRGRFTISRDNSKNTLYLQMNSLRAEDTAVYYCAARQ GQYIYSSMRSDSYDYWGQGTLVTVSS | 94 |
| CRL0502 (HSA/C5) | EVQLVESGGGLVKPGGSLRLSCAASGRPVSNYAAAWFRQAPGKERE FVSAINWQKTATYADSVKGRFTISRDNAKNSLYLQMNSLRAEDTAV YYCAAVFRVVAPKTQYDYDYWGQGTLVTVSSGGGGSGGGGSGGGGS EVQLVESGGGLVQPGGSLRLSCAASGRAHSDYAMAWFRQAPGQGLE FVAGIGWSGGDTLYADSVRGRFTISRDNSKNTLYLQMNSLRAEDTA VYYCAARQGQYIYSSMRSDSYDYWGQGTLVTVSS | 95 |

Figure 4:
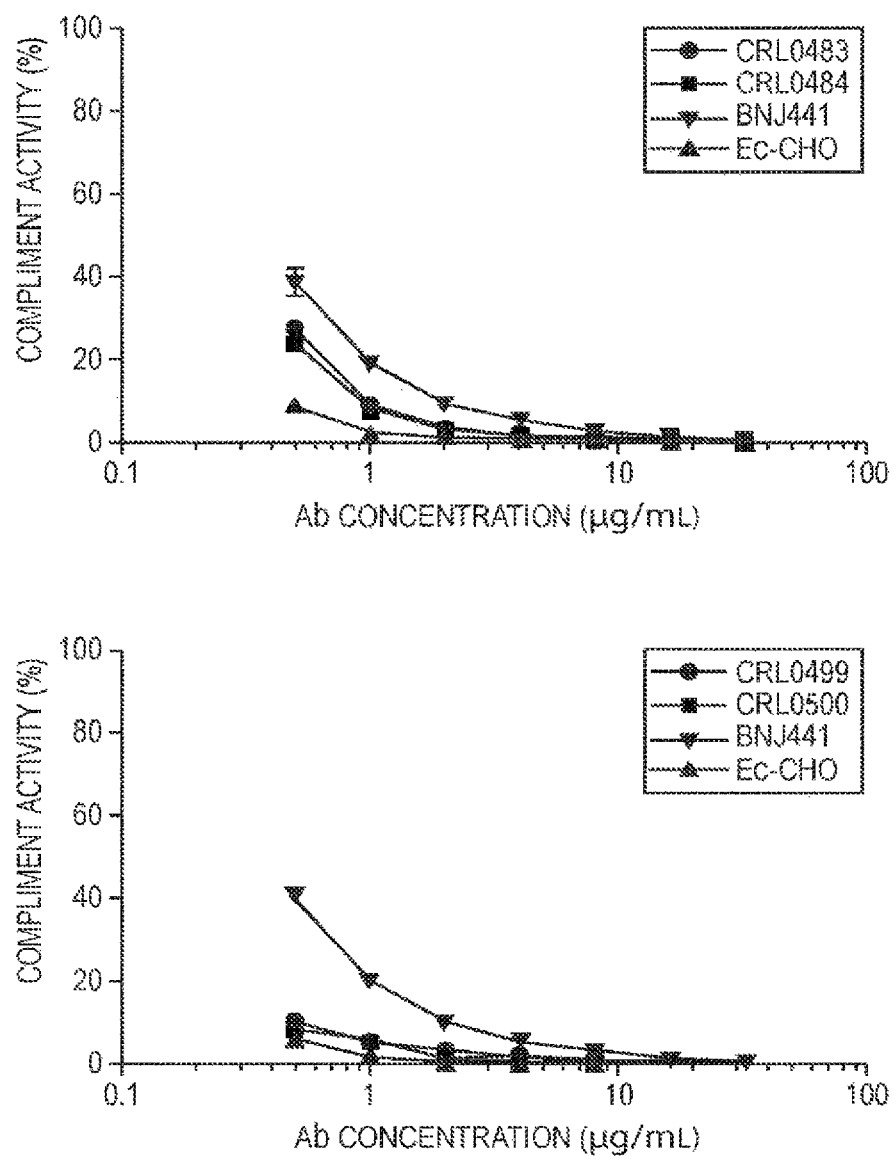
FIG. 4 shows the results of a Wieslab CCP assay for bispecific fusion proteins.
Figure 5:
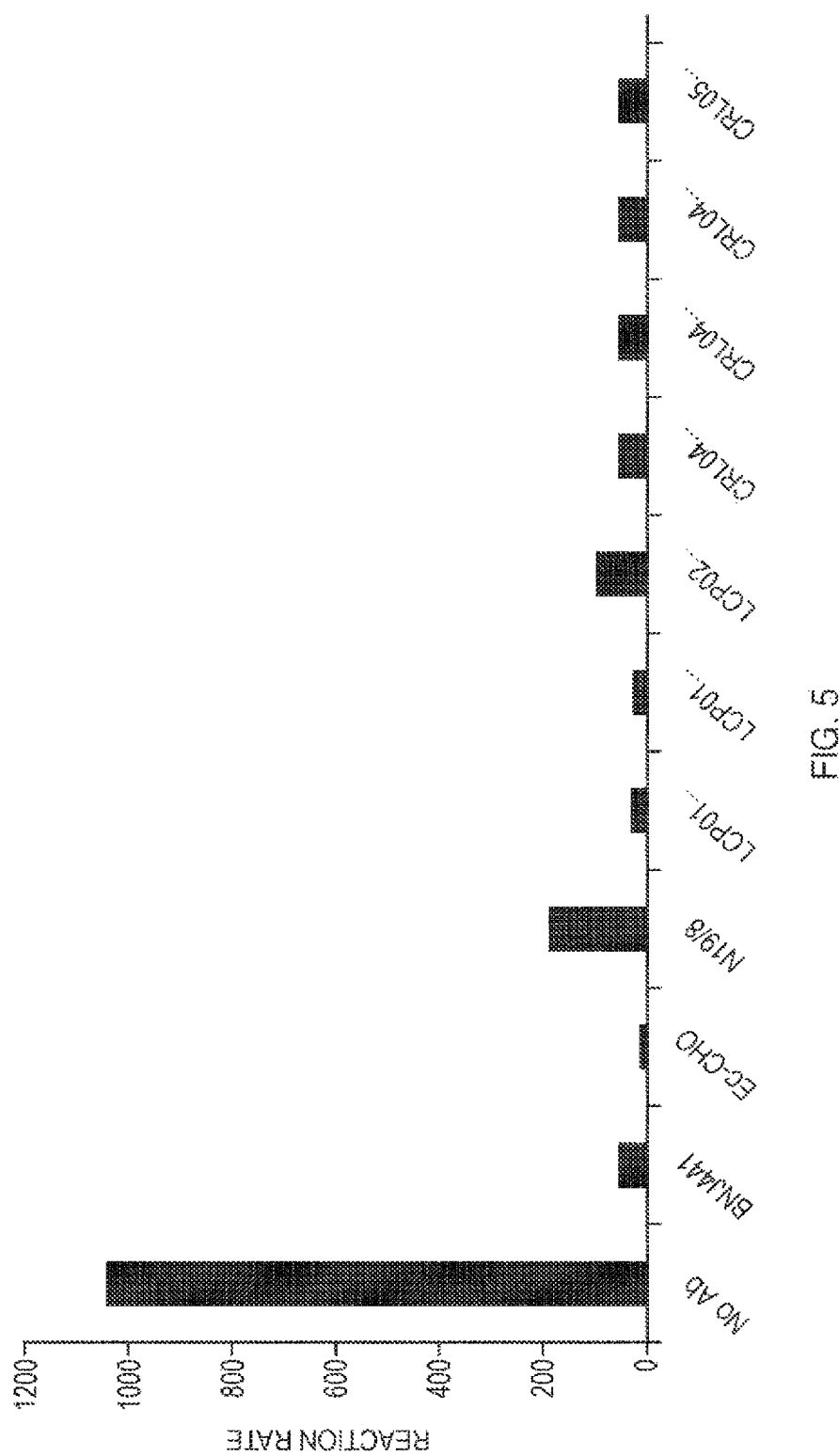
FIG. 5 shows the results of a C5a liberation assay for bispecific fusion proteins.

Four bispecific molecules CRL0483, CRL0484, CRL0499, and CRL0500 were prioritized based on binding and functional assays. Biacore affinity measurements for binding to human C5 for CRL0483, CRL0484, CRL0499, and CRL0500 are shown in Table 10 and functional assessments are shown in in FIGS. 3, 4 and 5. These four bispecific molecules were evaluated in in vivo pharmacokinetic studies in cynomolgus monkeys.

TABLE 10

Biacore measurements of prioritized fusions at pH 7.4 and pH 6.0

| Sample | C5 | pH | $k_a$ (1/Ms) | $k_d$ (1/s) | $K_D$ (M) | Chi$^2$ |
|---|---|---|---|---|---|---|
| CRL0483 | hC5 | 7.4 | 2.25e5 | 2.42e-4 | 1.07e-9 | 0.03 |
|  | cC5 | 7.4 | 9.15e4 | 2.20e-5 | 2.40e-10 | 0.01 |
| CRL0484 | hC5 | 7.4 | 7.01e4 | 7.69e-5 | 1.10e-9 | 0.04 |
|  | cC5 | 7.4 | 9.15e4 | 2.2e-5 | 2.40e-10 | 0.01 |
| CRL0499 | hC5* | 7.4 | 2.22e6 | 3.32e-4 | 1.5e-10 | 3.3 |
|  | cC5 | 7.4 | N.D. | N.D. | N.D. | N.D. |
| CRL0500 | hC5 | 7.4 | 2.88e6 | 6.72e-4 | 2.33e-10 | 0.65 |
|  | cC5 | 7.4 | 2.00e6 | 8.48e-4 | 4.2e-10 | 0.04 |
| CRL0483 | hC5 | 6.0 | 4.00e4 | 2.11e-04 | 5.27e-09 | 0.02 |
|  | cC5 | 6.0 | 3.71e4 | 4.62e-5 | 1.25e-9 | 0.02 |
| CRL0484 | hC5 | 6.0 | 4.25e5 | 2.36e-4 | 5.56e-10 | 0.02 |
|  | cC5 | 6.0 | 4.82e4 | 6.17e-6 | 1.28e-10 | 0.03 |
| CRL0499 | hC5* | 6.0 | 2.51e6 | 1.12e-3 | 4.48e-10 | 0.24 |
|  | cC5 | 6.0 | 1.92e6 | 3.88e-3 | 2.02e-9 | 0.31 |
| CRL0500 | hC5* | 6.0 | 8.02e6 | 1.519e-3 | 1.89e-10 | 1.06 |
|  | cC5* | 6.0 | 3.91e6 | 2.5e-3 | 6.41e-10 | 3.16 |

Example 13. Pharmacokinetic Analysis of Bispecific Fusion Proteins

Purified proteins were dosed at 10 mg/kg either intravenously or subcutaneously in cynomolgus monkeys. Three monkeys per dose group per test article were used. Pharmacokinetics properties of bispecific molecules were measured by LC-MS based quantitation using signature peptides to each construct. The PK profile is shown in FIG. 6, and the parameters are described in Table 11.

TABLE 11

PK parameters after 10 mg/kg of test articles in cynomolgus monkeys

| Test article | $t_{1/2}$ (h) | $t_{max}$ (h) | $C_{max}$ (μg/mL) | AUC (h * μg/mL) | $C_L$ (mL/h/kg) | V (mL/kg) | F (%) |
|---|---|---|---|---|---|---|---|
| CRL0483 IV | 139 | 1.33 | 324 | 47900 | 0.211 | 42.0 |  |
| CRL0484 IV | 125 | 1 | 382 | 43700 | 0.238 | 43.0 |  |
| CRL0483 SC | 103 | 20 | 238 | 46412 | 0.218 | 32.5 | 97 |
| CRL0484 SC | 75.9 | 24 | 161 | 32610 | 0.315 | 34.9 | 75 |
| CRL0499 IV | 170 | 2.11 | 299 | 53773 | 0.184 | 46.9 |  |
| CRL0500 IV | 239 | 0.167 | 351 | 51929 | 0.205 | 62.5 |  |
| CRL0499 SC | 220 | 32 | 146 | 58666 | 0.173 | 54.2 | 109 |
| CRL0500 SC | 209 | 32 | 161 | 61475 | 0.163 | 49.0 | 118 |

Variant linker sequences were also generated for the bispecific fusion proteins. The sequences including these variant linker sequences are shown in Table 12.

TABLE 12

Sequences of anti-C5/anti-albumin bi-specifics with different linkers

| Name | Sequence | SEQ ID NO |
|---|---|---|
| CRL0952 | EVQLVESGGGLVKPGGSLRLSCAASGRPVSNYAAAWFRQAPGKEREFVS<br>AINWQKTATYADSVKGRFTISRDNAKNSLYLQMNSLRAEDTAVYYCAAV<br>FRVVAPKTQYDYDYWGQGTLVTVSSGGGGAGGGGAGGGGSEVQLVESGG<br>GLVQPGGSLRLSCAASGRAHSDYAMAWFRQAPGQEREFVAGIGWSGGDT<br>LYADSVRGRFTNSRDNSKNTLYLQMNSLRAEDTAVYYCAARQGQYIYSS<br>MRSDSYDYWGQGTLVTVSS | 96 |
| CRL0953 | EVQLVESGGGLVQPGGSLRLSCAASGRTFSGILSPYAVGWFRQAPGKGL<br>EFVSTITSGGSAIYTDSVKGRFTISRDNAKDSLYLQMNSLRAEDTAVYY<br>CAVRTRRYGSNLGEVPQENEYGYWGQGTLVTVSSGGGGAGGGGAGGGGS<br>EVQLVESGGGLVKPGGSLRLSCAASGRPVSNYAAAWFRQAPGKEREFVS<br>AINWQKTATYADSVKGRFTISRDNAKNSLYLQMNSLRAEDTAVYYCAAV<br>FRVVAPKTQYDYDYWGQGTLVTVSS | 97 |
| CRL0954 | EVQLVESGGGVVQAGDSLTLTCTAPVGTISDYGMGWFRQAPGKEREFVA<br>SISWGGMWTDYADSVKGRFTISRDNDKNAVYLRMNSLNAEDTAVYYCGR<br>GRMYRGIGNSLAQPKSYGYWGQGTQVTVSSGGGGAGGGGAGGGGSEVQL<br>VESGGGLVKPGGSLRLSCAASGRPVSNYAAAWFRQAPGKEREFVSAINW<br>QKTATYADSVKGRFTISRDNAKNSLYLQMNSLRAEDTAVYYCAAVFRVV<br>APKTQYDYDYWGQGTLVTVSS | 98 |
| CRL0955 | EVQLVESGGGLVQAGGSLRLSCAASGRTFSGILSAYAVGWFRQAPGKER<br>EFVSTITSGGSTLSADSVKGRFTLSRDNAKDTVYLQMNSLKPEDTAVYY<br>CAVRTWPYGSNRGEVPTENEYGHWGQGTQVTVSSGGGGAGGGGAGGGGS<br>EVQLVESGGGLVKPGGSLRLSCAASGRPVSNYAAAWFRQAPGKEREFVS<br>AINWQKTATYADSVKGRFTISRDNAKNSLYLQMNSLRAEDTAVYYCAAV<br>FRVVAPKTQYDYDYWGQGTLVTVSS | 99 |
| CRL0956 | EVQLVESGGGLVKPGGSLRLSCAASGRPVSNYAAAWFRQAPGKEREFVS<br>AINWQKTATYADSVKGRFTISRDNAKNSLYLQMNSLRAEDTAVYYCAAV<br>FRVVAPKTQYDYDYWGQGTLVTVSSGGGGAGGGGAGGGGSEVQLVESGG | 100 |

TABLE 12-continued

Sequences of anti-C5/anti-albumin bi-specifics with different linkers

| Name | Sequence | SEQ ID NO |
|---|---|---|
| | GVVQAGDSLTLTCTAPVGTISDYGMGWFRQAPGKEREFVASISWGGMWT DYADSVKGRFTISRDNDKNAVYLRMNSLNAEDTAVYYCGRGRMYRGIGN SLAQPKSYGYWGQGTQVTVSS | |
| CRL0957 | EVQLVESGGGLVKPGGSLRLSCAASGRPVSNYAAAWFRQAPGKEREFVS AINWQKTATYADSVKGRFTISRDNAKNSLYLQMNSLRAEDTAVYYCAAV FRVVAPKTQYDYDYWGQGTLVTVSSGGGGAGGGGAGGGGSEVQLVESGG GLVQAGGSLRLSCAASGRTFSGILSAYAVGWFRQAPGKEREFVSTITSG GSTLSADSVKGRFTLSRDNAKDTVYLQMNSLKPEDTAVYYCAVRTWPYG SNRGEVPTENEYGHWGQGTQVTVSS | 101 |

Example 14. Varying Peptide Linker Sequences

Constructs were generates using the HAS042 (SEQ ID NO:26) albumin binding domain and the CRL0305 (SEQ ID NO:11) humanized anti-C5 VHH. The constructs that were evaluated are listed in Table 13.

TABLE 13

Linkers used for generating fusion proteins.

| Protein | Linker | SEQ ID NO | Octet Binding- Human C5 and Human Albumin |
|---|---|---|---|
| TPP-3211 | No anti-albumin domain (only anti-C5) | | no |
| TPP-3212 | No anti-C5 domain (only anti-albumin) | | no |
| TPP-3213 | No linker | | yes |
| TPP-3214 | GGGGS | 104 | yes |
| TPP-3215 | EAAAKEAAAKEAAAK | 110 | yes |
| TPP-3216 | PAPAP | 111 | yes |
| TPP-3217 | GGGGSPAPAP | 112 | yes |
| TPP-3218 | PAPAPGGGGS | 113 | yes |
| TPP-3219 | GSTSGKSSEGKG | 114 | yes |
| TPP-3220 | GGGDSGGGDS | 115 | yes |
| TPP-3221 | GGGESGGGES | 116 | yes |
| TPP-3222 | GGGGSGGGGS | 105 | yes |
| TPP-3223 | GGGDSGGGGS | 117 | yes |
| TPP-3224 | GGGASGGGGS | 118 | yes |
| TPP-3225 | GGGESGGGGS | 119 | yes |
| TPP-3226 | ASTKGP | 120 | yes |
| TPP-3227 | ASTKGPSVFPLAP | 121 | yes |
| TPP-3228 | GGGGGGGP | 123 | yes |
| TPP-3229 | GGGGGGGGP | 321 | yes |
| TPP-3230 | PAPNLLGGP | 124 | yes |
| TPP-3231 | PNLLGGP | 323 | yes |
| TPP-3232 | GGGGGG | 125 | yes |

TABLE 13-continued

Linkers used for generating fusion proteins.

| Protein | Linker | SEQ ID NO | Octet Binding- Human C5 and Human Albumin |
|---|---|---|---|
| TPP-3233 | GGGGGGGGGGGG | 126 | yes |
| TPP-3234 | APELPGGP | 127 | yes |
| TPP-3235 | SEPQPQPG | 128 | yes |
| TPP-1252 | GGGGSGGGSGGGGS | 106 | yes |

The 26 constructs listed in Table 13 were expressed and the fusion proteins were evaluated for binding to human C5 and albumin (Table 13—Octet binding), generation of aggregates, hydrophobicity (HIC HPLC) and glycosylation (electrospray mass spectrometry). For the octet analysis, biotinylated human C5 was captured on a CAP chip followed by an injection of a test bi-specific molecule. Various concentrations of albumin were subsequently injected. Kinetics were determined at pH 7.4 (Biacore 3000). All bi-specific molecules bound to both C5 and albumin, with each having a similar affinity for albumin (5-6 nM).

Figure 9A:
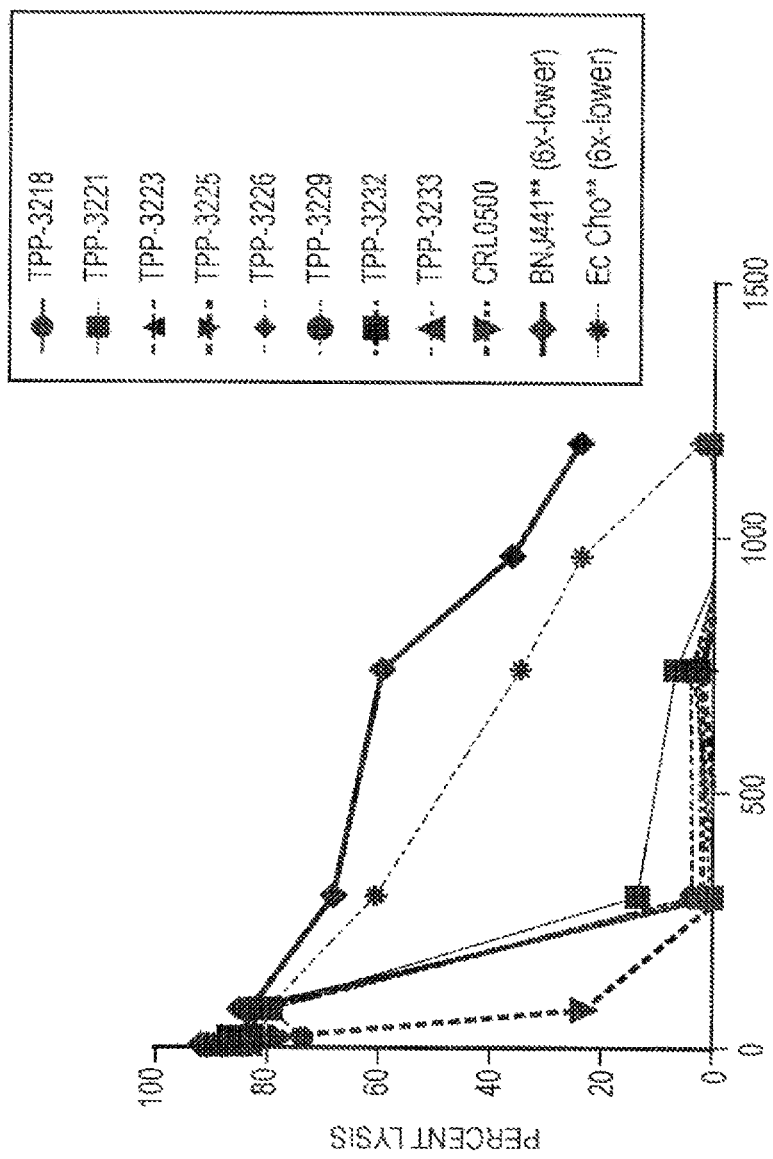
FIGS. 9A and 9B show the ability of various bi-specific fusion proteins to inhibit hemolysis.
Figure 9B:
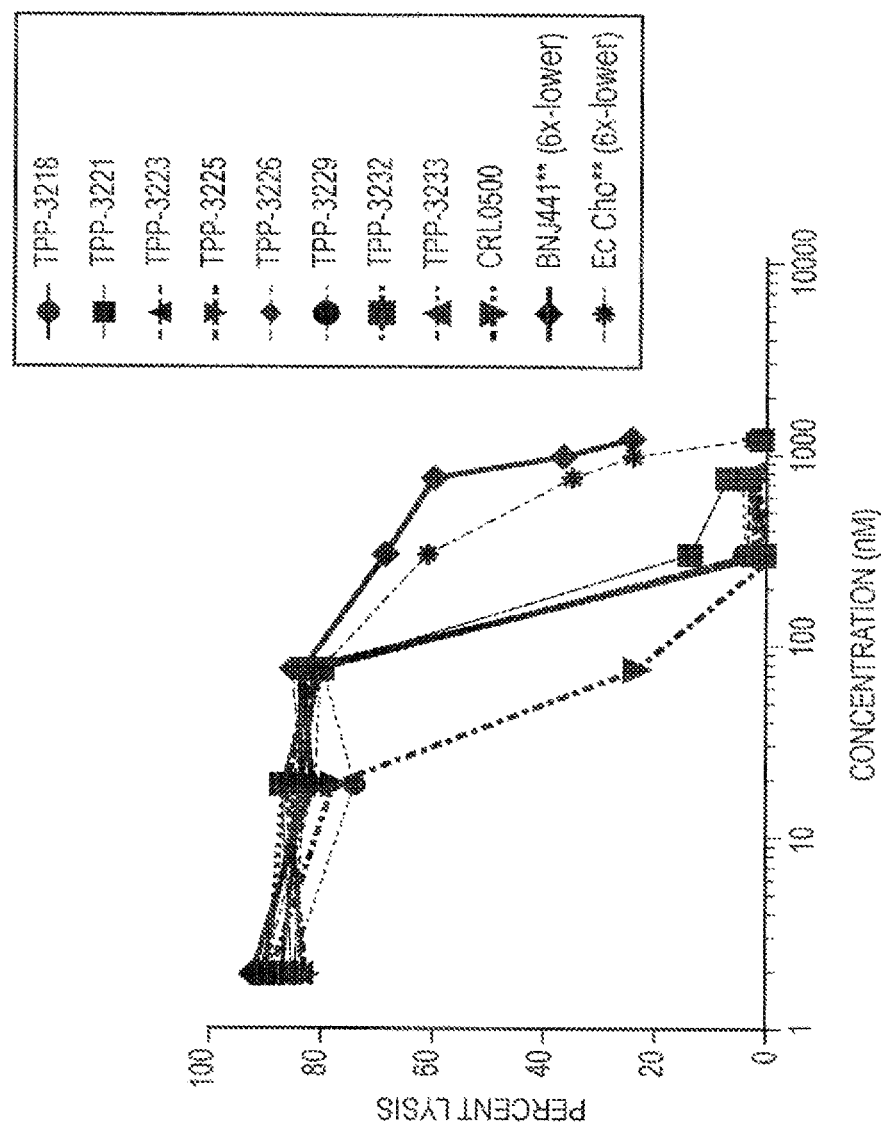
Figure 10:
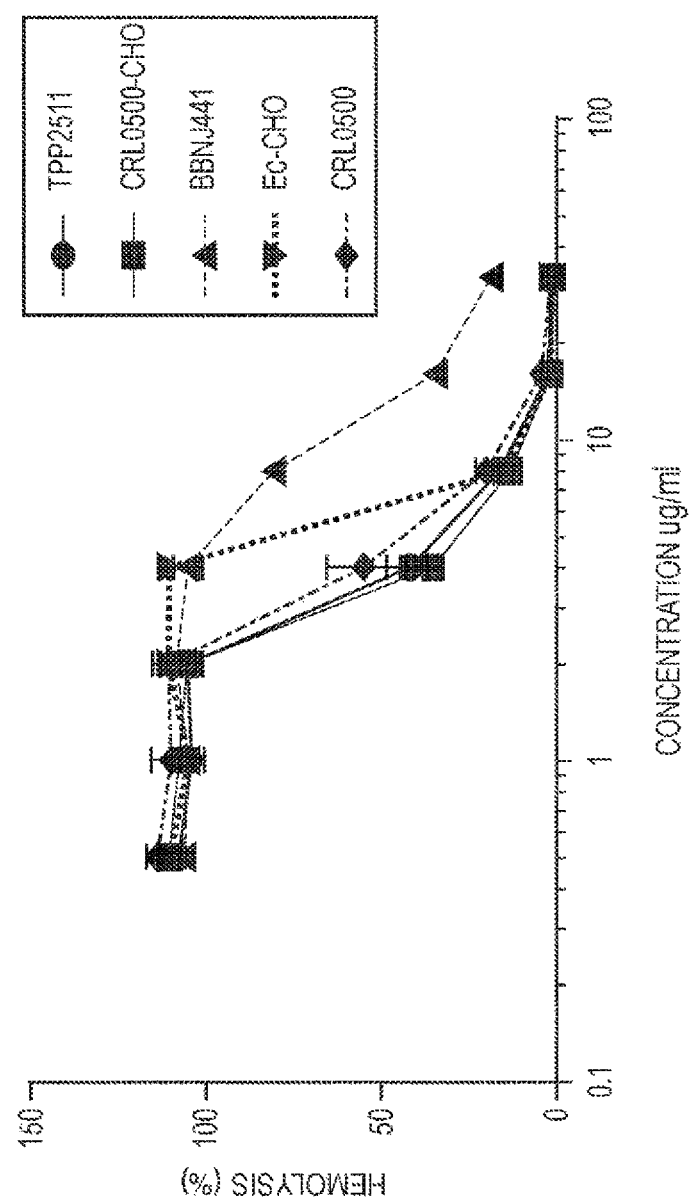
FIG. 10 shows CRL0952 (SEQ ID NO:96) is functionally highly similar to CRL0500 in preventing hemolysis. CRL0500 is a bi-specific C5 and albumin binding fusion protein with a $(G_4S)_3$ (SEQ ID NO:106) linker.
Figure 11A:
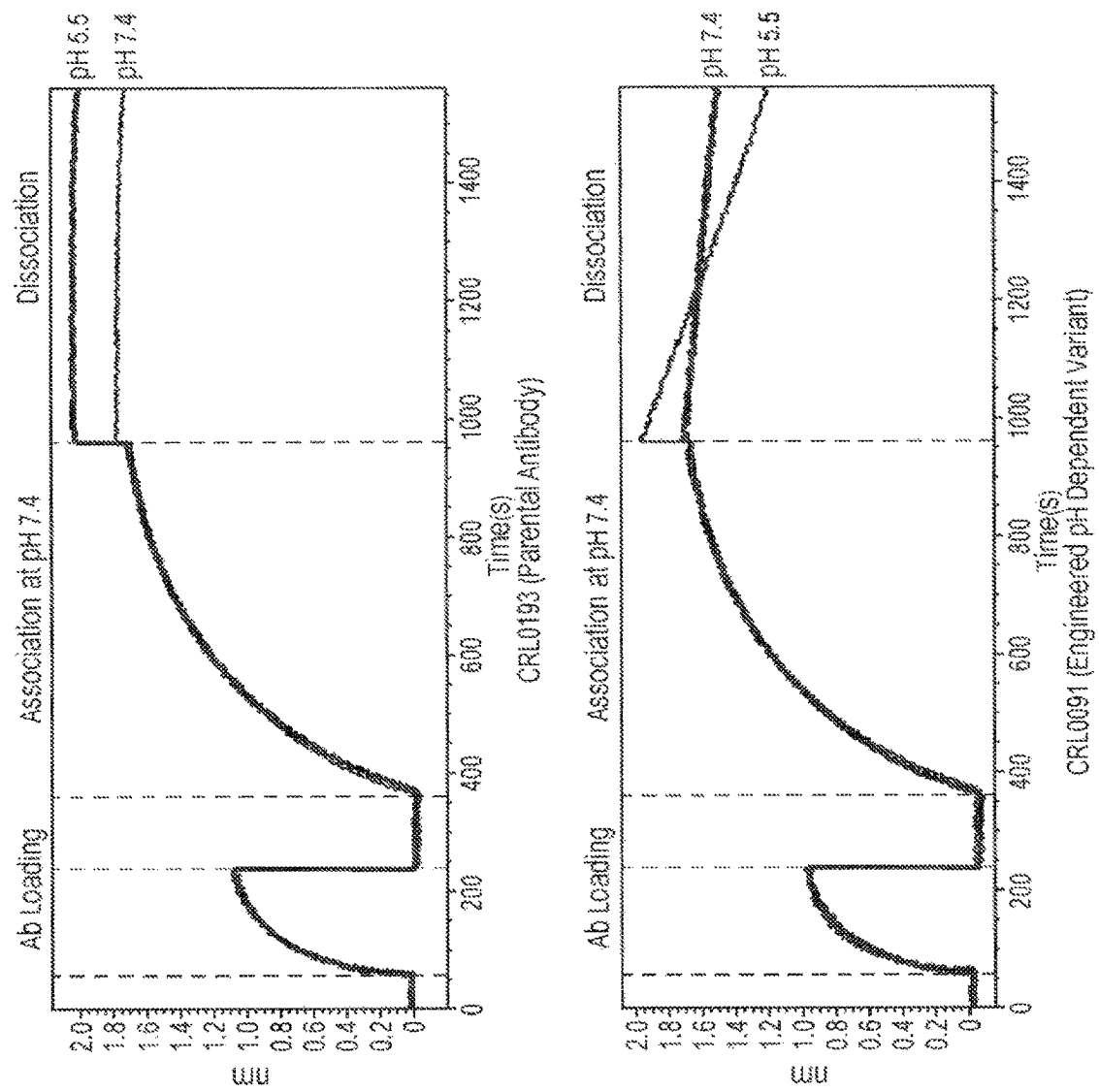
FIGS. 11A-11D show pH-dependent binding of histidine-substituted fusion proteins.
Figure 11B:
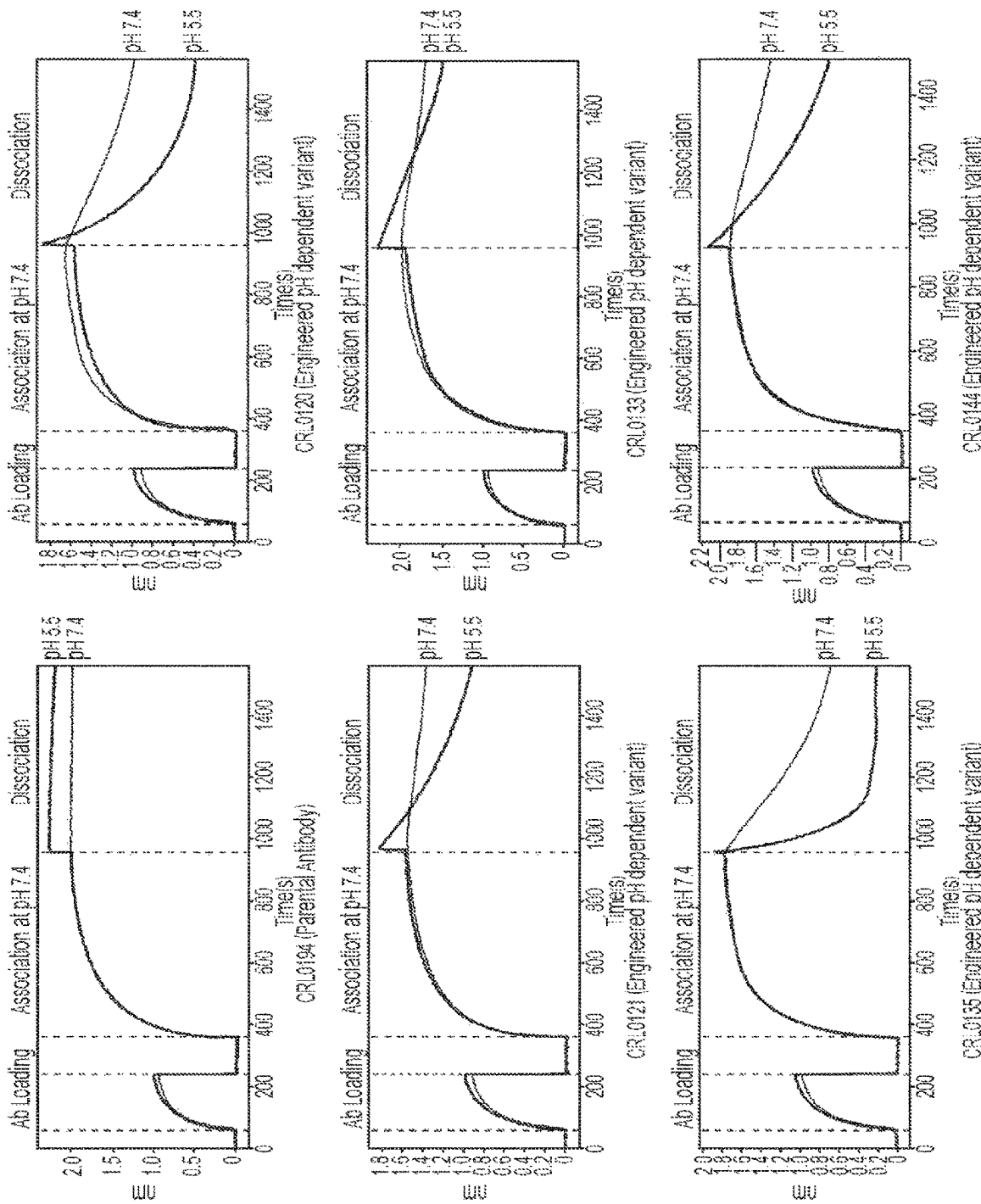
Figure 11C:
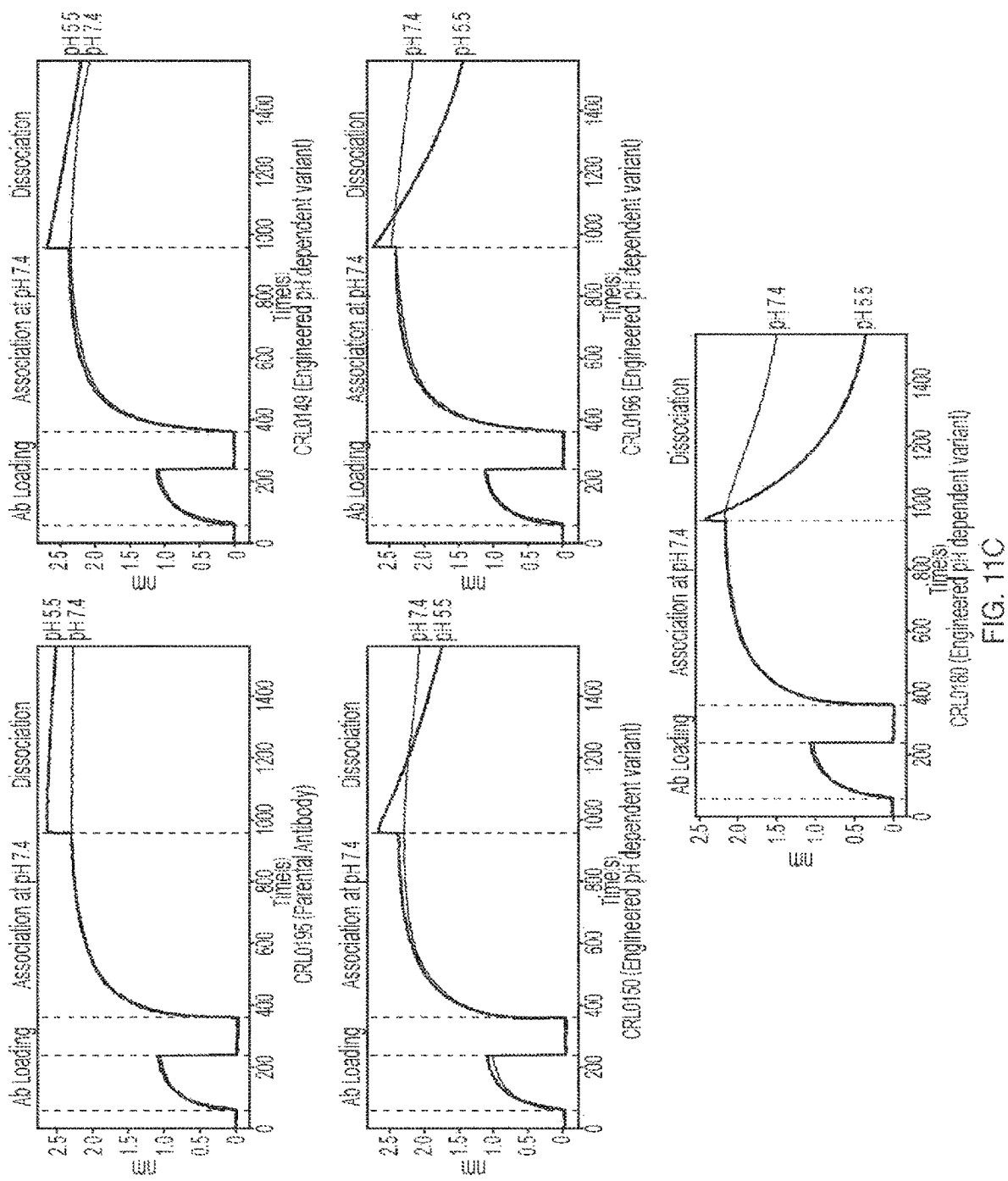
Figure 11D:
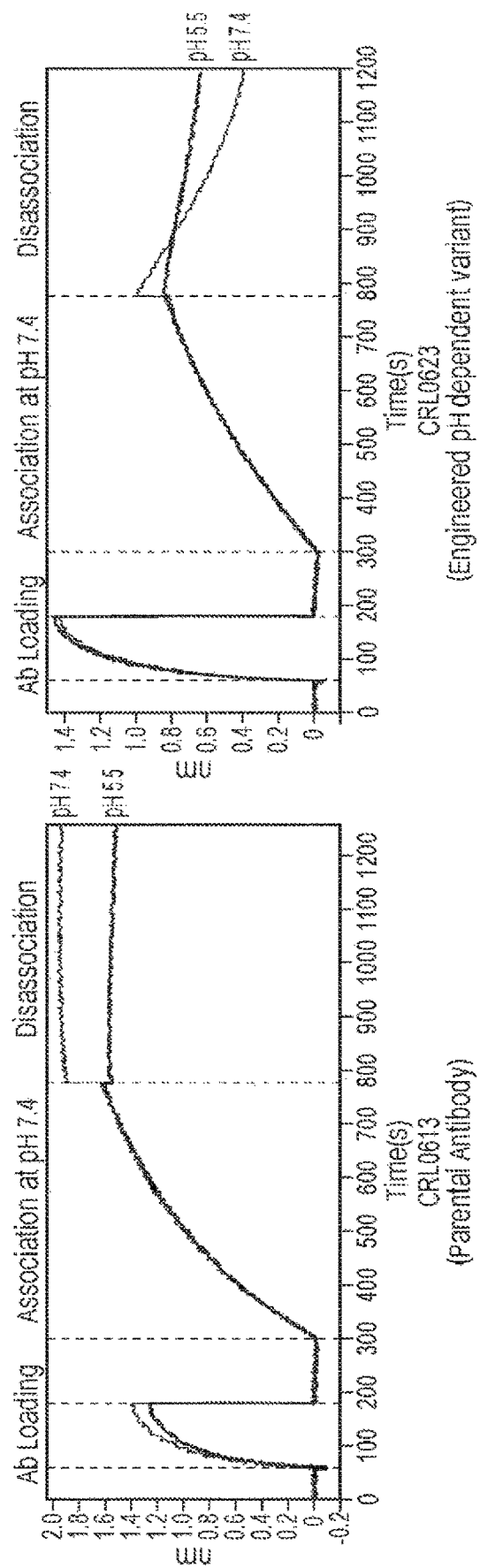

The bi-specific fusion proteins were tested for their ability to inhibit hemolysis in an in vitro hemolysis assay. Data are shown in FIGS. 9A and 9B.

Table 14 shows binding kinetics for CRL0500 and CRL0952 binding to human C5 (hC5) and cynomolgus C5 (cC5).

TABLE 14

Kinetics of bi-specific binding to C5

| Sample | Antigen | pH | $k_a$ (1/Ms) | $k_d$ (1/s) | $K_D$ (M) | Chi$^2$ |
|---|---|---|---|---|---|---|
| CRL0500 | hC5 | 7.4 | 9.60e+06 | 4.91e−04 | 5.12e−11 | 0.24 |
| CRL0500 | cC5 | 7.4 | 3.74e+06 | 8.18e−04 | 2.19e−10 | 0.01 |
| CRL0952 | hC5 | 7.4 | 1.01e+07 | 5.39e−04 | 5.36e−11 | 0.27 |
| CRL0952 | cC5 | 7.4 | 3.53e+06 | 7.86e−04 | 2.23e−10 | 0.01 |
| CRL0500 | hC5 | 6.0 | 7.56e+06 | 1.04e−03 | 1.38e−10 | 0.54 |
| CRL0500 | cC5 | 6.0 | 5.51e+06 | 4.10e−03 | 7.44e−10 | 0.07 |
| CRL0952 | hC5 | 6.0 | 5.84e+06 | 9.07e−04 | 1.55e−10 | 0.58 |
| CRL0952 | cC5 | 6.0 | 5.55e+06 | 3.99e−03 | 7.20e−10 | 0.06 |

Table 15 shows binding kinetics for CRL0500 and CRL0952 binding to Plasbumin® and cynomolgus albumin.

TABLE 15

Albumin bi-specific kinetics

| Sample | Albumin | pH | $k_a$ (1/Ms) | $k_d$ (1/s) | $K_D$ (M) | Chi² |
|---|---|---|---|---|---|---|
| CRL0500 | Plasbumin | 7.4 | 3.70e06 | 3.46e−03 | 9.36e−10 | 0.30 |
| CRL0500 | Plasbumin | 6.0 | 3.55e06 | 2.0e−03 | 5.63e−10 | 0.17 |
| CRL0952 | Plasbumin | 7.4 | 3.98e06 | 3.59e−03 | 9.01e−10 | 0.21 |
| CRL0952 | Plasbumin | 6.0 | 3.23e06 | 2.10e−03 | 6.49e−10 | 0.10 |
| CRL0500 | cyno | 7.4 | 3.32e06 | 1.26e−02 | 3.78e−09 | 0.42 |
| CRL0500 | cyno | 6.0 | 3.27e06 | 6.93e−03 | 2.12e−09 | 0.43 |
| CRL0952 | cyno | 7.4 | 2.93e06 | 1.52e−02 | 5.19e−09 | 0.17 |
| CRL0952 | cyno | 6.0 | 3.03e06 | 7.55e−03 | 2.49e−09 | 0.22 |

Example 15. pH-Dependent Binding of Anti-C5 VHH Domains

Histidine scanning was performed across all CDRs for anti-C5 VHH domains LCP0115, LCP0143, LCP0146 and LCP0302. Single histidine substitutions were generated at each position in the CDRs (shown in bold, underlined text). Variants were transfected in Expi293 cell culture and evaluated for pH-dependent binding at pH 7.4, 6.0 and 5.5. Several variants from each antibody exhibited pH-dependent binding. These variants are listed in Table 16 and their pH-dependent binding response is illustrated in FIGS. 11A-D.

TABLE 16

Pre-humanized histidine scanned variants of anti-C5 VHH domains.

| Variant name | Histidine variant sequence | SEQ ID NO |
|---|---|---|
| LCP0115 variants | | |
| CRL0085 | EVQLVESGGGLVQAGGSLRLSCAASGRTFSGILSPYAVGWFRQAPGKGREFVSTITSGGSAIYTDSVKGRFTLSRDNAKDTVYLQMNSLKPEDTAVYYCHVRTRRYGSNLGEVPQENEYGYWGQGTQVTVSS | 281 |
| CRL0091 | EVQLVESGGGLVQAGGSLRLSCAASGRTFSGILSPYAVGWFRQAPGKGREFVSTITSGGSAIYTDSVKGRFTLSRDNAKDTVYLQMNSLKPEDTAVYYCAVRTRRHGSNLGEVPQENEYGYWGQGTQVTVSS | 282 |
| LCP0143 variants | | |
| CRL0120 | EVQLVESGGGLVQAGGSLRLSCAAPEMGATINVMAWYRQAPGKQRELVARLPHDNNIDYGDFAKGRFTISRDITRNTVYLQMNNLKPDDTAVYYCNVLLSRQINGAYVHWGQGTQVTVSS | 283 |
| CRL0121 | EVQLVESGGGLVQAGGSLRLSCAAPEMGATINVMAWYRQAPGKQRELVARLPLHNNIDYGDFAKGRFTISRDITRNTVYLQMNNLKPDDTAVYYCNVLLSRQINGAYVHWGQGTQVTVSS | 284 |
| CRL0133 | EVQLVESGGGLVQAGGSLRLSCAAPEMGATINVMAWYRQAPGKQRELVARLPLDNNIDYGDFAKGRFTISRDITRNTVYLQMNNLKPDDTAVYYCHVLLSRQINGAYVHWGQGTQVTVSS | 285 |
| CRL0135 | EVQLVESGGGLVQAGGSLRLSCAAPEMGATINVMAWYRQAPGKQRELVARLPLDNNIDYGDFAKGRFTISRDITRNTVYLQMNNLKPDDTAVYYCNVHLSRQINGAYVHWGQGTQVTVSS | 286 |
| CRL0144 | EVQLVESGGGLVQAGGSLRLSCAAPEMGATINVMAWYRQAPGKQRELVARLPLDNNIDYGDFAKGRFTISRDITRNTVYLQMNNLKPDDTAVYYCNVLLSRQINGAHVHWGQGTQVTVSS | 287 |
| LCP0146 variants | | |
| CRL0149 | EVQLVESGGGLVQAGGSLRLSCAASGRHFSDYAMAWFRQAPGKEREFVAGIGWSGGDTLYADSVRGRFTNSKDNAKNRMSLQMNSLKPEDTAVYYCAARQGQYIYSSMRSDSYDYWGQGTQVTVSS | 288 |
| CRL0150 | EVQLVESGGGLVQAGGSLRLSCAASGRAHSDYAMAWFRQAPGKEREFVAGIGWSGGDTLYADSVRGRFTNSKDNAKNRMSLQMNSLKPEDTAVYYCAARQGQYIYSSMRSDSYDYWGQGTQVTVSS | 289 |
| CRL0166 | EVQLVESGGGLVQAGGSLRLSCAASGRAFSDYAMAWFRQAPGKEREFVAGIGWSGGDTHYADSVRGRFTNSKDNAKNRMSLQMNSLKPEDTAVYYCAARQGQYIYSSMRSDSYDYWGQGTQVTVSS | 290 |
| CRL0180 | EVQLVESGGGLVQAGGSLRLSCAASGRAFSDYAMAWFRQAPGKEREFVAGIGWSGGDTLYADSVRGRFTNSKDNAKNRMSLQMNSLKPEDTAVYYCAARQGQHIYSSMRSDSYDYWGQGTQVTVSS | 291 |
| LCP0302 | | |

TABLE 16-continued

Pre-humanized histidine scanned variants of anti-C5 VHH domains.

| Variant name | Histidine variant sequence | SEQ ID NO |
|---|---|---|
| variants | | |
| CRL0623 | EVQLVESGGGLVQAGGSLRLSCAASGRTFSGILSHYAVGWFRQ APGKEREFVSTITSGGSTLSADSVKGRFTLSRDNAKDTVYLQM NSLKPEDTAVYYCAVRTWPYGSNRGEVPTENEYGHWGQGTQVT VSS | 292 |

Figure 12A:
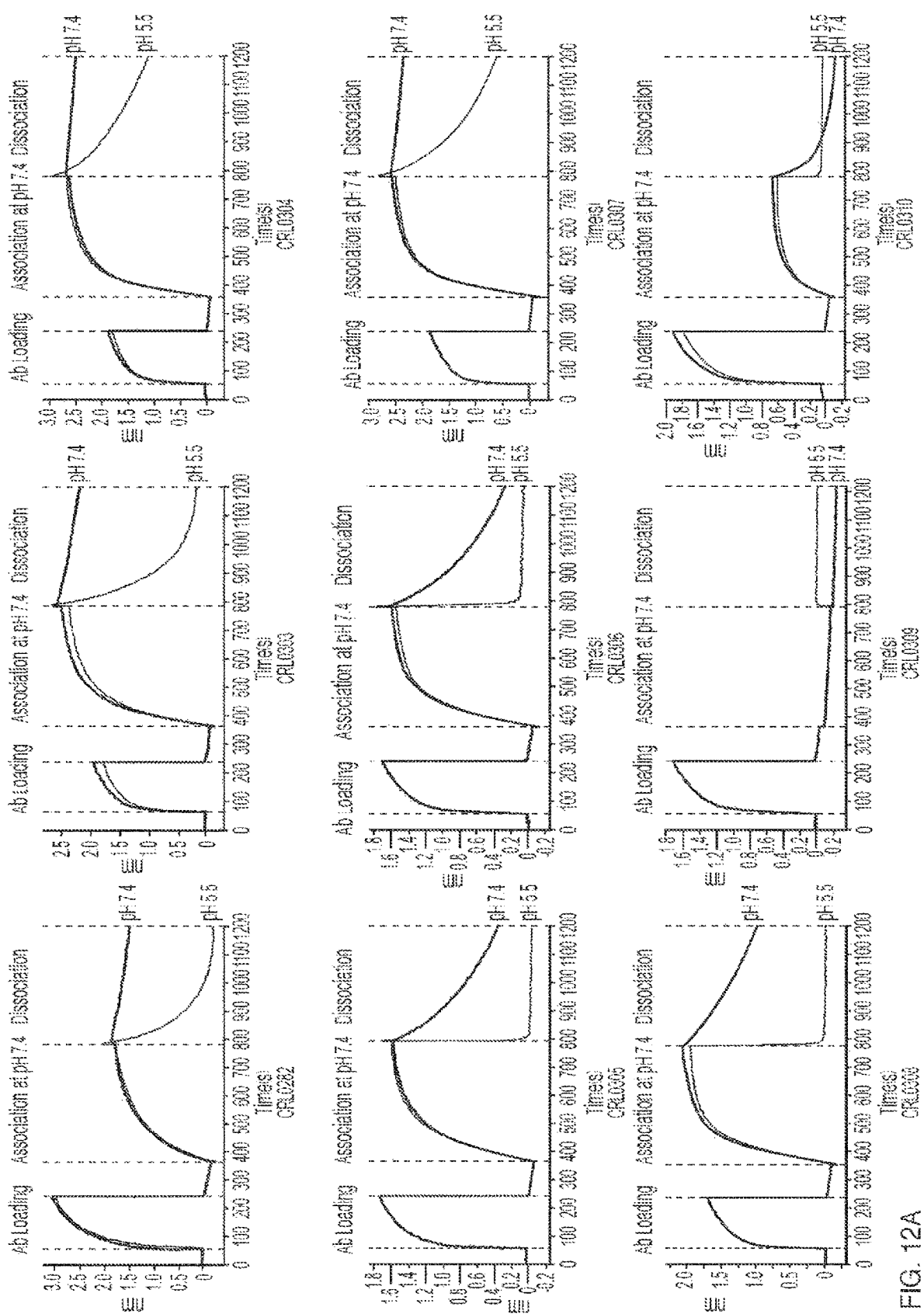
FIGS. 12A and 12B show pH-dependent binding of histidine-substituted fusion proteins.
Figure 12B:
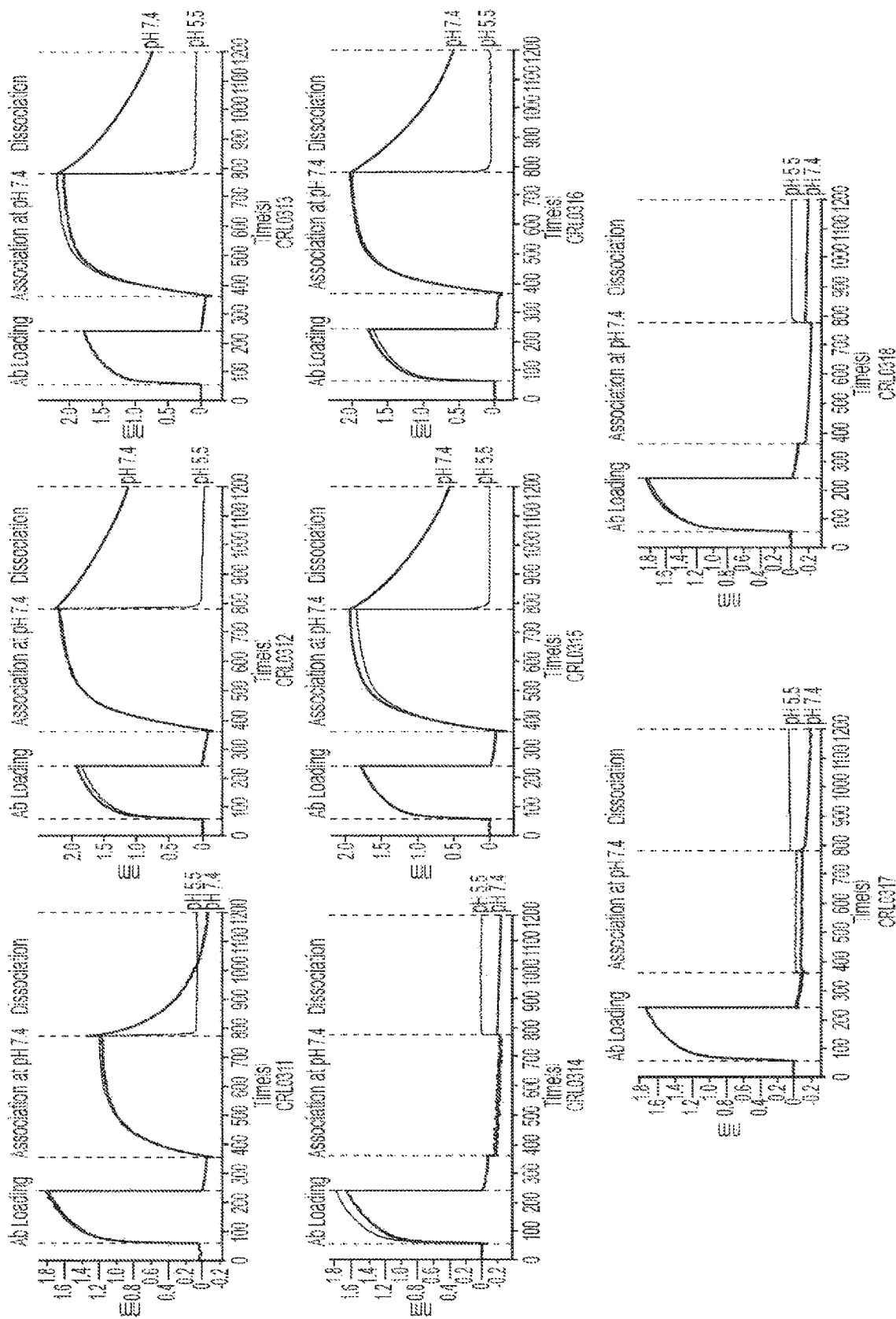

Single histidine mutations identified for pH-dependent binding were combined to enhance pH sensitivity. The sequences of these variants are shown in Table 17. These variants were evaluated in biolayer interferometry for pH-dependent binding and results are shown in FIGS. 12A and 12B.

TABLE 17

Histidine scanning combination variants of humanized anti-C5 VHH domains

| Variant name | Histidine variant sequence | SEQ ID NO |
|---|---|---|
| LCP0115 combination variants | | |
| CRL0282 | EVQLVESGGGLVQPGGSLRLSCAASGRTFSGILSPYAVGWFRQAPGKG LEFVSTITSGGSAIYTDSVKGRFTISRDNAKNSLYLQMNSLRAEDTAV YYCAVRTRRHGSNLGEVPQENEYGYWGQGTLVTVSS | 293 |
| LCP0146 combination variants | | |
| CRL0303 | EVQLVESGGGLVQPGGSLRLSCAASGRHFSDYAMAWFRQAPGQEREFV AGIGWSGGDTLYADSVRGRFTISRDNSKNTLYLQMNSLRAEDTAVYYC AARQGQYIYSSMRSDSYDYWGQGTLVTVSS | 9 |
| CRL0304 | EVQLVESGGGLVQPGGSLRLSCAASGRAHSDYAMAWFRQAPGQEREFV AGIGWSGGDTLYADSVRGRFTISRDNSKNTLYLQMNSLRAEDTAVYYC AARQGQYIYSSMRSDSYDYWGQGTLVTVSS | 10 |
| CRL0305 | EVQLVESGGGLVQPGGSLRLSCAASGRAFSDYAMAWFRQAPGQEREFV AGIGWSGGDTHYADSVRGRFTISRDNSKNTLYLQMNSLRAEDTAVYYC AARQGQYIYSSMRSDSYDYWGQGTLVTVSS | 294 |
| CRL0306 | EVQLVESGGGLVQPGGSLRLSCAASGRAFSDYAMAWFRQAPGQEREFV AGIGWSGGDTLYADSVRGRFTISRDNSKNTLYLQMNSLRAEDTAVYYC AARQGQHIYSSMRSDSYDYWGQGTLVTVSS | 295 |
| CRL0307 | EVQLVESGGGLVQPGGSLRLSCAASGRHHSDYAMAWFRQAPGQEREFV AGIGWSGGDTLYADSVRGRFTISRDNSKNTLYLQMNSLRAEDTAVYYC AARQGQYIYSSMRSDSYDYWGQGTLVTVSS | 12 |
| CRL0308 | EVQLVESGGGLVQPGGSLRLSCAASGRAHSDYAMAWFRQAPGQEREFV AGIGWSGGDTHYADSVRGRFTISRDNSKNTLYLQMNSLRAEDTAVYYC AARQGQYIYSSMRSDSYDYWGQGTLVTVSS | 296 |
| CRL0309 | EVQLVESGGGLVQPGGSLRLSCAASGRAFSDYAMAWFRQAPGQEREFV AGIGWSGGDTHYADSVRGRFTISRDNSKNTLYLQMNSLRAEDTAVYYC AARQGQHIYSSMRSDSYDYWGQGTLVTVSS | 297 |
| CRL0310 | EVQLVESGGGLVQPGGSLRLSCAASGRHFSDYAMAWFRQAPGQEREFV AGIGWSGGDTHYADSVRGRFTISRDNSKNTLYLQMNSLRAEDTAVYYC AARQGQYIYSSMRSDSYDYWGQGTLVTVSS | 298 |
| CRL0311 | EVQLVESGGGLVQPGGSLRLSCAASGRHFSDYAMAWFRQAPGQEREFV AGIGWSGGDTLYADSVRGRFTISRDNSKNTLYLQMNSLRAEDTAVYYC AARQGQHIYSSMRSDSYDYWGQGTLVTVSS | 299 |
| CRL0312 | EVQLVESGGGLVQPGGSLRLSCAASGRAHSDYAMAWFRQAPGQEREFV AGIGWSGGDTHYADSVRGRFTISRDNSKNTLYLQMNSLRAEDTAVYYC AARQGQYIYSSMRSDSYDYWGQGTLVTVSS | 296 |
| CRL0313 | EVQLVESGGGLVQPGGSLRLSCAASGRAHSDYAMAWFRQAPGQEREFV AGIGWSGGDTLYADSVRGRFTISRDNSKNTLYLQMNSLRAEDTAVYYC AARQGQHIYSSMRSDSYDYWGQGTLVTVSS | 300 |

TABLE 17-continued

Histidine scanning combination variants of humanized anti-C5 VHH domains

| Variant name | Histidine variant sequence | SEQ ID NO |
|---|---|---|
| CRL0314 | EVQLVESGGGLVQPGGSLRLSCAASGRAFSDYAMAWFRQAPGQEREFV AGIGWSGGDTHYADSVRGRFTISRDNSKNTLYLQMNSLRAEDTAVYYC AARQGQHIYSSMRSDSYDYWGQGTLVTVSS | 297 |
| CRL0315 | EVQLVESGGGLVQPGGSLRLSCAASGRHHSDYAMAWFRQAPGQEREFV AGIGWSGGDTHYADSVRGRFTISRDNSKNTLYLQMNSLRAEDTAVYYC AARQGQYIYSSMRSDSYDYWGQGTLVTVSS | 301 |
| CRL0316 | EVQLVESGGGLVQPGGSLRLSCAASGRHHSDYAMAWFRQAPGQEREFV AGIGWSGGDTLYADSVRGRFTISRDNSKNTLYLQMNSLRAEDTAVYYC AARQGQHIYSSMRSDSYDYWGQGTLVTVSS | 302 |
| CRL0317 | EVQLVESGGGLVQPGGSLRLSCAASGRAHSDYAMAWFRQAPGQEREFV AGIGWSGGDTHYADSVRGRFTISRDNSKNTLYLQMNSLRAEDTAVYYC AARQGQHIYSSMRSDSYDYWGQGTLVTVSS | 303 |
| CRL0318 | EVQLVESGGGLVQPGGSLRLSCAASGRHFSDYAMAWFRQAPGQEREFV AGIGWSGGDTHYADSVRGRFTISRDNSKNTLYLQMNSLRAEDTAVYYC AARQGQHIYSSMRSDSYDYWGQGTLVTVSS | 304 |

Example 16. Generation of Anti-C5 and Anti-Albumin Bispecific Fusions

Anti-C5 VHH domains were fused to an anti-albumin domain to generate bispecific molecules. Four different linker lengths $(G_4S)_3$ (SEQ ID NO: 106), $(G_4S)_4$ (SEQ ID NO: 107), $(G_4S)_5$ (SEQ ID NO: 108) and $(G_4S)_6$ (SEQ ID NO: 109) and two different orientations (N-terminal or C-terminal) of anti-albumin domain were evaluated. The sequences of the generated molecules are shown in Table 18. Constructs were expressed in HEK293F cells and purified using Protein A affinity chromatography. Purified fusion molecules were evaluated in Biacore experiments. Human C5 was biotinylated and immobilized on a biacore chip, purified bispecific molecules were injected to saturate the chip followed by three different concentrations of human serum albumin to obtain kinetics. Measured affinity to human serum albumin was used as a proxy to compare the different linker lengths. $(G_4S)_3$ (SEQ ID NO: 106) was chosen as the optimal linker length to generate bispecific fusions. N- or C-terminal anti-albumin fusion was also evaluated in the same experiment. Different orientations were found to be optimal for different anti-C5 VHH domains.

TABLE 8

Sequences of Linker length and Orientation Variants of anti-C5/anti-albumin bi-specifics

| Name | Sequence | SEQ ID NO |
|---|---|---|
| CRL0248 | EVQLVESGGGLVQPGGSLRLSCAASGRTFSGILSPYAVGWFRQAPGKGLEFVST ITSGGSAIYTDSVKGRFTISRDNAKNSLYLQMNSLRAEDTAVYYCAVRTRRYGS NLGEVPQENEYGYWGQGTLVTVSSGGGGSGGGGSGGGGSEVQLLESGGGLVQPG GSLRLSCAASGFTFRSFGMSWVRQAPGKGPEWVSSISGSGSDTLYADSVKGRFT ISRDNSKNTLYLQMNSLRPEDTAVYYCTIGGSLSRSSQGTLVTVSS | 305 |
| CRL0249 | EVQLVESGGGLVQPGGSLRLSCAASGRTFSGILSPYAVGWFRQAPGKGLEFVST ITSGGSAIYTDSVKGRFTISRDNAKNSLYLQMNSLRAEDTAVYYCAVRTRRYGS NLGEVPQENEYGYWGQGTLVTVSSGGGGSGGGGSGGGGSGGGGSEVQLLESGGG LVQPGGSLRLSCAASGFTFRSFGMSWVRQAPGKGPEWVSSISGSGSDTLYADSV KGRFTISRDNSKNTLYLQMNSLRPEDTAVYYCTIGGSLSRSSQGTLVTVSS | 306 |
| CRL0250 | EVQLVESGGGLVQPGGSLRLSCAASGRTFSGILSPYAVGWFRQAPGKGLEFVST ITSGGSAIYTDSVKGRFTISRDNAKNSLYLQMNSLRAEDTAVYYCAVRTRRYGS NLGEVPQENEYGYWGQGTLVTVSSGGGGSGGGGSGGGGSGGGGSGGGGSEVQLL ESGGGLVQPGGSLRLSCAASGFTFRSFGMSWVRQAPGKGPEWVSSISGSGSDTL YADSVKGRFTISRDNSKNTLYLQMNSLRPEDTAVYYCTIGGSLSRSSQGTLVTV SS | 307 |
| CRL0251 | EVQLVESGGGLVQPGGSLRLSCAASGRTFSGILSPYAVGWFRQAPGKGLEFVST ITSGGSAIYTDSVKGRFTISRDNAKNSLYLQMNSLRAEDTAVYYCAVRTRRYGS NLGEVPQENEYGYWGQGTLVTVSSGGGGSGGGGSGGGGSGGGGSGGGGSGGGGS EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSS | 308 |
| CRL0254 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSEVQLVESGGGLVQPGGSLRLSCAASGRTFSGI LSPYAVGWFRQAPGKGLEFVSTITSGGSAIYTDSVKGRFTTSRDNAKNSLYLQM NSLRAEDTAVYYCAVRTRRYGSNLGEVPQENEYGYWGQGTLVTVSS | 309 |

TABLE 8-continued

Sequences of Linker length and Orientation Variants of anti-C5/anti-albumin bi-specifics

| Name | Sequence | SEQ ID NO |
|---|---|---|
| CRL0255 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSEVQLVESGGGLVQPGGSLRLSCAASGR TFSGILSPYAVGWFRQAPGKGLEFVSTITSGGSAIYTDSVKGRFTISRDNAKNS LYLQMNSLRAEDTAVYYCAVRTRRYGSNLGEVPQENEYGYWGQGTLVTVSS | 310 |
| CRL0256 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSGGGGSEVQLVESGGGLVQPGGSLRLSC AASGRTFSGILSPYAVGWFRQAPGKGLEFVSTITSGGSAIYTDSVKGRFTISRD NAKNSLYLQMNSLRAEDTAVYYCAVRTRRYGSNLGEVPQENEYGYWGQGTLVTV SS | 311 |
| CRL0257 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSGGGGSEVQLVESGGGLVQPGGS LRLSCAASGRTFSGILSPYAVGWFRQAPGKGLEFVSTITSGGSAIYTDSVKGRF TISRDNAKNSLYLQMNSLRAEDTAVYYCAVRTRRYGSNLGEVPQENEYGYWGQG TLVTVSS | 312 |
| CRL0272 | EVQLVESGGGLVQPGGSLRLSCAASGRAFSDYAMAWFRQAPGQEREFVAGIGWS GGDTLYADSVRGRFTISRDNSKNTLYLQMNSLRAEDTAVYYCAARQGQYIYSSM RSDSYDYWGQGTLVTVSSGGGGSGGGGSGGGGSEVQLLESGGGLVQPGGSLRLS CAASGFTFRSFGMSWVRQAPGKGPEWVSSISGSGSDTLYADSVKGRFTISRDNS KNTLYLQMNSLRPEDTAVYYCTIGGSLSRSSQGTLVTVSS | 313 |
| CRL0273 | EVQLVESGGGLVQPGGSLRLSCAASGRAFSDYAMAWFRQAPGQEREFVAGIGWS GGDTLYADSVRGRFTISRDNSKNTLYLQMNSLRAEDTAVYYCAARQGQYIYSSM RSDSYDYWGQGTLVTVSSGGGGSGGGGSGGGGSGGGGSEVQLLESGGGLVQPGG SLRLSCAASGFTFRSFGMSWVRQAPGKGPEWVSSISGSGSDTLYADSVKGRFTI SRDNSKNTLYLQMNSLRPEDTAVYYCTIGGSLSRSSQGTLVTVSS | 314 |
| CRL0274 | EVQLVESGGGLVQPGGSLRLSCAASGRAFSDYAMAWFRQAPGQEREFVAGIGWS GGDTLYADSVRGRFTISRDNSKNTLYLQMNSLRAEDTAVYYCAARQGQYIYSSM RSDSYDYWGQGTLVTVSSGGGGSGGGGSGGGGSGGGGSGGGGSEVQLLESGGGL VQPGGSLRLSCAASGFTFRSFGMSWVRQAPGKGPEWVSSISGSGSDTLYADSVK GRFTISRDNSKNTLYLQMNSLRPEDTAVYYCTIGGSLSRSSQGTLVTVSS | 315 |
| CRL0275 | EVQLVESGGGLVQPGGSLRLSCAASGRAFSDYAMAWFRQAPGQEREFVAGIGWS GGDTLYADSVRGRFTISRDNSKNTLYLQMNSLRAEDTAVYYCAARQGQYIYSSM RSDSYDYWGQGTLVTVSSGGGGSGGGGSGGGGSGGGGSGGGGSGGGGSEVQLLE SGGGLVQPGGSLRLSCAASGFTFRSFGMSWVRQAPGKGPEWVSSISGSGSDTLY ADSVKGRFTISRDNSNTLYLQMNSLRPEDTAVYYCTIGGSLSRSSQGTLVTVSS | 316 |
| CRL0278 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSEVQLVESGGGLVQPGGSLRLSCAASGRAFSDY AMAWFRQAPGQEREFVAGIGWSGGDTLYADSVRGRFTISRDNSKNTLYLQMNSL RAEDTAVYYCAARQGQYIYSSMRSDSYDYWGQGTLVTVSS | 317 |
| CRL0279 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSEVQLVESGGGLVQPGGSLRLSCAASGR AFSDYAMAWFRQAPGQEREFVAGIGWSGGDTLYADSVRGRFTISRDNSKNTLYL QMNSLRAEDTAVYYCAARQGQYIYSSMRSDSYDYWGQGTLVTVSS | 318 |
| CRL0280 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSGGGGSEVQLVESGGGLVQPGGSLRLSC AASGRAFSDYAMAWFRQAPGQEREFVAGIGWSGGDTLYADSVRGRFTISRDNSK NTLYLQMNSLRAEDTAVYYCAARQGQYIYSSMRSDSYDYWGQGTLVTVSS | 319 |
| CRL0281 | EVQLLESGGGLVQPGGSLRLSCAASGFTFRSFGMSWVRQAPGKGPEWVSSISGS GSDTLYADSVKGRFTISRDNSKNTLYLQMNSLRPEDTAVYYCTIGGSLSRSSQG TLVTVSSGGGGSGGGGSGGGGSGGGGSGGGGSGGGGSEVQLVESGGGLVQPGGS LRLSCAASGRAFSDYAMAWFRQAPGQEREFVAGIGWSGGDTLYADSVRGRFTIS RDNSKNTLYLQMNSLRAEDTAVYYCAARQGQYIYSSMRSDSYDYWGQGTLVTVS S | 320 |

A series of different bi-specific fusion molecules were generated with humanized anti-C5 VHH domains with or without pH-dependent binding. The anti-C5 VHH domains were fused to two different anti-albumin domains to generate bi-specific molecules (shown in Table 9). These constructs were expressed in HEK293F cells and purified using Protein A chromatography. Purified bi-specifics were tested in hemolysis assays and the results are shown in FIGS. 3A-D.

Four bispecific molecules CRL0483, CRL0484, CRL0499 and CRL0500 were prioritized based on binding and functional assays. Biacore affinity measurements for binding to human C5 for CRL0483, CRL0484, CRL0499 and CRL0500 are shown in Table 10 and functional assessments in FIGS. 5, 6 and 7. These four bi-specific molecules were evaluated in in vivo pharmacokinetic studies in cynomolgus monkeys.

Example 17. Pharmacokinetic Analysis of Bispecific Fusion Molecules

Figure 6A:
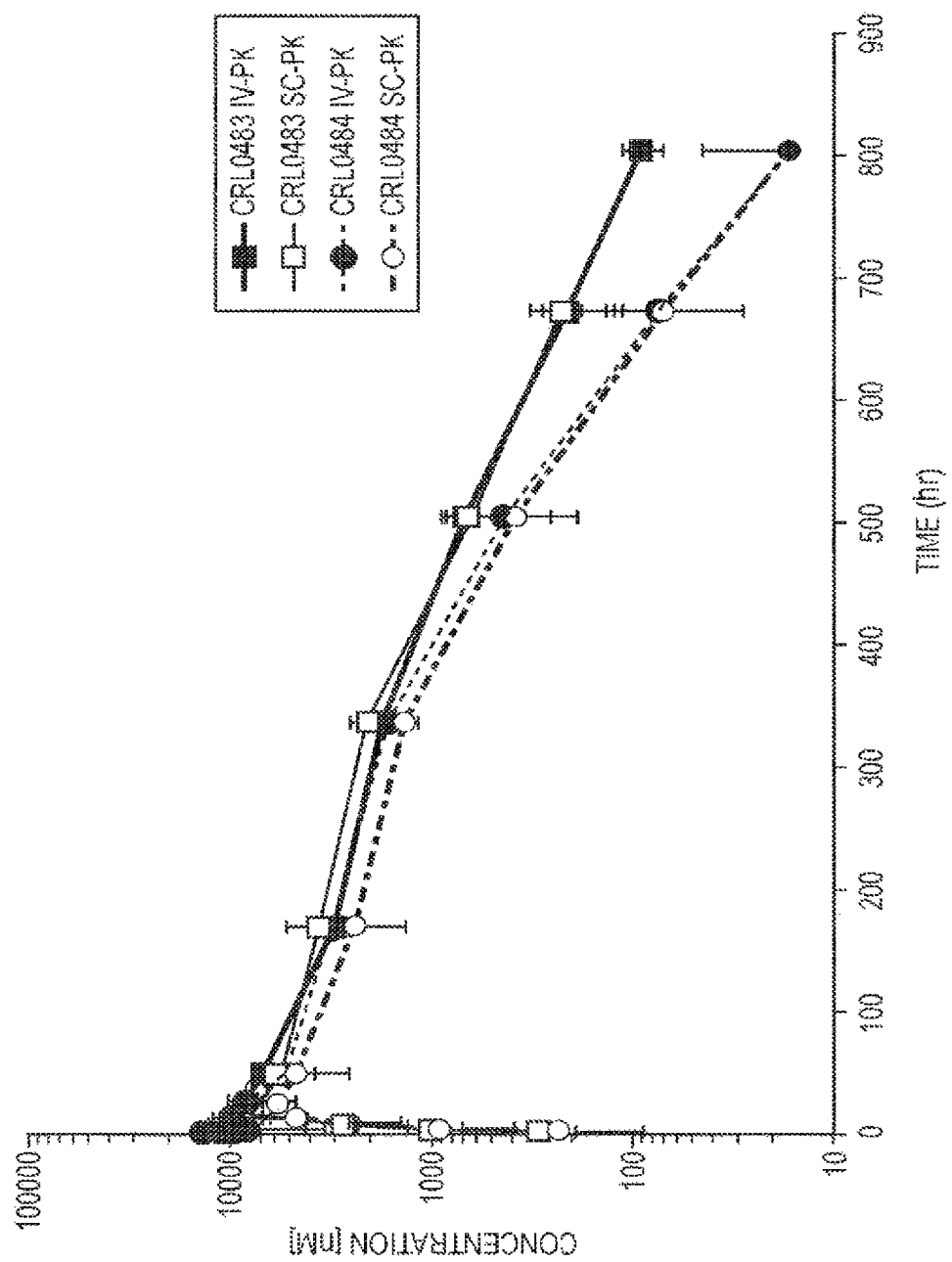
FIGS. 6A and 6B show the results of an LC-MS based quantitation assay demonstrating the pharmacokinetics of bispecific fusion proteins.
Figure 6B:
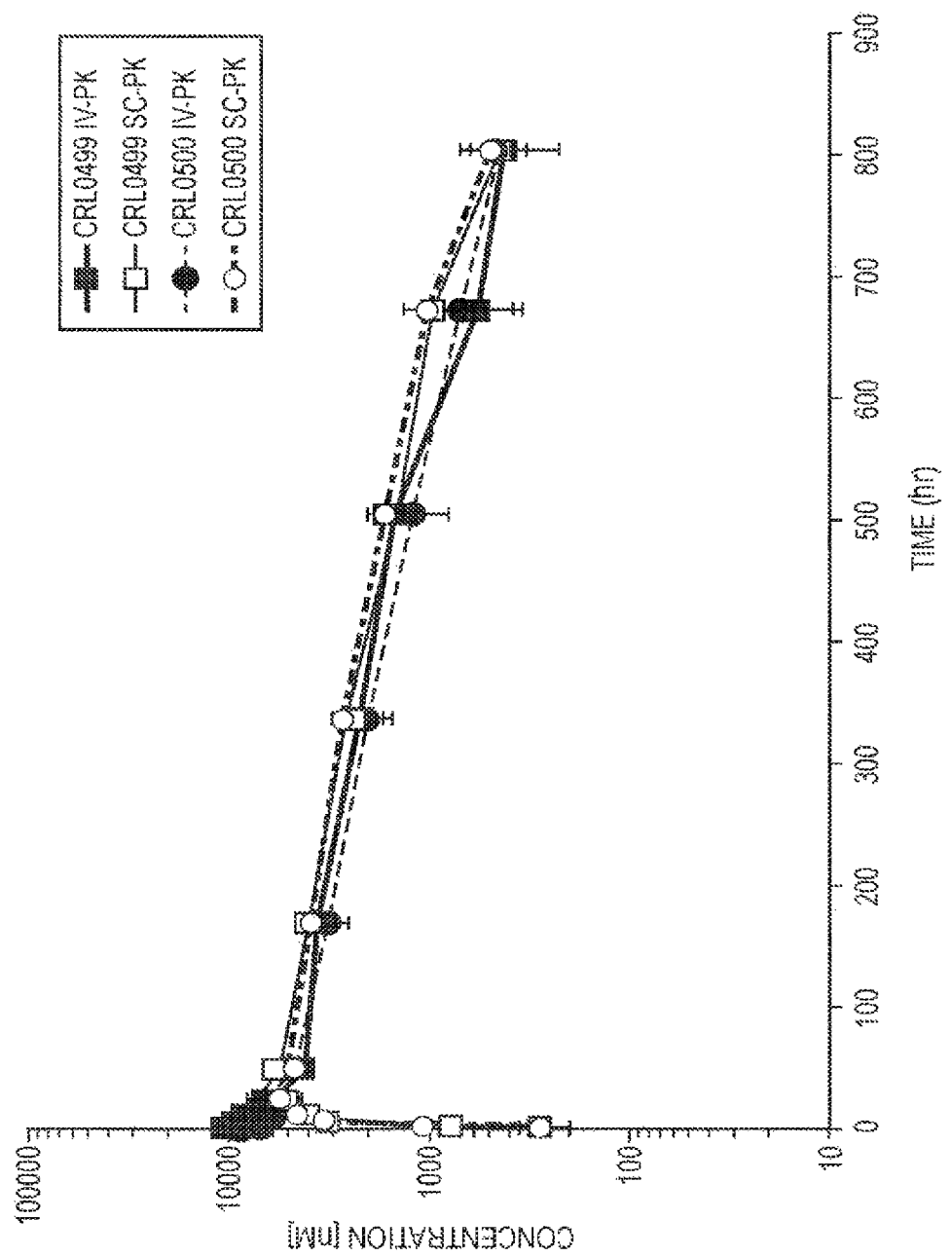
Figure 8B:
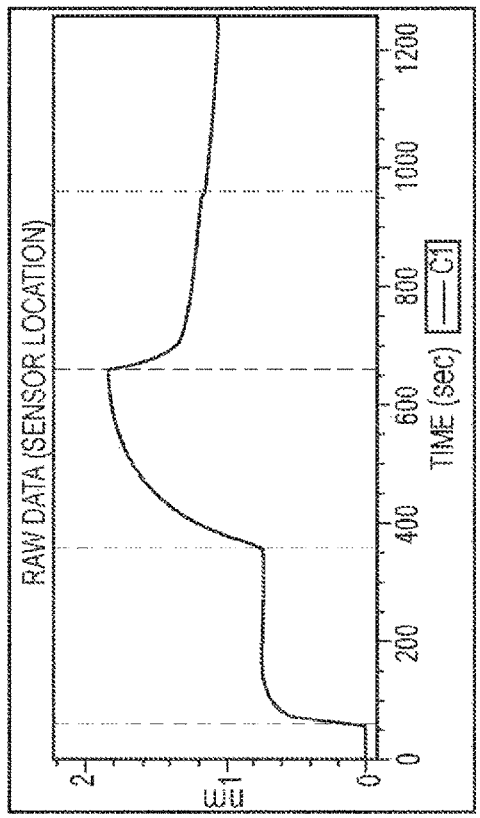
FIGS. 8A-8D show Biacore sensorgrams indicating the binding of albumin by the VHH domains HAS020, HAS040, HAS041 and HAS044 in competition with Alb1 VHH.
Figure 8D:
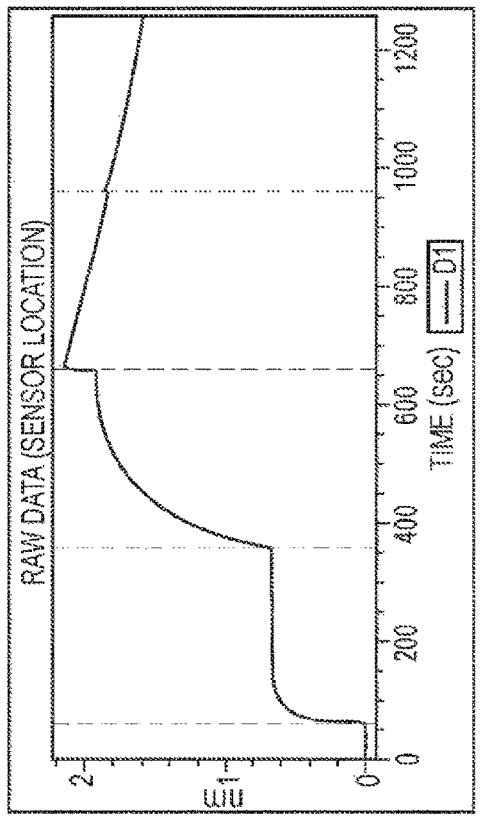
Figure 8A:
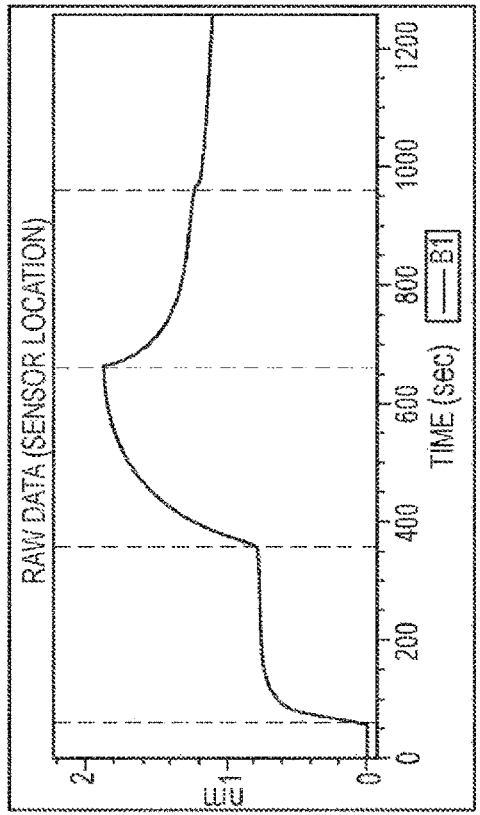
Figure 8C:
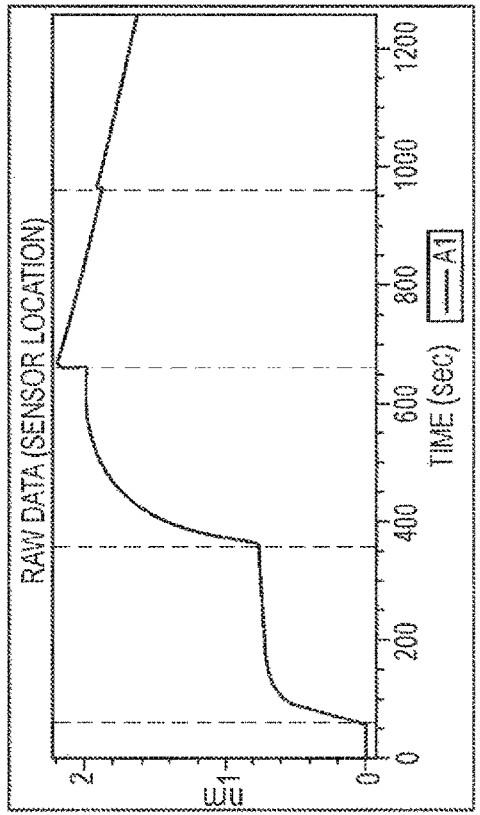

Purified proteins were dosed at 10 mg/kg either intravenously or subcutaneously in cynomolgus monkeys. Three monkeys per dose group per test article were used. Pharmacokinetics of bispecific molecules was measured by a LC-MS based quantitation assay using signature peptides specific to each construct. The PK profiles are shown in FIGS. 6A and 6B and the parameters are described in Table 20.

TABLE 20

PK parameters after 10 mg/kg of test articles in cynomolgus monkeys

| Test article | $t_{1/2}$ h | $t_{max}$ h | $C_{max}$ μg/mL | AUC h * μg/mL | $C_L$ mL/ h/kg | V mL/kg | F % |
|---|---|---|---|---|---|---|---|
| CRL0483 IV | 139 | 1.33 | 324 | 47900 | 0.211 | 42.0 | |
| CRL0484 IV | 125 | 1 | 382 | 43700 | 0.238 | 43.0 | |
| CRL0483 SC | 103 | 20 | 238 | 46412 | 0.218 | 32.5 | 97 |
| CRL0484 SC | 75.9 | 24 | 161 | 32610 | 0.315 | 34.9 | 75 |
| CRL0499 IV | 170 | 2.11 | 299 | 53773 | 0.184 | 46.9 | |
| CRL0500 IV | 239 | 0.167 | 351 | 51929 | 0.205 | 62.5 | |
| CRL0499 SC | 220 | 32 | 146 | 58666 | 0.173 | 54.2 | 109 |
| CRL0500 SC | 209 | 32 | 161 | 61475 | 0.163 | 49.0 | 118 |

While the disclosure describes various embodiments, it is understood that variations and modifications will occur to those skilled in the art. Therefore, it is intended that the appended claims cover all such equivalent variations. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

What is claimed is:

1. An engineered polypeptide that specifically binds to human serum albumin, wherein the engineered polypeptide comprises an amino acid sequence selected from the group consisting of SEQ ID NOS:22-25 and 27-34 and fragments thereof.

2. The engineered polypeptide of claim 1, wherein the engineered polypeptide comprises the amino acid sequence of SEQ ID NO:22.

3. The engineered polypeptide of claim 1, wherein the engineered polypeptide comprises the amino acid sequence of SEQ ID NO:23.

4. The engineered polypeptide of claim 1, wherein the engineered polypeptide comprises the amino acid sequence of SEQ ID NO:24.

5. The engineered polypeptide of claim 1, wherein the engineered polypeptide comprises the amino acid sequence of SEQ ID NO:25.

6. The engineered polypeptide of claim 1, wherein the engineered polypeptide comprises the amino acid sequence of SEQ ID NO:27.

7. The engineered polypeptide of claim 1, wherein the engineered polypeptide comprises the amino acid sequence of SEQ ID NO:28.

8. The engineered polypeptide of claim 1, wherein the engineered polypeptide comprises the amino acid sequence of SEQ ID NO:29.

9. The engineered polypeptide of claim 1, wherein the engineered polypeptide comprises the amino acid sequence of SEQ ID NO:30.

10. The engineered polypeptide of claim 1, wherein the engineered polypeptide comprises the amino acid sequence of SEQ ID NO:31.

11. The engineered polypeptide of claim 1, wherein the engineered polypeptide comprises the amino acid sequence of SEQ ID NO:32.

12. The engineered polypeptide of claim 1, wherein the engineered polypeptide comprises the amino acid sequence of SEQ ID NO:33.

13. The engineered polypeptide of claim 1, wherein the engineered polypeptide comprises the amino acid sequence of SEQ ID NO:34.

* * * * *

```
                          SEQUENCE LISTING

Sequence total quantity: 327
SEQ ID NO: 1           moltype = AA  length = 126
FEATURE                Location/Qualifiers
source                 1..126
                       mol_type = protein
                       organism = synthetic construct
                       note = Synthetic Construct
SEQUENCE: 1
EVQLVESGGG LVQPGGSLRL SCAASGRAFS DYAMAWFRQA PGQEREFVAG IGWSGGDTLY  60
ADSVRGRFTN SRDNSKNTLY LQMNSLRAED TAVYYCAARQ GQYIYSSMRS DSYDYWGQGT 120
LVTVSS                                                           126

SEQ ID NO: 2           moltype = AA  length = 126
FEATURE                Location/Qualifiers
source                 1..126
                       mol_type = protein
                       organism = synthetic construct
                       note = Synthetic Construct
SEQUENCE: 2
EVQLVESGGG LVQPGGSLRL SCAASGRAFS DYAMAWFRQA PGQEREFVAG IGWSGGDTLY  60
ADSVRGRFTI SRDNAKNTLY LQMNSLRAED TAVYYCAARQ GQYIYSSMRS DSYDYWGQGT 120
LVTVSS                                                           126

SEQ ID NO: 3           moltype = AA  length = 126
FEATURE                Location/Qualifiers
source                 1..126
                       mol_type = protein
                       organism = synthetic construct
                       note = Synthetic Construct
SEQUENCE: 3
EVQLVESGGG LVQPGGSLRL SCAASGRAFS DYAMAWFRQA PGQEREFVAG IGWSGGDTLY  60
ADSVRGRFTI SRDNSKNTMY LQMNSLRAED TAVYYCAARQ GQYIYSSMRS DSYDYWGQGT 120
LVTVSS                                                           126

SEQ ID NO: 4           moltype = AA  length = 126
FEATURE                Location/Qualifiers
source                 1..126
                       mol_type = protein
                       organism = synthetic construct
```

```
                                -continued
                        note = Synthetic Construct
SEQUENCE: 4
EVQLVESGGG LVQPGGSLRL SCAASGRAFS DYAMAWFRQA PGQGLEFVAG IGWSGGDTLY      60
ADSVRGRFTI SRDNSKNTLY LQMNSLRAED TAVYYCAARQ GQYIYSSMRS DSYDYWGQGT     120
LVTVSS                                                                126

SEQ ID NO: 5            moltype = AA   length = 132
FEATURE                 Location/Qualifiers
source                  1..132
                        mol_type = protein
                        organism = synthetic construct
                        note = Synthetic Construct
SEQUENCE: 5
EVQLVESGGG LVQPGGSLRL SCAASGRTFS GILSPYAVGW FRQAPGKGLE FVSTITSGGS      60
AIYTDSVKGR FTISRDNAKD SLYLQMNSLR AEDTAVYYCA VRTRRYGSNL GEVPQENEYG     120
YWGQGTLVTV SS                                                         132

SEQ ID NO: 6            moltype = AA   length = 132
FEATURE                 Location/Qualifiers
source                  1..132
                        mol_type = protein
                        organism = synthetic construct
                        note = Synthetic Construct
SEQUENCE: 6
EVQLVESGGG LVQPGGSLRL SCAASGRTFS GILSPYAVGW FRQAPGKGLE FVSTITSGGS      60
AIYTDSVKGR FTISRDNAKN TLYLQMNSLR AEDTAVYYCA VRTRRYGSNL GEVPQENEYG     120
YWGQGTLVTV SS                                                         132

SEQ ID NO: 7            moltype = AA   length = 132
FEATURE                 Location/Qualifiers
source                  1..132
                        mol_type = protein
                        organism = synthetic construct
                        note = Synthetic Construct
SEQUENCE: 7
EVQLVESGGG LVQPGGSLRL SCAASGRTFS GILSPYAVGW FRQAPGKGLE FVSTITSGGS      60
AIYTDSVKGR FTISRDNAKN SVYLQMNSLR AEDTAVYYCA VRTRRYGSNL GEVPQENEYG     120
YWGQGTLVTV SS                                                         132

SEQ ID NO: 8            moltype = AA   length = 132
FEATURE                 Location/Qualifiers
source                  1..132
                        mol_type = protein
                        organism = synthetic construct
                        note = Synthetic Construct
SEQUENCE: 8
EVQLVESGGG LVQPGGSLRL SCAASGRTFS GILSPYAVGW FRQAPGQGLE FVATITSGGS      60
AIYTDSVKGR FTISRDNSKN TLYLQMNSLR AEDTAVYYCA VRTRRYGSNL GEVPQENEYG     120
YWGQGTLVTV SS                                                         132

SEQ ID NO: 9            moltype = AA   length = 126
FEATURE                 Location/Qualifiers
source                  1..126
                        mol_type = protein
                        organism = synthetic construct
                        note = Synthetic Construct
SEQUENCE: 9
EVQLVESGGG LVQPGGSLRL SCAASGRHFS DYAMAWFRQA PGQEREFVAG IGWSGGDTLY      60
ADSVRGRFTI SRDNSKNTLY LQMNSLRAED TAVYYCAARQ GQYIYSSMRS DSYDYWGQGT     120
LVTVSS                                                                126

SEQ ID NO: 10           moltype = AA   length = 126
FEATURE                 Location/Qualifiers
source                  1..126
                        mol_type = protein
                        organism = synthetic construct
                        note = Synthetic Construct
SEQUENCE: 10
EVQLVESGGG LVQPGGSLRL SCAASGRAHS DYAMAWFRQA PGQEREFVAG IGWSGGDTLY      60
ADSVRGRFTI SRDNSKNTLY LQMNSLRAED TAVYYCAARQ GQYIYSSMRS DSYDYWGQGT     120
LVTVSS                                                                126

SEQ ID NO: 11           moltype = AA   length = 126
FEATURE                 Location/Qualifiers
source                  1..126
                        mol_type = protein
                        organism = synthetic construct
                        note = Synthetic Construct
SEQUENCE: 11
```

```
EVQLVESGGG LVQPGGSLRL SCAASGRAHS DYAMAWFRQA PGQEREFVAG IGWSGGDTLY    60
ADSVRGRFTN SRDNSKNTLY LQMNSLRAED TAVYYCAARQ GQYIYSSMRS DSYDYWGQGT   120
LVTVSS                                                             126

SEQ ID NO: 12           moltype = AA   length = 126
FEATURE                 Location/Qualifiers
source                  1..126
                        mol_type = protein
                        organism = synthetic construct
                        note = Synthetic Construct
SEQUENCE: 12
EVQLVESGGG LVQPGGSLRL SCAASGRHHS DYAMAWFRQA PGQEREFVAG IGWSGGDTLY    60
ADSVRGRFTI SRDNSKNTLY LQMNSLRAED TAVYYCAARQ GQYIYSSMRS DSYDYWGQGT   120
LVTVSS                                                             126

SEQ ID NO: 13           moltype = AA   length = 10
FEATURE                 Location/Qualifiers
source                  1..10
                        mol_type = protein
                        organism = synthetic construct
                        note = Synthetic Construct
SEQUENCE: 13
GRAFSDYAMA                                                          10

SEQ ID NO: 14           moltype = AA   length = 14
FEATURE                 Location/Qualifiers
source                  1..14
                        mol_type = protein
                        organism = synthetic construct
                        note = Synthetic Construct
SEQUENCE: 14
GRTFSGILSP YAVG                                                     14

SEQ ID NO: 15           moltype = AA   length = 10
FEATURE                 Location/Qualifiers
source                  1..10
                        mol_type = protein
                        organism = synthetic construct
                        note = Synthetic Construct
SEQUENCE: 15
GRHFSDYAMA                                                          10

SEQ ID NO: 16           moltype = AA   length = 10
FEATURE                 Location/Qualifiers
source                  1..10
                        mol_type = protein
                        organism = synthetic construct
                        note = Synthetic Construct
SEQUENCE: 16
GRAHSDYAMA                                                          10

SEQ ID NO: 17           moltype = AA   length = 10
FEATURE                 Location/Qualifiers
source                  1..10
                        mol_type = protein
                        organism = synthetic construct
                        note = Synthetic Construct
SEQUENCE: 17
GRHHSDYAMA                                                          10

SEQ ID NO: 18           moltype = AA   length = 17
FEATURE                 Location/Qualifiers
source                  1..17
                        mol_type = protein
                        organism = synthetic construct
                        note = Synthetic Construct
SEQUENCE: 18
GIGWSGGDTL YADSVRG                                                  17

SEQ ID NO: 19           moltype = AA   length = 16
FEATURE                 Location/Qualifiers
source                  1..16
                        mol_type = protein
                        organism = synthetic construct
                        note = Synthetic Construct
SEQUENCE: 19
TITSGGSAIY TDSVKG                                                   16

SEQ ID NO: 20           moltype = AA   length = 19
```

| FEATURE | Location/Qualifiers |
|---|---|
| source | 1..19<br>mol_type = protein<br>organism = synthetic construct<br>note = Synthetic Construct |

SEQUENCE: 20
AARQGQYIYS SMRSDSYDY                                              19

| SEQ ID NO: 21 | moltype = AA  length = 22 |
|---|---|
| FEATURE | Location/Qualifiers |
| source | 1..22<br>mol_type = protein<br>organism = synthetic construct<br>note = Synthetic Construct |

SEQUENCE: 21
AVRTRRYGSN LGEVPQENEY GY                                          22

| SEQ ID NO: 22 | moltype = AA  length = 127 |
|---|---|
| FEATURE | Location/Qualifiers |
| source | 1..127<br>mol_type = protein<br>organism = synthetic construct<br>note = Synthetic Construct |

SEQUENCE: 22
QVQLVESGGG LVQAGGSLRL SCAASGRTFG SDAAGWFRQA SGKEREFVAS ISWSGGYTYY   60
ADSVKGRFTI SSDNVKNTVY LQMNSLTPED TAVYFCATGN RYSDYRISLV TPSQYEYWGQ  120
GTLVTVS                                                          127

| SEQ ID NO: 23 | moltype = AA  length = 124 |
|---|---|
| FEATURE | Location/Qualifiers |
| source | 1..124<br>mol_type = protein<br>organism = synthetic construct<br>note = Synthetic Construct |

SEQUENCE: 23
QVQLVESGGG LVQPGGSLRL SCTGSGHSFS TYTVGWFRQA PGEERKFVAS ISWSGEVTLY   60
GDSVKGRFTI SRDNRKKTVY LQMHSLKPED SAIYYCAAKR GGRPTDSSDD YFYWGQGTQV  120
TVSS                                                             124

| SEQ ID NO: 24 | moltype = AA  length = 123 |
|---|---|
| FEATURE | Location/Qualifiers |
| source | 1..123<br>mol_type = protein<br>organism = synthetic construct<br>note = Synthetic Construct |

SEQUENCE: 24
QVQLNESGGG MVQAGGSLRL SCAASGRTVS NYAAGWFRQA PGKEREFVAA INWNKTTTYA   60
DSVKGRFIIS REYAKNTVAL QMNSLKPEDT AVYYCAAVFR IVAPKTQYEY DYWGQGTQVT  120
VSS                                                              123

| SEQ ID NO: 25 | moltype = AA  length = 123 |
|---|---|
| FEATURE | Location/Qualifiers |
| source | 1..123<br>mol_type = protein<br>organism = synthetic construct<br>note = Synthetic Construct |

SEQUENCE: 25
QVQLIESGGG LVQAGGSLGL SCAASGRPVS NYAAAWFRQA PGKEREFVAA INWNKTATYA   60
DSVKGRFTIS RDNAKSTVAL QMNSLKPEDT AVYYCAAVFR VVAPKTQYDY DYWGQGTQVT  120
VSS                                                              123

| SEQ ID NO: 26 | moltype = AA  length = 123 |
|---|---|
| FEATURE | Location/Qualifiers |
| source | 1..123<br>mol_type = protein<br>organism = synthetic construct<br>note = Synthetic Construct |

SEQUENCE: 26
EVQLVESGGG LVKPGGSLRL SCAASGRPVS NYAAAWFRQA PGKEREFVSA INWQKTATYA   60
DSVKGRFTIS RDNAKNSLYL QMNSLRAEDT AVYYCAAVFR VVAPKTQYDY DYWGQGTLVT  120
VSS                                                              123

| SEQ ID NO: 27 | moltype = AA  length = 123 |
|---|---|
| FEATURE | Location/Qualifiers |
| source | 1..123<br>mol_type = protein<br>organism = synthetic construct<br>note = Synthetic Construct |

SEQUENCE: 27

```
QVQLVESGGG LVQAGGSLRL SCAASGRTFS SYAIGWFRQA PGKAREFVAR VSTIAGDTDY    60
ADSVKGRFTI SRDNAKNTVY LQMNSLKPED TAVYYCAADS YNVRLVTGEA DYWGEGTQVT   120
VSS                                                                123

SEQ ID NO: 28           moltype = AA   length = 123
FEATURE                 Location/Qualifiers
source                  1..123
                        mol_type = protein
                        organism = synthetic construct
                        note = Synthetic Construct
SEQUENCE: 28
QVQLVESGGG LVQAGGSLRL SCAASGRTFS SYAIGWFRQA PGKAREFVAR VSTIAGDTDY    60
ADSVKGRFTI SRDNAKNTVY LQMNSLKPED TAVYYCAADS YNVRLGTGEA DYWGEGTQVT   120
VSS                                                                123

SEQ ID NO: 29           moltype = AA   length = 123
FEATURE                 Location/Qualifiers
source                  1..123
                        mol_type = protein
                        organism = synthetic construct
                        note = Synthetic Construct
SEQUENCE: 29
EVQLVESGGG LVQAGDSLRL SCAASGFTFS NYAIGWFRQA PGKAREFVAR VSTIAGDTDY    60
ANAVKGRFTI SRDNAKNTVY LQMNSLKPDD TAVYYCAAES YNVRLVTGEA DYWGEGTQVT   120
VSS                                                                123

SEQ ID NO: 30           moltype = AA   length = 127
FEATURE                 Location/Qualifiers
source                  1..127
                        mol_type = protein
                        organism = synthetic construct
                        note = Synthetic Construct
SEQUENCE: 30
QVRLAESGGG RVQAGESLRL SCVASGRTFS NDAAGWFREA SGKEREFVAS ISWSGNYTYY    60
ADSVKGRFTI SEDNVKNTVY LQMTSLKPED TAVYYCAAGN RYSDYRISLV TPRLYEYWGQ   120
GTQVTVS                                                            127

SEQ ID NO: 31           moltype = AA   length = 127
FEATURE                 Location/Qualifiers
source                  1..127
                        mol_type = protein
                        organism = synthetic construct
                        note = Synthetic Construct
SEQUENCE: 31
QVQLVESGGG LVQAGGSLRL SCAASGRTFS SDAAGWFRQA SGKEREFVAA ISWSGNYTYS    60
ADSVKGRFTI SSDNVKNTVY LQMNSLKPED TAVYLCAAGN RYSDYRISLV TPSQYEYWGQ   120
GTQVTVS                                                            127

SEQ ID NO: 32           moltype = AA   length = 127
FEATURE                 Location/Qualifiers
source                  1..127
                        mol_type = protein
                        organism = synthetic construct
                        note = Synthetic Construct
SEQUENCE: 32
QVQLVESGGG LVQAGGSLRL SCAASGRTFG SDAAGWFRQA SGKEREFVAS ISWSGGYTYY    60
ADSGTGRFTI SSDNVKNTVY LQMNSLTPED TAVYFCATGN RDSDYRISLV TPSQYEYWGQ   120
GTQVTVS                                                            127

SEQ ID NO: 33           moltype = AA   length = 127
FEATURE                 Location/Qualifiers
source                  1..127
                        mol_type = protein
                        organism = synthetic construct
                        note = Synthetic Construct
SEQUENCE: 33
QVQLVESGGG LVQAGGSLRL SCAASGRTFG SDAAGWFRQA SGKEREFVAS ISWSGGYTYY    60
ADSGKGRFTI SSDNVKNTVY LQMNSLTPED TAVYFCATGN RYSDYRISLV TPSQYDYWGQ   120
GTQVTVS                                                            127

SEQ ID NO: 34           moltype = AA   length = 127
FEATURE                 Location/Qualifiers
source                  1..127
                        mol_type = protein
                        organism = synthetic construct
                        note = Synthetic Construct
SEQUENCE: 34
QVQLVESGGG LVQAGGSLRL SCAASGRTFG SDAAGWFRQA SGKEREFVAS ISWSGGYTYY    60
ADSVKGRFTS SSDNVKNTVY LQMNSLTPED TAVYFCATVN RYSDYRISLV TPSQYEYWGQ   120
```

-continued

```
GTQVTVS                                                              127

SEQ ID NO: 35          moltype = AA  length = 8
FEATURE                Location/Qualifiers
source                 1..8
                       mol_type = protein
                       organism = synthetic construct
                       note = Synthetic Construct
SEQUENCE: 35
GRTFGSDA                                                             8

SEQ ID NO: 36          moltype = AA  length = 8
FEATURE                Location/Qualifiers
source                 1..8
                       mol_type = protein
                       organism = synthetic construct
                       note = Synthetic Construct
SEQUENCE: 36
GHSFSTYT                                                             8

SEQ ID NO: 37          moltype = AA  length = 8
FEATURE                Location/Qualifiers
source                 1..8
                       mol_type = protein
                       organism = synthetic construct
                       note = Synthetic Construct
SEQUENCE: 37
GRTVSNYA                                                             8

SEQ ID NO: 38          moltype = AA  length = 8
FEATURE                Location/Qualifiers
source                 1..8
                       mol_type = protein
                       organism = synthetic construct
                       note = Synthetic Construct
SEQUENCE: 38
GRPVSNYA                                                             8

SEQ ID NO: 39          moltype = AA  length = 8
FEATURE                Location/Qualifiers
source                 1..8
                       mol_type = protein
                       organism = synthetic construct
                       note = Synthetic Construct
SEQUENCE: 39
GRTFSSYA                                                             8

SEQ ID NO: 40          moltype = AA  length = 8
FEATURE                Location/Qualifiers
source                 1..8
                       mol_type = protein
                       organism = synthetic construct
                       note = Synthetic Construct
SEQUENCE: 40
GFTFSNYA                                                             8

SEQ ID NO: 41          moltype = AA  length = 8
FEATURE                Location/Qualifiers
source                 1..8
                       mol_type = protein
                       organism = synthetic construct
                       note = Synthetic Construct
SEQUENCE: 41
GRTFSNDA                                                             8

SEQ ID NO: 42          moltype = AA  length = 8
FEATURE                Location/Qualifiers
source                 1..8
                       mol_type = protein
                       organism = synthetic construct
                       note = Synthetic Construct
SEQUENCE: 42
GRTFSSDA                                                             8

SEQ ID NO: 43          moltype = AA  length = 8
FEATURE                Location/Qualifiers
source                 1..8
                       mol_type = protein
                       organism = synthetic construct
```

```
                                  note = Synthetic Construct
SEQUENCE: 43
GRTFGSDA                                                                                8

SEQ ID NO: 44           moltype = AA  length = 8
FEATURE                 Location/Qualifiers
source                  1..8
                        mol_type = protein
                        organism = synthetic construct
                        note = Synthetic Construct
SEQUENCE: 44
ISWSGGYT                                                                                8

SEQ ID NO: 45           moltype = AA  length = 8
FEATURE                 Location/Qualifiers
source                  1..8
                        mol_type = protein
                        organism = synthetic construct
                        note = Synthetic Construct
SEQUENCE: 45
ISWSGEVT                                                                                8

SEQ ID NO: 46           moltype = AA  length = 8
FEATURE                 Location/Qualifiers
source                  1..8
                        mol_type = protein
                        organism = synthetic construct
                        note = Synthetic Construct
SEQUENCE: 46
INWNKTTT                                                                                8

SEQ ID NO: 47           moltype = AA  length = 8
FEATURE                 Location/Qualifiers
source                  1..8
                        mol_type = protein
                        organism = synthetic construct
                        note = Synthetic Construct
SEQUENCE: 47
INWNKTAT                                                                                8

SEQ ID NO: 48           moltype = AA  length = 8
FEATURE                 Location/Qualifiers
source                  1..8
                        mol_type = protein
                        organism = synthetic construct
                        note = Synthetic Construct
SEQUENCE: 48
INWQKTAT                                                                                8

SEQ ID NO: 49           moltype = AA  length = 8
FEATURE                 Location/Qualifiers
source                  1..8
                        mol_type = protein
                        organism = synthetic construct
                        note = Synthetic Construct
SEQUENCE: 49
VSTIAGDT                                                                                8

SEQ ID NO: 50           moltype = AA  length = 8
FEATURE                 Location/Qualifiers
source                  1..8
                        mol_type = protein
                        organism = synthetic construct
                        note = Synthetic Construct
SEQUENCE: 50
ISWSGNYT                                                                                8

SEQ ID NO: 51           moltype = AA  length = 8
FEATURE                 Location/Qualifiers
source                  1..8
                        mol_type = protein
                        organism = synthetic construct
                        note = Synthetic Construct
SEQUENCE: 51
ISWSGGYT                                                                                8

SEQ ID NO: 52           moltype = AA  length = 21
FEATURE                 Location/Qualifiers
source                  1..21
```

```
                        mol_type = protein
                        organism = synthetic construct
                        note = Synthetic Construct
SEQUENCE: 52
ATGNRYSDYR ISLVTPSQYE Y                                               21

SEQ ID NO: 53           moltype = AA   length = 17
FEATURE                 Location/Qualifiers
source                  1..17
                        mol_type = protein
                        organism = synthetic construct
                        note = Synthetic Construct
SEQUENCE: 53
AAKRGGRPTD SSDDYFY                                                    17

SEQ ID NO: 54           moltype = AA   length = 17
FEATURE                 Location/Qualifiers
source                  1..17
                        mol_type = protein
                        organism = synthetic construct
                        note = Synthetic Construct
SEQUENCE: 54
AAVFRIVAPK TQYEYDY                                                    17

SEQ ID NO: 55           moltype = AA   length = 17
FEATURE                 Location/Qualifiers
source                  1..17
                        mol_type = protein
                        organism = synthetic construct
                        note = Synthetic Construct
SEQUENCE: 55
AAVFRVVAPK TQYDYDY                                                    17

SEQ ID NO: 56           moltype = AA   length = 16
FEATURE                 Location/Qualifiers
source                  1..16
                        mol_type = protein
                        organism = synthetic construct
                        note = Synthetic Construct
SEQUENCE: 56
AADSYNVRLV TGEADY                                                     16

SEQ ID NO: 57           moltype = AA   length = 16
FEATURE                 Location/Qualifiers
source                  1..16
                        mol_type = protein
                        organism = synthetic construct
                        note = Synthetic Construct
SEQUENCE: 57
AADSYNVRLG TGEADY                                                     16

SEQ ID NO: 58           moltype = AA   length = 16
FEATURE                 Location/Qualifiers
source                  1..16
                        mol_type = protein
                        organism = synthetic construct
                        note = Synthetic Construct
SEQUENCE: 58
AAESYNVRLV TGEADY                                                     16

SEQ ID NO: 59           moltype = AA   length = 21
FEATURE                 Location/Qualifiers
source                  1..21
                        mol_type = protein
                        organism = synthetic construct
                        note = Synthetic Construct
SEQUENCE: 59
AAGNRYSDYR ISLVTPRLYE Y                                               21

SEQ ID NO: 60           moltype = AA   length = 21
FEATURE                 Location/Qualifiers
source                  1..21
                        mol_type = protein
                        organism = synthetic construct
                        note = Synthetic Construct
SEQUENCE: 60
AAGNRYSDYR ISLVTPSQYE Y                                               21

SEQ ID NO: 61           moltype = AA   length = 21
```

```
FEATURE                     Location/Qualifiers
source                      1..21
                            mol_type = protein
                            organism = synthetic construct
                            note = Synthetic Construct
SEQUENCE: 61
ATGNRDSDYR ISLVTPSQYE Y                                                    21

SEQ ID NO: 62               moltype = AA   length = 21
FEATURE                     Location/Qualifiers
source                      1..21
                            mol_type = protein
                            organism = synthetic construct
                            note = Synthetic Construct
SEQUENCE: 62
ATGNRYSDYR ISLVTPSQYD Y                                                    21

SEQ ID NO: 63               moltype = AA   length = 21
FEATURE                     Location/Qualifiers
source                      1..21
                            mol_type = protein
                            organism = synthetic construct
                            note = Synthetic Construct
SEQUENCE: 63
ATVNRYSDYR ISLVTPSQYE Y                                                    21

SEQ ID NO: 64               moltype = AA   length = 256
FEATURE                     Location/Qualifiers
source                      1..256
                            mol_type = protein
                            organism = synthetic construct
                            note = Synthetic Construct
SEQUENCE: 64
EVQLLESGGG LVQPGGSLRL SCAASGFTFR SFGMSWVRQA PGKGPEWVSS ISGSGSDTLY           60
ADSVKGRFTI SRDNSKNTLY LQMNSLRPED TAVYYCTIGG SLSRSSQGTL VTVSSGGGGS          120
GGGGSGGGGS EVQLVESGGG LVQPGGSLRL SCAASGRHFS DYAMAWFRQA PGQEREFVAG          180
IGWSGGDTLY ADSVRGRFTI SRDNAKNTLY LQMNSLRAED TAVYYCAARQ GQYIYSSMRS          240
DSYDYWGQGT LVTVSS                                                         256

SEQ ID NO: 65               moltype = AA   length = 256
FEATURE                     Location/Qualifiers
source                      1..256
                            mol_type = protein
                            organism = synthetic construct
                            note = Synthetic Construct
SEQUENCE: 65
EVQLLESGGG LVQPGGSLRL SCAASGFTFR SFGMSWVRQA PGKGPEWVSS ISGSGSDTLY           60
ADSVKGRFTI SRDNSKNTLY LQMNSLRPED TAVYYCTIGG SLSRSSQGTL VTVSSGGGGS          120
GGGGSGGGGS EVQLVESGGG LVQPGGSLRL SCAASGRAHS DYAMAWFRQA PGQEREFVAG          180
IGWSGGDTLY ADSVRGRFTI SRDNAKNTLY LQMNSLRAED TAVYYCAARQ GQYIYSSMRS          240
DSYDYWGQGT LVTVSS                                                         256

SEQ ID NO: 66               moltype = AA   length = 256
FEATURE                     Location/Qualifiers
source                      1..256
                            mol_type = protein
                            organism = synthetic construct
                            note = Synthetic Construct
SEQUENCE: 66
EVQLLESGGG LVQPGGSLRL SCAASGFTFR SFGMSWVRQA PGKGPEWVSS ISGSGSDTLY           60
ADSVKGRFTI SRDNSKNTLY LQMNSLRPED TAVYYCTIGG SLSRSSQGTL VTVSSGGGGS          120
GGGGSGGGGS EVQLVESGGG LVQPGGSLRL SCAASGRHHS DYAMAWFRQA PGQEREFVAG          180
IGWSGGDTLY ADSVRGRFTI SRDNAKNTLY LQMNSLRAED TAVYYCAARQ GQYIYSSMRS          240
DSYDYWGQGT LVTVSS                                                         256

SEQ ID NO: 67               moltype = AA   length = 256
FEATURE                     Location/Qualifiers
source                      1..256
                            mol_type = protein
                            organism = synthetic construct
                            note = Synthetic Construct
SEQUENCE: 67
EVQLLESGGG LVQPGGSLRL SCAASGFTFR SFGMSWVRQA PGKGPEWVSS ISGSGSDTLY           60
ADSVKGRFTI SRDNSKNTLY LQMNSLRPED TAVYYCTIGG SLSRSSQGTL VTVSSGGGGS          120
GGGGSGGGGS EVQLVESGGG LVQPGGSLRL SCAASGRHFS DYAMAWFRQA PGQEREFVAG          180
IGWSGGDTLY ADSVRGRFTI SRDNSKNTMY LQMNSLRAED TAVYYCAARQ GQYIYSSMRS          240
DSYDYWGQGT LVTVSS                                                         256

SEQ ID NO: 68               moltype = AA   length = 256
```

| FEATURE | Location/Qualifiers |
|---|---|
| source | 1..256<br>mol_type = protein<br>organism = synthetic construct<br>note = Synthetic Construct |

SEQUENCE: 68
```
EVQLLESGGG LVQPGGSLRL SCAASGFTFR SFGMSWVRQA PGKGPEWVSS ISGSGSDTLY   60
ADSVKGRFTI SRDNSKNTLY LQMNSLRPED TAVYYCTIGG SLSRSSQGTL VTVSSGGGGS  120
GGGGSGGGGS EVQLVESGGG LVQPGGSLRL SCAASGRAHS DYAMAWFRQA PGQEREFVAG  180
IGWSGGDTLY ADSVRGRFTI SRDNSKNTMY LQMNSLRAED TAVYYCAARQ GQYIYSSMRS  240
DSYDYWGQGT LVTVSS                                                  256
```

| SEQ ID NO: 69 | moltype = AA length = 256 |
|---|---|
| FEATURE | Location/Qualifiers |
| source | 1..256<br>mol_type = protein<br>organism = synthetic construct<br>note = Synthetic Construct |

SEQUENCE: 69
```
EVQLLESGGG LVQPGGSLRL SCAASGFTFR SFGMSWVRQA PGKGPEWVSS ISGSGSDTLY   60
ADSVKGRFTI SRDNSKNTLY LQMNSLRPED TAVYYCTIGG SLSRSSQGTL VTVSSGGGGS  120
GGGGSGGGGS EVQLVESGGG LVQPGGSLRL SCAASGRHHS DYAMAWFRQA PGQEREFVAG  180
IGWSGGDTLY ADSVRGRFTI SRDNSKNTMY LQMNSLRAED TAVYYCAARQ GQYIYSSMRS  240
DSYDYWGQGT LVTVSS                                                  256
```

| SEQ ID NO: 70 | moltype = AA length = 264 |
|---|---|
| FEATURE | Location/Qualifiers |
| source | 1..264<br>mol_type = protein<br>organism = synthetic construct<br>note = Synthetic Construct |

SEQUENCE: 70
```
EVQLVESGGG LVKPGGSLRL SCAASGRPVS NYAAAWFRQA PGKEREFVSA INWQKTATYA   60
DSVKGRFTIS RDNAKNSLYL QMNSLRAEDT AVYYCAAVFR VVAPKTQYDY DYWGQGTLVT  120
VSSGGGGSGG GGSGGGGSEV QLVESGGGLV QPGGSLRLSC AASGRHFSDY AMAWFRQAPG  180
QEREFVAGIG WSGGDTLYAD SVRGRFTISR DNAKNTLYLQ MNSLRAEDTA VYYCAARQGQ  240
YIYSSMRSDS YDYWGQGTLV TVSS                                         264
```

| SEQ ID NO: 71 | moltype = AA length = 264 |
|---|---|
| FEATURE | Location/Qualifiers |
| source | 1..264<br>mol_type = protein<br>organism = synthetic construct<br>note = Synthetic Construct |

SEQUENCE: 71
```
EVQLVESGGG LVKPGGSLRL SCAASGRPVS NYAAAWFRQA PGKEREFVSA INWQKTATYA   60
DSVKGRFTIS RDNAKNSLYL QMNSLRAEDT AVYYCAAVFR VVAPKTQYDY DYWGQGTLVT  120
VSSGGGGSGG GGSGGGGSEV QLVESGGGLV QPGGSLRLSC AASGRAHSDY AMAWFRQAPG  180
QEREFVAGIG WSGGDTLYAD SVRGRFTISR DNAKNTLYLQ MNSLRAEDTA VYYCAARQGQ  240
YIYSSMRSDS YDYWGQGTLV TVSS                                         264
```

| SEQ ID NO: 72 | moltype = AA length = 264 |
|---|---|
| FEATURE | Location/Qualifiers |
| source | 1..264<br>mol_type = protein<br>organism = synthetic construct<br>note = Synthetic Construct |

SEQUENCE: 72
```
EVQLVESGGG LVKPGGSLRL SCAASGRPVS NYAAAWFRQA PGKEREFVSA INWQKTATYA   60
DSVKGRFTIS RDNAKNSLYL QMNSLRAEDT AVYYCAAVFR VVAPKTQYDY DYWGQGTLVT  120
VSSGGGGSGG GGSGGGGSEV QLVESGGGLV QPGGSLRLSC AASGRHHSDY AMAWFRQAPG  180
QEREFVAGIG WSGGDTLYAD SVRGRFTISR DNAKNTLYLQ MNSLRAEDTA VYYCAARQGQ  240
YIYSSMRSDS YDYWGQGTLV TVSS                                         264
```

| SEQ ID NO: 73 | moltype = AA length = 264 |
|---|---|
| FEATURE | Location/Qualifiers |
| source | 1..264<br>mol_type = protein<br>organism = synthetic construct<br>note = Synthetic Construct |

SEQUENCE: 73
```
EVQLVESGGG LVKPGGSLRL SCAASGRPVS NYAAAWFRQA PGKEREFVSA INWQKTATYA   60
DSVKGRFTIS RDNAKNSLYL QMNSLRAEDT AVYYCAAVFR VVAPKTQYDY DYWGQGTLVT  120
VSSGGGGSGG GGSGGGGSEV QLVESGGGLV QPGGSLRLSC AASGRHFSDY AMAWFRQAPG  180
QEREFVAGIG WSGGDTLYAD SVRGRFTISR DNSKNTMYLQ MNSLRAEDTA VYYCAARQGQ  240
YIYSSMRSDS YDYWGQGTLV TVSS                                         264
```

| SEQ ID NO: 74 | moltype = AA length = 264 |
|---|---|
| FEATURE | Location/Qualifiers |

| | | |
|---|---|---|
| source | 1..264<br>mol_type = protein<br>organism = synthetic construct<br>note = Synthetic Construct | |
| SEQUENCE: 74 | | |
| EVQLVESGGG LVKPGGSLRL SCAASGRPVS NYAAAWFRQA PGKEREFVSA INWQKTATYA | | 60 |
| DSVKGRFTIS RDNAKNSLYL QMNSLRAEDT AVYYCAAVFR VVAPKTQYDY DYWGQGTLVT | | 120 |
| VSSGGGGSGG GGSGGGGSEV QLVESGGGLV QPGGSLRLSC AASGRAHSDY AMAWFRQAPG | | 180 |
| QEREFVAGIG WSGGDTLYAD SVRGRFTISR DNSKNTMYLQ MNSLRAEDTA VYYCAARQGQ | | 240 |
| YIYSSMRSDS YDYWGQGTLV TVSS | | 264 |
| | | |
| SEQ ID NO: 75 | moltype = AA length = 264 | |
| FEATURE | Location/Qualifiers | |
| source | 1..264<br>mol_type = protein<br>organism = synthetic construct<br>note = Synthetic Construct | |
| SEQUENCE: 75 | | |
| EVQLVESGGG LVKPGGSLRL SCAASGRPVS NYAAAWFRQA PGKEREFVSA INWQKTATYA | | 60 |
| DSVKGRFTIS RDNAKNSLYL QMNSLRAEDT AVYYCAAVFR VVAPKTQYDY DYWGQGTLVT | | 120 |
| VSSGGGGSGG GGSGGGGSEV QLVESGGGLV QPGGSLRLSC AASGRHHSDY AMAWFRQAPG | | 180 |
| QEREFVAGIG WSGGDTLYAD SVRGRFTISR DNSKNTMYLQ MNSLRAEDTA VYYCAARQGQ | | 240 |
| YIYSSMRSDS YDYWGQGTLV TVSS | | 264 |
| | | |
| SEQ ID NO: 76 | moltype = AA length = 262 | |
| FEATURE | Location/Qualifiers | |
| source | 1..262<br>mol_type = protein<br>organism = synthetic construct<br>note = Synthetic Construct | |
| SEQUENCE: 76 | | |
| EVQLVESGGG LVQPGGSLRL SCAASGRTFS GILSPYAVGW FRQAPGKGLE FVSTITSGGS | | 60 |
| AIYTDSVKGR FTISRDNAKD SLYLQMNSLR AEDTAVYYCA VRTRRYGSNL GEVPQENEYG | | 120 |
| YWGQGTLVTV SSGGGGSGGG GSGGGGSEVQ LLESGGGLVQ PGGSLRLSCA ASGFTFRSFG | | 180 |
| MSWVRQAPGK GPEWVSSISG SGSDTLYADS VKGRFTISRD NSKNTLYLQM NSLRPEDTAV | | 240 |
| YYCTIGGSLS RSSQGTLVTV SS | | 262 |
| | | |
| SEQ ID NO: 77 | moltype = AA length = 270 | |
| FEATURE | Location/Qualifiers | |
| source | 1..270<br>mol_type = protein<br>organism = synthetic construct<br>note = Synthetic Construct | |
| SEQUENCE: 77 | | |
| EVQLVESGGG LVQPGGSLRL SCAASGRTFS GILSPYAVGW FRQAPGKGLE FVSTITSGGS | | 60 |
| AIYTDSVKGR FTISRDNAKD SLYLQMNSLR AEDTAVYYCA VRTRRYGSNL GEVPQENEYG | | 120 |
| YWGQGTLVTV SSGGGGSGGG GSGGGGSEVQ LVESGGGLVK PGGSLRLSCA ASGRPVSNYA | | 180 |
| AAWFRQAPGK EREFVSAINW QKTATYADSV KGRFTISRDN AKNSLYLQMN SLRAEDTAVY | | 240 |
| YCAAVFRVVA PKTQYDYDYW GQGTLVTVSS | | 270 |
| | | |
| SEQ ID NO: 78 | moltype = AA length = 262 | |
| FEATURE | Location/Qualifiers | |
| source | 1..262<br>mol_type = protein<br>organism = synthetic construct<br>note = Synthetic Construct | |
| SEQUENCE: 78 | | |
| EVQLVESGGG LVQPGGSLRL SCAASGRTFS GILSPYAVGW FRQAPGKGLE FVSTITSGGS | | 60 |
| AIYTDSVKGR FTISRDNAKN TLYLQMNSLR AEDTAVYYCA VRTRRYGSNL GEVPQENEYG | | 120 |
| YWGQGTLVTV SSGGGGSGGG GSGGGGSEVQ LLESGGGLVQ PGGSLRLSCA ASGFTFRSFG | | 180 |
| MSWVRQAPGK GPEWVSSISG SGSDTLYADS VKGRFTISRD NSKNTLYLQM NSLRPEDTAV | | 240 |
| YYCTIGGSLS RSSQGTLVTV SS | | 262 |
| | | |
| SEQ ID NO: 79 | moltype = AA length = 270 | |
| FEATURE | Location/Qualifiers | |
| source | 1..270<br>mol_type = protein<br>organism = synthetic construct<br>note = Synthetic Construct | |
| SEQUENCE: 79 | | |
| EVQLVESGGG LVQPGGSLRL SCAASGRTFS GILSPYAVGW FRQAPGKGLE FVSTITSGGS | | 60 |
| AIYTDSVKGR FTISRDNAKN TLYLQMNSLR AEDTAVYYCA VRTRRYGSNL GEVPQENEYG | | 120 |
| YWGQGTLVTV SSGGGGSGGG GSGGGGSEVQ LVESGGGLVK PGGSLRLSCA ASGRPVSNYA | | 180 |
| AAWFRQAPGK EREFVSAINW QKTATYADSV KGRFTISRDN AKNSLYLQMN SLRAEDTAVY | | 240 |
| YCAAVFRVVA PKTQYDYDYW GQGTLVTVSS | | 270 |
| | | |
| SEQ ID NO: 80 | moltype = AA length = 262 | |
| FEATURE | Location/Qualifiers | |
| source | 1..262 | |

```
                            mol_type = protein
                            organism = synthetic construct
                            note = Synthetic Construct
SEQUENCE: 80
EVQLVESGGG LVQPGGSLRL SCAASGRTFS GILSPYAVGW FRQAPGKGLE FVSTITSGGS    60
AIYTDSVKGR FTISRDNAKN SVYLQMNSLR AEDTAVYYCA VRTRRYGSNL GEVPQENEYG   120
YWGQGTLVTV SSGGGGSGGG GSGGGGSEVQ LLESGGGLVQ PGGSLRLSCA ASGFTFRSFG   180
MSWVRQAPGK GPEWVSSISG SGSDTLYADS VKGRFTISRD NSKNTLYLQM NSLRPEDTAV   240
YYCTIGGSLS RSSQGTLVTV SS                                           262

SEQ ID NO: 81           moltype = AA  length = 270
FEATURE                 Location/Qualifiers
source                  1..270
                        mol_type = protein
                        organism = synthetic construct
                        note = Synthetic Construct
SEQUENCE: 81
EVQLVESGGG LVQPGGSLRL SCAASGRTFS GILSPYAVGW FRQAPGKGLE FVSTITSGGS    60
AIYTDSVKGR FTISRDNAKN SVYLQMNSLR AEDTAVYYCA VRTRRYGSNL GEVPQENEYG   120
YWGQGTLVTV SSGGGGSGGG GSGGGGSEVQ LVESGGGLVK PGGSLRLSCA ASGRPVSNYA   180
AAWFRQAPGK EREFVSAINW QKTATYADSV KGRFTISRDN AKNSLYLQMN SLRAEDTAVY   240
YCAAVFRVVA PKTQYDYDYW GQGTLVTVSS                                   270

SEQ ID NO: 82           moltype = AA  length = 262
FEATURE                 Location/Qualifiers
source                  1..262
                        mol_type = protein
                        organism = synthetic construct
                        note = Synthetic Construct
SEQUENCE: 82
EVQLVESGGG LVQPGGSLRL SCAASGRTFS GILSPYAVGW FRQAPGQGLE FVATITSGGS    60
AIYTDSVKGR FTISRDNSKN TLYLQMNSLR AEDTAVYYCA VRTRRYGSNL GEVPQENEYG   120
YWGQGTLVTV SSGGGGSGGG GSGGGGSEVQ LLESGGGLVQ PGGSLRLSCA ASGFTFRSFG   180
MSWVRQAPGK GPEWVSSISG SGSDTLYADS VKGRFTISRD NSKNTLYLQM NSLRPEDTAV   240
YYCTIGGSLS RSSQGTLVTV SS                                           262

SEQ ID NO: 83           moltype = AA  length = 270
FEATURE                 Location/Qualifiers
source                  1..270
                        mol_type = protein
                        organism = synthetic construct
                        note = Synthetic Construct
SEQUENCE: 83
EVQLVESGGG LVQPGGSLRL SCAASGRTFS GILSPYAVGW FRQAPGQGLE FVATITSGGS    60
AIYTDSVKGR FTISRDNSKN TLYLQMNSLR AEDTAVYYCA VRTRRYGSNL GEVPQENEYG   120
YWGQGTLVTV SSGGGGSGGG GSGGGGSEVQ LVESGGGLVK PGGSLRLSCA ASGRPVSNYA   180
AAWFRQAPGK EREFVSAINW QKTATYADSV KGRFTISRDN AKNSLYLQMN SLRAEDTAVY   240
YCAAVFRVVA PKTQYDYDYW GQGTLVTVSS                                   270

SEQ ID NO: 84           moltype = AA  length = 256
FEATURE                 Location/Qualifiers
source                  1..256
                        mol_type = protein
                        organism = synthetic construct
                        note = Synthetic Construct
SEQUENCE: 84
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SLSRSSQGTL VTVSSGGGGS   120
GGGGSGGGGS EVQLVESGGG LVQPGGSLRL SCAASGRAFS DYAMAWFRQA PGQEREFVAG   180
IGWSGGDTLY ADSVRGRFTN SRDNSKNTLY LQMNSLRAED TAVYYCAARQ GQYIYSSMRS   240
DSYDYWGQGT LVTVSS                                                  256

SEQ ID NO: 85           moltype = AA  length = 264
FEATURE                 Location/Qualifiers
source                  1..264
                        mol_type = protein
                        organism = synthetic construct
                        note = Synthetic Construct
SEQUENCE: 85
EVQLVESGGG LVKPGGSLRL SCAASGRPVS NYAAAWFRQA PGKEREFVSA INWQKTATYA    60
DSVKGRFTIS RDNAKNSLYL QMNSLRAEDT AVYYCAAVFR VVAPKTQYDY DYWGQGTLVT   120
VSSGGGGSGG GGSGGGGSEV QLVESGGGLV QPGGSLRLSC AASGRAFSDY AMAWFRQAPG   180
QEREFVAGIG WSGGDTLYAD SVRGRFTNSR DNSKNTLYLQ MNSLRAEDTA VYYCAARQGQ   240
YIYSSMRSDS YDYWGQGTLV TVSS                                         264

SEQ ID NO: 86           moltype = AA  length = 256
FEATURE                 Location/Qualifiers
source                  1..256
                        mol_type = protein
```

```
                        organism = synthetic construct
                        note = Synthetic Construct
SEQUENCE: 86
EVQLLESGGG LVQPGGSLRL SCAASGFTFR SFGMSWVRQA PGKGPEWVSS ISGSGSDTLY     60
ADSVKGRFTI SRDNSKNTLY LQMNSLRPED TAVYYCTIGG SLSRSSQGTL VTVSSGGGGS    120
GGGGSGGGGS EVQLVESGGG LVQPGGSLRL SCAASGRAFS DYAMAWFRQA PGQEREFVAG    180
IGWSGGDTLY ADSVRGRFTI SRDNAKNTLY LQMNSLRAED TAVYYCAARQ GQYIYSSMRS    240
DSYDYWGQGT LVTVSS                                                    256

SEQ ID NO: 87           moltype = AA  length = 264
FEATURE                 Location/Qualifiers
source                  1..264
                        mol_type = protein
                        organism = synthetic construct
                        note = Synthetic Construct
SEQUENCE: 87
EVQLVESGGG LVKPGGSLRL SCAASGRPVS NYAAAWFRQA PGKEREFVSA INWQKTATYA     60
DSVKGRFTIS RDNAKNSLYL QMNSLRAEDT AVYYCAAVFR VVAPKTQYDY DYWGQGTLVT    120
VSSGGGGSGG GGSGGGGSEV QLVESGGGLV QPGGSLRLSC AASGRAFSDY AMAWFRQAPG    180
QEREFVAGIG WSGGDTLYAD SVRGRFTISR DNAKNTLYLQ MNSLRAEDTA VYYCAARQGQ    240
YIYSSMRSDS YDYWGQGTLV TVSS                                           264

SEQ ID NO: 88           moltype = AA  length = 256
FEATURE                 Location/Qualifiers
source                  1..256
                        mol_type = protein
                        organism = synthetic construct
                        note = Synthetic Construct
SEQUENCE: 88
EVQLLESGGG LVQPGGSLRL SCAASGFTFR SFGMSWVRQA PGKGPEWVSS ISGSGSDTLY     60
ADSVKGRFTI SRDNSKNTLY LQMNSLRPED TAVYYCTIGG SLSRSSQGTL VTVSSGGGGS    120
GGGGSGGGGS EVQLVESGGG LVQPGGSLRL SCAASGRAFS DYAMAWFRQA PGQEREFVAG    180
IGWSGGDTLY ADSVRGRFTI SRDNSKNTMY LQMNSLRAED TAVYYCAARQ GQYIYSSMRS    240
DSYDYWGQGT LVTVSS                                                    256

SEQ ID NO: 89           moltype = AA  length = 264
FEATURE                 Location/Qualifiers
source                  1..264
                        mol_type = protein
                        organism = synthetic construct
                        note = Synthetic Construct
SEQUENCE: 89
EVQLVESGGG LVKPGGSLRL SCAASGRPVS NYAAAWFRQA PGKEREFVSA INWQKTATYA     60
DSVKGRFTIS RDNAKNSLYL QMNSLRAEDT AVYYCAAVFR VVAPKTQYDY DYWGQGTLVT    120
VSSGGGGSGG GGSGGGGSEV QLVESGGGLV QPGGSLRLSC AASGRAFSDY AMAWFRQAPG    180
QEREFVAGIG WSGGDTLYAD SVRGRFTISR DNSKNTMYLQ MNSLRAEDTA VYYCAARQGQ    240
YIYSSMRSDS YDYWGQGTLV TVSS                                           264

SEQ ID NO: 90           moltype = AA  length = 256
FEATURE                 Location/Qualifiers
source                  1..256
                        mol_type = protein
                        organism = synthetic construct
                        note = Synthetic Construct
SEQUENCE: 90
EVQLLESGGG LVQPGGSLRL SCAASGFTFR SFGMSWVRQA PGKGPEWVSS ISGSGSDTLY     60
ADSVKGRFTI SRDNSKNTLY LQMNSLRPED TAVYYCTIGG SLSRSSQGTL VTVSSGGGGS    120
GGGGSGGGGS EVQLVESGGG LVQPGGSLRL SCAASGRAFS DYAMAWFRQA PGQGLEFVAG    180
IGWSGGDTLY ADSVRGRFTI SRDNSKNTLY LQMNSLRAED TAVYYCAARQ GQYIYSSMRS    240
DSYDYWGQGT LVTVSS                                                    256

SEQ ID NO: 91           moltype = AA  length = 264
FEATURE                 Location/Qualifiers
source                  1..264
                        mol_type = protein
                        organism = synthetic construct
                        note = Synthetic Construct
SEQUENCE: 91
EVQLVESGGG LVKPGGSLRL SCAASGRPVS NYAAAWFRQA PGKEREFVSA INWQKTATYA     60
DSVKGRFTIS RDNAKNSLYL QMNSLRAEDT AVYYCAAVFR VVAPKTQYDY DYWGQGTLVT    120
VSSGGGGSGG GGSGGGGSEV QLVESGGGLV QPGGSLRLSC AASGRAFSDY AMAWFRQAPG    180
QGLEFVAGIG WSGGDTLYAD SVRGRFTISR DNSKNTLYLQ MNSLRAEDTA VYYCAARQGQ    240
YIYSSMRSDS YDYWGQGTLV TVSS                                           264

SEQ ID NO: 92           moltype = AA  length = 256
FEATURE                 Location/Qualifiers
source                  1..256
                        mol_type = protein
                        organism = synthetic construct
```

```
                          note = Synthetic Construct
SEQUENCE: 92
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SLSRSSQGTL VTVSSGGGGS   120
GGGGSGGGGS EVQLVESGGG LVQPGGSLRL SCAASGRAHS DYAMAWFRQA PGQEREFVAG   180
IGWSGGDTLY ADSVRGRFTN SRDNSKNTLY LQMNSLRAED TAVYYCAARQ GQYIYSSMRS   240
DSYDYWGQGT LVTVSS                                                  256

SEQ ID NO: 93               moltype = AA  length = 264
FEATURE                     Location/Qualifiers
source                      1..264
                            mol_type = protein
                            organism = synthetic construct
                            note = Synthetic Construct
SEQUENCE: 93
EVQLVESGGG LVKPGGSLRL SCAASGRPVS NYAAAWFRQA PGKEREFVSA INWQKTATYA    60
DSVKGRFTIS RDNAKNSLYL QMNSLRAEDT AVYYCAAVFR VVAPKTQYDY DYWGQGTLVT   120
VSSGGGGSGG GGSGGGGSEV QLVESGGGLV QPGGSLRLSC AASGRAHSDY AMAWFRQAPG   180
QEREFVAGIG WSGGDTLYAD SVRGRFTNSR DNSKNTLYLQ MNSLRAEDTA VYYCAARQGQ   240
YIYSSMRSDS YDWGQGTLV TVSS                                          264

SEQ ID NO: 94               moltype = AA  length = 256
FEATURE                     Location/Qualifiers
source                      1..256
                            mol_type = protein
                            organism = synthetic construct
                            note = Synthetic Construct
SEQUENCE: 94
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SLSRSSQGTL VTVSSGGGGS   120
GGGGSGGGGS EVQLVESGGG LVQPGGSLRL SCAASGRAHS DYAMAWFRQA PGQGLEFVAG   180
IGWSGGDTLY ADSVRGRFTI SRDNSKNTLY LQMNSLRAED TAVYYCAARQ GQYIYSSMRS   240
DSYDYWGQGT LVTVSS                                                  256

SEQ ID NO: 95               moltype = AA  length = 264
FEATURE                     Location/Qualifiers
source                      1..264
                            mol_type = protein
                            organism = synthetic construct
                            note = Synthetic Construct
SEQUENCE: 95
EVQLVESGGG LVKPGGSLRL SCAASGRPVS NYAAAWFRQA PGKEREFVSA INWQKTATYA    60
DSVKGRFTIS RDNAKNSLYL QMNSLRAEDT AVYYCAAVFR VVAPKTQYDY DYWGQGTLVT   120
VSSGGGGSGG GGSGGGGSEV QLVESGGGLV QPGGSLRLSC AASGRAHSDY AMAWFRQAPG   180
QGLEFVAGIG WSGGDTLYAD SVRGRFTISR DNSKNTLYLQ MNSLRAEDTA VYYCAARQGQ   240
YIYSSMRSDS YDYWGQGTLV TVSS                                         264

SEQ ID NO: 96               moltype = AA  length = 264
FEATURE                     Location/Qualifiers
source                      1..264
                            mol_type = protein
                            organism = synthetic construct
                            note = Synthetic Construct
SEQUENCE: 96
EVQLVESGGG LVKPGGSLRL SCAASGRPVS NYAAAWFRQA PGKEREFVSA INWQKTATYA    60
DSVKGRFTIS RDNAKNSLYL QMNSLRAEDT AVYYCAAVFR VVAPKTQYDY DYWGQGTLVT   120
VSSGGGGAGG GGAGGGGSEV QLVESGGGLV QPGGSLRLSC AASGRAHSDY AMAWFRQAPG   180
QEREFVAGIG WSGGDTLYAD SVRGRFTNSR DNSKNTLYLQ MNSLRAEDTA VYYCAARQGQ   240
YIYSSMRSDS YDYWGQGTLV TVSS                                         264

SEQ ID NO: 97               moltype = AA  length = 270
FEATURE                     Location/Qualifiers
source                      1..270
                            mol_type = protein
                            organism = synthetic construct
                            note = Synthetic Construct
SEQUENCE: 97
EVQLVESGGG LVQPGGSLRL SCAASGRTFS GILSPYAVGW FRQAPGKGLE FVSTITSGGS    60
AIYTDSVKGR FTISRDNAKD SLYLQMNSLR AEDTAVYYCA VRTRRYGSNL GEVPQENEYG   120
YWGQGTLVTV SSGGGGAGGG GAGGGGSEVQ LVESGGGLVK PGGSLRLSCA ASGRPVSNYA   180
AAWFRQAPGK EREFVSAINW QKTATYADSV KGRFTISRDN AKNSLYLQMN SLRAEDTAVY   240
YCAAVFRVVA PKTQYDYDYW GQGTLVTVSS                                   270

SEQ ID NO: 98               moltype = AA  length = 266
FEATURE                     Location/Qualifiers
source                      1..266
                            mol_type = protein
                            organism = synthetic construct
                            note = Synthetic Construct
```

```
SEQUENCE: 98
EVQLVESGGG VVQAGDSLTL TCTAPVGTIS DYGMGWFRQA PGKEREFVAS ISWGGMWTDY    60
ADSVKGRFTI SRDNDKNAVY LRMNSLNAED TAVYYCGRGR MYRGIGNSLA QPKSYGYWGQ   120
GTQVTVSSGG GGAGGGGAGG GGSEVQLVES GGGLVKPGGS LRLSCAASGR PVSNYAAAWF   180
RQAPGKEREF VSAINWQKTA TYADSVKGRF TISRDNAKNS LYLQMNSLRA EDTAVYYCAA   240
VFRVVAPKTQ YDYDYWGQGT LVTVSS                                       266

SEQ ID NO: 99              moltype = AA  length = 270
FEATURE                    Location/Qualifiers
source                     1..270
                           mol_type = protein
                           organism = synthetic construct
                           note = Synthetic Construct
SEQUENCE: 99
EVQLVESGGG LVQAGGSLRL SCAASGRTFS GILSAYAVGW FRQAPGKERE FVSTITSGGS    60
TLSADSVKGR FTLSRDNAKD TVYLQMNSLK PEDTAVYYCA VRTWPYGSNR GEVPTENEYG   120
HWGQGTQVTV SSGGGGAGGG GAGGGGSEVQ LVESGGGLVK PGGSLRLSCA ASGRPVSNYA   180
AAWFRQAPGK EREFVSAINW QKTATYADSV KGRFTISRDN AKNSLYLQMN SLRAEDTAVY   240
YCAAVFRVVA PKTQYDYDYW GQGTLVTVSS                                   270

SEQ ID NO: 100             moltype = AA  length = 266
FEATURE                    Location/Qualifiers
source                     1..266
                           mol_type = protein
                           organism = synthetic construct
                           note = Synthetic Construct
SEQUENCE: 100
EVQLVESGGG LVKPGGSLRL SCAASGRPVS NYAAAWFRQA PGKEREFVSA INWQKTATYA    60
DSVKGRFTIS RDNAKNSLYL QMNSLRAEDT AVYYCAAVFR VVAPKTQYDY DYWGQGTLVT   120
VSSGGGGAGG GGAGGGGSEV QLVESGGGVV QAGDSLTLTC TAPVGTISDY GMGWFRQAPG   180
KEREFVASIS WGGMWTDYAD SVKGRFTISR DNDKNAVYLR MNSLNAEDTA VYYCGRGRMY   240
RGIGNSLAQP KSYGYWGQGT QVTVSS                                       266

SEQ ID NO: 101             moltype = AA  length = 270
FEATURE                    Location/Qualifiers
source                     1..270
                           mol_type = protein
                           organism = synthetic construct
                           note = Synthetic Construct
SEQUENCE: 101
EVQLVESGGG LVKPGGSLRL SCAASGRPVS NYAAAWFRQA PGKEREFVSA INWQKTATYA    60
DSVKGRFTIS RDNAKNSLYL QMNSLRAEDT AVYYCAAVFR VVAPKTQYDY DYWGQGTLVT   120
VSSGGGGAGG GGAGGGGSEV QLVESGGGLV QAGGSLRLSC AASGRTFSGI LSAYAVGWFR   180
QAPGKEREFV STITSGGSTL SADSVKGRFT LSRDNAKDTV YLQMNSLKPE DTAVYYCAVR   240
TWPYGSNRGE VPTENEYGHW GQGTQVTVSS                                   270

SEQ ID NO: 102             moltype = AA  length = 15
FEATURE                    Location/Qualifiers
source                     1..15
                           mol_type = protein
                           organism = synthetic construct
                           note = Synthetic Construct
SEQUENCE: 102
GGGGAGGGGA GGGGS                                                    15

SEQ ID NO: 103             moltype = AA  length = 15
FEATURE                    Location/Qualifiers
source                     1..15
                           mol_type = protein
                           organism = synthetic construct
                           note = Synthetic Construct
SEQUENCE: 103
GGGGSGGGGS GGGGS                                                    15

SEQ ID NO: 104             moltype = AA  length = 5
FEATURE                    Location/Qualifiers
source                     1..5
                           mol_type = protein
                           organism = synthetic construct
                           note = Synthetic Construct
SEQUENCE: 104
GGGGS                                                                5

SEQ ID NO: 105             moltype = AA  length = 10
FEATURE                    Location/Qualifiers
source                     1..10
                           mol_type = protein
                           organism = synthetic construct
                           note = Synthetic Construct
```

```
SEQUENCE: 105
GGGGSGGGGS                                                              10

SEQ ID NO: 106          moltype = AA  length = 15
FEATURE                 Location/Qualifiers
source                  1..15
                        mol_type = protein
                        organism = synthetic construct
                        note = Synthetic Construct
SEQUENCE: 106
GGGGSGGGGS GGGGS                                                        15

SEQ ID NO: 107          moltype = AA  length = 20
FEATURE                 Location/Qualifiers
source                  1..20
                        mol_type = protein
                        organism = synthetic construct
                        note = Synthetic Construct
SEQUENCE: 107
GGGGSGGGGS GGGGSGGGGS                                                   20

SEQ ID NO: 108          moltype = AA  length = 25
FEATURE                 Location/Qualifiers
source                  1..25
                        mol_type = protein
                        organism = synthetic construct
                        note = Synthetic Construct
SEQUENCE: 108
GGGGSGGGGS GGGGSGGGGS GGGGS                                             25

SEQ ID NO: 109          moltype = AA  length = 30
FEATURE                 Location/Qualifiers
source                  1..30
                        mol_type = protein
                        organism = synthetic construct
                        note = Synthetic Construct
SEQUENCE: 109
GGGGSGGGGS GGGGSGGGGS GGGGSGGGGS                                        30

SEQ ID NO: 110          moltype = AA  length = 15
FEATURE                 Location/Qualifiers
source                  1..15
                        mol_type = protein
                        organism = synthetic construct
                        note = Synthetic Construct
SEQUENCE: 110
EAAAKEAAAK EAAAK                                                        15

SEQ ID NO: 111          moltype = AA  length = 5
FEATURE                 Location/Qualifiers
source                  1..5
                        mol_type = protein
                        organism = synthetic construct
                        note = Synthetic Construct
SEQUENCE: 111
PAPAP                                                                    5

SEQ ID NO: 112          moltype = AA  length = 10
FEATURE                 Location/Qualifiers
source                  1..10
                        mol_type = protein
                        organism = synthetic construct
                        note = Synthetic Construct
SEQUENCE: 112
GGGGSPAPAP                                                              10

SEQ ID NO: 113          moltype = AA  length = 10
FEATURE                 Location/Qualifiers
source                  1..10
                        mol_type = protein
                        organism = synthetic construct
                        note = Synthetic Construct
SEQUENCE: 113
PAPAPGGGGS                                                              10

SEQ ID NO: 114          moltype = AA  length = 12
FEATURE                 Location/Qualifiers
source                  1..12
                        mol_type = protein
```

```
SEQUENCE: 114
GSTSGKSSEG KG                                                           12

SEQ ID NO: 115          moltype = AA  length = 10
FEATURE                 Location/Qualifiers
source                  1..10
                        mol_type = protein
                        organism = synthetic construct
                        note = Synthetic Construct
SEQUENCE: 115
GGGDSGGGDS                                                              10

SEQ ID NO: 116          moltype = AA  length = 10
FEATURE                 Location/Qualifiers
source                  1..10
                        mol_type = protein
                        organism = synthetic construct
                        note = Synthetic Construct
SEQUENCE: 116
GGGESGGGES                                                              10

SEQ ID NO: 117          moltype = AA  length = 10
FEATURE                 Location/Qualifiers
source                  1..10
                        mol_type = protein
                        organism = synthetic construct
                        note = Synthetic Construct
SEQUENCE: 117
GGGDSGGGGS                                                              10

SEQ ID NO: 118          moltype = AA  length = 10
FEATURE                 Location/Qualifiers
source                  1..10
                        mol_type = protein
                        organism = synthetic construct
                        note = Synthetic Construct
SEQUENCE: 118
GGGASGGGGS                                                              10

SEQ ID NO: 119          moltype = AA  length = 10
FEATURE                 Location/Qualifiers
source                  1..10
                        mol_type = protein
                        organism = synthetic construct
                        note = Synthetic Construct
SEQUENCE: 119
GGGESGGGGS                                                              10

SEQ ID NO: 120          moltype = AA  length = 6
FEATURE                 Location/Qualifiers
source                  1..6
                        mol_type = protein
                        organism = synthetic construct
                        note = Synthetic Construct
SEQUENCE: 120
ASTKGP                                                                   6

SEQ ID NO: 121          moltype = AA  length = 13
FEATURE                 Location/Qualifiers
source                  1..13
                        mol_type = protein
                        organism = synthetic construct
                        note = Synthetic Construct
SEQUENCE: 121
ASTKGPSVFP LAP                                                          13

SEQ ID NO: 122          moltype = AA  length = 4
FEATURE                 Location/Qualifiers
source                  1..4
                        mol_type = protein
                        organism = synthetic construct
                        note = Synthetic Construct
SEQUENCE: 122
GGGP                                                                     4

SEQ ID NO: 123          moltype = AA  length = 8
FEATURE                 Location/Qualifiers
```

```
source                  1..8
                        mol_type = protein
                        organism = synthetic construct
                        note = Synthetic Construct
SEQUENCE: 123
GGGGGGGP                                                                        8

SEQ ID NO: 124          moltype = AA  length = 9
FEATURE                 Location/Qualifiers
source                  1..9
                        mol_type = protein
                        organism = synthetic construct
                        note = Synthetic Construct
SEQUENCE: 124
PAPNLLGGP                                                                       9

SEQ ID NO: 125          moltype = AA  length = 6
FEATURE                 Location/Qualifiers
source                  1..6
                        mol_type = protein
                        organism = synthetic construct
                        note = Synthetic Construct
SEQUENCE: 125
GGGGGG                                                                          6

SEQ ID NO: 126          moltype = AA  length = 12
FEATURE                 Location/Qualifiers
source                  1..12
                        mol_type = protein
                        organism = synthetic construct
                        note = Synthetic Construct
SEQUENCE: 126
GGGGGGGGGG GG                                                                  12

SEQ ID NO: 127          moltype = AA  length = 8
FEATURE                 Location/Qualifiers
source                  1..8
                        mol_type = protein
                        organism = synthetic construct
                        note = Synthetic Construct
SEQUENCE: 127
APELPGGP                                                                        8

SEQ ID NO: 128          moltype = AA  length = 8
FEATURE                 Location/Qualifiers
source                  1..8
                        mol_type = protein
                        organism = synthetic construct
                        note = Synthetic Construct
SEQUENCE: 128
SEPQPQPG                                                                        8

SEQ ID NO: 129          moltype = AA  length = 15
FEATURE                 Location/Qualifiers
source                  1..15
                        mol_type = protein
                        organism = synthetic construct
                        note = Synthetic Construct
SEQUENCE: 129
GGGSSGGGSS GGGSS                                                               15

SEQ ID NO: 130          moltype = AA  length = 14
FEATURE                 Location/Qualifiers
source                  1..14
                        mol_type = protein
                        organism = synthetic construct
                        note = Synthetic Construct
SEQUENCE: 130
GGGGGGGGGS GGGS                                                                14

SEQ ID NO: 131          moltype = AA  length = 15
FEATURE                 Location/Qualifiers
source                  1..15
                        mol_type = protein
                        organism = synthetic construct
                        note = Synthetic Construct
SEQUENCE: 131
GGGGSGGGGG GGGGS                                                               15
```

```
SEQ ID NO: 132           moltype = AA   length = 15
FEATURE                  Location/Qualifiers
source                   1..15
                         mol_type = protein
                         organism = synthetic construct
                         note = Synthetic Construct
SEQUENCE: 132
GGSSSGGSSS GGSSS                                                         15

SEQ ID NO: 133           moltype = AA   length = 15
FEATURE                  Location/Qualifiers
source                   1..15
                         mol_type = protein
                         organism = synthetic construct
                         note = Synthetic Construct
SEQUENCE: 133
GSSSSGSSSS GSSSS                                                         15

SEQ ID NO: 134           moltype = AA   length = 15
FEATURE                  Location/Qualifiers
source                   1..15
                         mol_type = protein
                         organism = synthetic construct
                         note = Synthetic Construct
SEQUENCE: 134
GGGGAGGGGS GGGGS                                                         15

SEQ ID NO: 135           moltype = AA   length = 15
FEATURE                  Location/Qualifiers
source                   1..15
                         mol_type = protein
                         organism = synthetic construct
                         note = Synthetic Construct
SEQUENCE: 135
GGGGSGGGGA GGGGS                                                         15

SEQ ID NO: 136           moltype = AA   length = 15
FEATURE                  Location/Qualifiers
source                   1..15
                         mol_type = protein
                         organism = synthetic construct
                         note = Synthetic Construct
SEQUENCE: 136
GGGASGGGGS GGGGS                                                         15

SEQ ID NO: 137           moltype = AA   length = 15
FEATURE                  Location/Qualifiers
source                   1..15
                         mol_type = protein
                         organism = synthetic construct
                         note = Synthetic Construct
SEQUENCE: 137
GGGGSGGGAS GGGGS                                                         15

SEQ ID NO: 138           moltype = AA   length = 15
FEATURE                  Location/Qualifiers
source                   1..15
                         mol_type = protein
                         organism = synthetic construct
                         note = Synthetic Construct
SEQUENCE: 138
GGGGSAGGGS GGGGS                                                         15

SEQ ID NO: 139           moltype = AA   length = 15
FEATURE                  Location/Qualifiers
source                   1..15
                         mol_type = protein
                         organism = synthetic construct
                         note = Synthetic Construct
SEQUENCE: 139
GGGGSGGGGS AGGGS                                                         15

SEQ ID NO: 140           moltype = AA   length = 15
FEATURE                  Location/Qualifiers
source                   1..15
                         mol_type = protein
                         organism = synthetic construct
                         note = Synthetic Construct
SEQUENCE: 140
```

```
GGGGSAGGGS AGGGS                                                              15

SEQ ID NO: 141           moltype = AA  length = 15
FEATURE                  Location/Qualifiers
source                   1..15
                         mol_type = protein
                         organism = synthetic construct
                         note = Synthetic Construct SEQUENCE: 141
GGGGDGGGGS GGGGS                                                              15

SEQ ID NO: 142           moltype = AA  length = 15
FEATURE                  Location/Qualifiers
source                   1..15
                         mol_type = protein
                         organism = synthetic construct
                         note = Synthetic Construct SEQUENCE: 142
GGGGSGGGGD GGGGS                                                              15

SEQ ID NO: 143           moltype = AA  length = 15
FEATURE                  Location/Qualifiers
source                   1..15
                         mol_type = protein
                         organism = synthetic construct
                         note = Synthetic Construct SEQUENCE: 143
GGGGDGGGGD GGGGS                                                              15

SEQ ID NO: 144           moltype = AA  length = 15
FEATURE                  Location/Qualifiers
source                   1..15
                         mol_type = protein
                         organism = synthetic construct
                         note = Synthetic Construct SEQUENCE: 144
GGGGEGGGGS GGGGS                                                              15

SEQ ID NO: 145           moltype = AA  length = 15
FEATURE                  Location/Qualifiers
source                   1..15
                         mol_type = protein
                         organism = synthetic construct
                         note = Synthetic Construct SEQUENCE: 145
GGGGSGGGGE GGGGS                                                              15

SEQ ID NO: 146           moltype = AA  length = 15
FEATURE                  Location/Qualifiers
source                   1..15
                         mol_type = protein
                         organism = synthetic construct
                         note = Synthetic Construct SEQUENCE: 146
GGGGEGGGGE GGGGS                                                              15

SEQ ID NO: 147           moltype = AA  length = 5
FEATURE                  Location/Qualifiers
source                   1..5
                         mol_type = protein
                         organism = synthetic construct
                         note = Synthetic Construct SEQUENCE: 147
EVQLV                                                                          5

SEQ ID NO: 148           moltype = AA  length = 11
FEATURE                  Location/Qualifiers
source                   1..11
                         mol_type = protein
                         organism = synthetic construct
                         note = Synthetic Construct SEQUENCE: 148
WGQGTLVTVS S                                                                  11

SEQ ID NO: 149           moltype = AA  length = 115
FEATURE                  Location/Qualifiers
source                   1..115
                         mol_type = protein
                         organism = synthetic construct
```

-continued

```
                        note = Synthetic Construct
SEQUENCE: 149
AVQLVESGGG LVQPGNSLRL SCAASGFTFR SFGMSWVRQA PGKEPEWVSS ISGSGSDTLY    60
ADSVKGRFTI SRDNAKTTLY LQMNSLKPED TAVYYCTIGG SLSRSSQGTQ VTVSS        115

SEQ ID NO: 150          moltype = AA   length = 114
FEATURE                 Location/Qualifiers
source                  1..114
                        mol_type = protein
                        organism = synthetic construct
                        note = Synthetic Construct
SEQUENCE: 150
EVQLVESGGG LVQTGGSLRL SCAASTSGSD FSGKKMAWYR QAPGNGREFV AIIFSNKVTD    60
YADSVKGRFT ISRDNAKKTV YLQMSSLTPT DTAVYYCHDQ EISWGQGTQV TVSS         114

SEQ ID NO: 151          moltype = AA   length = 122
FEATURE                 Location/Qualifiers
source                  1..122
                        mol_type = protein
                        organism = synthetic construct
                        note = Synthetic Construct
SEQUENCE: 151
EVQLVESGGG LVQAGGSLRL SCAASGTSVV INSMGWYRQA PGKQRELVAT IDLSGTTNYA    60
DSAQGRFTIS RDNAENLNLV YLQMNNLNPD DTAVYYCNAL LSRAVSGSYV YWGQGTQVTV   120
SS                                                                  122

SEQ ID NO: 152          moltype = AA   length = 118
FEATURE                 Location/Qualifiers
source                  1..118
                        mol_type = protein
                        organism = synthetic construct
                        note = Synthetic Construct
SEQUENCE: 152
EVQLVESGGG LVQPGGSLRL SCTSRIGTIS NIDLMNWYRQ APGKQREFVA SLQSNGATNY    60
ADSVKGRFTI SRDNAKNTLF LQMNSLNPED TAVYFCHALL PRSPYNSWGQ GTQVTVSS     118

SEQ ID NO: 153          moltype = AA   length = 116
FEATURE                 Location/Qualifiers
source                  1..116
                        mol_type = protein
                        organism = synthetic construct
                        note = Synthetic Construct
SEQUENCE: 153
EVQLVESGGG LVQAGGSLRL SCAASSIIPN IYAMGWYRQA PGKQRELVAS IENGLPANYA    60
DSVKGRFTIS RDNAKNTVFL QMHSLKSEDT AVYYCYAFRP GVPTTWGQGT QVTVSS       116

SEQ ID NO: 154          moltype = AA   length = 116
FEATURE                 Location/Qualifiers
source                  1..116
                        mol_type = protein
                        organism = synthetic construct
                        note = Synthetic Construct
SEQUENCE: 154
EVQLVESGGG LVQAGESLRL SCAASGSISA INAMGWYRQA PGKQREFVAD ITRAGVSDYA    60
DAVKGRFTIS RDNAKNTFYL QMNDLKPEDT AVYYCDALLI AGGVYWGQGT QVTVSS       116

SEQ ID NO: 155          moltype = AA   length = 126
FEATURE                 Location/Qualifiers
source                  1..126
                        mol_type = protein
                        organism = synthetic construct
                        note = Synthetic Construct
SEQUENCE: 155
EVQLVESGGG LVQAGGSLRL SCTASGRTIS TTVMGWFRQA PGKEREFVAA VHWGDGNTVY    60
ADSVKGRFTI SRDDAKNTVY LQLNYLKPED TSVYYCAARP PTYVGTSRNS RSYDWGQGT   120
QVTVSS                                                              126

SEQ ID NO: 156          moltype = AA   length = 125
FEATURE                 Location/Qualifiers
source                  1..125
                        mol_type = protein
                        organism = synthetic construct
                        note = Synthetic Construct
SEQUENCE: 156
EVQLVESGGG LVQAGGSLRL SCVVSGRAID RNAMGWFRQA PGKERESVAA ISASSGNTYY    60
SDSVTGRFTI SRDNTKNTVY LQMNSLKPED TAVYYCAAGS RGSWYLFDRR EYDYWGQGTQ  120
VTVSS                                                               125

SEQ ID NO: 157          moltype = AA   length = 120
```

```
FEATURE                   Location/Qualifiers
source                    1..120
                          mol_type = protein
                          organism = synthetic construct
                          note = Synthetic Construct
SEQUENCE: 157
EVQLVESGGG LVQAGGSLRL TCTASETSFD INVMGWYRQA PGKQRELVAI ITASGNTEYA    60
DSAKGRFTIS RDNTKNTVAM QMNNLKPDDT AVYYCYVLLS GAVSGVYAHW GQGTQVTVSS   120

SEQ ID NO: 158            moltype = AA  length = 130
FEATURE                   Location/Qualifiers
source                    1..130
                          mol_type = protein
                          organism = synthetic construct
                          note = Synthetic Construct
SEQUENCE: 158
EVQLVESGGG LVQAGGSLTL SCAASGRTDS RYAMGWFRQA PGKERELMAA ISWSGRPTYY    60
ADSVKGRFTI SRDNAKNTVS LQMNSLKPED TAVYYCAYKR LPAWTGSAY YSQESEYDYW   120
GQGTQVTVSS                                                          130

SEQ ID NO: 159            moltype = AA  length = 118
FEATURE                   Location/Qualifiers
source                    1..118
                          mol_type = protein
                          organism = synthetic construct
                          note = Synthetic Construct
SEQUENCE: 159
EVQLVESGGG LVQPGGSLRL SCTSRIGTIS NIDLMNWYRQ APGKQREFVA SLQSTGTTDY    60
ADSVKGRFTI SRDNAKNTLF LQMNSLNPED TAVYYCHALI PRSPYNVWGQ GTQVTVSS    118

SEQ ID NO: 160            moltype = AA  length = 126
FEATURE                   Location/Qualifiers
source                    1..126
                          mol_type = protein
                          organism = synthetic construct
                          note = Synthetic Construct
SEQUENCE: 160
EVQLVESGGG LVQAGGSLRL SCTASGRTIS TTVMAWFRQA PGKEREFVAA DHWGDAGTVY    60
ADSVKGRFTI SRDNAKNTVY LQMNYLKPED TSVYYCAARP PTYVGTSRDS RAYDYWGQGT   120
QVTVSS                                                              126

SEQ ID NO: 161            moltype = AA  length = 117
FEATURE                   Location/Qualifiers
source                    1..117
                          mol_type = protein
                          organism = synthetic construct
                          note = Synthetic Construct
SEQUENCE: 161
EVQLVESGGG LVQPGGSLRL SCAASESISS DSPMAWYRQA PGKQREMVAR ILPIGPPDYA    60
DAVKDRFSIS RENAKNTVYL QMNSLKPEDT AVYYCNLLHL PSGLNYWGQG TQVTVSS     117

SEQ ID NO: 162            moltype = AA  length = 109
FEATURE                   Location/Qualifiers
source                    1..109
                          mol_type = protein
                          organism = synthetic construct
                          note = Synthetic Construct
SEQUENCE: 162
EVQLVESGGD LVQAGGSLRL SCVASRSISS AMNWYRQPPG KQRELVALIT RGFNTNYADS    60
VKGRFTISRD NAKNTVYLQM NSLKPEDTGV YYCNSLNYWG QGTQVTVSS              109

SEQ ID NO: 163            moltype = AA  length = 124
FEATURE                   Location/Qualifiers
source                    1..124
                          mol_type = protein
                          organism = synthetic construct
                          note = Synthetic Construct
SEQUENCE: 163
EVQLVESGGG LVQAGGSLRL SCAASGRTDS MWSMGWFRQA PGQEREFVAA ISWSVGTYYE    60
DSVKGRFTLS RDDDKDTAYL EMSDLKLEDT ADYYCAASTR HGTNLVLPRD YDYWGQGTQV   120
TVSS                                                                124

SEQ ID NO: 164            moltype = AA  length = 118
FEATURE                   Location/Qualifiers
source                    1..118
                          mol_type = protein
                          organism = synthetic construct
                          note = Synthetic Construct
SEQUENCE: 164
```

```
EVQLVESGGG LVQPGGSLRL SCTSRIGTIS NIDLMNWYRQ APGKQREFVA SLQSTGTTDY    60
ADSVKGRFTI SRDNAKNTLF LQMNSLNPED TAVYYCHALL PRSPYNAWGQ GTQVTVSS    118

SEQ ID NO: 165          moltype = AA  length = 116
FEATURE                 Location/Qualifiers
source                  1..116
                        mol_type = protein
                        organism = synthetic construct
                        note = Synthetic Construct
SEQUENCE: 165
EVQLVESGGG LVQAGGSLRL SCAASGIIPN IYAMGWYRQA PGKQRELVAS IENGGSTNYA    60
DSVKGRFTIS RDNARNTVFL QMHSLKSEDT AVYYCYAFRP GVPTDWGQGT QVTVSS      116

SEQ ID NO: 166          moltype = AA  length = 118
FEATURE                 Location/Qualifiers
source                  1..118
                        mol_type = protein
                        organism = synthetic construct
                        note = Synthetic Construct
SEQUENCE: 166
EVQLVESGGG LVQAGGSLTL SCVASGRTFS NYRMGWFRQA PGAEREFVGT IYWSTGRSYY    60
GDSVKGRFII SGDNAKNTIH LQMNSLKPED TGVYYCASGP ENSAFDSWGQ GTQVTVSS   118

SEQ ID NO: 167          moltype = AA  length = 124
FEATURE                 Location/Qualifiers
source                  1..124
                        mol_type = protein
                        organism = synthetic construct
                        note = Synthetic Construct
SEQUENCE: 167
EVQLVESGGG LVQAGDSLRL SCAASGRPFS SYTMGWFRQA PGKERDFVAT ISWSGGIKYY    60
ADSVEGRFSI SRDNAKNMVY LQMNSLKPED TAVYYCAATE LRTWSRQTFE YDYWGQGTQV  120
TVSS                                                              124

SEQ ID NO: 168          moltype = AA  length = 126
FEATURE                 Location/Qualifiers
source                  1..126
                        mol_type = protein
                        organism = synthetic construct
                        note = Synthetic Construct
SEQUENCE: 168
EVQLVESGGG LVQAGGSLRL SCTASGRTIS TTVMAWFRQA PGKEREFVAA VHWGDESTVY    60
ADSVKGRFTI SRDNAKNTVY LQMNYLKPED TSVYYCAARP PTYVGSSRSS RAYDYWGQGT  120
QVTVSS                                                            126

SEQ ID NO: 169          moltype = AA  length = 120
FEATURE                 Location/Qualifiers
source                  1..120
                        mol_type = protein
                        organism = synthetic construct
                        note = Synthetic Construct
SEQUENCE: 169
EVQLVESGGG LVQAGGSLRL SCVVSGSILD INVMAWYRQA PGKQREFVAR ITSGGDIDYA    60
DPVKGRFTIS TNGAKNTVYL QMNSLKPEDT AAYYCNVLLS RSSAGRYTHW GQGTQVTVSS  120

SEQ ID NO: 170          moltype = AA  length = 112
FEATURE                 Location/Qualifiers
source                  1..112
                        mol_type = protein
                        organism = synthetic construct
                        note = Synthetic Construct
SEQUENCE: 170
EVQLVESGGG LVQPGGSLRL SCAASGFPFS LYDMGWYRQA PEKQRESVAI ITQSGSTDYA    60
DSVKGRFTIS RDNAKNTLYL QMNSLKPEDT AVYYCRLVGV TWGQGTQVTV SS          112

SEQ ID NO: 171          moltype = AA  length = 120
FEATURE                 Location/Qualifiers
source                  1..120
                        mol_type = protein
                        organism = synthetic construct
                        note = Synthetic Construct
SEQUENCE: 171
EVQLVESGGG LVQAGGSLTL SCAASGRTFS SYGIGWFRQA PGKEREFVAA ISRTGQTTHY    60
ADSIRFTISR DNAKNTVYLQ MNSLKPEDTA VYYCAARTGG PIYGSEYHYW GQGTQVTVSS  120

SEQ ID NO: 172          moltype = AA  length = 124
FEATURE                 Location/Qualifiers
source                  1..124
                        mol_type = protein
```

```
                             organism = synthetic construct
                             note = Synthetic Construct
SEQUENCE: 172
EVQLVESGGG LVQAGDSLTL SCAASGRPFS SLTMGWFRQA PGKGREFVAT TSWSGDIKYY    60
ADFVKGRFTI SRDNAKNMVY LQMNSLKPED TAVYYCAATL LRTWSRQTNE YEYWGQGTQV   120
TVSS                                                                124

SEQ ID NO: 173               moltype = AA  length = 118
FEATURE                      Location/Qualifiers
source                       1..118
                             mol_type = protein
                             organism = synthetic construct
                             note = Synthetic Construct
SEQUENCE: 173
EVQLVESGGG LVQPGGSLRL SCTSRIGTIS NIDLMNWYRQ APGKQREFVA SLQSTGTTDY    60
ADSVRGRFTI SRDNAKNTLF LQMNSLNPED TAVYYCHALL PRSPYNVWGQ GTQVTVSS    118

SEQ ID NO: 174               moltype = AA  length = 132
FEATURE                      Location/Qualifiers
source                       1..132
                             mol_type = protein
                             organism = synthetic construct
                             note = Synthetic Construct
SEQUENCE: 174
EVQLVESGGG LVQAGGSLRL SCAASGRTFS GILSPYAVGW FRQAPGKGRE FVSTITSGGS    60
AIYTDSVKGR FTLSRDNAKD TVYLQMNSLK PEDTAVYYCA VRTRRYGSNL GEVPQENEYG   120
YWGQGTQVTV SS                                                       132

SEQ ID NO: 175               moltype = AA  length = 120
FEATURE                      Location/Qualifiers
source                       1..120
                             mol_type = protein
                             organism = synthetic construct
                             note = Synthetic Construct
SEQUENCE: 175
EVQLVESGGG LVQAGGSLRL SCAAPETGAT INVMAWYRQA PGKQRELVAR VAIDNNTDYA    60
DHAKGRFTIS RDNTKNTVYL QMNNLKPDDT AVYYCNVLLS RQISGSYGHW GQGTQVTVSS   120

SEQ ID NO: 176               moltype = AA  length = 133
FEATURE                      Location/Qualifiers
source                       1..133
                             mol_type = protein
                             organism = synthetic construct
                             note = Synthetic Construct
SEQUENCE: 176
EVQLVESGGG LVQAGGSLTL SCAMSGGTRP FEDYVMAWFR QATGKEREFV ATITWMGETT    60
YYKDSVNGRF AISRDNAENT VALQMNSLEP EDTAVYFCAA HSRSSFSTSG GRYNPRPTEY   120
DYWGQGTQVT VSS                                                      133

SEQ ID NO: 177               moltype = AA  length = 126
FEATURE                      Location/Qualifiers
source                       1..126
                             mol_type = protein
                             organism = synthetic construct
                             note = Synthetic Construct
SEQUENCE: 177
EVQLVESGGG LVQAGGSLRL SCTASGRTIS TTVMGWFRQA PGKEREFVAA VHWGDEGTVY    60
ADSVKGRFTI SRDNAKNTVY LQMNALKPED TSVYYCAAKP PTYVGTSRSS RAYVYWGQGT   120
QVTVSS                                                              126

SEQ ID NO: 178               moltype = AA  length = 120
FEATURE                      Location/Qualifiers
source                       1..120
                             mol_type = protein
                             organism = synthetic construct
                             note = Synthetic Construct
SEQUENCE: 178
EVQLVESGGG LVQAGDSLTL SCAASGSGFS INVMAWYRQA PGKQRDLVAS MTIGGRTNYK    60
DSLKGRFTIS RDNTKNTAYL QMNSLKPEDT AVYYCYALLD RGIGGNYVYW GQGTQVTVSS   120

SEQ ID NO: 179               moltype = AA  length = 125
FEATURE                      Location/Qualifiers
source                       1..125
                             mol_type = protein
                             organism = synthetic construct
                             note = Synthetic Construct
SEQUENCE: 179
EVQLVESGGG LVQAGGSLRL SCAASGLTFS DYYMGWFRQA PGKERDFLAR IGKSGIGKSY    60
ADSVRGRFTI SRDNAKNTVY LQMNNLKLED TAVYYCAADR DIAYDARLTA EYDYWGQGTQ   120
```

```
VTVSS                                                                            125

SEQ ID NO: 180            moltype = AA  length = 126
FEATURE                   Location/Qualifiers
source                    1..126
                          mol_type = protein
                          organism = synthetic construct
                          note = Synthetic Construct
SEQUENCE: 180
EVQLVESGGG LVQAGGSLRL SCTASGRTIS TTVMGWFRQA PGKEREFVAA VHWGDESTVY    60
ADSVKGRFTI SRDNAKNTVY LQMNYLKPED TAVYYCAARP PTYVGTSRSS RAYDYWGQGT   120
QVTVSS                                                              126

SEQ ID NO: 181            moltype = AA  length = 123
FEATURE                   Location/Qualifiers
source                    1..123
                          mol_type = protein
                          organism = synthetic construct
                          note = Synthetic Construct
SEQUENCE: 181
EVQLVESGGG LVQAGGSLRL SCAASVASET IVSINDMAWY RQAPGKQREL VASITIHNNR    60
DYADSAKGRF TISRDDTKNT VYLQMTHLKP DDTAVYYCTV LLSRALSGSY RFWGQGTQVT   120
VSS                                                                 123

SEQ ID NO: 182            moltype = AA  length = 123
FEATURE                   Location/Qualifiers
source                    1..123
                          mol_type = protein
                          organism = synthetic construct
                          note = Synthetic Construct
SEQUENCE: 182
EVQLVESGGG LVQAGGSLRL SCTGSETSGT IFNINVMGWY RQAPGKQREL VAIMDIGGTT    60
DYADSVKGRF TISRDNAKNT VYVQMNNLKS EDTAVYYCYC ALDRAVAGRY TYWGQGTQVT   120
VSS                                                                 123

SEQ ID NO: 183            moltype = AA  length = 124
FEATURE                   Location/Qualifiers
source                    1..124
                          mol_type = protein
                          organism = synthetic construct
                          note = Synthetic Construct
SEQUENCE: 183
EVQLVESGGG LVQPGGSLRL SCEASGISLN DYNMGWFRQA PGKDREIVAA LSRRSHGIYQ    60
SDSVKYRFSI SRDNTKNMVS LQMDSLRPED TAVYYCAADG DPYFTGRDMN PEYWGQGTQV   120
TVSS                                                                124

SEQ ID NO: 184            moltype = AA  length = 124
FEATURE                   Location/Qualifiers
source                    1..124
                          mol_type = protein
                          organism = synthetic construct
                          note = Synthetic Construct
SEQUENCE: 184
EVQLVESGGG SVQAGGSLRL SCAFSGGRFS DYGMAWFRQG PGKEREFVSR ISGNGRGTQY    60
TDSVSGRFII SRDNDKNTVY LQMNDLKVED TAIYYCARGS GPSSFNEGSV YDYWGQGTQV   120
TVSS                                                                124

SEQ ID NO: 185            moltype = AA  length = 113
FEATURE                   Location/Qualifiers
source                    1..113
                          mol_type = protein
                          organism = synthetic construct
                          note = Synthetic Construct
SEQUENCE: 185
EVQLVESGGG LVQSGGSLTL SCVLSGSIFS SNTMGWHRQA PGKQREWVAI TTSGGTTKYA    60
DSVKGRFTIS RDNAKNTVYL RMNNLKPEDT GVYFCYASLA GIWGQGTQVT VSS          113

SEQ ID NO: 186            moltype = AA  length = 120
FEATURE                   Location/Qualifiers
source                    1..120
                          mol_type = protein
                          organism = synthetic construct
                          note = Synthetic Construct
SEQUENCE: 186
EVQLVESGGG LVQAGGSLRL SCAAPETEAT YNVMGWYRRA PGKQRELVAT MTIDYNTNYA    60
DSAKGRFTIS RDNTKNTVYL QMNNLRPDDT AVYYCRVDLS RQISGSYNYW GQGTQVTVSS   120

SEQ ID NO: 187            moltype = AA  length = 125
FEATURE                   Location/Qualifiers
```

```
source                  1..125
                        mol_type = protein
                        organism = synthetic construct
                        note = Synthetic Construct
SEQUENCE: 187
EVQLVESGGG LVQPGESLRL SCAISGFAFT DVGMSWVRQA PGKGLEWVSS ISSGSSITTY    60
SDSVKGRFTI SRDNARNTLF LQMNSLKPED TAVYYCGRYY CTGLGCHPRR DSALWGQGTQ   120
VTVSS                                                                125

SEQ ID NO: 188          moltype = AA   length = 127
FEATURE                 Location/Qualifiers
source                  1..127
                        mol_type = protein
                        organism = synthetic construct
                        note = Synthetic Construct
SEQUENCE: 188
EVQLVESGGG LVQPGGSLRL SCRASGFTYS TAAMGWVRQA PGKGLEWVSS ISSLGSDRKS    60
ADSVKGRFTI SRDNAKNTLY LQMNSLKPED TAVYYCARFI SNRWSRDVHA PSDFGSRGQG   120
TQVTVSS                                                              127

SEQ ID NO: 189          moltype = AA   length = 122
FEATURE                 Location/Qualifiers
source                  1..122
                        mol_type = protein
                        organism = synthetic construct
                        note = Synthetic Construct
SEQUENCE: 189
EVQLVESGGG SVPAGGSLRL SCAAFGFTFD NYAIAWFRQA PGKEREGVSC LSTNDGETYY    60
ADSVKGRFTI SSDHAKNTVY LQMDSLRPED TAVYYCAAAE GSWCHKYEYD YWGQGTQVTV   120
SS                                                                   122

SEQ ID NO: 190          moltype = AA   length = 125
FEATURE                 Location/Qualifiers
source                  1..125
                        mol_type = protein
                        organism = synthetic construct
                        note = Synthetic Construct
SEQUENCE: 190
EVQLVESGGG LVQAGESLRL SCAASGRTSD LYVVGWFRQT PGKEREFVAG IAWTGDASYY    60
ADSVEGRFTI ARDNAENRID LQMTSLKPED TAVYYCAADS RARFERQRYN DMNYWGQGTQ   120
VTVSS                                                                125

SEQ ID NO: 191          moltype = AA   length = 120
FEATURE                 Location/Qualifiers
source                  1..120
                        mol_type = protein
                        organism = synthetic construct
                        note = Synthetic Construct
SEQUENCE: 191
EVQLVESGGG LVQAGGSLRL SCIASVTIAD INVMGWYRQA PGKQREFVAS IPTTGDKNYA    60
ESAKGRFTIS RDNSQNTVAM QMNNLKPDDT AVYYCYVLLS RAVSGSYGHW GQGTQVTVSS   120

SEQ ID NO: 192          moltype = AA   length = 123
FEATURE                 Location/Qualifiers
source                  1..123
                        mol_type = protein
                        organism = synthetic construct
                        note = Synthetic Construct
SEQUENCE: 192
EVQLVESGGG LVQVGGSLRL SCAASGSIVD IKVMGWYRQA PGNERELVAL INDADDSEYS    60
PSMRGRFTIS RDNSKNTVYL QMNSLKPEDT AAYYCAADRD SSWFKSPYIP GSWGQGTQVT   120
VSS                                                                  123

SEQ ID NO: 193          moltype = AA   length = 120
FEATURE                 Location/Qualifiers
source                  1..120
                        mol_type = protein
                        organism = synthetic construct
                        note = Synthetic Construct
SEQUENCE: 193
EVQLVESGGG LVQAGGSLRL SCAAPEMGAT INVMAWYRQA PGKQRELVAR LPLDNNIDYG    60
DFAKGRFTIS RDITRNTVYL QMNNLKPDDT AVYYCNVLLS RQINGAYVHW GQGTQVTVSS   120

SEQ ID NO: 194          moltype = AA   length = 120
FEATURE                 Location/Qualifiers
source                  1..120
                        mol_type = protein
                        organism = synthetic construct
                        note = Synthetic Construct
```

```
SEQUENCE: 194
EVQLVESGGG LVQAGGSLRL SCAASGIDGD INVMAWYRQA PGKQRELVAS ITIGGNTNYA   60
DSVKGRFTIA RDNAKNRMSL EMNSLKSEDT AVYYCNTLLS RVHDGQYVFW GQGTQVTVSS  120

SEQ ID NO: 195          moltype = AA  length = 125
FEATURE                 Location/Qualifiers
source                  1..125
                        mol_type = protein
                        organism = synthetic construct
                        note = Synthetic Construct
SEQUENCE: 195
EVQLVESGGG LVQAGGSLRL SCVASEDAFK TDTLGWFRQA PGEEREFVAA FVWAGGPFYA   60
DSVKGRFTIS MDEDRNTVYL QMNSLKPEDT GVYYCAASLS RLRVGEITPR HMNYWGQGTQ  120
VTVSS                                                              125

SEQ ID NO: 196          moltype = AA  length = 126
FEATURE                 Location/Qualifiers
source                  1..126
                        mol_type = protein
                        organism = synthetic construct
                        note = Synthetic Construct
SEQUENCE: 196
EVQLVESGGG LVQAGGSLRL SCAASGRAFS DYAMAWFRQA PGKEREFVAG IGWSGGDTLY   60
ADSVRGRFTN SKDNAKNRMS LQMNSLKPED TAVYYCAARQ GQYIYSSMRS DSYDWGQGT   120
QVTVSS                                                             126

SEQ ID NO: 197          moltype = AA  length = 124
FEATURE                 Location/Qualifiers
source                  1..124
                        mol_type = protein
                        organism = synthetic construct
                        note = Synthetic Construct
SEQUENCE: 197
EVQLVESGGG LVQAGGSLRL SCAASGRTFS SSNMGWFRQA PGEEREFVTA IDWSGGRTYY   60
ADSVKGRFTI SRDNAKNTVY LQMDSLKPED TAVYYCAAQG SGLDWGYPWT YDYWGQGTQV  120
TVSS                                                               124

SEQ ID NO: 198          moltype = AA  length = 115
FEATURE                 Location/Qualifiers
source                  1..115
                        mol_type = protein
                        organism = synthetic construct
                        note = Synthetic Construct
SEQUENCE: 198
EVQLVESGGG LVQPGGSLKL SCATSGSVLN IDSMAWYRQA PGKQRELVAE MLWGGTKNYG   60
DSVKGRFTIS GDADWGTELQ MSSLKPEDTA VYYCNAVGRG FRDAWGQGTQ VTVSS        115

SEQ ID NO: 199          moltype = AA  length = 116
FEATURE                 Location/Qualifiers
source                  1..116
                        mol_type = protein
                        organism = synthetic construct
                        note = Synthetic Construct
SEQUENCE: 199
EVQLVESGGG LVQAGGSLRL SCVASGSGFG ILDMGWYRQA PGSRRELVGY VTRDGTTNYG   60
NSVKGRSIIS EDITKNTVIL QMNSLKPEDT AVYFCTAGLT NQPRAWGQGT QVTVSS       116

SEQ ID NO: 200          moltype = AA  length = 119
FEATURE                 Location/Qualifiers
source                  1..119
                        mol_type = protein
                        organism = synthetic construct
                        note = Synthetic Construct
SEQUENCE: 200
EVQLVESGGG LVQPGGSLRL SCAASGSVSS INVMGWYRQT PGKQRELVAA INRGGSTNVA   60
DSVKGRFTIS RDNAKNTVYL QMNSLKPEDT AVYYCNAEPY GLDWRYDYWG QGTQVTVSS   119

SEQ ID NO: 201          moltype = AA  length = 129
FEATURE                 Location/Qualifiers
source                  1..129
                        mol_type = protein
                        organism = synthetic construct
                        note = Synthetic Construct
SEQUENCE: 201
EVQLVESGGG LEQAGGSLRL SCTASGGTDS IYQMGWFRQT PGKEREFVAA INWNYGGAYY   60
PDSVKGRFTI SRDKAKNIGF LQMNSLKPED TAVYYCATSQ TSVDAFSVPI TTARRYQYWG  120
QGTQVTVSS                                                          129

SEQ ID NO: 202          moltype = AA  length = 118
```

| FEATURE | Location/Qualifiers |
|---|---|
| source | 1..118<br>mol_type = protein<br>organism = synthetic construct<br>note = Synthetic Construct |

SEQUENCE: 202
```
EVQLVESGGG LVQAGGSLTL SCVASGRTFS NYRMGWFRQA PGKEREFVGT IYWSTGRSYY   60
GDSVKGRFII SGDNAKNTIH LQMNSLKPGD TGVYYCASGP EMSAFDSWGQ GTQVTVSS    118
```

| SEQ ID NO: 203 | moltype = AA length = 127 |
|---|---|
| FEATURE | Location/Qualifiers |
| source | 1..127<br>mol_type = protein<br>organism = synthetic construct<br>note = Synthetic Construct |

SEQUENCE: 203
```
EVQLVESGGG LVQPGGSLRL SCAASGFTLD DYAIGWFRQA PGKEREGVSC ISSSDGSTYY   60
GDSVKGRFTI SRDNAKNTMY LQMNSLKPED TAVYYCATGT PLSSYYGSCL DYDMAYWGQG  120
TQVTVSS                                                           127
```

| SEQ ID NO: 204 | moltype = AA length = 124 |
|---|---|
| FEATURE | Location/Qualifiers |
| source | 1..124<br>mol_type = protein<br>organism = synthetic construct<br>note = Synthetic Construct |

SEQUENCE: 204
```
EVQLVESGGG LVQAGGSLRL SCAASGVTFS NYGMAWFRQA PEKEREFVAR ISSNGRRTEY   60
ADGVSGRFTI SRDNAKNTVY LQMNGLKPED TAVYYCARAA GPSGFHEQSI YDDWGQGTQV  120
TVSS                                                              124
```

| SEQ ID NO: 205 | moltype = AA length = 123 |
|---|---|
| FEATURE | Location/Qualifiers |
| source | 1..123<br>mol_type = protein<br>organism = synthetic construct<br>note = Synthetic Construct |

SEQUENCE: 205
```
EVQLVESGGG LVQAGGSLRL SCAVSGRSIS TYVAGWFRQG PGKEREFVAL ISRGGGDIQY   60
SDSVKGRFTI SRDNAKNAVY LQMNSLKPAD TAVYYCSLDA SFGSRLVSRW DYWGQGTQVT  120
VSS                                                               123
```

| SEQ ID NO: 206 | moltype = AA length = 128 |
|---|---|
| FEATURE | Location/Qualifiers |
| source | 1..128<br>mol_type = protein<br>organism = synthetic construct<br>note = Synthetic Construct |

SEQUENCE: 206
```
EVQLVESGGG VVQAGDSLTL TCTAPVGTIS DYGMGWFRQA PGKEREFVAS ISWGGMWTDY   60
ADSVKGRFTI SRDNDKNAVY LRMNSLNAED TAVYYCGRGR MYRGIGNSLA QPKSYGYWGQ  120
GTQVTVSS                                                          128
```

| SEQ ID NO: 207 | moltype = AA length = 126 |
|---|---|
| FEATURE | Location/Qualifiers |
| source | 1..126<br>mol_type = protein<br>organism = synthetic construct<br>note = Synthetic Construct |

SEQUENCE: 207
```
EVQLVESGGG LVQAGGSLRL SCAGSGFTSD DYAIAWFRQA PGKEREGVSC IGSGDGTTYY   60
ADSVKGRFII SSENAKKTVY LQMNSLKPED TGIYYCAADL YPPADYALDH TWYDYWGQGT  120
QVTVSS                                                            126
```

| SEQ ID NO: 208 | moltype = AA length = 113 |
|---|---|
| FEATURE | Location/Qualifiers |
| source | 1..113<br>mol_type = protein<br>organism = synthetic construct<br>note = Synthetic Construct |

SEQUENCE: 208
```
EVQLVESGGG VVQPGGSLRL SCVVSGRFS LDTVGWHHQA PGKLRELVAR IRDDGDTMYV   60
ASVKGRFIIS RDDAKNTVYL QMNSLKPEDT GVYYCYFSRN GAWGQGTQVT VSS         113
```

| SEQ ID NO: 209 | moltype = AA length = 120 |
|---|---|
| FEATURE | Location/Qualifiers |
| source | 1..120<br>mol_type = protein<br>organism = synthetic construct |

```
                          note = Synthetic Construct
SEQUENCE: 209
EVQLVESGGG LVQAGGSLRL SCGASGRISD INVMGWYRQA PGKQREMVAD IDIRGYTNYA    60
DSVKGRFTVS RDNAETMYLE MNSLKPEDTA VYRCNALTSR DWGTGKYVYW GQGTQVTVSS   120

SEQ ID NO: 210            moltype = AA  length = 111
FEATURE                   Location/Qualifiers
source                    1..111
                          mol_type = protein
                          organism = synthetic construct
                          note = Synthetic Construct
SEQUENCE: 210
EVQLVESGGD LVQVGGSLRL SCAFPGSMSS RNSVNWYRQP PGKQREWVAT ISVSGFTQYA    60
DSAKGRFTIS RDSAKNTVHL QMNSLKPEDT GVYYCNYMDY WGQGTQVTVS S            111

SEQ ID NO: 211            moltype = AA  length = 113
FEATURE                   Location/Qualifiers
source                    1..113
                          mol_type = protein
                          organism = synthetic construct
                          note = Synthetic Construct
SEQUENCE: 211
EVQLVESGGG VVRAGGSLKL SCTAAGTDIN IVTVGWHRQA PGKHRELVAT IVGSGSRTNY    60
ADSVKGRFTI SRDNPKNTVY LQMNSLKPED TAVYYCYATS IGWGQGTQVT VSS          113

SEQ ID NO: 212            moltype = AA  length = 132
FEATURE                   Location/Qualifiers
source                    1..132
                          mol_type = protein
                          organism = synthetic construct
                          note = Synthetic Construct
SEQUENCE: 212
EVQLVESGGG LVQAGGSLRL SCAASGRTFS GILSAYAVGW FRQAPGKERE FVSTITSGGS    60
TLSADSVKGR FTLSRDNAKD TVYLQMNSLK PEDTAVYYCA VRTWPYGSNR GEVPTENEYG   120
HWGQGTQVTV SS                                                      132

SEQ ID NO: 213            moltype = AA  length = 118
FEATURE                   Location/Qualifiers
source                    1..118
                          mol_type = protein
                          organism = synthetic construct
                          note = Synthetic Construct
SEQUENCE: 213
EVQLVESGGG SVQAGGSLRL TCTASGNVRS IFTMAWYRQA PGKQRELVAS AAKGGDTYYA    60
DSAKGRFTIS RDDAKAIVSL QMNSLKPEDT AVYYCKTDGR PWFSEDYWGQ GTQVTVSS     118

SEQ ID NO: 214            moltype = AA  length = 111
FEATURE                   Location/Qualifiers
source                    1..111
                          mol_type = protein
                          organism = synthetic construct
                          note = Synthetic Construct
SEQUENCE: 214
EVQLVESGGG LVQVGDSMRL SCAVFGNIFT RDPVMWFRQP PGKQREWVAT ITPSGFANYA    60
DSVKGRFTIS RYAANNTVHL QMNSLKPEDT GVYFCNFGTY WGQGTQVTVS S            111

SEQ ID NO: 215            moltype = AA  length = 120
FEATURE                   Location/Qualifiers
source                    1..120
                          mol_type = protein
                          organism = synthetic construct
                          note = Synthetic Construct
SEQUENCE: 215
EVQLVESGGG LVQAGGSLRL SCAASKGAFN INVMAWYRQA PGKQRELVAR VALGGTTDYA    60
DSVKGRFTIS RNNAQDTVYL QMNSLKPEDT AVYYCNVLLD RGVRGSYAYW GQGTQVTVSS   120

SEQ ID NO: 216            moltype = AA  length = 122
FEATURE                   Location/Qualifiers
source                    1..122
                          mol_type = protein
                          organism = synthetic construct
                          note = Synthetic Construct
SEQUENCE: 216
EVQLVESGGG LVQAGGSLRL SCAASGRTYS SYVIGWFRQA PGKEREFVAS IRWAGGDSHY    60
QESVKGRSTI SKDNARNTVY LQMNSLKPED TAVYYCAGAA PVPGQSYEWS SWGQGTQVTV   120
SS                                                                 122

SEQ ID NO: 217            moltype = AA  length = 121
FEATURE                   Location/Qualifiers
```

```
source                    1..121
                          mol_type = protein
                          organism = synthetic construct
                          note = Synthetic Construct
SEQUENCE: 217
EVQLVESGGG LVQAGGSLRL SCVASGSAFY VGPMAWYRQA PGKERESVAS ITKGGITNYA    60
DSVKGRFTIS RDNAKNTVYL QMNSLKPEDT DVYVCNARVK LQEDRLFRDY WGQGTQVTVS   120
S                                                                   121

SEQ ID NO: 218            moltype = AA   length = 116
FEATURE                   Location/Qualifiers
source                    1..116
                          mol_type = protein
                          organism = synthetic construct
                          note = Synthetic Construct
SEQUENCE: 218
EVQLVESGGG MVQPGGSLRL SCVVSGASGN IDFVTVGWHR QAPGKHREMV AVITGDGTRN    60
YRDSVKGRFS ISRDNAKNTI YLQMNSLKPE DTAVYYCYMS NPISSWGQGT QVTVSS       116

SEQ ID NO: 219            moltype = AA   length = 126
FEATURE                   Location/Qualifiers
source                    1..126
                          mol_type = protein
                          organism = synthetic construct
                          note = Synthetic Construct
SEQUENCE: 219
EVQLVESGGG LVQAGGSRRL SCAVSGRTLS SFGMGWFRQA PEKPREFVAA ITWQGGTFY     60
ADSVKGRFTI SRDIVKNTVY LQMNDLKPDD TGLYFCVSAP HFHEAFPSRP PAYAYWGQGT   120
QVTVSS                                                              126

SEQ ID NO: 220            moltype = AA   length = 122
FEATURE                   Location/Qualifiers
source                    1..122
                          mol_type = protein
                          organism = synthetic construct
                          note = Synthetic Construct
SEQUENCE: 220
EVQLVESGGG LVQAGGSLRL SCAASGRTYG SYVIGWFRQA PGKEREFVAS IRWAGGDSHY    60
GDPLKGRSTI SKDNAKNTVY LQMNSLKPED AAVYYCAGAA PVPGSSYEWT NWGQGTQVTV   120
SS                                                                  122

SEQ ID NO: 221            moltype = AA   length = 120
FEATURE                   Location/Qualifiers
source                    1..120
                          mol_type = protein
                          organism = synthetic construct
                          note = Synthetic Construct
SEQUENCE: 221
EVQLVESGGG LVQAGGSLRL SCAASGSISS VNTMGWYRQA PGKQRELVAF ITSGDDTNYA    60
DSMKGRFTIS RDNAKNTLYL QMNSLKPEDT AVYYCVATLG RSSSGTYTYW GQGTQVTVSS   120

SEQ ID NO: 222            moltype = AA   length = 127
FEATURE                   Location/Qualifiers
source                    1..127
                          mol_type = protein
                          organism = synthetic construct
                          note = Synthetic Construct
SEQUENCE: 222
EVQLVESGGG LVQAGGSLRL SCAASLRTLD NYGVGWFRQT PGREREFVSA VSWNGDRTYY    60
QDSVKGRFTI SREYAKNTVY LQMDSLKPED TAVYYCAVNM YGSTFPGLSV ESHYDYWGQG   120
TQVTVSS                                                             127

SEQ ID NO: 223            moltype = AA   length = 117
FEATURE                   Location/Qualifiers
source                    1..117
                          mol_type = protein
                          organism = synthetic construct
                          note = Synthetic Construct
SEQUENCE: 223
EVQLVESGGG LVQAGGSLRL SCAASGSIFS INAMAWYRQA QGKQRELVAD ITKNDITDYA    60
DSVKGRFTIA RDNAKNTVDL QMNSLKPEDT AVYYCTAALS RHPYRSWGQG TQVTVSS      117

SEQ ID NO: 224            moltype = AA   length = 122
FEATURE                   Location/Qualifiers
source                    1..122
                          mol_type = protein
                          organism = synthetic construct
                          note = Synthetic Construct
SEQUENCE: 224
```

```
EVQLVESGGG LVQAGGSLRL SCAAAGRSLS DYYIIWFRQP PGKEYEFVSS IRWNTGSTTY    60
GDSVKGRFTI SRDNAKSTVY LQMNSLKPED TALYWCAAGL HLTPTSRTYN YRGQGTQVTV   120
SS                                                                 122

SEQ ID NO: 225          moltype = AA  length = 120
FEATURE                 Location/Qualifiers
source                  1..120
                        mol_type = protein
                        organism = synthetic construct
                        note = Synthetic Construct
SEQUENCE: 225
EVQLVESGGG LVQAGGSLRL SCAAPETIFT INSMGWYRQA PGKQRELVAF INLDGNTNYA    60
DSAKGRFTIS RDNAENTVYL QMDNLKPDDT AVYYCNVLLS RAISGSYVHW GQGTQVTVSS   120

SEQ ID NO: 226          moltype = AA  length = 132
FEATURE                 Location/Qualifiers
source                  1..132
                        mol_type = protein
                        organism = synthetic construct
                        note = Synthetic Construct
SEQUENCE: 226
EVQLVESGGG LVQPGGSLRL SCAASGRTFS GILSPYAVGW FRQAPGQGLE AVATITSGGS    60
AIYTDSVKGR FTISRDNSKN TLYLQMNSLR AEDTAVYYCA VRTRRYGSNL GEVPQENEYG   120
YWGQGTLVTV SS                                                      132

SEQ ID NO: 227          moltype = AA  length = 120
FEATURE                 Location/Qualifiers
source                  1..120
                        mol_type = protein
                        organism = synthetic construct
                        note = Synthetic Construct
SEQUENCE: 227
EVQLVESGGG LVQPGGSLRL SCAASEMGAT INVMAWFRQA PGQGLEAVAR LPLDNNIDYG    60
DFAKGRFTIS RDNSKNTLYL QMNSLRAEDT AVYYCNVLLS RQINGAYVHW GQGTLVTVSS   120

SEQ ID NO: 228          moltype = AA  length = 126
FEATURE                 Location/Qualifiers
source                  1..126
                        mol_type = protein
                        organism = synthetic construct
                        note = Synthetic Construct
SEQUENCE: 228
EVQLVESGGG LVQPGGSLRL SCAASGRAFS DYAMAWFRQA PGQGLEAVAG IGWSGGDTLY    60
ADSVRGRFTI SRDNSKNTLY LQMNSLRAED TAVYYCAARQ GQYIYSSMRS DSYDYWGQGT   120
LVTVSS                                                             126

SEQ ID NO: 229          moltype = AA  length = 132
FEATURE                 Location/Qualifiers
source                  1..132
                        mol_type = protein
                        organism = synthetic construct
                        note = Synthetic Construct
SEQUENCE: 229
EVQLVESGGG LVQPGGSLRL SCAASGRTFS GILSPYAVGW FRQAPGQGRE FVATITSGGS    60
AIYTDSVKGR FTISRDNSKN TLYLQMNSLR AEDTAVYYCA VRTRRYGSNL GEVPQENEYG   120
YWGQGTLVTV SS                                                      132

SEQ ID NO: 230          moltype = AA  length = 120
FEATURE                 Location/Qualifiers
source                  1..120
                        mol_type = protein
                        organism = synthetic construct
                        note = Synthetic Construct
SEQUENCE: 230
EVQLVESGGG LVQPGGSLRL SCAAPEMGAT INVMAWYRQA PGQQRELVAR LPLDNNIDYG    60
DFAKGRFTIS RDNSKNTLYL QMNSLRAEDT AVYYCNVLLS RQINGAYVHW GQGTLVTVSS   120

SEQ ID NO: 231          moltype = AA  length = 126
FEATURE                 Location/Qualifiers
source                  1..126
                        mol_type = protein
                        organism = synthetic construct
                        note = Synthetic Construct
SEQUENCE: 231
EVQLVESGGG LVQPGGSLRL SCAASGRAFS DYAMAWFRQA PGQEREFVAG IGWSGGDTLY    60
ADSVRGRFTI SRDNSKNTLY LQMNSLRAED TAVYYCAARQ GQYIYSSMRS DSYDYWGQGT   120
LVTVSS                                                             126

SEQ ID NO: 232          moltype = AA  length = 132
```

```
FEATURE                  Location/Qualifiers
source                   1..132
                         mol_type = protein
                         organism = synthetic construct
                         note = Synthetic Construct
SEQUENCE: 232
EVQLVESGGG LVQPGGSLRL SCAASGRTFS GILSPYAVGW FRQAPGKGRE FVSTITSGGS   60
AIYTDSVKGR FTISRDNAKN SLYLQMNSLR AEDTAVYYCA VRTRRYGSNL GEVPQENEYG  120
YWGQGTLVTV SS                                                      132

SEQ ID NO: 233           moltype = AA  length = 132
FEATURE                  Location/Qualifiers
source                   1..132
                         mol_type = protein
                         organism = synthetic construct
                         note = Synthetic Construct
SEQUENCE: 233
EVQLVESGGG LVQPGGSLRL SCAASGRTFS GILSPYAVGW FRQAPGKGLE FVSTITSGGS   60
AIYTDSVKGR FTISRDNAKN SLYLQMNSLR AEDTAVYYCA VRTRRYGSNL GEVPQENEYG  120
YWGQGTLVTV SS                                                      132

SEQ ID NO: 234           moltype = AA  length = 120
FEATURE                  Location/Qualifiers
source                   1..120
                         mol_type = protein
                         organism = synthetic construct
                         note = Synthetic Construct
SEQUENCE: 234
EVQLVESGGG LVKPGGSLRL SCAASEMGAT INVMAWYRQA PGKQRELVSR LPLDNNIDYG   60
DFAKGRFTIS RDNAKNSLYL QMNSLRAEDT AVYYCNVLLS RQINGAYVHW GQGTLVTVSS  120

SEQ ID NO: 235           moltype = AA  length = 120
FEATURE                  Location/Qualifiers
source                   1..120
                         mol_type = protein
                         organism = synthetic construct
                         note = Synthetic Construct
SEQUENCE: 235
EVQLVESGGG LVKPGGSLRL SCAASEMGAT INVMAWYRQA PGKGLELVSR LPLDNNIDYG   60
DFAKGRFTIS RDNAKNSLYL QMNSLRAEDT AVYYCNVLLS RQINGAYVHW GQGTLVTVSS  120

SEQ ID NO: 236           moltype = AA  length = 126
FEATURE                  Location/Qualifiers
source                   1..126
                         mol_type = protein
                         organism = synthetic construct
                         note = Synthetic Construct
SEQUENCE: 236
EVQLVESGGG LVQPGRSLRL SCAASGRAFS DYAMAWFRQA PGKEREFVSG IGWSGGDTLY   60
ADSVRGRFTI SRDNAKNSLY LQMNSLRAED TALYYCAARQ GQYIYSSMRS DSYDYWGQGT  120
LVTVSS                                                             126

SEQ ID NO: 237           moltype = AA  length = 126
FEATURE                  Location/Qualifiers
source                   1..126
                         mol_type = protein
                         organism = synthetic construct
                         note = Synthetic Construct
SEQUENCE: 237
EVQLVESGGG LVQPGRSLRL SCAASGRAFS DYAMAWFRQA PGKGLEFVSG IGWSGGDTLY   60
ADSVRGRFTI SRDNAKNSLY LQMNSLRAED TALYYCAARQ GQYIYSSMRS DSYDYWGQGT  120
LVTVSS                                                             126

SEQ ID NO: 238           moltype = AA  length = 128
FEATURE                  Location/Qualifiers
source                   1..128
                         mol_type = protein
                         organism = synthetic construct
                         note = Synthetic Construct
SEQUENCE: 238
EVQLVESGGG LVQPGGSLRL SCAASVGTIS DYGMGWFRQA PGQGLEAVAS ISWGGMWTDY   60
ADSVKGRFTI SRDNSKNTLY LQMNSLRAED TAVYYCGRGR MYRGIGNSLA QPKSYGYWGQ  120
GTLVTVSS                                                           128

SEQ ID NO: 239           moltype = AA  length = 132
FEATURE                  Location/Qualifiers
source                   1..132
                         mol_type = protein
                         organism = synthetic construct
```

```
                            note = Synthetic Construct
SEQUENCE: 239
EVQLVESGGG LVQPGGSLRL SCAASGRTFS GILSAYAVGW FRQAPGQGLE AVATITSGGS    60
TLSADSVKGR FTISRDNSKN TLYLQMNSLR AEDTAVYYCA VRTWPYGSNR GEVPTENEYG   120
HWGQGTLVTV SS                                                      132

SEQ ID NO: 240          moltype = AA  length = 128
FEATURE                 Location/Qualifiers
source                  1..128
                        mol_type = protein
                        organism = synthetic construct
                        note = Synthetic Construct
SEQUENCE: 240
EVQLVESGGG LVQPGGSLRL SCAASVGTIS DYGMGWFRQA PGQEREFVAS ISWGGMWTDY    60
ADSVKGRFTI SRDNSKNTLY LQMNSLRAED TAVYYCGRGR MYRGIGNSLA QPKSYGYWGQ  120
GTLVTVSS                                                           128

SEQ ID NO: 241          moltype = AA  length = 132
FEATURE                 Location/Qualifiers
source                  1..132
                        mol_type = protein
                        organism = synthetic construct
                        note = Synthetic Construct
SEQUENCE: 241
EVQLVESGGG LVQPGGSLRL SCAASGRTFS GILSAYAVGW FRQAPGQERE FVATITSGGS    60
TLSADSVKGR FTISRDNSKN TLYLQMNSLR AEDTAVYYCA VRTWPYGSNR GEVPTENEYG   120
HWGQGTLVTV SS                                                      132

SEQ ID NO: 242          moltype = AA  length = 128
FEATURE                 Location/Qualifiers
source                  1..128
                        mol_type = protein
                        organism = synthetic construct
                        note = Synthetic Construct
SEQUENCE: 242
EVQLVESGGG LVKPGGSLRL SCAASVGTIS DYGMGWFRQA PGKEREFVSS ISWGGMWTDY    60
ADSVKGRFTI SRDNAKNSLY LQMNSLRAED TAVYYCGRGR MYRGIGNSLA QPKSYGYWGQ  120
GTLVTVSS                                                           128

SEQ ID NO: 243          moltype = AA  length = 128
FEATURE                 Location/Qualifiers
source                  1..128
                        mol_type = protein
                        organism = synthetic construct
                        note = Synthetic Construct
SEQUENCE: 243
EVQLVESGGG LVKPGGSLRL SCAASVGTIS DYGMGWFRQA PGKGLEFVSS ISWGGMWTDY    60
ADSVKGRFTI SRDNAKNSLY LQMNSLRAED TAVYYCGRGR MYRGIGNSLA QPKSYGYWGQ  120
GTLVTVSS                                                           128

SEQ ID NO: 244          moltype = AA  length = 132
FEATURE                 Location/Qualifiers
source                  1..132
                        mol_type = protein
                        organism = synthetic construct
                        note = Synthetic Construct
SEQUENCE: 244
EVQLLESGGG LVQPGGSLRL SCAASGRTFS GILSAYAVGW FRQAPGKERE FVSTITSGGS    60
TLSADSVKGR FTISRDNSKN TLYLQMNSLR AEDTAVYYCA VRTWPYGSNR GEVPTENEYG   120
HWGQGTLVTV SS                                                      132

SEQ ID NO: 245          moltype = AA  length = 132
FEATURE                 Location/Qualifiers
source                  1..132
                        mol_type = protein
                        organism = synthetic construct
                        note = Synthetic Construct
SEQUENCE: 245
EVQLLESGGG LVQPGGSLRL SCAASGRTFS GILSAYAVGW FRQAPGKGLE FVSTITSGGS    60
TLSADSVKGR FTISRDNSKN TLYLQMNSLR AEDTAVYYCA VRTWPYGSNR GEVPTENEYG   120
HWGQGTLVTV SS                                                      132

SEQ ID NO: 246          moltype = AA  length = 132
FEATURE                 Location/Qualifiers
source                  1..132
                        mol_type = protein
                        organism = synthetic construct
                        note = Synthetic Construct
SEQUENCE: 246
```

```
QVQLVQSGAE VKKPGASVKV SCKASGRAFS DYAMAWVRQA PGQGLEWMGG IGWSGGDTLY    60
ADSVRGYTEN FKDRVTMTRD TSTSTVYMEL SSLRSEDTAV YYCARQGQYI YSSMRSDSYD   120
YWGQGTLVTV SS                                                      132

SEQ ID NO: 247         moltype = AA   length = 132
FEATURE                Location/Qualifiers
source                 1..132
                       mol_type = protein
                       organism = synthetic construct
                       note = Synthetic Construct
SEQUENCE: 247
QVQLVQSGAE VKKPGASVKV SCKASGRAFS DYAMAWFRQA PGQEREFMGG IGWSGGDTLY    60
ADSVRGYTEN FKDRVTMTRD TSTSTVYMEL SSLRSEDTAV YYCARQGQYI YSSMRSDSYD   120
YWGQGTLVTV SS                                                      132

SEQ ID NO: 248         moltype = AA   length = 132
FEATURE                Location/Qualifiers
source                 1..132
                       mol_type = protein
                       organism = synthetic construct
                       note = Synthetic Construct
SEQUENCE: 248
QVQLVQSGAE VKKPGASVKV SCKASGRAFS DYAMAWFRQA PGQGLEFMGG IGWSGGDTLY    60
ADSVRGYTEN FKDRVTMTRD TSTSTVYMEL SSLRSEDTAV YYCARQGQYI YSSMRSDSYD   120
YWGQGTLVTV SS                                                      132

SEQ ID NO: 249         moltype = AA   length = 137
FEATURE                Location/Qualifiers
source                 1..137
                       mol_type = protein
                       organism = synthetic construct
                       note = Synthetic Construct
SEQUENCE: 249
QVQLVQSGAE VKKPGASVKV SCKASVGTIS DYGMGWVRQA PGQGLEWMGS ISWGGMWTDY    60
ADSVKGYTEN FKDRVTMTRD TSTSTVYMEL SSLRSEDTAV YYCARGRGRM YRGIGNSLAQ   120
PKSYGYWGQG TLVTVSS                                                 137

SEQ ID NO: 250         moltype = AA   length = 137
FEATURE                Location/Qualifiers
source                 1..137
                       mol_type = protein
                       organism = synthetic construct
                       note = Synthetic Construct
SEQUENCE: 250
QVQLVQSGAE VKKPGASVKV SCKASVGTIS DYGMGWFRQA PGQEREFMGS ISWGGMWTDY    60
ADSVKGYTEN FKDRVTMTRD TSTSTVYMEL SSLRSEDTAV YYCARGRGRM YRGIGNSLAQ   120
PKSYGYWGQG TLVTVSS                                                 137

SEQ ID NO: 251         moltype = AA   length = 137
FEATURE                Location/Qualifiers
source                 1..137
                       mol_type = protein
                       organism = synthetic construct
                       note = Synthetic Construct
SEQUENCE: 251
QVQLVQSGAE VKKPGASVKV SCKASVGTIS DYGMGWFRQA PGQGLEFMGS ISWGGMWTDY    60
ADSVKGYTEN FKDRVTMTRD TSTSTVYMEL SSLRSEDTAV YYCARGRGRM YRGIGNSLAQ   120
PKSYGYWGQG TLVTVSS                                                 137

SEQ ID NO: 252         moltype = AA   length = 141
FEATURE                Location/Qualifiers
source                 1..141
                       mol_type = protein
                       organism = synthetic construct
                       note = Synthetic Construct
SEQUENCE: 252
QVQLVQSGAE VKKPGASVKV SCKASGRTFS GILSAYAVGW VRQAPGQGLE WMGTITSGGS    60
TLSADSVKGY TENFKDRVTM TRDTSTSTVY MELSSLRSED TAVYYCARAV RTWPYGSNRG   120
EVPTENEYGH WGQGTLVTVS S                                            141

SEQ ID NO: 253         moltype = AA   length = 141
FEATURE                Location/Qualifiers
source                 1..141
                       mol_type = protein
                       organism = synthetic construct
                       note = Synthetic Construct
SEQUENCE: 253
QVQLVQSGAE VKKPGASVKV SCKASGRTFS GILSAYAVGW FRQAPGQERE FMGTITSGGS    60
TLSADSVKGY TENFKDRVTM TRDTSTSTVY MELSSLRSED TAVYYCARAV RTWPYGSNRG   120
```

```
EVPTENEYGH WGQGTLVTVS S                                                  141

SEQ ID NO: 254           moltype = AA  length = 141
FEATURE                  Location/Qualifiers
source                   1..141
                         mol_type = protein
                         organism = synthetic construct
                         note = Synthetic Construct
SEQUENCE: 254
QVQLVQSGAE VKKPGASVKV SCKASGRTFS GILSAYAVGW FRQAPGQGLE FMGTITSGGS          60
TLSADSVKGY TENFKDRVTM TRDTSTSTVY MELSSLRSED TAVYYCARAV RTWPYGSNRG         120
EVPTENEYGH WGQGTLVTVS S                                                  141

SEQ ID NO: 255           moltype = AA  length = 126
FEATURE                  Location/Qualifiers
source                   1..126
                         mol_type = protein
                         organism = synthetic construct
                         note = Synthetic Construct
SEQUENCE: 255
EVQLVESGGG VVRPGGSLRL SFAASGRAFS DYAMAWFRQA PGKEREFVSG IGWSGGDTLY          60
ADSVRGRFTI SRDNAKNSLY LQMNSLRAED TALYHCAARQ GQYIYSSMRS DSYDYWGQGT         120
LVTVSS                                                                   126

SEQ ID NO: 256           moltype = AA  length = 126
FEATURE                  Location/Qualifiers
source                   1..126
                         mol_type = protein
                         organism = synthetic construct
                         note = Synthetic Construct
SEQUENCE: 256
EVQLLESGGG LVQPGGSLRL SCAASGRAFS DYAMAWFRQA PGKEREFVSG IGWSGGDTLY          60
ADSVRGRFTI SRDNSKNTLY LQMNSLRAED TAVYYCAARQ GQYIYSSMRS DSYDYWGQGT         120
LVTVSS                                                                   126

SEQ ID NO: 257           moltype = AA  length = 126
FEATURE                  Location/Qualifiers
source                   1..126
                         mol_type = protein
                         organism = synthetic construct
                         note = Synthetic Construct
SEQUENCE: 257
EVQLVESGGV VVQPGGSLRL SCAASGRAFS DYAMAWFRQA PGKEREFVSG IGWSGGDTLY          60
ADSVRGRFTI SRDNSKNSLY LQMNSLRAED TALYYCAARQ GQYIYSSMRS DSYDYWGQGT         120
LVTVSS                                                                   126

SEQ ID NO: 258           moltype = AA  length = 128
FEATURE                  Location/Qualifiers
source                   1..128
                         mol_type = protein
                         organism = synthetic construct
                         note = Synthetic Construct
SEQUENCE: 258
EVQLVESGGG LVQPGGSLRL SCAASVGTIS DYGMGWFRQA PGKEREFVSS ISWGGMWTDY          60
ADSVKGRFTI SRDNSKNTLY LQMNSLRAED TAVYYCGRGR MYRGIGNSLA QPKSYGYWGQ         120
GTQVTVSS                                                                 128

SEQ ID NO: 259           moltype = AA  length = 128
FEATURE                  Location/Qualifiers
source                   1..128
                         mol_type = protein
                         organism = synthetic construct
                         note = Synthetic Construct
SEQUENCE: 259
EVQLVESGGG LVQPGGSLRL SCAASVGTIS DYGMGWFHQA PGKEREFVSS ISWGGMWTDY          60
ADSVKGRFII SRDNSRNTLY LQTNSLRAED TAVYYCGRGR MYRGIGNSLA QPKSYGYWGQ         120
GTLVTVSS                                                                 128

SEQ ID NO: 260           moltype = AA  length = 128
FEATURE                  Location/Qualifiers
source                   1..128
                         mol_type = protein
                         organism = synthetic construct
                         note = Synthetic Construct
SEQUENCE: 260
EVQLVESGGG VVQPGRSLRL SCAASVGTIS DYGMGWFRQA PGKEREFVAS ISWGGMWTDY          60
ADSVKGRFTI SRDNSKNTLY LQMNSLRAED TAVYYCGRGR MYRGIGNSLA QPKSYGYWGQ         120
GTQVTVSS                                                                 128
```

```
SEQ ID NO: 261            moltype = AA   length = 132
FEATURE                   Location/Qualifiers
source                    1..132
                          mol_type = protein
                          organism = synthetic construct
                          note = Synthetic Construct
SEQUENCE: 261
EVQLVESGGG LVKPGGSLRL SCAASGRTFS GILSAYAVGW FRQAPGKERE FVSTITSGGS    60
TLSADSVKGR FTISRDNAKN SLYLQMNSLR AEDTAVYYCA VRTWPYGSNR GEVPTENEYG   120
HWGQGTQVTV SS                                                      132

SEQ ID NO: 262            moltype = AA   length = 132
FEATURE                   Location/Qualifiers
source                    1..132
                          mol_type = protein
                          organism = synthetic construct
                          note = Synthetic Construct
SEQUENCE: 262
EVQLVESGGG LVQPGGSLRL SCAASGRTFS GILSAYAVGW FRQAPGKERE FVSTITSGGS    60
TLSADSVKGR FTISRDNSKN TLYVQMSSLR AEDTAVYYCA VRTWPYGSNR GEVPTENEYG   120
HWGQGTQVTV SS                                                      132

SEQ ID NO: 263            moltype = AA   length = 132
FEATURE                   Location/Qualifiers
source                    1..132
                          mol_type = protein
                          organism = synthetic construct
                          note = Synthetic Construct
SEQUENCE: 263
EVQLVESGGG VVQPGGSLRL SCAASGRTFS GILSAYAVGW FRQAPGKERE FVSTITSGGS    60
TLSADSVKGR FTISRDNSKN SLYLQMNSLR TEDTALYYCA VRTWPYGSNR GEVPTENEYG   120
HWGQGTQVTV SS                                                      132

SEQ ID NO: 264            moltype = AA   length = 10
FEATURE                   Location/Qualifiers
source                    1..10
                          mol_type = protein
                          organism = synthetic construct
                          note = Synthetic Construct
SEQUENCE: 264
VGTISDYGMG                                                          10

SEQ ID NO: 265            moltype = AA   length = 14
FEATURE                   Location/Qualifiers
source                    1..14
                          mol_type = protein
                          organism = synthetic construct
                          note = Synthetic Construct
SEQUENCE: 265
GRTFSGILSA YAVG                                                     14

SEQ ID NO: 266            moltype = AA   length = 17
FEATURE                   Location/Qualifiers
source                    1..17
                          mol_type = protein
                          organism = synthetic construct
                          note = Synthetic Construct
SEQUENCE: 266
SISWGGMWTD YADSVKG                                                  17

SEQ ID NO: 267            moltype = AA   length = 16
FEATURE                   Location/Qualifiers
source                    1..16
                          mol_type = protein
                          organism = synthetic construct
                          note = Synthetic Construct
SEQUENCE: 267
TITSGGSTLS ADSVKG                                                   16

SEQ ID NO: 268            moltype = AA   length = 21
FEATURE                   Location/Qualifiers
source                    1..21
                          mol_type = protein
                          organism = synthetic construct
                          note = Synthetic Construct
SEQUENCE: 268
GRGRMYRGIG NSLAQPKSYG Y                                             21

SEQ ID NO: 269            moltype = AA   length = 22
```

| FEATURE | Location/Qualifiers |
|---|---|
| source | 1..22 |
| | mol_type = protein |
| | organism = synthetic construct |
| | note = Synthetic Construct |

SEQUENCE: 269
AVRTWPYGSN RGEVPTENEY GH                                                22

| SEQ ID NO: 270 | moltype = AA   length = 132 |
|---|---|
| FEATURE | Location/Qualifiers |
| source | 1..132 |
| | mol_type = protein |
| | organism = synthetic construct |
| | note = Synthetic Construct |

SEQUENCE: 270
EVQLVESGGG LVQAGGSLRL SCAASGRTFS GILSPYAVGW FRQAPGKGLE FVSTITSGGS    60
AIYTDSVKGR FTISRDNAKN SLYLQMNSLR AEDTAVYYCA VRTRRYGSNL GEVPQENEYG  120
YWGQGTLVTV SS                                                      132

| SEQ ID NO: 271 | moltype = AA   length = 132 |
|---|---|
| FEATURE | Location/Qualifiers |
| source | 1..132 |
| | mol_type = protein |
| | organism = synthetic construct |
| | note = Synthetic Construct |

SEQUENCE: 271
EVQLVESGGG LVQPGGSLRL SCAASGRTFS GILSPYAVGW FRQAPGKGLE FVSTITSGGS    60
AIYTDSVKGR FTLSRDNAKN SLYLQMNSLR AEDTAVYYCA VRTRRYGSNL GEVPQENEYG  120
YWGQGTLVTV SS                                                      132

| SEQ ID NO: 272 | moltype = AA   length = 132 |
|---|---|
| FEATURE | Location/Qualifiers |
| source | 1..132 |
| | mol_type = protein |
| | organism = synthetic construct |
| | note = Synthetic Construct |

SEQUENCE: 272
EVQLVESGGG LVQPGGSLRL SCAASGRTFS GILSPYAVGW FRQAPGKGLE FVSTITSGGS    60
AIYTDSVKGR FTISRDNAKN SLYLQMNSLK AEDTAVYYCA VRTRRYGSNL GEVPQENEYG  120
YWGQGTLVTV SS                                                      132

| SEQ ID NO: 273 | moltype = AA   length = 132 |
|---|---|
| FEATURE | Location/Qualifiers |
| source | 1..132 |
| | mol_type = protein |
| | organism = synthetic construct |
| | note = Synthetic Construct |

SEQUENCE: 273
EVQLVESGGG LVQPGGSLRL SCAASGRTFS GILSPYAVGW FRQAPGKGLE FVSTITSGGS    60
AIYTDSVKGR FTISRDNAKN SLYLQMNSLR PEDTAVYYCA VRTRRYGSNL GEVPQENEYG  120
YWGQGTLVTV SS                                                      132

| SEQ ID NO: 274 | moltype = AA   length = 126 |
|---|---|
| FEATURE | Location/Qualifiers |
| source | 1..126 |
| | mol_type = protein |
| | organism = synthetic construct |
| | note = Synthetic Construct |

SEQUENCE: 274
EVQLVESGGG LVQAGGSLRL SCAASGRAFS DYAMAWFRQA PGQEREFVAG IGWSGGDTLY    60
ADSVRGRFTI SRDNSKNTLY LQMNSLRAED TAVYYCAARQ GQYIYSSMRS DSYDWGQGT  120
LVTVSS                                                             126

| SEQ ID NO: 275 | moltype = AA   length = 126 |
|---|---|
| FEATURE | Location/Qualifiers |
| source | 1..126 |
| | mol_type = protein |
| | organism = synthetic construct |
| | note = Synthetic Construct |

SEQUENCE: 275
EVQLVESGGG LVQPGGSLRL SCAASGRAFS DYAMAWFRQA PGKEREFVAG IGWSGGDTLY    60
ADSVRGRFTI SRDNSKNTLY LQMNSLRAED TAVYYCAARQ GQYIYSSMRS DSYDWGQGT  120
LVTVSS                                                             126

| SEQ ID NO: 276 | moltype = AA   length = 126 |
|---|---|
| FEATURE | Location/Qualifiers |
| source | 1..126 |
| | mol_type = protein |
| | organism = synthetic construct |

```
                            note = Synthetic Construct
SEQUENCE: 276
EVQLVESGGG LVQPGGSLRL SCAASGRAFS DYAMAWFRQA PGQEREFVAG IGWSGGDTLY     60
ADSVRGRFTI SKDNSKNTLY LQMNSLRAED TAVYYCAARQ GQYIYSSMRS DSYDYWGQGT    120
LVTVSS                                                               126

SEQ ID NO: 277          moltype = AA   length = 126
FEATURE                 Location/Qualifiers
source                  1..126
                        mol_type = protein
                        organism = synthetic construct
                        note = Synthetic Construct
SEQUENCE: 277
EVQLVESGGG LVQPGGSLRL SCAASGRAFS DYAMAWFRQA PGQEREFVAG IGWSGGDTLY     60
ADSVRGRFTI SRDNSKNRLY LQMNSLRAED TAVYYCAARQ GQYIYSSMRS DSYDYWGQGT    120
LVTVSS                                                               126

SEQ ID NO: 278          moltype = AA   length = 126
FEATURE                 Location/Qualifiers
source                  1..126
                        mol_type = protein
                        organism = synthetic construct
                        note = Synthetic Construct
SEQUENCE: 278
EVQLVESGGG LVQPGGSLRL SCAASGRAFS DYAMAWFRQA PGQEREFVAG IGWSGGDTLY     60
ADSVRGRFTI SRDNSKNTLS LQMNSLRAED TAVYYCAARQ GQYIYSSMRS DSYDYWGQGT    120
LVTVSS                                                               126

SEQ ID NO: 279          moltype = AA   length = 126
FEATURE                 Location/Qualifiers
source                  1..126
                        mol_type = protein
                        organism = synthetic construct
                        note = Synthetic Construct
SEQUENCE: 279
EVQLVESGGG LVQPGGSLRL SCAASGRAFS DYAMAWFRQA PGQEREFVAG IGWSGGDTLY     60
ADSVRGRFTI SRDNSKNTLY LQMNSLKAED TAVYYCAARQ GQYIYSSMRS DSYDYWGQGT    120
LVTVSS                                                               126

SEQ ID NO: 280          moltype = AA   length = 126
FEATURE                 Location/Qualifiers
source                  1..126
                        mol_type = protein
                        organism = synthetic construct
                        note = Synthetic Construct
SEQUENCE: 280
EVQLVESGGG LVQPGGSLRL SCAASGRAFS DYAMAWFRQA PGQEREFVAG IGWSGGDTLY     60
ADSVRGRFTI SRDNSKNTLY LQMNSLRPED TAVYYCAARQ GQYIYSSMRS DSYDYWGQGT    120
LVTVSS                                                               126

SEQ ID NO: 281          moltype = AA   length = 132
FEATURE                 Location/Qualifiers
source                  1..132
                        mol_type = protein
                        organism = synthetic construct
                        note = Synthetic Construct
SEQUENCE: 281
EVQLVESGGG LVQAGGSLRL SCAASGRTFS GILSPYAVGW FRQAPGKGRE FVSTITSGGS     60
AIYTDSVKGR FTLSRDNAKD TVYLQMNSLK PEDTAVYYCH VRTRRYGSNL GEVPQENEYG    120
YWGQGTQVTV SS                                                        132

SEQ ID NO: 282          moltype = AA   length = 132
FEATURE                 Location/Qualifiers
source                  1..132
                        mol_type = protein
                        organism = synthetic construct
                        note = Synthetic Construct
SEQUENCE: 282
EVQLVESGGG LVQAGGSLRL SCAASGRTFS GILSPYAVGW FRQAPGKGRE FVSTITSGGS     60
AIYTDSVKGR FTLSRDNAKD TVYLQMNSLK PEDTAVYYCA VRTRRHGSNL GEVPQENEYG    120
YWGQGTQVTV SS                                                        132

SEQ ID NO: 283          moltype = AA   length = 120
FEATURE                 Location/Qualifiers
source                  1..120
                        mol_type = protein
                        organism = synthetic construct
                        note = Synthetic Construct
SEQUENCE: 283
```

```
EVQLVESGGG LVQAGGSLRL SCAAPEMGAT INVMAWYRQA PGKQRELVAR LPHDNNIDYG    60
DFAKGRFTIS RDITRNTVYL QMNNLKPDDT AVYYCNVLLS RQINGAYVHW GQGTQVTVSS   120

SEQ ID NO: 284          moltype = AA  length = 120
FEATURE                 Location/Qualifiers
source                  1..120
                        mol_type = protein
                        organism = synthetic construct
                        note = Synthetic Construct
SEQUENCE: 284
EVQLVESGGG LVQAGGSLRL SCAAPEMGAT INVMAWYRQA PGKQRELVAR LPLHNNIDYG    60
DFAKGRFTIS RDITRNTVYL QMNNLKPDDT AVYYCNVLLS RQINGAYVHW GQGTQVTVSS   120

SEQ ID NO: 285          moltype = AA  length = 120
FEATURE                 Location/Qualifiers
source                  1..120
                        mol_type = protein
                        organism = synthetic construct
                        note = Synthetic Construct
SEQUENCE: 285
EVQLVESGGG LVQAGGSLRL SCAAPEMGAT INVMAWYRQA PGKQRELVAR LPLDNNIDYG    60
DFAKGRFTIS RDITRNTVYL QMNNLKPDDT AVYYCHVLLS RQINGAYVHW GQGTQVTVSS   120

SEQ ID NO: 286          moltype = AA  length = 120
FEATURE                 Location/Qualifiers
source                  1..120
                        mol_type = protein
                        organism = synthetic construct
                        note = Synthetic Construct
SEQUENCE: 286
EVQLVESGGG LVQAGGSLRL SCAAPEMGAT INVMAWYRQA PGKQRELVAR LPLDNNIDYG    60
DFAKGRFTIS RDITRNTVYL QMNNLKPDDT AVYYCNVHLS RQINGAYVHW GQGTQVTVSS   120

SEQ ID NO: 287          moltype = AA  length = 120
FEATURE                 Location/Qualifiers
source                  1..120
                        mol_type = protein
                        organism = synthetic construct
                        note = Synthetic Construct
SEQUENCE: 287
EVQLVESGGG LVQAGGSLRL SCAAPEMGAT INVMAWYRQA PGKQRELVAR LPLDNNIDYG    60
DFAKGRFTIS RDITRNTVYL QMNNLKPDDT AVYYCNVLLS RQINGAHVHW GQGTQVTVSS   120

SEQ ID NO: 288          moltype = AA  length = 126
FEATURE                 Location/Qualifiers
source                  1..126
                        mol_type = protein
                        organism = synthetic construct
                        note = Synthetic Construct
SEQUENCE: 288
EVQLVESGGG LVQAGGSLRL SCAASGRHFS DYAMAWFRQA PGKEREFVAG IGWSGGDTLY    60
ADSVRGRFTN SKDNAKNRMS LQMNSLKPED TAVYYCAARQ GQYIYSSMRS DSYDYWGQGT   120
QVTVSS                                                              126

SEQ ID NO: 289          moltype = AA  length = 126
FEATURE                 Location/Qualifiers
source                  1..126
                        mol_type = protein
                        organism = synthetic construct
                        note = Synthetic Construct
SEQUENCE: 289
EVQLVESGGG LVQAGGSLRL SCAASGRAHS DYAMAWFRQA PGKEREFVAG IGWSGGDTLY    60
ADSVRGRFTN SKDNAKNRMS LQMNSLKPED TAVYYCAARQ GQYIYSSMRS DSYDYWGQGT   120
QVTVSS                                                              126

SEQ ID NO: 290          moltype = AA  length = 126
FEATURE                 Location/Qualifiers
source                  1..126
                        mol_type = protein
                        organism = synthetic construct
                        note = Synthetic Construct
SEQUENCE: 290
EVQLVESGGG LVQAGGSLRL SCAASGRAFS DYAMAWFRQA PGKEREFVAG IGWSGGDTHY    60
ADSVRGRFTN SKDNAKNRMS LQMNSLKPED TAVYYCAARQ GQYIYSSMRS DSYDYWGQGT   120
QVTVSS                                                              126

SEQ ID NO: 291          moltype = AA  length = 126
FEATURE                 Location/Qualifiers
source                  1..126
```

```
                        mol_type = protein
                        organism = synthetic construct
                        note = Synthetic Construct
SEQUENCE: 291
EVQLVESGGG LVQAGGSLRL SCAASGRAFS DYAMAWFRQA PGKEREFVAG IGWSGGDTLY     60
ADSVRGRFTN SKDNAKNRMS LQMNSLKPED TAVYYCAARQ GQHIYSSMRS DSYDYWGQGT    120
QVTVSS                                                               126

SEQ ID NO: 292          moltype = AA  length = 132
FEATURE                 Location/Qualifiers
source                  1..132
                        mol_type = protein
                        organism = synthetic construct
                        note = Synthetic Construct
SEQUENCE: 292
EVQLVESGGG LVQAGGSLRL SCAASGRTFS GILSHYAVGW FRQAPGKERE FVSTITSGGS     60
TLSADSVKGR FTLSRDNAKD TVYLQMNSLK PEDTAVYYCA VRTWPYGSNR GEVPTENEYG    120
HWGQGTQVTV SS                                                        132

SEQ ID NO: 293          moltype = AA  length = 132
FEATURE                 Location/Qualifiers
source                  1..132
                        mol_type = protein
                        organism = synthetic construct
                        note = Synthetic Construct
SEQUENCE: 293
EVQLVESGGG LVQPGGSLRL SCAASGRTFS GILSPYAVGW FRQAPGKGLE FVSTITSGGS     60
AIYTDSVKGR FTISRDNAKN SLYLQMNSLR AEDTAVYYCA VRTRRHGSNL GEVPQENEYG    120
YWGQGTLVTV SS                                                        132

SEQ ID NO: 294          moltype = AA  length = 126
FEATURE                 Location/Qualifiers
source                  1..126
                        mol_type = protein
                        organism = synthetic construct
                        note = Synthetic Construct
SEQUENCE: 294
EVQLVESGGG LVQPGGSLRL SCAASGRAFS DYAMAWFRQA PGQEREFVAG IGWSGGDTHY     60
ADSVRGRFTI SRDNSKNTLY LQMNSLRAED TAVYYCAARQ GQYIYSSMRS DSYDYWGQGT    120
LVTVSS                                                               126

SEQ ID NO: 295          moltype = AA  length = 126
FEATURE                 Location/Qualifiers
source                  1..126
                        mol_type = protein
                        organism = synthetic construct
                        note = Synthetic Construct
SEQUENCE: 295
EVQLVESGGG LVQPGGSLRL SCAASGRAFS DYAMAWFRQA PGQEREFVAG IGWSGGDTLY     60
ADSVRGRFTI SRDNSKNTLY LQMNSLRAED TAVYYCAARQ GQHIYSSMRS DSYDYWGQGT    120
LVTVSS                                                               126

SEQ ID NO: 296          moltype = AA  length = 126
FEATURE                 Location/Qualifiers
source                  1..126
                        mol_type = protein
                        organism = synthetic construct
                        note = Synthetic Construct
SEQUENCE: 296
EVQLVESGGG LVQPGGSLRL SCAASGRAHS DYAMAWFRQA PGQEREFVAG IGWSGGDTHY     60
ADSVRGRFTI SRDNSKNTLY LQMNSLRAED TAVYYCAARQ GQYIYSSMRS DSYDYWGQGT    120
LVTVSS                                                               126

SEQ ID NO: 297          moltype = AA  length = 126
FEATURE                 Location/Qualifiers
source                  1..126
                        mol_type = protein
                        organism = synthetic construct
                        note = Synthetic Construct
SEQUENCE: 297
EVQLVESGGG LVQPGGSLRL SCAASGRAFS DYAMAWFRQA PGQEREFVAG IGWSGGDTHY     60
ADSVRGRFTI SRDNSKNTLY LQMNSLRAED TAVYYCAARQ GQHIYSSMRS DSYDYWGQGT    120
LVTVSS                                                               126

SEQ ID NO: 298          moltype = AA  length = 126
FEATURE                 Location/Qualifiers
source                  1..126
                        mol_type = protein
                        organism = synthetic construct
```

```
                            note = Synthetic Construct
SEQUENCE: 298
EVQLVESGGG LVQPGGSLRL SCAASGRHFS DYAMAWFRQA PGQEREFVAG IGWSGGDTHY    60
ADSVRGRFTI SRDNSKNTLY LQMNSLRAED TAVYYCAARQ GQYIYSSMRS DSYDYWGQGT   120
LVTVSS                                                              126

SEQ ID NO: 299          moltype = AA  length = 126
FEATURE                 Location/Qualifiers
source                  1..126
                        mol_type = protein
                        organism = synthetic construct
                        note = Synthetic Construct
SEQUENCE: 299
EVQLVESGGG LVQPGGSLRL SCAASGRHFS DYAMAWFRQA PGQEREFVAG IGWSGGDTLY    60
ADSVRGRFTI SRDNSKNTLY LQMNSLRAED TAVYYCAARQ GQHIYSSMRS DSYDYWGQGT   120
LVTVSS                                                              126

SEQ ID NO: 300          moltype = AA  length = 126
FEATURE                 Location/Qualifiers
source                  1..126
                        mol_type = protein
                        organism = synthetic construct
                        note = Synthetic Construct
SEQUENCE: 300
EVQLVESGGG LVQPGGSLRL SCAASGRAHS DYAMAWFRQA PGQEREFVAG IGWSGGDTLY    60
ADSVRGRFTI SRDNSKNTLY LQMNSLRAED TAVYYCAARQ GQHIYSSMRS DSYDYWGQGT   120
LVTVSS                                                              126

SEQ ID NO: 301          moltype = AA  length = 126
FEATURE                 Location/Qualifiers
source                  1..126
                        mol_type = protein
                        organism = synthetic construct
                        note = Synthetic Construct
SEQUENCE: 301
EVQLVESGGG LVQPGGSLRL SCAASGRHHS DYAMAWFRQA PGQEREFVAG IGWSGGDTHY    60
ADSVRGRFTI SRDNSKNTLY LQMNSLRAED TAVYYCAARQ GQYIYSSMRS DSYDYWGQGT   120
LVTVSS                                                              126

SEQ ID NO: 302          moltype = AA  length = 126
FEATURE                 Location/Qualifiers
source                  1..126
                        mol_type = protein
                        organism = synthetic construct
                        note = Synthetic Construct
SEQUENCE: 302
EVQLVESGGG LVQPGGSLRL SCAASGRHHS DYAMAWFRQA PGQEREFVAG IGWSGGDTLY    60
ADSVRGRFTI SRDNSKNTLY LQMNSLRAED TAVYYCAARQ GQHIYSSMRS DSYDYWGQGT   120
LVTVSS                                                              126

SEQ ID NO: 303          moltype = AA  length = 126
FEATURE                 Location/Qualifiers
source                  1..126
                        mol_type = protein
                        organism = synthetic construct
                        note = Synthetic Construct
SEQUENCE: 303
EVQLVESGGG LVQPGGSLRL SCAASGRAHS DYAMAWFRQA PGQEREFVAG IGWSGGDTHY    60
ADSVRGRFTI SRDNSKNTLY LQMNSLRAED TAVYYCAARQ GQHIYSSMRS DSYDYWGQGT   120
LVTVSS                                                              126

SEQ ID NO: 304          moltype = AA  length = 126
FEATURE                 Location/Qualifiers
source                  1..126
                        mol_type = protein
                        organism = synthetic construct
                        note = Synthetic Construct
SEQUENCE: 304
EVQLVESGGG LVQPGGSLRL SCAASGRHFS DYAMAWFRQA PGQEREFVAG IGWSGGDTHY    60
ADSVRGRFTI SRDNSKNTLY LQMNSLRAED TAVYYCAARQ GQHIYSSMRS DSYDYWGQGT   120
LVTVSS                                                              126

SEQ ID NO: 305          moltype = AA  length = 262
FEATURE                 Location/Qualifiers
source                  1..262
                        mol_type = protein
                        organism = synthetic construct
                        note = Synthetic Construct
SEQUENCE: 305
```

```
EVQLVESGGG LVQPGGSLRL SCAASGRTFS GILSPYAVGW FRQAPGKGLE FVSTITSGGS    60
AIYTDSVKGR FTISRDNAKN SLYLQMNSLR AEDTAVYYCA VRTRRYGSNL GEVPQENEYG   120
YWGQGTLVTV SSGGGGSGGG GSGGGGSEVQ LLESGGGLVQ PGGSLRLSCA ASGFTFRSFG   180
MSWVRQAPGK GPEWVSSISG SGSDTLYADS VKGRFTISRD NSKNTLYLQM NSLRPEDTAV   240
YYCTIGGSLS RSSQGTLVTV SS                                            262

SEQ ID NO: 306          moltype = AA   length = 267
FEATURE                 Location/Qualifiers
source                  1..267
                        mol_type = protein
                        organism = synthetic construct
                        note = Synthetic Construct
SEQUENCE: 306
EVQLVESGGG LVQPGGSLRL SCAASGRTFS GILSPYAVGW FRQAPGKGLE FVSTITSGGS    60
AIYTDSVKGR FTISRDNAKN SLYLQMNSLR AEDTAVYYCA VRTRRYGSNL GEVPQENEYG   120
YWGQGTLVTV SSGGGGSGGG GSGGGGSGGG GSEVQLLESG GLVQPGGSL RLSCAASGFT    180
FRSFGMSWVR QAPGKGPEWV SSISGSGSDT LYADSVKGRF TISRDNSKNT LYLQMNSLRP   240
EDTAVYYCTI GGSLSRSSQG TLVTVSS                                      267

SEQ ID NO: 307          moltype = AA   length = 272
FEATURE                 Location/Qualifiers
source                  1..272
                        mol_type = protein
                        organism = synthetic construct
                        note = Synthetic Construct
SEQUENCE: 307
EVQLVESGGG LVQPGGSLRL SCAASGRTFS GILSPYAVGW FRQAPGKGLE FVSTITSGGS    60
AIYTDSVKGR FTISRDNAKN SLYLQMNSLR AEDTAVYYCA VRTRRYGSNL GEVPQENEYG   120
YWGQGTLVTV SSGGGGSGGG GSGGGGSGGG GSGGGGSEVQ LLESGGGLVQ PGGSLRLSCA   180
ASGFTFRSFG MSWVRQAPGK GPEWVSSISG SGSDTLYADS VKGRFTISRD NSKNTLYLQM   240
NSLRPEDTAV YYCTIGGSLS RSSQGTLVTV SS                                 272

SEQ ID NO: 308          moltype = AA   length = 277
FEATURE                 Location/Qualifiers
source                  1..277
                        mol_type = protein
                        organism = synthetic construct
                        note = Synthetic Construct
SEQUENCE: 308
EVQLVESGGG LVQPGGSLRL SCAASGRTFS GILSPYAVGW FRQAPGKGLE FVSTITSGGS    60
AIYTDSVKGR FTISRDNAKN SLYLQMNSLR AEDTAVYYCA VRTRRYGSNL GEVPQENEYG   120
YWGQGTLVTV SSGGGGSGGG GSGGGGSGGG GSGGGGSGGG GSEVQLLESG GLVQPGGSL    180
RLSCAASGFT FRSFGMSWVR QAPGKGPEWV SSISGSGSDT LYADSVKGRF TISRDNSKNT   240
LYLQMNSLRP EDTAVYYCTI GGSLSRSSQG TLVTVSS                           277

SEQ ID NO: 309          moltype = AA   length = 262
FEATURE                 Location/Qualifiers
source                  1..262
                        mol_type = protein
                        organism = synthetic construct
                        note = Synthetic Construct
SEQUENCE: 309
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SLSRSSQGTL VTVSSGGGGS   120
GGGGSGGGGS EVQLVESGGG LVQPGGSLRL SCAASGRTFS GILSPYAVGW FRQAPGKGLE   180
FVSTITSGGS AIYTDSVKGR FTISRDNAKN SLYLQMNSLR AEDTAVYYCA VRTRRYGSNL   240
GEVPQENEYG YWGQGTLVTV SS                                            262

SEQ ID NO: 310          moltype = AA   length = 267
FEATURE                 Location/Qualifiers
source                  1..267
                        mol_type = protein
                        organism = synthetic construct
                        note = Synthetic Construct
SEQUENCE: 310
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SLSRSSQGTL VTVSSGGGGS   120
GGGGSGGGGS GGGGSEVQLV ESGGGLVQPG GSLRLSCAAS GRTFSGILSP YAVGWFRQAP   180
GKGLEFVSTI TSGGSAIYTD SVKGRFTISR DNAKNSLYLQ MNSLRAEDTA VYYCAVRTRR   240
YGSNLGEVPQ ENEYGYWGQG TLVTVSS                                      267

SEQ ID NO: 311          moltype = AA   length = 272
FEATURE                 Location/Qualifiers
source                  1..272
                        mol_type = protein
                        organism = synthetic construct
                        note = Synthetic Construct
SEQUENCE: 311
EVQLLESGGG LVQPGGSLRL SCAASGFTFR SFGMSWVRQA PGKGPEWVSS ISGSGSDTLY    60
```

```
ADSVKGRFTI SRDNSKNTLY LQMNSLRPED TAVYYCTIGG SLSRSSQGTL VTVSSGGGS      120
GGGGSGGGGS GGGGSGGGGS EVQLVESGGG LVQPGGSLRL SCAASGRTFS GILSPYAVGW     180
FRQAPGKGLE FVSTITSGGS AIYTDSVKGR FTISRDNAKN SLYLQMNSLR AEDTAVYYCA     240
VRTRRYGSNL GEVPQENEYG YWGQGTLVTV SS                                   272

SEQ ID NO: 312          moltype = AA   length = 277
FEATURE                 Location/Qualifiers
source                  1..277
                        mol_type = protein
                        organism = synthetic construct
                        note = Synthetic Construct
SEQUENCE: 312
EVQLLESGGG LVQPGGSLRL SCAASGFTFR SFGMSWVRQA PGKGPEWVSS ISGSGSDTLY      60
ADSVKGRFTI SRDNSKNTLY LQMNSLRPED TAVYYCTIGG SLSRSSQGTL VTVSSGGGGS     120
GGGGSGGGGS GGGGSGGGGS GGGGSEVQLV ESGGGLVQPG GSLRLSCAAS GRTFSGILSP     180
YAVGWFRQAP GKGLEFVSTI TSGGSAIYTD SVKGRFTISR DNAKNSLYLQ MNSLRAEDTA     240
VYYCAVRTRR YGSNLGEVPQ ENEYGYWGQG TLVTVSS                              277

SEQ ID NO: 313          moltype = AA   length = 256
FEATURE                 Location/Qualifiers
source                  1..256
                        mol_type = protein
                        organism = synthetic construct
                        note = Synthetic Construct
SEQUENCE: 313
EVQLVESGGG LVQPGGSLRL SCAASGRAFS DYAMAWFRQA PGQEREFVAG IGWSGGDTLY      60
ADSVRGRFTI SRDNSKNTLY LQMNSLRAED TAVYYCAARQ GQYIYSSMRS DSYDYWGQGT     120
LVTVSSGGGG SGGGGSGGGG SEVQLLESGG GLVQPGGSLR LSCAASGFTF RSFGMSWVRQ     180
APGKGPEWVS SISGSGSDTL YADSVKGRFT ISRDNSKNTL YLQMNSLRPE DTAVYYCTIG     240
GSLSRSSQGT LVTVSS                                                     256

SEQ ID NO: 314          moltype = AA   length = 261
FEATURE                 Location/Qualifiers
source                  1..261
                        mol_type = protein
                        organism = synthetic construct
                        note = Synthetic Construct
SEQUENCE: 314
EVQLVESGGG LVQPGGSLRL SCAASGRAFS DYAMAWFRQA PGQEREFVAG IGWSGGDTLY      60
ADSVRGRFTI SRDNSKNTLY LQMNSLRAED TAVYYCAARQ GQYIYSSMRS DSYDYWGQGT     120
LVTVSSGGGG SGGGGSGGGG SGGGGSEVQL LESGGGLVQP GGSLRLSCAA SGFTFRSFGM     180
SWVRQAPGKG PEWVSSISGS GSDTLYADSV KGRFTISRDN SKNTLYLQMN SLRPEDTAVY     240
YCTIGGSLSR SSQGTLVTVS S                                               261

SEQ ID NO: 315          moltype = AA   length = 266
FEATURE                 Location/Qualifiers
source                  1..266
                        mol_type = protein
                        organism = synthetic construct
                        note = Synthetic Construct
SEQUENCE: 315
EVQLVESGGG LVQPGGSLRL SCAASGRAFS DYAMAWFRQA PGQEREFVAG IGWSGGDTLY      60
ADSVRGRFTI SRDNSKNTLY LQMNSLRAED TAVYYCAARQ GQYIYSSMRS DSYDYWGQGT     120
LVTVSSGGGG SGGGGSGGGG SGGGGSGGGG SEVQLLESGG GLVQPGGSLR LSCAASGFTF     180
RSFGMSWVRQ APGKGPEWVS SISGSGSDTL YADSVKGRFT ISRDNSKNTL YLQMNSLRPE     240
DTAVYYCTIG GSLSRSSQGT LVTVSS                                          266

SEQ ID NO: 316          moltype = AA   length = 270
FEATURE                 Location/Qualifiers
source                  1..270
                        mol_type = protein
                        organism = synthetic construct
                        note = Synthetic Construct
SEQUENCE: 316
EVQLVESGGG LVQPGGSLRL SCAASGRAFS DYAMAWFRQA PGQEREFVAG IGWSGGDTLY      60
ADSVRGRFTI SRDNSKNTLY LQMNSLRAED TAVYYCAARQ GQYIYSSMRS DSYDYWGQGT     120
LVTVSSGGGG SGGGGSGGGG SGGGGSGGGG SGGGGSEVQL LESGGGLVQP GGSLRLSCAA     180
SGFTFRSFGM SWVRQAPGKG PEWVSSISGS GSDTLYADSV KGRFTISRDN SNTLYLQMNS     240
LRPEDTAVYY CTIGGSLSRS SQGTLVTVSS                                      270

SEQ ID NO: 317          moltype = AA   length = 256
FEATURE                 Location/Qualifiers
source                  1..256
                        mol_type = protein
                        organism = synthetic construct
                        note = Synthetic Construct
SEQUENCE: 317
EVQLLESGGG LVQPGGSLRL SCAASGFTFR SFGMSWVRQA PGKGPEWVSS ISGSGSDTLY      60
ADSVKGRFTI SRDNSKNTLY LQMNSLRPED TAVYYCTIGG SLSRSSQGTL VTVSSGGGGS     120
```

```
GGGGSGGGGS EVQLVESGGG LVQPGGSLRL SCAASGRAFS DYAMAWFRQA PGQEREFVAG    180
IGWSGGDTLY ADSVRGRFTI SRDNSKNTLY LQMNSLRAED TAVYYCAARQ GQYIYSSMRS    240
DSYDYWGQGT LVTVSS                                                    256

SEQ ID NO: 318          moltype = AA  length = 261
FEATURE                 Location/Qualifiers
source                  1..261
                        mol_type = protein
                        organism = synthetic construct
                        note = Synthetic Construct
SEQUENCE: 318
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SLSRSSQGTL VTVSSGGGGS    120
GGGGSGGGGS GGGGSEVQLV ESGGGLVQPG GSLRLSCAAS GRAFSDYAMA WFRQAPGQER    180
EFVAGIGWSG GDTLYADSVR GRFTISRDNS KNTLYLQMNS LRAEDTAVYY CAARQGQYIY    240
SSMRSDSYDY WGQGTLVTVS S                                              261

SEQ ID NO: 319          moltype = AA  length = 266
FEATURE                 Location/Qualifiers
source                  1..266
                        mol_type = protein
                        organism = synthetic construct
                        note = Synthetic Construct
SEQUENCE: 319
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SLSRSSQGTL VTVSSGGGGS    120
GGGGSGGGGS GGGGSGGGGS EVQLVESGGG LVQPGGSLRL SCAASGRAFS DYAMAWFRQA    180
PGQEREFVAG IGWSGGDTLY ADSVRGRFTI SRDNSKNTLY LQMNSLRAED TAVYYCAARQ    240
GQYIYSSMRS DSYDYWGQGT LVTVSS                                         266

SEQ ID NO: 320          moltype = AA  length = 271
FEATURE                 Location/Qualifiers
source                  1..271
                        mol_type = protein
                        organism = synthetic construct
                        note = Synthetic Construct
SEQUENCE: 320
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SLSRSSQGTL VTVSSGGGGS    120
GGGGSGGGGS GGGGSGGGGS GGGGSEVQLV ESGGGLVQPG GSLRLSCAAS GRAFSDYAMA    180
WFRQAPGQER EFVAGIGWSG GDTLYADSVR GRFTISRDNS KNTLYLQMNS LRAEDTAVYY    240
CAARQGQYIY SSMRSDSYDY WGQGTLVTVS S                                   271

SEQ ID NO: 321          moltype = AA  length = 9
FEATURE                 Location/Qualifiers
source                  1..9
                        mol_type = protein
                        organism = synthetic construct
                        note = Synthetic Construct
SEQUENCE: 321
GGGGGGGGP                                                            9

SEQ ID NO: 322          moltype = AA  length = 117
FEATURE                 Location/Qualifiers
source                  1..117
                        mol_type = protein
                        organism = synthetic construct
                        note = Synthetic Construct
SEQUENCE: 322
LEQVQLQESG GGLVQPGGSL RLSCEASGFT FSRFGMTWVR QAPGKGVEWV SGISSLGDST    60
LYADSVKGRF TISRDNAKNT LYLQMNSLKP EDTAVYYCTI GGSLNPGGQG TQVTVSS       117

SEQ ID NO: 323          moltype = AA  length = 7
FEATURE                 Location/Qualifiers
source                  1..7
                        mol_type = protein
                        organism = synthetic construct
                        note = Synthetic Construct
SEQUENCE: 323
PNLLGGP                                                              7

SEQ ID NO: 324          moltype = AA  length = 6
FEATURE                 Location/Qualifiers
source                  1..6
                        mol_type = protein
                        organism = synthetic construct
                        note = Synthetic Construct
SEQUENCE: 324
HHHHHH                                                               6
```

```
SEQ ID NO: 325          moltype = AA  length = 16
FEATURE                 Location/Qualifiers
source                  1..16
                        mol_type = protein
                        organism = synthetic construct
                        note = Synthetic Construct
SEQUENCE: 325
RLPLDNNIDY GDFAKG                                                    16

SEQ ID NO: 326          moltype = AA  length = 14
FEATURE                 Location/Qualifiers
source                  1..14
                        mol_type = protein
                        organism = synthetic construct
                        note = Synthetic Construct
SEQUENCE: 326
NVLLSRQING AYVH                                                      14

SEQ ID NO: 327          moltype = AA  length = 10
FEATURE                 Location/Qualifiers
source                  1..10
                        mol_type = protein
                        organism = synthetic construct
                        note = Synthetic Construct
SEQUENCE: 327
EMGATINVMA                                                           10
```